United States Patent
Naso et al.

(10) Patent No.: US 11,661,459 B2
(45) Date of Patent: *May 30, 2023

(54) ARTIFICIAL CELL DEATH POLYPEPTIDE FOR CHIMERIC ANTIGEN RECEPTOR AND USES THEREOF

(71) Applicant: Century Therapeutics, Inc., Philadelphia, PA (US)

(72) Inventors: Michael Naso, Philadelphia, PA (US); Jill Carton, Philadelphia, PA (US); John Wheeler, Philadelphia, PA (US); Luis Borges, Philadelphia, PA (US)

(73) Assignee: Century Therapeutics, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/457,142

(22) Filed: Dec. 1, 2021

(65) Prior Publication Data

US 2022/0177592 A1   Jun. 9, 2022

Related U.S. Application Data

(60) Provisional application No. 63/120,948, filed on Dec. 3, 2020.

(51) Int. Cl.
| | | |
|---|---|---|
| *C07K 16/28* | (2006.01) | |
| *A61K 35/545* | (2015.01) | |
| *C12N 15/63* | (2006.01) | |
| *C07K 14/54* | (2006.01) | |
| *A61K 38/00* | (2006.01) | |
| *C07K 14/55* | (2006.01) | |

(52) U.S. Cl.
CPC ........ *C07K 16/2863* (2013.01); *A61K 35/545* (2013.01); *C07K 14/5443* (2013.01); *C07K 14/55* (2013.01); *C12N 15/63* (2013.01); *A61K 38/00* (2013.01)

(58) Field of Classification Search
CPC ............ C07K 16/2863; C07K 14/5443; C07K 14/55; A61K 35/545; A61K 38/00; C12N 15/63
See application file for complete search history.

(56) References Cited

U.S. PATENT DOCUMENTS

| | | |
|---|---|---|
| 5,843,728 A | 12/1998 | Seed |
| 6,139,835 A | 10/2000 | Kucherlapati |
| 6,140,081 A | 10/2000 | Barbas |
| 6,453,242 B1 | 9/2002 | Eisenberg |
| 6,534,261 B1 | 3/2003 | Cox, III |
| 7,446,179 B2 | 11/2008 | Jensen |
| 7,446,190 B2 | 11/2008 | Sadelain |
| 7,741,465 B1 | 6/2010 | Eshhar |
| 7,888,121 B2 | 2/2011 | Urnov |
| 7,972,854 B2 | 7/2011 | Miller |
| 7,998,736 B2 | 8/2011 | Morgan |
| 8,163,879 B2 | 4/2012 | Wong |
| 8,211,422 B2 | 7/2012 | Eshhar |
| 8,318,491 B2 | 11/2012 | Choi |
| 8,338,172 B2 | 12/2012 | Funaro |
| 8,389,282 B2 | 3/2013 | Sadelain |
| 8,399,645 B2 | 3/2013 | Campana |
| 8,530,636 B2 | 9/2013 | Wandless |
| 8,546,140 B2 | 10/2013 | Mack |
| 8,765,470 B2 | 7/2014 | Thomson |
| 8,802,374 B2 | 8/2014 | Jensen |
| 8,846,395 B2 | 9/2014 | Slukvin |
| 8,906,682 B2 | 12/2014 | June |
| 8,911,993 B2 | 12/2014 | June |
| 8,916,381 B1 | 12/2014 | June |
| 8,945,922 B2 | 2/2015 | Watarai |
| 8,946,385 B2 | 2/2015 | Kawai |
| 8,975,071 B1 | 3/2015 | June |
| 9,034,650 B2 | 5/2015 | Padidam |
| 9,181,322 B2 | 11/2015 | Campbell |
| 9,181,527 B2 | 11/2015 | Sentman |
| 9,206,394 B2 | 12/2015 | Nakauchi |
| 9,303,080 B2 | 4/2016 | Felber |
| 9,328,332 B2 | 5/2016 | Mack |
| 9,371,386 B2 | 6/2016 | Vallera |
| 9,428,573 B2 | 8/2016 | Wong |
| 9,447,194 B2 | 9/2016 | Jensen |
| 9,475,883 B2 | 10/2016 | Chang |
| 9,493,569 B2 | 11/2016 | Igawa |
| 9,511,092 B2 | 12/2016 | Campana |
| 9,629,877 B2 | 4/2017 | Cooper |
| 9,644,184 B2 | 5/2017 | Mack |

(Continued)

FOREIGN PATENT DOCUMENTS

| | | |
|---|---|---|
| CA | 3048979 | 7/2018 |
| CN | 108624608 | 10/2018 |

(Continued)

OTHER PUBLICATIONS

Altschul, Stephen F., et al., "Gapped BLAST and PSI-BLAST: a new generation of protein database search programs", Nucleic Acids Research, vol. 25, No. 7, pp. 3389-3402, 1997.

Binz, H. Kaspar, et al., "Engineering novel binding proteins from nonimmunoglobulin domains", Nature Biotechnology, vol. 23, No. 10, pp. 1257-1268, 2005.

Bix, Mark, et al., "Rejection of class I MHC-deficient haemopoietic cells by irradiated MHC-matched mice", Nature, vol. 349, pp. 329-331, 1991.

(Continued)

*Primary Examiner* — Ruixiang Li
(74) *Attorney, Agent, or Firm* — Ice Miller LLP

(57) ABSTRACT

Provided are polynucleotides encoding inactivated cell surface receptors. Also provided are genetically engineered induced pluripotent stem cells (iPSCs) and derivative cells thereof expressing a chimeric antigen receptor (CAR) and methods of using the same. Also provided are compositions, polypeptides, vectors, and methods of manufacturing.

11 Claims, 46 Drawing Sheets

Specification includes a Sequence Listing.

(56) References Cited

U.S. PATENT DOCUMENTS

| | | |
|---|---|---|
| 9,757,458 B2 | 9/2017 | Chang |
| 9,765,330 B1 | 9/2017 | Niazi |
| 9,782,462 B2 | 10/2017 | Bancel |
| 9,833,476 B2 | 12/2017 | Zhang |
| 9,855,297 B2 | 1/2018 | Duchateau |
| 9,868,774 B2 | 1/2018 | Orentas |
| 9,932,607 B2 | 4/2018 | Calos |
| 10,077,312 B2 | 9/2018 | Urech |
| 10,081,817 B2 | 9/2018 | Padidam |
| 10,093,738 B2 | 10/2018 | Johnson |
| 10,098,926 B2 | 10/2018 | Pulé |
| 10,144,770 B2 | 12/2018 | Campana |
| 10,166,255 B2 | 1/2019 | Moriarity |
| 10,189,880 B2 | 1/2019 | Heemskerk |
| 10,189,903 B2 | 1/2019 | Jensen |
| 10,221,245 B2 | 3/2019 | Brogdon |
| 10,253,086 B2 | 4/2019 | Bitter |
| 10,266,805 B2 | 4/2019 | Zuniga-Pflucker |
| 10,287,606 B2 | 5/2019 | Valamehr |
| 10,344,280 B1 | 7/2019 | Niazi |
| 10,358,477 B2 | 7/2019 | Jacques |
| 10,370,452 B2 | 8/2019 | Themeli |
| 10,391,126 B2 | 8/2019 | Cooper |
| 10,406,177 B2 | 9/2019 | Moriarity |
| 10,428,305 B2 | 10/2019 | Campana |
| 10,464,989 B2 | 11/2019 | Walcheck |
| 10,494,645 B2 | 12/2019 | Auricchio |
| 10,500,229 B2 | 12/2019 | Lee |
| 10,519,248 B2 | 12/2019 | Cheung |
| 10,525,110 B2 | 1/2020 | Slawin |
| 10,538,739 B2 | 1/2020 | Campana |
| 10,590,205 B2 | 3/2020 | Williams |
| 10,603,378 B2 | 3/2020 | June |
| 10,603,380 B2 | 3/2020 | Wiltzius |
| 10,633,450 B2 | 4/2020 | Kohrt |
| 10,633,451 B2 | 4/2020 | Bourquin |
| 10,654,928 B2 | 5/2020 | Kloss |
| 10,682,378 B2 | 6/2020 | Zhang |
| 10,696,723 B2 | 6/2020 | Winston |
| 10,703,816 B2 | 7/2020 | Orentas |
| 10,709,775 B2 | 7/2020 | Dusseaux |
| 10,724,052 B2 | 7/2020 | Rezania |
| 10,738,116 B2 | 8/2020 | Fry |
| 10,774,309 B2 | 9/2020 | Campana |
| 10,780,118 B2 | 9/2020 | Jensen |
| 10,787,642 B2 | 9/2020 | Nakauchi |
| 10,801,012 B2 | 10/2020 | Campana |
| 10,813,952 B2 | 10/2020 | Childs |
| 10,827,606 B2 | 11/2020 | Chen |
| 10,829,556 B2 | 11/2020 | Jensen |
| 10,829,737 B2 | 11/2020 | Campana |
| 10,836,998 B2 | 11/2020 | Duchateau |
| 10,836,999 B2 | 11/2020 | Campana |
| 10,858,628 B2 | 12/2020 | Valamehr |
| 10,865,424 B2 | 12/2020 | Rezania |
| 10,912,797 B2 | 2/2021 | Moriarity |
| 10,912,799 B2 | 2/2021 | Mukherjee |
| 10,927,346 B2 | 2/2021 | Valamehr |
| 10,934,336 B2 | 3/2021 | Zhao |
| 10,941,381 B2 | 3/2021 | Cui |
| 10,960,024 B2 | 3/2021 | Klingemann |
| 10,960,064 B2 | 3/2021 | O'Dwyer |
| 10,975,149 B2 | 4/2021 | Huntington |
| 10,975,392 B2 | 4/2021 | Tsai |
| 10,981,970 B2 | 4/2021 | Pulé |
| 11,028,143 B2 | 6/2021 | Zhao |
| 11,041,021 B2 | 6/2021 | Chang |
| 11,058,723 B2 | 7/2021 | Klingemann |
| 11,072,781 B2 | 7/2021 | Valamehr |
| 11,077,143 B2 | 8/2021 | Klingemann |
| 11,090,335 B2 | 8/2021 | Dai |
| 11,104,735 B2 | 8/2021 | Huntington |
| 11,129,850 B2 | 9/2021 | Klingemann |
| 11,154,574 B2 | 10/2021 | Moriarity |
| 11,207,350 B2 | 12/2021 | Lee |
| 11,214,619 B2 | 1/2022 | Prinz |
| 11,220,551 B2 | 1/2022 | Moffat |
| 11,229,669 B2 | 1/2022 | Sadelain |
| 11,230,699 B2 | 1/2022 | Lee |
| 11,242,375 B2 | 2/2022 | Adusumilli |
| 11,253,547 B2 | 2/2022 | Trager |
| 11,254,912 B2 | 2/2022 | Terrett |
| 11,266,692 B2 | 3/2022 | Moriarity |
| 11,267,901 B2 | 3/2022 | Fedorov |
| 11,344,577 B2 | 5/2022 | Cooper |
| 11,365,394 B2 | 6/2022 | Valamehr |
| 2002/0114781 A1 | 8/2002 | Strom |
| 2005/0196404 A1 | 9/2005 | Crew |
| 2006/0046294 A1 | 3/2006 | Ow |
| 2010/0068815 A1 | 3/2010 | Ow |
| 2011/0136237 A1 | 6/2011 | Ow |
| 2011/0145940 A1 | 6/2011 | Voytas |
| 2013/0071414 A1 | 3/2013 | Dotti |
| 2014/0134195 A1 | 5/2014 | Russell |
| 2015/0140665 A1 | 5/2015 | Calos |
| 2016/0036472 A1 | 2/2016 | Chang |
| 2017/0005308 A1 | 1/2017 | Fujii |
| 2017/0369850 A1 | 12/2017 | Kaneko |
| 2018/0044686 A1 | 2/2018 | Nagy |
| 2018/0153977 A1 | 6/2018 | Wu |
| 2018/0171298 A1 | 6/2018 | Duchateau |
| 2018/0273601 A1 | 9/2018 | Adusumilli |
| 2018/0273903 A1 | 9/2018 | Zhang |
| 2018/0362975 A1 | 12/2018 | Chen |
| 2019/0010514 A1 | 1/2019 | Poirot |
| 2019/0019269 A1 | 1/2019 | Itagaki |
| 2019/0048060 A1 | 2/2019 | Conway |
| 2019/0054122 A1 | 2/2019 | Moriarity |
| 2019/0060363 A1 | 2/2019 | Moriarity |
| 2019/0060364 A1 | 2/2019 | Moriarity |
| 2019/0062394 A1 | 2/2019 | Yarlagadda |
| 2019/0062735 A1 | 2/2019 | Welstead |
| 2019/0091310 A1 | 3/2019 | Wright |
| 2019/0119638 A1 | 4/2019 | Sadelain |
| 2019/0144515 A1 | 5/2019 | Sievers |
| 2019/0161530 A1 | 5/2019 | Certo |
| 2019/0161727 A1 | 5/2019 | Kawamoto |
| 2019/0175651 A1 | 6/2019 | Lee |
| 2019/0183936 A1 | 6/2019 | Shum Shum |
| 2019/0202918 A1 | 7/2019 | Lim |
| 2019/0271005 A1 | 9/2019 | Valamehr |
| 2019/0314418 A1 | 10/2019 | Mukherjee |
| 2019/0338309 A1 | 11/2019 | Vallier |
| 2019/0365876 A1 | 12/2019 | Russell |
| 2019/0375850 A1 | 12/2019 | Themeli |
| 2019/0381154 A1 | 12/2019 | Russell |
| 2019/0382759 A1 | 12/2019 | Nelles |
| 2019/0388472 A1 | 12/2019 | Cooper |
| 2020/0054675 A1 | 2/2020 | Dipersio |
| 2020/0063100 A1 | 2/2020 | Terrett |
| 2020/0069734 A1 | 3/2020 | Valamehr |
| 2020/0080107 A1 | 3/2020 | Rezania |
| 2020/0087681 A1 | 3/2020 | Qasim |
| 2020/0095543 A1 | 3/2020 | Bhattacharya |
| 2020/0109364 A1 | 4/2020 | Dipersio |
| 2020/0147134 A1 | 5/2020 | Qin |
| 2020/0172879 A1 | 6/2020 | Suri |
| 2020/0224163 A1 | 7/2020 | Busser |
| 2020/0283489 A1 | 9/2020 | Winston |
| 2020/0283522 A1 | 9/2020 | Orentas |
| 2020/0289571 A1 | 9/2020 | Moriarity |
| 2020/0299661 A1 | 9/2020 | Gori |
| 2020/0318067 A1 | 10/2020 | Gilham |
| 2020/0352998 A1 | 11/2020 | Albertson |
| 2020/0354673 A1 | 11/2020 | Schrepfer |
| 2020/0407728 A1 | 12/2020 | Zhao |
| 2021/0013950 A1 | 1/2021 | Yang |
| 2021/0015859 A1 | 1/2021 | Valamehr |
| 2021/0024959 A1 | 1/2021 | Valamehr |
| 2021/0060072 A1 | 3/2021 | Terrett |
| 2021/0062227 A1 | 3/2021 | Qi |
| 2021/0069242 A1 | 3/2021 | Genkin |
| 2021/0079347 A1 | 3/2021 | Terrett |
| 2021/0087537 A1 | 3/2021 | Valamehr |

(56) References Cited

U.S. PATENT DOCUMENTS

| | | | |
|---|---|---|---|
| 2021/0115404 A1 | 4/2021 | Campana |
| 2021/0138051 A1 | 5/2021 | O'Dwyer |
| 2021/0139935 A1 | 5/2021 | Carson |
| 2021/0161954 A1 | 6/2021 | Smith |
| 2021/0163895 A1 | 6/2021 | Valamehr |
| 2021/0180017 A1 | 6/2021 | Valamehr |
| 2021/0187025 A1 | 6/2021 | Dipierro |
| 2021/0198342 A1 | 7/2021 | Boissel |
| 2021/0205362 A1 | 7/2021 | Davila |
| 2021/0230289 A1 | 7/2021 | Chen |
| 2021/0230548 A1 | 7/2021 | Daher |
| 2021/0246425 A1 | 8/2021 | Terrett |
| 2021/0252073 A1 | 8/2021 | Mukherjee |
| 2021/0254005 A1 | 8/2021 | Kang |
| 2021/0260116 A1 | 8/2021 | Boissel |
| 2021/0260117 A1 | 8/2021 | Moriarity |
| 2021/0261919 A1 | 8/2021 | Terrett |
| 2021/0309713 A1 | 10/2021 | Xie |
| 2021/0347850 A1 | 11/2021 | Boissel |
| 2021/0363212 A1 | 11/2021 | Ghonime |
| 2021/0386785 A1 | 12/2021 | Klingemann |
| 2022/0002424 A1 | 1/2022 | Trager |
| 2022/0017594 A1 | 1/2022 | Navarro |
| 2022/0025329 A1 | 1/2022 | Lee |
| 2022/0047634 A1 | 2/2022 | Marasco |
| 2022/0054544 A1 | 2/2022 | Lin |
| 2022/0074945 A1 | 3/2022 | Sadelain |
| 2022/0127328 A1 | 4/2022 | Valamehr |
| 2022/0127366 A1 | 4/2022 | Fotakis |
| 2022/0162301 A1 | 5/2022 | Wang |
| 2022/0169988 A1 | 6/2022 | Kyrychenko |
| 2022/0184123 A1 | 6/2022 | Naso |
| 2022/0184142 A1 | 6/2022 | Valamehr |
| 2022/0195396 A1 | 6/2022 | Naso |
| 2022/0323480 A1 | 10/2022 | Goodman |
| 2022/0332782 A1 | 10/2022 | Naso |

FOREIGN PATENT DOCUMENTS

| | | |
|---|---|---|
| CN | 110272493 A | 9/2019 |
| EP | 0638119 | 6/2003 |
| EP | 2694549 | 2/2014 |
| EP | 2699593 | 2/2014 |
| EP | 2768863 | 8/2014 |
| EP | 2814846 | 12/2014 |
| EP | 2819701 | 1/2015 |
| EP | 2838548 | 2/2015 |
| EP | 2958943 | 12/2015 |
| EP | 2981607 | 2/2016 |
| EP | 2997134 | 3/2016 |
| EP | 3004337 | 4/2016 |
| EP | 3048112 | 7/2016 |
| EP | 3105317 | 12/2016 |
| EP | 3116902 | 1/2017 |
| EP | 3143134 | 3/2017 |
| EP | 3234144 | 10/2017 |
| EP | 3268480 | 1/2018 |
| EP | 3298032 | 3/2018 |
| EP | 3307877 | 4/2018 |
| EP | 3317401 | 5/2018 |
| EP | 3334442 | 6/2018 |
| EP | 3344284 | 7/2018 |
| EP | 3368689 | 9/2018 |
| EP | 3421590 | 1/2019 |
| EP | 3434762 | 1/2019 |
| EP | 3459560 | 3/2019 |
| EP | 3545079 | 10/2019 |
| EP | 3694546 | 8/2020 |
| EP | 3728563 | 10/2020 |
| EP | 3732205 | 11/2020 |
| EP | 3775228 | 2/2021 |
| EP | 3789487 | 3/2021 |
| EP | 3791892 | 3/2021 |
| EP | 3845638 | 7/2021 |
| WO | 9527722 | 10/1995 |
| WO | 9853058 | 11/1998 |
| WO | 9853059 | 11/1998 |
| WO | 9853060 | 11/1998 |
| WO | 0216536 | 2/2002 |
| WO | 03016496 | 2/2003 |
| WO | 2007060406 A1 | 5/2007 |
| WO | 2008102274 | 8/2008 |
| WO | 2009152529 A2 | 12/2009 |
| WO | 2010099539 | 9/2010 |
| WO | 2011056894 A2 | 5/2011 |
| WO | 2012109208 | 8/2012 |
| WO | 2012145384 | 10/2012 |
| WO | 2013044225 A1 | 3/2013 |
| WO | 2013074916 | 5/2013 |
| WO | 2013153391 | 10/2013 |
| WO | 2013158292 | 10/2013 |
| WO | 2013176915 | 11/2013 |
| WO | 2014031687 A1 | 2/2014 |
| WO | 2014055771 A1 | 4/2014 |
| WO | 2014065961 A1 | 5/2014 |
| WO | 2014165707 | 10/2014 |
| WO | 2015105522 | 7/2015 |
| WO | 2015142675 | 9/2015 |
| WO | 2016010148 | 1/2016 |
| WO | 2016044811 A1 | 3/2016 |
| WO | 2017040945 | 3/2017 |
| WO | 2017070333 | 4/2017 |
| WO | 2017078807 | 5/2017 |
| WO | 2017079673 A1 | 5/2017 |
| WO | 2017093969 | 6/2017 |
| WO | 2017106537 | 6/2017 |
| WO | 2017179720 | 10/2017 |
| WO | 2017180989 | 10/2017 |
| WO | 2017222593 A1 | 12/2017 |
| WO | 2018002358 A1 | 1/2018 |
| WO | 2018048828 | 3/2018 |
| WO | 2018058002 | 3/2018 |
| WO | 2018096343 | 5/2018 |
| WO | 2018108106 | 6/2018 |
| WO | 2018127585 A1 | 7/2018 |
| WO | 2018132783 | 7/2018 |
| WO | 2018161038 | 9/2018 |
| WO | 2018213731 | 11/2018 |
| WO | 2018226897 | 12/2018 |
| WO | 2018226958 | 12/2018 |
| WO | 2018236548 | 12/2018 |
| WO | 2019023396 | 1/2019 |
| WO | 2019023396 A1 | 1/2019 |
| WO | 2019033023 | 2/2019 |
| WO | 2019060695 | 3/2019 |
| WO | 2019067805 | 4/2019 |
| WO | 2019070856 | 4/2019 |
| WO | 2019076149 | 4/2019 |
| WO | 2019112899 | 6/2019 |
| WO | 2019126724 | 6/2019 |
| WO | 2019126748 | 6/2019 |
| WO | 2019157597 | 8/2019 |
| WO | 2019160956 | 8/2019 |
| WO | 2019161271 | 8/2019 |
| WO | 2019191495 | 10/2019 |
| WO | 2019204643 | 10/2019 |
| WO | 2019204661 | 10/2019 |
| WO | 2019205403 | 10/2019 |
| WO | 2019209991 | 10/2019 |
| WO | 2019220109 | 11/2019 |
| WO | 2019220110 | 11/2019 |
| WO | 2019241688 | 12/2019 |
| WO | 2019246563 | 12/2019 |
| WO | 2020000035 | 1/2020 |
| WO | 2020006126 | 1/2020 |
| WO | 2020010235 | 1/2020 |
| WO | 2020019983 | 1/2020 |
| WO | 2020088631 | 5/2020 |
| WO | 2020092467 | 5/2020 |
| WO | 2020097395 | 5/2020 |
| WO | 2020123716 | 6/2020 |
| WO | 2020124021 | 6/2020 |
| WO | 2020150702 | 7/2020 |
| WO | 2020168300 | 8/2020 |

(56) References Cited

FOREIGN PATENT DOCUMENTS

| | | |
|---|---|---|
| WO | 2020172177 | 8/2020 |
| WO | 2020223445 | 11/2020 |
| WO | 2020237227 A1 | 11/2020 |
| WO | 2020247392 | 12/2020 |
| WO | 2020261219 | 12/2020 |
| WO | 2021013950 | 1/2021 |
| WO | 2021015997 | 1/2021 |
| WO | 2021041316 | 3/2021 |
| WO | 2021069508 | 4/2021 |
| WO | 2021076427 | 4/2021 |
| WO | 2021077117 | 4/2021 |
| WO | 2021081133 | 4/2021 |
| WO | 2021087466 | 5/2021 |
| WO | 2021092252 | 5/2021 |
| WO | 2021095009 | 5/2021 |
| WO | 2021099944 | 5/2021 |
| WO | 2021127594 | 6/2021 |
| WO | 2021146627 | 7/2021 |
| WO | 2021154218 | 8/2021 |
| WO | 2021226151 | 11/2021 |
| WO | 2021252804 | 12/2021 |
| WO | 2021258016 | 12/2021 |
| WO | 2022036041 | 2/2022 |
| WO | 2022038158 | 2/2022 |
| WO | 2022076910 | 4/2022 |
| WO | 2022087453 | 4/2022 |
| WO | 2022093825 | 5/2022 |
| WO | 2022099297 | 5/2022 |

OTHER PUBLICATIONS

Borges, Luis, et al., "Development of Multi-Engineered iPSC-Derived CAR-NK Cells for the Treatment of B-Cell Malignancies", Blood, 138 (Supplement 1), 1729, 2021.

Braud, Veronique M., et al., "HLA-E binds to natural killer cell receptors CD94/NKG2A, B and C", Nature, vol. 391, pp. 795-799, 1998.

Brentjens, Renier, et al., "CD19-targeted T cells rapidly induce molecular remissions in adults with chemotherapy-refractory acute lymphoblastic leukemia", Sci Transl Med., vol. 177, No. 5, 19 pages, 2013.

Byla, Povilas, et al., "Selection of a Novel and Highly Specific Tumor Necrosis Factor a(TNFa) Antagonist", Journal of Biological Chemistry, vol. 285, No. 16, pp. 12096-12100, 2010.

Curran, Kevin J., et al., "Chimeric Antigen Receptor T Cells for Cancer Immunotherapy", Journal of Clinical Oncology, vol. 33, No. 15, 6 pages, 2015.

Depil, S., et al., "Off-the-shelf allogeneic CAR T cells: development and challenges", Nature, 15 pages, published online 2020.

Donnelly, Michelle L.L., et al., "Analysis of the aphthovirus 2A/2B polyprotein 'cleavage' mechanism indicates not a proteolytic reaction, but a novel translational effect: a putative ribosomal 'skip'", Journal of General Virology, 82, pp. 1013-1025, 2001.

Felix, Nathan J., et al., "Specificity of T-cell alloreactivity", Nature, vol. 7, pp. 942-953, 2007.

Gill, Davinder S., et al., "Biopharmaceutical drug discovery using novel protein scaffolds", ScienceDirect, 17, pp. 653-658, 2006.

Gornalusse, German G., et al., "HLA-E-expressing pluripotent stem cells escape allogeneic responses and lysis by NK cells", Nature Biotechnology—HHS Public Access, vol. 35, No. 8, pp. 765-772, 2017.

Gornalusse, German G., et al., "HLA-E-expressing pluripotent stem cells escape allogeneic responses and lysis by NK cells", Nature Biotechnology, vol. 35, No. 8, pp. 765-775, 2017.

Henikoff, Steven, et al., "Amino acid substitution matrices from protein blocks", Proc. Natl. Acad. Sci. USA, vol. 89, pp. 10915-10919, 1992.

Hey, Thomas, et al., "Artificial, non-antibody binding proteins for pharmaceutical and industrial applications", TRENDS in Biotechnology, vol. 23, No. 10, pp. 514-522, 2005.

Hollinger, Philipp, et al., "Engineered antibody fragments and the rise of single domains", Nature Biotechnology, vol. 23, No. 9, pp. 1126-1136, 2005.

International Search Report and Written Opinion issued in App. No. PCT/US2021/072646, dated Mar. 29, 2022, 19 pages.

Jena, Bipulendu, et al., "Redirecting T-cell specificity by introducing a tumor-specific chimeric antigen receptor", Blood, 116, pp. 1035-1044, 2010.

Jones, Benjamin S., et al., "Improving the safety of cell therapy products by suicide gene transfer", Frontiers in Phamacology, vol. 5, Article 254, 8 pages, 2014.

Karabekian, Zaruhi, et al., "Downregulation of beta-microglobulin to diminish T-lymphocyte lysis of non-syngeneic cell sources of engineered heart tissue constructs", Biomed Mater., 10(3):034101, 2021.

Karlin, Samuel, et al., "Applications and statistics for multiple high-scoring segments in molecular sequences", Proc. Natl. Acad. Sci. USA, vol. 90, pp. 5873-5877, 1993.

Kochenderfer, James N., et al., "Construction and Pre-clinical Evaluation of an Anti-CD19 Chimeric Antigen Receptor", J Immunother., 32(7), pp. 689-702, 2009.

Koide, Akiko, et al., "Antibody Mimics Based on the Scaffold of the Fibronectin Type III Domain", Methods in Molecular Biology, vol. 352, pp. 95-109, 2007.

Krangel, Michael S., et al., "Assembly and Maturation of HLA-A and HLA-B Antigens In Vivo", Cell, vol. 18, pp. 979-991, 1979.

Lanza, Robert, et al., "Engineering universal cells that evade immune detection", Nature Reviews, vol. 19, pp. 723-733, 2019.

Liao, Nan-Shih, et al., "MHC ClassI Deficiency: Susceptibility to Natural Killer (NK) Cells and Impaired NK Activity", Science, 253, pp. 199-202, 1991.

Liu, M.D., Enli, et al., "Use of CAR-Transduced Natural Killer Cells in CD19-Positive Lymphoid Tumors", N Engl J Med., 382(6), pp. 545-553, 2020.

Matsunaga, Yusuke, et al., "Activation of Antigen-Specific Cytotoxic T Lymphocytes by ☐ 2-Microglobulin or TAP1 Gene Disruption and the Introduction of Recipient-Matched MHC Class I Gene in Allogeneic Embryonic Stem Cell-Derived Dendritic Cells", J Immunol, 181, pp. 6635-6643, 2008.

Miller, Joseph D., et al., "Analysis of HLA-E Peptide-Binding Specificity and Contact Residues in Bound Peptide Required for Recognition by CD94/NKG2", The Journal of Immunology, 171, pp. 1369-1375, 2003.

Needleman, Saul B., et al., "A General Method Applicable to the Search for Similarities in the Amino Acid Sequence of Two Proteins", J. Mel. Biol., 48, pp. 443-453, 1970.

Nishimura, Toshinobu, et al., "Generation of Rejuvenated Antigen-Specific T Cells by Reprogramming to Pluripotency and Rediferentiation", Cell Stem Cell, 12, pp. 114-126, 2013.

Pearson, William R., et al., "Improved tools for biological sequence comparison", Proc. Natl. Acad. Sci. USA, vol. 85, pp. 2444-2448, 1988.

Ryan, Martin D., et al., "Cleavage of foot-and-mouth disease virus polyprotein is mediated by residues located within a 19 amino acid sequence", Journal of General Virology, 72, pp. 2727-2732, 1991.

Seki, Tomohisa, et al., "Generation of Induced Pluripotent Stem Cells from Human Terminally Differentiated Circulating T Cells", Cell Stem Cell, 7, pp. 11-14, 2010.

Skerra, Arne, "Alternative non-antibody scaffolds for molecular recognition", Current Opinion in Biotechnology, 18, pp. 295-304, 2007.

Smith, Temple F., "Comparison of Biosequences", Advances in Applied Mathematics, 2, pp. 482-489, 1981.

Themeli, Maria, et al., "Generation of tumor-targeted human T lymphocytes from induced pluripotent stem cells for cancer therapy", Nat Biotechnol., 31, 10, pp. 928-933, 2013.

Wikman, M., et al., "Selection and characterization of HER2/neu-binding affibody ligands", Protein Engineering, Design & Selection, vol. 17, No. 5, pp. 455-462, 2004.

Worn, Arne, et al., "Stability Engineering of Antibody Single-chain Fv Fragments", J. Mol. Biol., 305, pp. 989-1010, 2001.

(56) References Cited

OTHER PUBLICATIONS

Wypych, Jette, et al., "Human IgG2 Antibodies Display Disulfide-mediated Structural Isoforms", Journal of biological Chemistry, vol. 283, No. 23, pp. 16194-16205, 2008.

Zijlstra, Maarten, et al., "Germ-line transmission of a disrupted B2-microglobulin gene produced by homologous recombination in embryonic stem cells", Nature, vol. 342, pp. 435-438, 1989.

Zoller, Frederic, et al., "Miniproteins as Phage Display-Scaffolds for Clinical Applications", Molecules, 16, pp. 2467-2485, 2011.

Bibeau F, et al., "Impact of Fcgamma RIIa-Fcgamma RIIIa polymorphisms and KRAS mutations on the clinical outcome of patients with metastatic colorectal cancer treated with cetuximab plus irinotecan", J Clin Oncol (2009) 27 (7):1122-9.

Blazquez-Moreno, Alfonso et al., "Transmembrane features governing Fc receptor CD16A assembly with CD16A signaling adaptor molecules", PNAS, Published online Jun. 26, 2017, E5645-E5654.

Challita PM, et al., "Multiple modifications in cis elements of the long terminal repeat of retroviral vectors lead to increased expression and decreased DNA methylation in embryonic carcinoma cells", J Virol. Feb. 1995;69(2):748-55. https://doi.org/10.1128/JVI.69.2.748-755.1995 PMID: 7815539; PMCID: PMC188638.

Chen I-Ju, et al., "Bispecific antibody (HER2 × mPEG) enhances anti-cancer effects by precise targeting and accumulation of mPEGylated liposomes," Acta Biomaterialia, vol. 111 (2020) pp. 386-397.

Clemenceau et al., "Antibody-dependent cellular cytotoxicity (ADCC) is mediated by genetically modified antigen-specific human T lymphocytes", CD16-FceR1G CAR, Blood 2006;107:4669-4677.

Halene S, et al., "Improved expression in hematopoietic and lymphoid cells in mice after transplantation of bone marrow transduced with a modified retroviral vector", Blood. Nov. 15, 1999;94(10):3349-57.

Hara, et al. "Neuron-like differentiation and selective ablation of undifferentiated embryonic stem cells containing suicide gene with Oct-4 promoter." Stem Cells and Develop., 2008, vol. 17, pp. 619-628.

Huang WC, et al., "Engineering Chimeric Receptors to Investigate the Size- and Rigidity-Dependent Interaction of PEGylated Nanoparticles with Cells", ACS Nano. Jan. 26, 2016;10(1):648-62.

Inniss, Mara C. et al. "A Novel Bxb1 Integrase RMCE System for High Fidelity Site-Specific Integration of mAb Expression Cassette in CHO cells" BioTechnology BioEngineering, vol. 114, No. 8 (Aug. 2017) pp. 1837-1846.

Jing, Yawu et al. "Identification of an ADAM17 clavage region in human CD16 and the engineering of a non-cleavable version in NK cells", Plos One 2015; 10(3) 14 pages.

Koene, Harry R., et al. "FcγRIIIa-158V/F Polymorphism Influences the Binding of IgG by Natural Killer Cell FcγRIIIa, Independently of the FcγRIIIa-48L/R/H Phenotype," Blood. 1997; 90: 1109-1114.

Kudo, Ko, et al. "T lymphocytes expressing a CD16 signaling receptor exert antibody-dependent cancer cell killing." Cancer Research; 74(1) (2014) pp. 93-103.

Kyba, Michael et al. "Enhanced hematopoietic differentiation of embryonic stem cells conditionally expressing Stat5." PNAS, 2003, vol. 100, pp. 11904-11910.

Lasek, Witold et al. "Interleukin 12: still a promising candidate for tumor immunotherapy?" Cancer Immunol Immunother. 2014; 63(5): 419-435.

Li, Xiaoli et al. "The unique cytoplasmic domain of human FcγRIIIA regulates receptor-mediated function." J Immunol. Nov. 2012, 189(9):4284-4294.

Matreyek, Kenneth A. et al. "A platform for functional assessment of large variant libraries in mammalian cells," Nucleic Acids Research, vol. 45, No. 11 (Mar. 15, 2017).

Mirlekar, Bhalchandra et al. "IL-12 Family Cytokines in Cancer and Immunotherapy", Cancers (Basel). Jan. 2021; 13(2): 167.

Ochi, Fumihiro, et al. "Gene-modified human α/β-T cells expressing a chimeric CD16-CD3 receptor as adoptively transferable effector cells for anticancer monoclonal antibody therapy." Cancer Immunol Res (2014) 2(3):249-62.

Qin, Haiying et al. "Preclinical Development of Bivalent Chimeric Antigen Receptors Targeting Both CD19 and CD22," Molecular Therapy Oncolytics, vol. 11 (Dec. 21, 2018) pp. 127-137.

Rong, Zhili et al. "A scalable approach to prevent teratoma formation of human embryonic stem cells." J. Biol. Chem., 2012, vol. 287, No. 39, pp. 32338-32345.

Sarin, Kavita Y. et al. "Conditional telomerase induction causes proliferation of hair follicle stem cells." Nature, 2005, vol. 436, pp. 1048-1052.

Suri, Vipin et al. "Small Molecule Regulated Cytokine Expression Enables Potent and Durable Responses to Engineered T-Cell Therapy." Blood, vol. 132, supplemental 1; (Nov. 29, 2018).

Tanaka, Hiroki et al. "Development of Engineered T Cells Expressing a Chimeric CD16-CD3. Receptor to Improve the Clinical Efficacy of Mogamulizumab Therapy Against Adult T-Cell Leukemia." Clin Cancer Res, vol. 22, issue 17, (Sep. 1, 2016), pp. 4405-4416.

Wilkin MS, Ciarlo C, Peari J, et al. Regulatory DNA keyholes enable specific and persistent multi-gene expression programs in primary T cells without genome modification. bioRxiv (2020): 2020-02.

Wu, J et al., "A novel polymorphism of FcgammaRIIIa (CD16) alters receptor function and predisposes to autoimmune disease", J Clin Invest. 1997, 100(5): 1059-1070.

Zenatti, Priscila P., et al. "Oncogenic IL7R gain-of-function mutations in childhood T-cell acute lymphoblastic leukemia," Nature Genetics.; 43(10), Sep. 4, 2011, pp. 932-939.

Zhang, Ling et al. "Enhanced efficacy and limited systemic cytokine exposure with membrane-anchored interleukin-12 T-cell therapy in murine tumor models" J Immunother Cancer. Jan. 2020;8(1).

Zhu, Huang et al., "Pluripotent stem cell-derived NK cells with high-affinity noncleavable CD16a mediate improved antitumor activity", Blood 2020, 135(6): 399-410.

Wang et al., "A transgene-encoded truncated human epidermal growth factor receptor for depletion of anti- B-cell maturation antigen CAR-T cells," Cellular Immunology 363 (2021) 104342.

Duong et al., "Two-Dimensional Regulation of CAR-T Cell Therapy with Orthogonal Switches," Molecular Therapy: Oncolytics vol. Mar. 12, 2019.

ARTIFICIAL CELL DEATH POLYPEPTIDE FOR CHIMERIC ANTIGEN RECEPTOR AND USES THEREOF

CROSS-REFERENCE TO RELATED APPLICATIONS

This application claims the benefit of U.S. Provisional Patent Application No. 63/120,948 filed Dec. 3, 2020, the disclosure of which is incorporated by reference herein in its entirety.

TECHNICAL FIELD

This application provides genetically engineered induced pluripotent stem cells (iPSCs) and derivative cells thereof. Also provided are uses of the iPSCs or derivative cells thereof to express a chimeric antigen receptor for allogenic cell therapy. Also provided are related vectors, polynucleotides, and pharmaceutical compositions.

REFERENCE TO SEQUENCE LISTING SUBMITTED ELECTRONICALLY

This application contains a sequence listing, which is submitted electronically via EFS-Web as an ASCII formatted sequence listing with a file name "066461-3US2_Sequence Listing" and a creation date of Nov. 1, 2021, and having a size of 113 kb. The sequence listing submitted via EFS-Web is part of the specification and is herein incorporated by reference in its entirety.

BACKGROUND

Chimeric antigen receptors (CARs) significantly enhance anti-tumor activity of immune effector cells. CARs are engineered receptors typically comprising an extracellular targeting domain that is linked to a linker peptide, a transmembrane (TM) domain, and one or more intracellular signaling domains. Traditionally, the extracellular domain consists of an antigen binding fragment of an antibody (such as a single chain Fv, scFv) that is specific for a given tumor-associated antigen (TAA) or cell surface target. The extracellular domain confers the tumor specificity of the CAR, while the intracellular signaling domain activates the T cell that has been genetically engineered to express the CAR upon TAA/target engagement. The engineered immune effector cells are re-infused into cancer patients, where they specifically engage and kill cells expressing the TAA target of the CAR (Maus et al., Blood. 2014 Apr. 24; 123(17):2625-35; Curran and Brentjens, J Clin Oncol. 2015 May 20; 33(15):1703-6).

Autologous, patient-specific CAR-T therapy has emerged as a powerful and potentially curative therapy for cancer, especially for CD19-positive hematological malignancies. However, the autologous T cells must be generated on a custom-made basis, which remains a significant limiting factor for large-scale clinical application due to the production costs and the risk of production failure. The development of CAR-T technology and its wider application is also limited due to a number of other key shortcomings, including, e.g., a) an inefficient anti-tumor response in solid tumors, b) limited penetration and susceptibility of adoptively transferred CAR T cells to an immunosuppressive tumor microenvironment (TME), c) poor persistence of CAR-T cells in vivo, d) serious adverse events in the patients including cytokine release syndrome (CRS) and graft-versus-host disease (GVHD) mediated by the CAR-T, and e) the time required for manufacturing.

Therefore, there is an unmet need for therapeutically sufficient and functional antigen-specific immune cells for effective use in immunotherapy.

BRIEF SUMMARY

In one general aspect, provided is a polynucleotide encoding an artificial cell death polypeptide. In certain embodiments, the polynucleotide encodes an inactivated cell surface receptor that comprises a monoclonal antibody-specific epitope and an interleukin 15 (IL-15), wherein the inactivated cell surface receptor and the IL-15 are operably linked by an autoprotease peptide.

In certain embodiments, the inactivated cell surface receptor is selected from the group of monoclonal antibody specific epitopes selected from epitopes specifically recognized by ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, polatuzumab vedotin, ranibizumab, tocilizumab, trastuzumab, vedolizumab, adalimumab, belimumab, canakinumab, denosumab, golimumab, ipilimumab, ofatumumab, panitumumab, and ustekinumab.

In certain embodiments, the inactivated cell surface receptor is a truncated epithelial growth factor receptor (tEGFR) variant.

In certain embodiments, the autoprotease peptide comprises or is a porcine tesehovirus-1 2A (P2A) peptide.

In certain embodiments, the tEGFR variant consists of an amino acid sequence having at least 90%, 91%, 92%, 93%, 94%, 95%, 96%, 97%, 98%, 99% or 100% sequence identity to SEQ ID NO: 71, preferably SEQ ID NO: 71.

In certain embodiments, the IL-15 comprises an amino acid sequence having at least 90%, 91%, 92%, 93%, 94%, 95%, 96%, 97%, 98%, 99% or 100% sequence identity to SEQ ID NO: 72, preferably SEQ ID NO: 72.

In certain embodiments, the autoprotease peptide comprises an amino acid sequence having at least 90%, 91%, 92%, 93%, 94%, 95%, 96%, 97%, 98%, 99% or 100% sequence identity to SEQ ID NO: 73, preferably SEQ ID NO: 73.

In certain embodiments, the polynucleotide consists of operably linked polynucleotides encoding a truncated epithelial growth factor receptor (tEGFR) variant having the amino acid sequence of SEQ ID NO: 71, an autoprotease peptide having the amino acid sequence of SEQ ID NO: 73, and an interleukin 15 (IL-15) having the amino acid sequence of SEQ ID NO: 72.

Also provided is a polynucleotide encoding an inactivated cell surface receptor that comprises an epitope specifically recognized by an antibody selected from the group consisting of cetuximab, matuzumab, necitumumab, panitumumab, polatuzumab vedotin, rituximab and trastuzumab, and an IL-15, wherein the epitope and the cytokine are operably linked by a P2A sequence.

In certain embodiments, the inactivated cell surface receptor comprises an amino acid sequence selected from the group consisting of SEQ ID NO: 74, 79, 81, and 83.

Also provided is a protein encoded by a polynucleotide of the application.

Also provided is an induced pluripotent stem cell (iPSC) or a derivative cell thereof comprising a polynucleotide of the application Also provided is a vector comprising a polynucleotide of the application.

In certain embodiments, the vector further comprises:
(i) a promoter;
(ii) a terminator and/or a polyadenylation signal sequence;
(iii) a left homology sequence; and
(iv) a right homology sequence.

In certain embodiments, the left homology sequence comprises a polynucleotide sequence having at least 90%, 91%, 92%, 93%, 94%, 95%, 96%, 97%, 98%, 99% or 100% sequence identity to the polynucleotide sequence of SEQ ID NO: 84.

In certain embodiments, the right homology sequence comprises a polynucleotide sequence having at least 90%, 91%, 92%, 93%, 94%, 95%, 96%, 97%, 98%, 99% or 100% sequence identity to the polynucleotide sequence of SEQ ID NO: 85.

In certain embodiments, the vector comprises a polynucleotide sequence having at least 85%, 90%, 91%, 92%, 93%, 94%, 95%, 96%, 97%, 98%, 99% or 100% sequence identity to SEQ ID NO: 86.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1A shows CIITA targeting transgene plasmid with a CMV early enhancer/chicken β actin (CAG) promoter, SV40 terminator/polyadenylation signal, and tEGFR-IL15 coding sequence. FIG. 1B shows AAVS1 targeting transgene plasmid with a CAG promoter, SV40 terminator/polyadenylation, and anti-CD19 scFv chimeric antigen receptor (CAR) coding sequence. FIG. 1C shows B2M targeting transgene plasmid with a CAG promoter, SV40 terminator/polyadenylation, and Peptide-B2M-HLA-E coding sequence.

FIG. 3A shows a graph demonstrating IL-15 concentration (pg/ml/1e6 cells/24 hours) released from CAR iNK cells and CAR/IL15 iNK cells. FIG. 3B shows graphs demonstrating percentage iNK cells after 20 days in the blood and lungs of mice injected with CAR iNK cells or CAR-IL15 iNK cells. FIG. 3C shows graphs demonstrating percentage iNK cells in the lungs of mice injected with CAR iNK cells or CAR-IL15 iNK cells and with and without recombinant IL-15.

FIG. 4A shows a graph demonstrating the serial killing of CD19+ Reh cells by CAG-CAR/IL15-iNK cells over time. FIG. 4B shows a graph demonstrating the increased proliferation of CAG-CAR/IL-15 iNK cells compared to CAG-CAR iNK cells. FIG. 4C shows a graph demonstrating the increased target serial killing of CD19+ Raji cells over time by CAG-CAR/IL-15 iNK cells compared to CAG-CAR iNK cells.

FIG. 5A shows a graph demonstrating Raji cell death overtime when cultured with CAG-CAR-IL15 iNK cells with and without IL12. FIG. 5B shows a graph demonstrating tumor growth measured as mean whole body luminescent average radiance of mice infused with IL12-primed and unprimed CAG-CAR-IL15 iNK cells.

FIG. 6A shows a graph demonstrating percentage Annexin-V staining in CAG-CAR expressing cells. FIG. 6B shows a graph demonstrating percentage Annexin-V staining in CAG-CAR-IL15-tEGFR expressing cells.

FIG. 18A shows gating on iNK and T cells. FIG. 18B shows specific lysis of iNK cells co-cultured with CTL at 5:1 CTL:iNK ratio. Each symbol represents one donor, open bar is the parental wild-type iNK cells, and the shaded bar is the edited β2MKO iNK cells.

FIG. 19A shows a histogram plot of CD25 expression of CD8+ T cells. Dashed line indicates T cells alone, the solid open histogram indicates T cells co-cultured with parental wild-type iNK cells, and the shaded histogram indicates T cells co-cultured with edited 132MKO iNK cells.

FIG. 19B shows frequencies of activated T cells in co-cultures with parental iNK cells (open bar), β2MKO iNK cells (shaded bar), or T cells alone with no targets (hatched bar). Each symbol represents one donor.

DETAILED DESCRIPTION

Figure 1A:
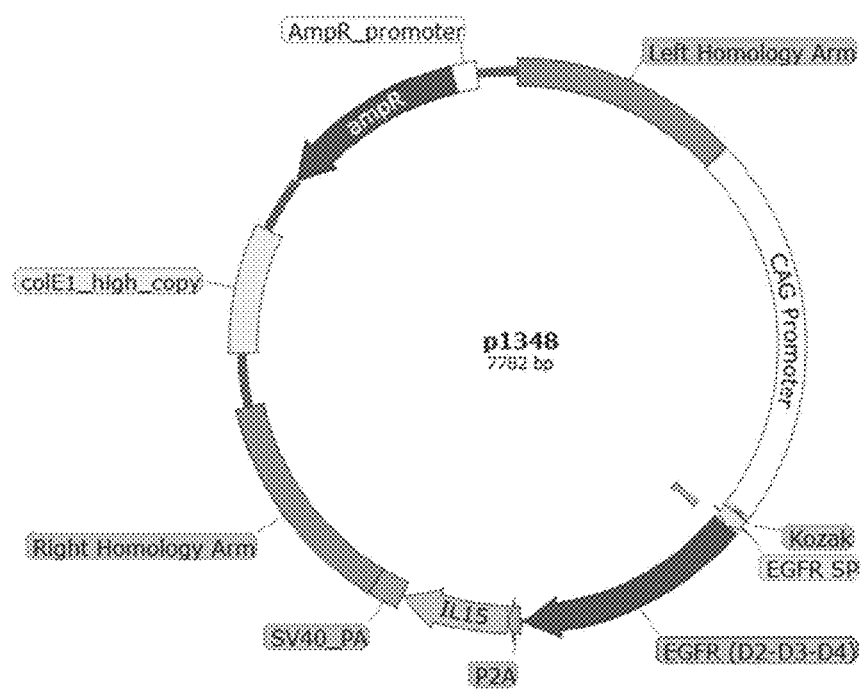
FIGS. 1A-1C show schematics of vectors (plasmids) according to embodiments of the application.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this application pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the application described herein. Such equivalents are intended to be encompassed by the application.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., CAR polypeptides and the CAR polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1997) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et at, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "isolated" means a biological component (such as a nucleic acid, peptide, protein, or cell) has been substantially separated, produced apart from, or purified away from other biological components of the organism in which the component naturally occurs, i.e., other chromosomal and extrachromosomal DNA and RNA, proteins, cells, and tissues. Nucleic acids, peptides, proteins, and cells that have been "isolated" thus include nucleic acids, peptides, proteins, and cells purified by standard purification methods and purification methods described herein. "Isolated" nucleic acids, peptides, proteins, and cells can be part of a composition and still be isolated if the composition is not part of the native environment of the nucleic acid, peptide, protein, or cell. The term also embraces nucleic acids, peptides and proteins prepared by recombinant expression in a host cell as well as chemically synthesized nucleic acids.

As used herein, the term "polynucleotide," synonymously referred to as "nucleic acid molecule," "nucleotides," "nucleic acids," or "polynucleic acids," refers to any polyribonucleotide or polydeoxyribonucleotide, which can be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

A "construct" refers to a macromolecule or complex of molecules comprising a polynucleotide to be delivered to a host cell, either in vitro or in vivo. A "vector," as used herein refers to any nucleic acid construct capable of directing the delivery or transfer of a foreign genetic material to target cells, where it can be replicated and/or expressed. The term "vector" as used herein comprises the construct to be delivered. A vector can be a linear or a circular molecule. A vector can be integrating or non-integrating. The major types of vectors include, but are not limited to, plasmids, episomal vector, viral vectors, cosmids, and artificial chromosomes. Viral vectors include, but are not limited to, adenovirus vector, adeno-associated virus vector, retrovirus vector, lentivirus vector, Sendai virus vector, and the like.

By "integration" it is meant that one or more nucleotides of a construct is stably inserted into the cellular genome, i.e., covalently linked to the nucleic acid sequence within the cell's chromosomal DNA. By "targeted integration" it is meant that the nucleotide(s) of a construct is inserted into the cell's chromosomal or mitochondrial DNA at a pre-selected site or "integration site". The term "integration" as used herein further refers to a process involving insertion of one or more exogenous sequences or nucleotides of the construct, with or without deletion of an endogenous sequence or nucleotide at the integration site. In the case, where there is a deletion at the insertion site, "integration" can further comprise replacement of the endogenous sequence or a nucleotide that is deleted with the one or more inserted nucleotides.

As used herein, the term "exogenous" is intended to mean that the referenced molecule or the referenced activity is introduced into, or non-native to, the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell in its native form. Similarly, the term when used in reference to expression of an encoding nucleic acid refers to expression of an encoding nucleic acid natively contained within the cell and not exogenously introduced.

As used herein, a "gene of interest" or "a polynucleotide sequence of interest" is a DNA sequence that is transcribed into RNA and in some instances translated into a polypeptide in vivo when placed under the control of appropriate regulatory sequences. A gene or polynucleotide of interest can include, but is not limited to, prokaryotic sequences, cDNA from eukaryotic mRNA, genomic DNA sequences from eukaryotic (e.g., mammalian) DNA, and synthetic DNA sequences. For example, a gene of interest may encode an miRNA, an shRNA, a native polypeptide (i.e. a polypeptide found in nature) or fragment thereof; a variant polypeptide (i.e. a mutant of the native polypeptide having less than 100% sequence identity with the native polypeptide) or fragment thereof; an engineered polypeptide or peptide fragment, a therapeutic peptide or polypeptide, an imaging marker, a selectable marker, and the like.

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences can be operably-linked to regulatory sequences in sense or antisense orientation.

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed CAR can be within the cytoplasm of a host cell, into the extracellular milieu such as the growth medium of a cell culture or anchored to the cell membrane.

As used herein, the terms "peptide," "polypeptide," or "protein" can refer to a molecule comprised of amino acids and can be recognized as a protein by those of skill in the art. The conventional one-letter or three-letter code for amino acid residues is used herein. The terms "peptide," "polypeptide," and "protein" can be used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

As used herein, the term "engineered immune cell" refers to an immune cell, also referred to as an immune effector cell, that has been genetically modified by the addition of exogenous genetic material in the form of DNA or RNA to the total genetic material of the cell.

As used herein, a "porcine tesehovirus-1 2A peptide" or "P2A peptide" or "P2A", refers to a "self-cleaving peptide" of a picornavirus. The average length of P2A peptides is 18-22 amino acids. A P2A peptide was first identified in a foot-and-mouth disease virus (FMDV), a member of the picornavirus (Ryan et al., *J Gen Virol*, 1991, 72(Pt 11): 2727-2732). It was reported that ribosomes skip the synthesis of the glycyl-prolyl peptide bond at the C-terminus of a 2A peptide, leading to the cleavage between a 2A peptide and its immediate downstream peptide (see, e.g., Donnelly et al., *J Gen Virol.*, 2001, 82: 1013-1025. An exemplary P2A peptide useful for the application comprises an amino acid sequence at least 90%, such as 90%, 91%, 92%, 93%, 04%, 95%, 96%, 97%, 98%, 99% or 100% identical to SEQ ID NO: 73. In some embodiment, the P2A peptide useful for the application comprises the amino acid sequence of SEQ ID NO: 73.

Induced Pluripotent Stem Cells (IPSCs) and Immune Effector Cells

IPSCs have unlimited self-renewing capacity. Use of iPSCs enables cellular engineering to produce a controlled cell bank of modified cells that can be expanded and differentiated into desired immune effector cells, supplying large amounts of homogeneous allogeneic therapeutic products.

Provided herein are genetically engineered IPSCs and derivative cells thereof. The selected genomic modifications provided herein enhance the therapeutic properties of the derivative cells. The derivative cells are functionally improved and suitable for allogenic off-the-shelf cell therapies following a combination of selective modalities being introduced to the cells at the level of iPSC through genomic engineering. This approach can help to reduce the side effects mediated by CRS/GVHD and prevent long-term autoimmunity while providing excellent efficacy.

As used herein, the term "differentiation" is the process by which an unspecialized ("uncommitted") or less specialized cell acquires the features of a specialized cell. Specialized cells include, for example, a blood cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. As used herein, the term "pluripotent" refers to the ability of a cell to form all lineages of the body or soma or the embryo proper. For example, embryonic stem cells are a type of pluripotent stem cells that are able to form cells from each of the three germs layers, the ectoderm, the mesoderm, and the endoderm. Pluripotency is a continuum of developmental potencies ranging from the incompletely or partially pluripotent cell (e.g., an epiblast stem cell or EpiSC), which is unable to give rise to a complete organism to the more primitive, more pluripotent cell, which is able to give rise to a complete organism (e.g., an embryonic stem cell).

As used herein, the terms "reprogramming" or "dedifferentiation" refers to a method of increasing the potency of a cell or dedifferentiating the cell to a less differentiated state. For example, a cell that has an increased cell potency has more developmental plasticity (i.e., can differentiate into more cell types) compared to the same cell in the non-reprogrammed state. In other words, a reprogrammed cell is one that is in a less differentiated state than the same cell in a non-reprogrammed state.

As used herein, the term "induced pluripotent stem cells" or, iPSCs, means that the stem cells are produced from differentiated adult, neonatal or fetal cells that have been induced or changed or reprogrammed into cells capable of differentiating into tissues of all three germ or dermal layers: mesoderm, endoderm, and ectoderm. The iPSCs produced do not refer to cells as they are found in nature.

The term "hematopoietic stem and progenitor cells," "hematopoietic stem cells," "hematopoietic progenitor cells," or "hematopoietic precursor cells" or "HPCs" refers to cells which are committed to a hematopoietic lineage but are capable of further hematopoietic differentiation. Hematopoietic stem cells include, for example, multipotent hematopoietic stem cells (hematoblasts), myeloid progenitors, megakaryocyte progenitors, erythrocyte progenitors, and lymphoid progenitors. Hematopoietic stem and progenitor cells (HSCs) are multipotent stem cells that give rise to all the blood cell types including myeloid (monocytes and macrophages, neutrophils, basophils, eosinophils, erythrocytes, megakaryocytes/platelets, dendritic cells), and lymphoid lineages (T cells, B cells, NK cells). As used herein, "CD34+ hematopoietic progenitor cell" refers to an HPC that expresses CD34 on its surface.

As used herein, the term "immune cell" or "immune effector cell" refers to a cell that is involved in an immune response. Immune response includes, for example, the promotion of an immune effector response. Examples of immune cells include T cells, B cells, natural killer (NK) cells, mast cells, and myeloid-derived phagocytes.

As used herein, the terms "T lymphocyte" and "T cell" are used interchangeably and refer to a type of white blood cell that completes maturation in the thymus and that has various roles in the immune system. A T cell can have the roles including, e.g., the identification of specific foreign antigens in the body and the activation and deactivation of other immune cells. A T cell can be any T cell, such as a cultured T cell, e.g., a primary T cell, or a T cell from a cultured T cell line, e.g., Jurkat, SupT1, etc., or a T cell obtained from a mammal. The T cell can be CD3+ cells. The T cell can be any type of T cell and can be of any developmental stage, including but not limited to, CD4+/CD8+ double positive T cells, CD4+ helper T cells (e.g., Th1 and Th2 cells), CD8+ T cells (e.g., cytotoxic T cells), peripheral blood mononuclear cells (PBMCs), peripheral blood leukocytes (PBLs), tumor infiltrating lymphocytes (TILs), memory T cells, naive T cells, regulator T cells, gamma delta T cells (gd T cells), and the like. Additional types of helper T cells include cells such as Th3 (Treg), Th17, Th9, or Tfh cells. Additional types of memory T cells include cells such as central memory T cells (Tcm cells), effector memory T cells (Tern cells and TEMRA cells). The T cell can also refer to a genetically engineered T cell, such as a T cell modified to express a T cell receptor (TCR) or a chimeric antigen receptor (CAR). The T cell can also be differentiated from a stem cell or progenitor cell.

"CD4+ T cells" refers to a subset of T cells that express CD4 on their surface and are associated with cell-mediated immune response. They are characterized by the secretion profiles following stimulation, which may include secretion of cytokines such as IFN-gamma, TNF-alpha, IL2, IL4 and IL10. "CD4" are 55-kD glycoproteins originally defined as differentiation antigens on T-lymphocytes, but also found on other cells including monocytes/macrophages. CD4 antigens are members of the immunoglobulin supergene family and are implicated as associative recognition elements in MHC (major histocompatibility complex) class II-restricted immune responses. On T-lymphocytes they define the helper/inducer subset.

"CD8+ T cells" refers to a subset of T cells which express CD8 on their surface, are MHC class I-restricted, and function as cytotoxic T cells. "CD8" molecules are differentiation antigens found on thymocytes and on cytotoxic and suppressor T-lymphocytes. CD8 antigens are members of the immunoglobulin supergene family and are associative recognition elements in major histocompatibility complex class I-restricted interactions.

As used herein, the term "NK cell" or "Natural Killer cell" refers to a subset of peripheral blood lymphocytes defined by the expression of CD56 and CD45 and the absence of the T cell receptor (TCR chains). The NK cell can also refer to a genetically engineered NK cell, such as a NK cell modified to express a chimeric antigen receptor (CAR). The NK cell can also be differentiated from a stem cell or progenitor cell.

As used herein, the term "genetic imprint" refers to genetic or epigenetic information that contributes to preferential therapeutic attributes in a source cell or an iPSC, and is retainable in the source cell derived iPSCs, and/or the iPSC-derived hematopoietic lineage cells. As used herein, "a source cell" is a non-pluripotent cell that may be used for generating iPSCs through reprogramming, and the source cell derived iPSCs may be further differentiated to specific cell types including any hematopoietic lineage cells. The source cell derived iPSCs, and differentiated cells therefrom are sometimes collectively called "derived" or "derivative" cells depending on the context. For example, derivative effector cells, or derivative NK or "iNK" cells or derivative T or "iT" cells, as used throughout this application are cells differentiated from an iPSC, as compared to their primary counterpart obtained from natural/native sources such as peripheral blood, umbilical cord blood, or other donor tissues. As used herein, the genetic imprint(s) conferring a preferential therapeutic attribute is incorporated into the iPSCs either through reprogramming a selected source cell that is donor-, disease-, or treatment response-specific, or through introducing genetically modified modalities to iPSC using genomic editing.

The induced pluripotent stem cell (iPSC) parental cell lines may be generated from peripheral blood mononuclear cells (PBMCs) or T-cells using any known method for introducing re-programming factors into non-pluripotent cells such as the episomal plasmid-based process as previously described in U.S. Pat. Nos. 8,546,140; 9,644,184; 9,328,332; and 8,765,470, the complete disclosures of which are incorporated herein by reference. The reprogramming factors may be in a form of polynucleotides, and thus are introduced to the non-pluripotent cells by vectors such as a retrovirus, a Sendai virus, an adenovirus, an episome, and a mini-circle. In particular embodiments, the one or more polynucleotides encoding at least one reprogramming factor are introduced by a lentiviral vector. In some embodiments, the one or more polynucleotides introduced by an episomal vector. In various other embodiments, the one or more polynucleotides are introduced by a Sendai viral vector. In some embodiments, the iPSC's are clonal iPSC's or are obtained from a pool of iPSCs and the genome edits are introduced by making one or more targeted integration and/or in/del at one or more selected sites. In another embodiment, the iPSC's are obtained from human T cells having antigen specificity and a reconstituted TCR gene (hereinafter, also refer to as "T-iPS" cells) as described in US Pat. Nos. 9206394, and 10787642 hereby incorporated by reference into the present application.

According to a particular aspect, the application relates to an induced pluripotent stem cell (iPSC) cell or a derivative cell thereof comprising: (i) a first exogenous polynucleotide encoding a chimeric antigen receptor (CAR); (ii) a second exogenous polynucleotide encoding a truncated epithelial growth factor receptor (tEGFR) variant and an interleukin 15 (IL-15), wherein the tEGFR variant and IL-15 are operably linked by an autoprotease peptide, such as a porcine tesehovirus-1 2A (P2A) peptide; and (iii) a deletion or reduced expression of B2M and CIITA genes.

I. Chimeric Antigen Receptor (CAR) Expression

According to embodiments of the application, an iPSC cell or a derivative cell thereof comprises a first exogenous polynucleotide encoding a chimeric antigen receptor (CAR), such as a CAR targeting a tumor antigen. In one embodiment, the CAR targets a CD19 antigen.

As used herein, the term "chimeric antigen receptor" (CAR) refers to a recombinant polypeptide comprising at least an extracellular domain that binds specifically to an antigen or a target, a transmembrane domain and an intracellular signaling domain. Engagement of the extracellular domain of the CAR with the target antigen on the surface of a target cell results in clustering of the CAR and delivers an activation stimulus to the CAR-containing cell. CARs redirect the specificity of immune effector cells and trigger proliferation, cytokine production, phagocytosis and/or production of molecules that can mediate cell death of the target antigen-expressing cell in a major histocompatibility (MHC)-independent manner.

As used herein, the term "signal peptide" refers to a leader sequence at the amino-terminus (N-terminus) of a nascent CAR protein, which co-translationally or post-translationally directs the nascent protein to the endoplasmic reticulum and subsequent surface expression.

As used herein, the term "extracellular antigen binding domain," "extracellular domain," or "extracellular ligand binding domain" refers to the part of a CAR that is located outside of the cell membrane and is capable of binding to an antigen, target or ligand.

As used herein, the term "hinge region" or "hinge domain" refers to the part of a CAR that connects two adjacent domains of the CAR protein, i.e., the extracellular domain and the transmembrane domain of the CAR protein.

As used herein, the term "transmembrane domain" refers to the portion of a CAR that extends across the cell membrane and anchors the CAR to cell membrane.

As used herein, the term "intracellular signaling domain," "cytoplasmic signaling domain," or "intracellular signaling domain" refers to the part of a CAR that is located inside of the cell membrane and is capable of transducing an effector signal.

As used herein, the term "stimulatory molecule" refers to a molecule expressed by an immune cell (e.g., NK cell or T cell) that provides the primary cytoplasmic signaling sequence(s) that regulate primary activation of receptors in a stimulatory way for at least some aspect of the immune cell signaling pathway. Stimulatory molecules comprise two distinct classes of cytoplasmic signaling sequence, those that initiate antigen-dependent primary activation (referred to as "primary signaling domains"), and those that act in an antigen-independent manner to provide a secondary of co-stimulatory signal (referred to as "co-stimulatory signaling domains").

In certain embodiments, the extracellular domain comprises an antigen binding domain and/or an antigen binding fragment. The antigen binding fragment can, for example, be an antibody or antigen binding fragment thereof that specifically binds a tumor antigen. The antigen binding fragments of the application possess one or more desirable functional properties, including but not limited to high-affinity binding to a tumor antigen, high specificity to a tumor antigen, the ability to stimulate complement-dependent cytotoxicity (CDC), antibody-dependent phagocytosis (ADPC), and/or antibody-dependent cellular-mediated cytotoxicity (ADCC) against cells expressing a tumor antigen, and the ability to inhibit tumor growth in subjects in need thereof and in animal models when administered alone or in combination with other anti-cancer therapies.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the application can be of any of the five major classes or corresponding sub-classes. Preferably, the antibodies of the application are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the application can contain a kappa or lambda light chain constant domain. According to particular embodiments, the antibodies of the application include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to the specific tumor antigen is substantially free of antibodies that do not bind to the tumor antigen). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that can be present in minor amounts. The monoclonal antibodies of the application can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), a single domain antibody (sdAb), a scFv dimer (bivalent diabody), a multi-specific antibody formed from a portion of an antibody comprising one or more CDRs, a camelized single domain antibody, a minibody, a nanobody, a domain antibody, a bivalent domain antibody, a light chain variable domain (VL), a variable domain ($V_HH$) of a camelid antibody, or any other antibody fragment that binds to an antigen but does not comprise a complete antibody structure. An antigen-binding fragment is capable of binding to the same antigen to which the parent antibody or a parent antibody fragment binds.

As used herein, the term "single-chain antibody" refers to a conventional single-chain antibody in the field, which comprises a heavy chain variable region and a light chain variable region connected by a short peptide of about 15 to about 20 amino acids (e.g., a linker peptide).

As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, a multispecific antibody comprises a third, fourth, or fifth immunoglobulin variable domain. In an embodiment, a multi specific antibody is a bispecific antibody molecule, a trispecific antibody molecule, or a tetraspecific antibody molecule.

As used herein, the term "bispecific antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes are on different antigens, e.g., the different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, a bispecific antibody comprises a $V_HH$ having binding specificity for a first epitope, and a $V_HH$ having binding specificity for a second epitope.

As used herein, an antigen binding domain or antigen binding fragment that "specifically binds to a tumor antigen" refers to an antigen binding domain or antigen binding fragment that binds a tumor antigen, with a KD of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antigen binding domain or antigen binding fragment can be determined by using surface plasmon resonance, such as by using a biosensor system, e.g., a Biacore® system, or by using bio-layer interferometry technology, such as an Octet RED96 system.

The smaller the value of the KD of an antigen binding domain or antigen binding fragment, the higher affinity that the antigen binding domain or antigen binding fragment binds to a target antigen.

In various embodiments, antibodies or antibody fragments suitable for use in the CAR of the present disclosure include, but are not limited to, monoclonal antibodies, bispecific antibodies, multispecific antibodies, chimeric antibodies, polypeptide-Fc fusions, single-chain Fvs (scFv), single chain antibodies, Fab fragments, F(ab') fragments, disulfide-linked Fvs (sdFv), masked antibodies (e.g., Probodies®), Small Modular ImmunoPharmaceuticals ("SMIPs™"), intrabodies, minibodies, single domain antibody variable domains, nanobodies, VHHs, diabodies, tandem diabodies (TandAb®), anti-idiotypic (anti-Id) antibodies (including, e.g., anti-Id antibodies to antigen-specific TCR), and epitope-binding fragments of any of the above. Antibodies and/or antibody fragments may be derived from murine antibodies, rabbit antibodies, human antibodies, fully humanized antibodies, camelid antibody variable domains and humanized versions, shark antibody variable domains and humanized versions, and camelized antibody variable domains.

In some embodiments, the antigen-binding fragment is an Fab fragment, an Fab' fragment, an F(ab')2 fragment, an scFv fragment, an Fv fragment, a dsFv diabody, a VHH, a VNAR, a single-domain antibody (sdAb) or nanobody, a dAb fragment, a Fd' fragment, a Fd fragment, a heavy chain variable region, an isolated complementarity determining region (CDR), a diabody, a triabody, or a decabody. In some embodiments, the antigen-binding fragment is an scFv fragment. In some embodiments, the antigen-binding fragment is a VHH.

In some embodiments, at least one of the extracellular tag-binding domain, the antigen-binding domain, or the tag comprises a single-domain antibody or nanobody.

In some embodiments, at least one of the extracellular tag-binding domain, the antigen-binding domain, or the tag comprises a VHH.

In some embodiments, the extracellular tag-binding domain and the tag each comprise a VHH.

In some embodiments, the extracellular tag-binding domain, the tag, and the antigen-binding domain each comprise a VHH.

In some embodiments, at least one of the extracellular tag-binding domain, the antigen-binding domain, or the tag comprises an scFv.

In some embodiments, the extracellular tag-binding domain and the tag each comprise an scFv.

In some embodiments, the extracellular tag-binding domain, the tag, and the antigen-binding domain each comprise a scFv.

Alternative scaffolds to immunoglobulin domains that exhibit similar functional characteristics, such as high-affinity and specific binding of target biomolecules, may also be used in the CARs of the present disclosure. Such scaffolds have been shown to yield molecules with improved characteristics, such as greater stability or reduced immunogenicity. Non-limiting examples of alternative scaffolds that may be used in the CAR of the present disclosure include engineered, tenascin-derived, tenascin type III domain (e.g., Centyrin™); engineered, gamma-B crystallin-derived scaffold or engineered, ubiquitin-derived scaffold (e.g., Affilins); engineered, fibronectin-derived, 10th fibronectin type III (10Fn3) domain (e.g., monobodies, AdNectins™ or AdNexins™); engineered, ankyrin repeat motif containing polypeptide (e.g., DARPins™); engineered, low-density-lipoprotein-receptor-derived, A domain (LDLR-A) (e.g., Avimers™); lipocalin (e.g., anticalins); engineered, protease inhibitor-derived, Kunitz domain (e.g., EETI-II/AGRP, BPTI/LACI-D1/ITI-D2); engineered, Protein-A-derived, Z domain (Affibodies™); Sac7d-derived polypeptides (e.g., Nanoffitins® or affitins); engineered, Fyn-derived, SH2 domain (e.g., Fynomers®); $CTLD_3$ (e.g., Tetranectin); thioredoxin (e.g., peptide aptamer); KALBITOR®; the β-sandwich (e.g., iMab); miniproteins; C-type lectin-like domain scaffolds; engineered antibody mimics; and any genetically manipulated counterparts of the foregoing that retains its binding functionality (Wörn A, Pluckthun A, J Mol Biol 305: 989-1010 (2001); Xu L et al., Chem Biol 9: 933-42 (2002); Wikman M et al., Protein Eng Des Sel 17: 455-62 (2004); Binz H et al., Nat Biotechnol 23: 1257-68

(2005); Hey T et al., Trends Biotechnol 23:514-522 (2005); Holliger P, Hudson P, Nat Biotechnol 23: 1126-36 (2005); Gill D, Damle N, Curr Opin Biotech 17: 653-8 (2006); Koide A, Koide S, Methods Mol Biol 352: 95-109 (2007); Skerra, Current Opin. in Biotech., 2007 18: 295-304; Byla P et al., J Biol Chem 285: 12096 (2010); Zoller F et al., Molecules 16: 2467-85 (2011), each of which is incorporated by reference in its entirety).

In some embodiments, the alternative scaffold is Affilin or Centyrin.

In some embodiments, the first polypeptide of the CARs of the present disclosure comprises a leader sequence. The leader sequence may be positioned at the N-terminus the extracellular tag-binding domain. The leader sequence may be optionally cleaved from the extracellular tag-binding domain during cellular processing and localization of the CAR to the cellular membrane. Any of various leader sequences known to one of skill in the art may be used as the leader sequence. Non-limiting examples of peptides from which the leader sequence may be derived include granulocyte-macrophage colony-stimulating factor receptor (GMCSFR), FcεR, human immunoglobulin (IgG) heavy chain (HC) variable region, CD8α, or any of various other proteins secreted by T cells. In various embodiments, the leader sequence is compatible with the secretory pathway of a T cell. In certain embodiments, the leader sequence is derived from human immunoglobulin heavy chain (HC).

In some embodiments, the leader sequence is derived from GMCSFR. In one embodiment, the GMCSFR leader sequence comprises the amino acid sequence set forth in SEQ ID NO: 1, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 1.

In some embodiments, the first polypeptide of the CARs of the present disclosure comprise a transmembrane domain, fused in frame between the extracellular tag-binding domain and the cytoplasmic domain.

The transmembrane domain may be derived from the protein contributing to the extracellular tag-binding domain, the protein contributing the signaling or co-signaling domain, or by a totally different protein. In some instances, the transmembrane domain can be selected or modified by amino acid substitution, deletions, or insertions to minimize interactions with other members of the CAR complex. In some instances, the transmembrane domain can be selected or modified by amino acid substitution, deletions, or insertions to avoid binding of proteins naturally associated with the transmembrane domain. In certain embodiments, the transmembrane domain includes additional amino acids to allow for flexibility and/or optimal distance between the domains connected to the transmembrane domain.

The transmembrane domain may be derived either from a natural or from a synthetic source. Where the source is natural, the domain may be derived from any membrane-bound or transmembrane protein. Non-limiting examples of transmembrane domains of particular use in this disclosure may be derived from (i.e. comprise at least the transmembrane region(s) of) the α, β or ζ chain of the T-cell receptor (TCR), CD28, CD3 epsilon, CD45, CD4, CD5, CD8, CD8α, CD9, CD16, CD22, CD33, CD37, CD40, CD64, CD80, CD86, CD134, CD137, or CD154. Alternatively, the transmembrane domain may be synthetic, in which case it will comprise predominantly hydrophobic residues such as leucine and valine. For example, a triplet of phenylalanine, tryptophan and/or valine can be found at each end of a synthetic transmembrane domain.

In some embodiments, it will be desirable to utilize the transmembrane domain of the ζ, η or FcεR1γ chains which contain a cysteine residue capable of disulfide bonding, so that the resulting chimeric protein will be able to form disulfide linked dimers with itself, or with unmodified versions of the ζ, η or FcεR1γ chains or related proteins. In some instances, the transmembrane domain will be selected or modified by amino acid substitution to avoid binding of such domains to the transmembrane domains of the same or different surface membrane proteins to minimize interactions with other members of the receptor complex. In other cases, it will be desirable to employ the transmembrane domain of ζ, η or FcεR1γ and –β, MB1 (Igα), B29 or CD3-γ, ζ, or η, in order to retain physical association with other members of the receptor complex.

In some embodiments, the transmembrane domain is derived from CD8 or CD28. In one embodiment, the CD8 transmembrane domain comprises the amino acid sequence set forth in SEQ ID NO: 23, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 23. In one embodiment, the CD28 transmembrane domain comprises the amino acid sequence set forth in SEQ ID NO: 24, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 24.

In some embodiments, the first polypeptide of the CAR of the present disclosure comprises a spacer region between the extracellular tag-binding domain and the transmembrane domain, wherein the tag-binding domain, linker, and the transmembrane domain are in frame with each other.

The term "spacer region" as used herein generally means any oligo- or polypeptide that functions to link the tag-binding domain to the transmembrane domain. A spacer region can be used to provide more flexibility and accessibility for the tag-binding domain. A spacer region may comprise up to 300 amino acids, preferably 10 to 100 amino acids and most preferably 25 to 50 amino acids. A spacer region may be derived from all or part of naturally occurring molecules, such as from all or part of the extracellular region of CD8, CD4 or CD28, or from all or part of an antibody constant region. Alternatively, the spacer region may be a synthetic sequence that corresponds to a naturally occurring spacer region sequence, or may be an entirely synthetic spacer region sequence. Non-limiting examples of spacer regions which may be used in accordance to the disclosure include a part of human CD8a chain, partial extracellular domain of CD28, FcyRllla receptor, IgG, IgM, IgA, IgD, IgE, an Ig hinge, or functional fragment thereof. In some embodiments, additional linking amino acids are added to the spacer region to ensure that the antigen-binding domain is an optimal distance from the transmembrane domain. In some embodiments, when the spacer is derived from an Ig, the spacer may be mutated to prevent Fc receptor binding.

In some embodiments, the spacer region comprises a hinge domain. The hinge domain may be derived from CD8α, CD28, or an immunoglobulin (IgG). For example, the IgG hinge may be from IgG1, IgG2, IgG3, IgG4, IgM1, IgM2, IgA1, IgA2, IgD, IgE, or a chimera thereof.

In certain embodiments, the hinge domain comprises an immunoglobulin IgG hinge or functional fragment thereof. In certain embodiments, the IgG hinge is from IgG1, IgG2, IgG3, IgG4, IgM1, IgM2, IgA1, IgA2, IgD, IgE, or a chimera thereof. In certain embodiments, the hinge domain comprises the CH1, CH2, CH3 and/or hinge region of the immunoglobulin. In certain embodiments, the hinge domain comprises the core hinge region of the immunoglobulin. The term "core hinge" can be used interchangeably with the term "short hinge" (a.k.a "SH"). Non-limiting examples of suitable hinge domains are the core immunoglobulin hinge regions include EPKSCDKTHTCPPCP (SEQ ID NO: 57) from IgG1, ERKCCVECPPCP (SEQ ID NO: 58) from IgG2, ELKTPLGDTTHTCPRCP(EPKSCDTPPPCPRCP)$_3$ (SEQ ID NO: 59) from IgG3, and ESKYGPPCPSCP (SEQ ID NO: 60) from IgG4 (see also Wypych et al., *JBC* 2008 283(23): 16194-16205, which is incorporated herein by reference in its entirety for all purposes). In certain embodiments, the hinge domain is a fragment of the immunoglobulin hinge.

In some embodiments, the hinge domain is derived from CD8 or CD28. In one embodiment, the CD8 hinge domain comprises the amino acid sequence set forth in SEQ ID NO: 21, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 21. In one embodiment, the CD28 hinge domain comprises the amino acid sequence set forth in SEQ ID NO: 22, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 22.

In some embodiments, the transmembrane domain and/or hinge domain is derived from CD8 or CD28. In some embodiments, both the transmembrane domain and hinge domain are derived from CD8. In some embodiments, both the transmembrane domain and hinge domain are derived from CD28.

In certain aspects, the first polypeptide of CARs of the present disclosure comprise a cytoplasmic domain, which comprises at least one intracellular signaling domain. In some embodiments, cytoplasmic domain also comprises one or more co-stimulatory signaling domains.

The cytoplasmic domain is responsible for activation of at least one of the normal effector functions of the host cell (e.g., T cell) in which the CAR has been placed in. The term "effector function" refers to a specialized function of a cell. Effector function of a T-cell, for example, may be cytolytic activity or helper activity including the secretion of cytokines. Thus, the term "signaling domain" refers to the portion of a protein which transduces the effector function signal and directs the cell to perform a specialized function. While usually the entire signaling domain is present, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the signaling domain sufficient to transduce the effector function signal.

Non-limiting examples of signaling domains which can be used in the CARs of the present disclosure include, e.g., signaling domains derived from DAP10, DAP12, Fc epsilon receptor I γ chain (FCER1G), FcR β, CD3δ, CD3ε, CD3γ, CD3ζ, CD5, CD22, CD226, CD66d, CD79A, and CD79B.

In some embodiments, the cytoplasmic domain comprises a CD3ζ signaling domain. In one embodiment, the CD3ζ signaling domain comprises the amino acid sequence set forth in SEQ ID NO: 6, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 6.

In some embodiments, the cytoplasmic domain further comprises one or more co-stimulatory signaling domains. In some embodiments, the one or more co-stimulatory signaling domains are derived from CD28, 41BB, IL2Rb, CD40, OX40 (CD134), CD80, CD86, CD27, ICOS, NKG2D, DAP10, DAP12, 2B4 (CD244), BTLA, CD30, GITR, CD226, CD79A, and HVEM.

In one embodiment, the co-stimulatory signaling domain is derived from 41BB. In one embodiment, the 41BB co-stimulatory signaling domain comprises the amino acid sequence set forth in SEQ ID NO: 8, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 8.

In one embodiment, the co-stimulatory signaling domain is derived from IL2Rb. In one embodiment, the IL2Rb co-stimulatory signaling domain comprises the amino acid sequence set forth in SEQ ID NO: 9, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 9.

In one embodiment, the co-stimulatory signaling domain is derived from CD40. In one embodiment, the CD40 co-stimulatory signaling domain comprises the amino acid sequence set forth in SEQ ID NO: 10, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 10.

In one embodiment, the co-stimulatory signaling domain is derived from OX40. In one embodiment, the OX40 co-stimulatory signaling domain comprises the amino acid sequence set forth in SEQ ID NO: 11, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 11.

In one embodiment, the co-stimulatory signaling domain is derived from CD80. In one embodiment, the CD80 co-stimulatory signaling domain comprises the amino acid sequence set forth in SEQ ID NO: 12, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 12.

In one embodiment, the co-stimulatory signaling domain is derived from CD86. In one embodiment, the CD86 co-stimulatory signaling domain comprises the amino acid sequence set forth in SEQ ID NO: 13, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 13.

In one embodiment, the co-stimulatory signaling domain is derived from CD27. In one embodiment, the CD27 co-stimulatory signaling domain comprises the amino acid sequence set forth in SEQ ID NO: 14, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 14.

In one embodiment, the co-stimulatory signaling domain is derived from ICOS. In one embodiment, the ICOS co-stimulatory signaling domain comprises the amino acid sequence set forth in SEQ ID NO: 15, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 15.

In one embodiment, the co-stimulatory signaling domain is derived from NKG2D. In one embodiment, the NKG2D co-stimulatory signaling domain comprises the amino acid sequence set forth in SEQ ID NO: 16, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 16.

In one embodiment, the co-stimulatory signaling domain is derived from DAP10. In one embodiment, the DAP10 co-stimulatory signaling domain comprises the amino acid sequence set forth in SEQ ID NO: 17, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 17.

In one embodiment, the co-stimulatory signaling domain is derived from DAP12. In one embodiment, the DAP12 co-stimulatory signaling domain comprises the amino acid sequence set forth in SEQ ID NO: 18, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 18.

In one embodiment, the co-stimulatory signaling domain is derived from 2B4 (CD244). In one embodiment, the 2B4 (CD244) co-stimulatory signaling domain comprises the amino acid sequence set forth in SEQ ID NO: 19, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 19.

In some embodiments, the CAR of the present disclosure comprises one costimulatory signaling domains. In some embodiments, the CAR of the present disclosure comprises two or more costimulatory signaling domains. In certain embodiments, the CAR of the present disclosure comprises two, three, four, five, six or more costimulatory signaling domains.

In some embodiments, the signaling domain(s) and costimulatory signaling domain(s) can be placed in any order. In some embodiments, the signaling domain is upstream of the costimulatory signaling domains. In some embodiments, the signaling domain is downstream from the costimulatory signaling domains. In the cases where two or more costimulatory domains are included, the order of the costimulatory signaling domains could be switched.

Non-limiting exemplary CAR regions and sequences are provided in Table 1.

TABLE 1

| CAR regions | Sequence | UniProt Id | SEQ ID NO |
|---|---|---|---|
| CD19 CAR: | | | |
| GMCSFR Signal Peptide | MLLLVTSLLLCELPHPAFLLIP | | 1 |
| FMC63 VH | EVKLQESGPGLVAPSQSLSVTCTVSGVSLPDYG VSWIRQPPRKGLEWLGVIWGSETTYYNSALKSR LTIIKDNSKSQVFLKMNSLQTDDTAIYYCAKHY YYGGSYAMDYWGQGTSVTVSS | | 2 |
| Whitlow Linker | GSTSGSGKPGSGEGSTKG | | 3 |
| FMC63 VL | DIQMTQTTSSLSASLGDRVTISCRASQDISKYLN WYQQKPDGTVKLLIYHTSRLHSGVPSRFSGSGS GTDYSLTISNLEQEDIATYFCQQGNTLPYTFGG GTKLEIT | | 4 |
| CD28 (AA 114-220) | IEVMYPPPYLDNEKSNGTIIHVKGKHLCPSPLFP GPSKPFWVLVVVGGVLACYSLLVTVAFIIFWV RSKRSRLLHSDYMNMTPRRPGPTRKHYQPYAP PRDFAAYRS | P10747-1 | 5 |
| CD3-zeta isoform 3 (AA 52-163) | RVKFSRSADAPAYQQGQNQLYNELNLGRREEY DVLDKRRGRDPEMGGKPRRKNPQEGLYNELQ KDKMAEAYSEIGMKGERRRGKGHDGLYQGLS TATKDTYDALHMQALPPR | P20963-3 | 6 |
| FMC63 scFV | EVKLQESGPGLVAPSQSLSVTCTVSGVSLPDYG VSWIRQPPRKGLEWLGVIWGSETTYYNSALKS RLTIIKDNSKSQVFLKMNSLQTDDTAIYYCAKH YYYGGSYAMDYWGQGTSVTVSSGSTSGSGKP GSGEGSTKGDIQMTQTTSSLSASLGDRVTISCR ASQDISKYLNWYQQKPDGTVKLLIYHTSRLHS GVPSRFSGSGSGTDYSLTISNLEQEDIATYFCQQ GNTLPYTFGGGTKLEIT | | 7 |

TABLE 1-continued

| CAR regions | Sequence | UniProt Id | SEQ ID NO |
|---|---|---|---|
| Signaling Domains: | | | |
| 41BB (AA 214-255) | KRGRKKLLYIFKQPFMRPVQTTQEEDGCSCRFP EEEEGGCEL | Q07011 | 8 |
| IL2Rb (AA 266-551) | NCRNTGPWLKKVLKCNTPDPSKFFSQLSSEHG GDVQKWLSSPFPSSSFSPGGLAPEISPLEVLERD KVTQLLPLNTDAYLSLQELQGQDPTHLV | P14784 | 9 |
| CD40 (AA 216-277) | KKVAKKPTNKAPHPKQEPQEINFPDDLPGSNTA APVQETLHGCQPVTQEDGKESRISVQERQ | P25942 | 10 |
| OX40 (AA 236-277) | ALYLLRRDQRLPPDAHKPPGGGSFRTPIQEEQA DAHSTLAKI | P43489 | 11 |
| CD80 (AA 264-288) | TYCFAPRCRERRRNERLRRESVRPV | P33681 | 12 |
| CD86 (AA269-329) | KWKKKKRPRNSYKCGTNTMEREESEQTKKRE KIHIPERSDEAQRVFKSSKTSSCDKSDTCF | P42081 | 13 |
| CD27 (AA 213-260) | QRRKYRSNKGESPVEPAEPCHYSCPREEEGSTIP IQEDYRKPEPACSP | P26842 | 14 |
| ICOS (AA 162-199) | CWLTKKKYSSSVHDPNGEYMFMRAVNTAKKS RLTDVTL | Q9Y6W8 | 15 |
| NKG2D (AA 1-51) | MGWIRGRRSR HSWEMSEFHN YNLDLKKSDF STRWQKQRCPVVKSKCRENAS | P26718 | 16 |
| DAP10 (AA 70-93) | LCARPRRSPAQEDGKVYINMPGRG | Q9UBK5 | 17 |
| DAP12 (AA 62-113) | YFLGRLVPRGRGAAEAATRKQRITETESPYQEL QGQRSDVYSDLNTQRPYYK | O54885 | 18 |
| 2B4/CD244 (AA 251-370) | WRRKRKEKQSETSPKEFLTIYEDVKDLKTRRN HEQEQTFPGGGSTIYSMIQSQSSAPTSQEPAYTL YSLIQPSRKSGSRKRNHSPSFNSTIYEVIGKSQP KAQNPARLSRKELENFDVYS | Q9BZW8 | 19 |
| CD3-zeta isoform 3 (AA 52-163) | RVKFSRSADAPAYQQGQNQLYNELNLGRREEY DVLDKRRGRDPEMGGKPRRKNPQEGLYNELQ KDKMAEAYSEIGMKGERRRGKGHDGLYQGLS TATKDTYDALHMQALPPR | P20963-3 | 6 |
| CD28 (AA 180-220) | RSKRSRLLHSDYMNMTPRRPGPTRKHYQPYAP PRDFAAYRS | P10747-1 | 20 |
| Spacer/Hinge: | | | |
| CD8 (AA 136-182) | TTTPAPRPPTPAPTIASQPLSLRPEACRPAAGGA VHTRGLDFACDIY | P01732 | 21 |
| CD28 (AA 114-151) | IEVMYPPPYLDNEKSNGTIIHVKGKHLCPSPLFP GPSKP | P10747-1 | 22 |
| Transmembrane: | | | |
| CD8 (AA 183-203) | IYIWAPLAGTCGVLLLSLVIT | P01732 | 23 |
| CD28 (AA 153-179) | FWVLVVVGGVLACYSLLVTVAFIIFWV | P10747-1 | 24 |
| Linkers: | | | |
| Whitlow Linker | GSTSGSGKPGSGEGSTKG | | 3 |
| (G$_4$S)$_3$ | GGGGSGGGGSGGGGS | | 25 |
| Linker 3 | GGSEGKSSGSGSESKSTGGS | | 26 |
| Linker 4 | GGGSGGGS | | 27 |

TABLE 1-continued

| CAR regions | Sequence | UniProt Id | SEQ ID NO |
|---|---|---|---|
| Linker 5 | GGGSGGGSGGGS | | 28 |
| Linker 6 | GGGSGGGSGGGSGGGS | | 29 |
| Linker 7 | GGGSGGGSGGGSGGGSGGGS | | 30 |
| Linker 8 | GGGGSGGGGSGGGGSGGGGS | | 31 |
| Linker 9 | GGGGSGGGGSGGGGSGGGGSGGGGS | | 32 |
| Linker 10 | IRPRAIGGSKPRVA | | 33 |
| Linker 11 | GKGGSGKGGSGKGGS | | 34 |
| Linker 12 | GGKGSGGKGSGGKGS | | 35 |
| Linker 13 | GGGKSGGGKSGGGKS | | 36 |
| Linker 14 | GKGKSGKGKSGKGKS | | 37 |
| Linker 15 | GGGKSGGKGSGKGGS | | 38 |
| Linker 16 | GKPGSGKPGSGKPGS | | 39 |
| Linker 17 | GKPGSGKPGSGKPGSGKPGS | | 40 |
| Linker 18 | GKGKSGKGKSGKGKSGKGKS | | 41 |
| Linker 19 | STAGDTHLGGEDFD | | 42 |
| Linker 20 | GEGGSGEGGSGEGGS | | 43 |
| Linker 21 | GGEGSGGEGSGGEGS | | 44 |
| Linker 22 | GEGESGEGESGEGES | | 45 |
| Linker 23 | GGGESGGEGSGEGGS | | 46 |
| Linker 24 | GEGESGEGESGEGESGEGES | | 47 |
| Linker 25 | GSTSGSGKPGSGEGSTKG | | 48 |
| Linker 26 | PRGASKSGSASQTGSAPGS | | 49 |
| Linker 27 | GTAAAGAGAAGGAAAGAAG | | 50 |
| Linker 28 | GTSGSSGSGSGGSGSGGGG | | 51 |
| Linker 29 | GKPGSGKPGSGKPGSGKPGS | | 52 |
| Linker 30 | GSGS | | 53 |
| Linker 31 | APAPAPAPAP | | 54 |
| Linker 32 | APAPAPAPAPAPAPAPAPAP | | 55 |
| Linker 33 | AEAAAKEAAAKEAAAAKEAAAAKEAAAAKAAA | | 56 |

In some embodiments, the antigen-binding domain of the second polypeptide binds to an antigen. The antigen-binding domain of the second polypeptide may bind to more than one antigen or more than one epitope in an antigen. For example, the antigen-binding domain of the second polypeptide may bind to two, three, four, five, six, seven, eight or more antigens. As another example, the antigen-binding domain of the second polypeptide may bind to two, three, four, five, six, seven, eight or more epitopes in the same antigen.

The choice of antigen-binding domain may depend upon the type and number of antigens that define the surface of a target cell. For example, the antigen-binding domain may be chosen to recognize an antigen that acts as a cell surface marker on target cells associated with a particular disease state. In certain embodiments, the CARs of the present disclosure can be genetically modified to target a tumor antigen of interest by way of engineering a desired antigen-binding domain that specifically binds to an antigen (e.g., on a tumor cell). Non-limiting examples of cell surface markers that may act as targets for the antigen-binding domain in the CAR of the disclosure include those associated with tumor cells or autoimmune diseases.

In some embodiments, the antigen-binding domain binds to at least one tumor antigen or autoimmune antigen.

In some embodiments, the antigen-binding domain binds to at least one tumor antigen. In some embodiments, the antigen-binding domain binds to two or more tumor antigens. In some embodiments, the two or more tumor antigens are associated with the same tumor. In some embodiments, the two or more tumor antigens are associated with different tumors.

In some embodiments, the antigen-binding domain binds to at least one autoimmune antigen. In some embodiments, the antigen-binding domain binds to two or more autoimmune antigens. In some embodiments, the two or more autoimmune antigens are associated with the same autoimmune disease. In some embodiments, the two or more autoimmune antigens are associated with different autoimmune diseases.

In some embodiments, the tumor antigen is associated with glioblastoma, ovarian cancer, cervical cancer, head and neck cancer, liver cancer, prostate cancer, pancreatic cancer, renal cell carcinoma, bladder cancer, or hematologic malignancy. Non-limiting examples of tumor antigen associated with glioblastoma include HER2, EGFRvIII, EGFR, CD133, PDGFRA, FGFR1, FGFR3, MET, CD70, ROBO1 and IL13Rα2. Non-limiting examples of tumor antigens associated with ovarian cancer include FOLR1, FSHR, MUC16, MUC1, Mesothelin, CA125, EpCAM, EGFR, PDGFRα, Nectin-4, and B7H4. Non-limiting examples of the tumor antigens associated with cervical cancer or head and neck cancer include GD2, MUC1, Mesothelin, HER2, and EGFR. Non-limiting examples of tumor antigen associated with liver cancer include Claudin 18.2, GPC-3, EpCAM, cMET, and AFP. Non-limiting examples of tumor antigens associated with hematological malignancies include CD22, CD79, BCMA, GPRC5D, SLAM F7, CD33, CLL1, CD123, and CD70. Non-limiting examples of tumor antigens associated with bladder cancer include Nectin-4 and SLITRK6.

Additional examples of antigens that may be targeted by the antigen-binding domain include, but are not limited to, alpha-fetoprotein, A3, antigen specific for A33 antibody, Ba 733, BrE3-antigen, carbonic anhydrase EX, CD1, CD1a, CD3, CD5, CD15, CD16, CD19, CD20, CD21, CD22, CD23, CD25, CD30, CD33, CD38, CD45, CD74, CD79a, CD80, CD123, CD138, colon-specific antigen-p (CSAp), CEA (CEACAM5), CEACAM6, CSAp, EGFR, EGP-I, EGP-2, Ep-CAM, EphA1, EphA2, EphA3, EphA4, EphA5, EphA6, EphA7, EphA8, EphA10, EphB1, EphB2, EphB3, EphB4, EphB6, FIt-I, Flt-3, folate receptor, HLA-DR, human chorionic gonadotropin (HCG) and its subunits, hypoxia inducible factor (HIF-I), Ia, IL-2, IL-6, IL-8, insulin growth factor-1 (IGF-I), KC4-antigen, KS-1-antigen, KS1-4, Le-Y, macrophage inhibition factor (MIF), MAGE, MUC2, MUC3, MUC4, NCA66, NCA95, NCA90, antigen specific for PAM-4 antibody, placental growth factor, p53, prostatic acid phosphatase, PSA, PSMA, RS5, S100, TAC, TAG-72, tenascin, TRAIL receptors, Tn antigen, Thomson-Friedenreich antigens, tumor necrosis antigens, VEGF, ED-B fibronectin, 17-1A-antigen, an angiogenesis marker, an oncogene marker or an oncogene product.

In one embodiment, the antigen targeted by the antigen-binding domain is CD19. In one embodiment, the antigen-binding domain comprises an anti-CD19 scFv. In one embodiment, the anti-CD19 scFv comprises a heavy chain variable region (VH) comprising the amino acid sequence set forth in SEQ ID NO: 2, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 2. In one embodiment, the anti-CD19 scFv comprises a light chain variable region (VL) comprising the amino acid sequence set forth in SEQ ID NO: 4, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 4. In one embodiment, the anti-CD19 scFv comprises the amino acid sequence set forth in SEQ ID NO: 7, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 7.

In some embodiments, the antigen is associated with an autoimmune disease or disorder. Such antigens may be derived from cell receptors and cells which produce "self"-directed antibodies. In some embodiments, the antigen is associated with an autoimmune disease or disorder such as Rheumatoid arthritis (RA), multiple sclerosis (MS), Sjögren's syndrome, Systemic lupus erythematosus, sarcoidosis, Type 1 diabetes mellitus, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Myasthenia gravis, Hashimoto's thyroiditis, Graves' disease, chronic inflammatory demyelinating polyneuropathy, Guillain-Barre syndrome, Crohn's disease or ulcerative colitis.

In some embodiments, autoimmune antigens that may be targeted by the CAR disclosed herein include but are not limited to platelet antigens, myelin protein antigen, Sm antigens in snRNPs, islet cell antigen, Rheumatoid factor, and anticitrullinated protein. citrullinated proteins and peptides such as CCP-1, CCP-2 (cyclical citrullinated peptides), fibrinogen, fibrin, vimentin, filaggrin, collagen I and II peptides, alpha-enolase, translation initiation factor 4G1, perinuclear factor, keratin, Sa (cytoskeletal protein vimentin), components of articular cartilage such as collagen II, IX, and XI, circulating serum proteins such as RFs (IgG, IgM), fibrinogen, plasminogen, ferritin, nuclear components such as RA33/hnRNP A2, Sm, eukaryotic translation elongation factor 1 alpha 1, stress proteins such as HSP-65, -70, -90, BiP, inflammatory/immune factors such as B7-H1, IL-1 alpha, and IL-8, enzymes such as calpastatin, alpha-enolase, aldolase-A, dipeptidyl peptidase, osteopontin, glucose-6-phosphate isomerase, receptors such as lipocortin 1, neutrophil nuclear proteins such as lactoferrin and 25-35 kD nuclear protein, granular proteins such as bactericidal permeability increasing protein (BPI), elastase, cathepsin G, myeloperoxidase, proteinase 3, platelet antigens, myelin protein antigen, islet cell antigen, rheumatoid factor, histones, ribosomal P proteins, cardiolipin, vimentin, nucleic acids such as dsDNA, ssDNA, and RNA, ribonuclear particles and proteins such as Sm antigens (including but not limited to SmD's and SmB'/B), U1RNP, A2/B1 hnRNP, Ro (SSA), and La (SSB) antigens.

In various embodiments, the scFv fragment used in the CAR of the present disclosure may include a linker between the VH and VL domains. The linker can be a peptide linker and may include any naturally occurring amino acid. Exemplary amino acids that may be included into the linker are Gly, Ser Pro, Thr, Glu, Lys, Arg, Ile, Leu, His and The. The linker should have a length that is adequate to link the VH and the VL in such a way that they form the correct conformation relative to one another so that they retain the desired activity, such as binding to an antigen. The linker may be about 5-50 amino acids long. In some embodiments, the linker is about 10-40 amino acids long. In some embodiments, the linker is about 10-35 amino acids long. In some embodiments, the linker is about 10-30 amino acids long. In some embodiments, the linker is about 10-25 amino acids long. In some embodiments, the linker is about 10-20 amino acids long. In some embodiments, the linker is about 15-20 amino acids long. Exemplary linkers that may be used are Gly rich linkers, Gly and Ser containing linkers, Gly and Ala containing linkers, Ala and Ser containing linkers, and other flexible linkers.

In one embodiment, the linker is a Whitlow linker. In one embodiment, the Whitlow linker comprises the amino acid sequence set forth in SEQ ID NO: 3, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 3. In another embodiment, the linker is a $(G_4S)_3$ linker. In one embodiment, the $(G_4S)_3$ linker comprises the amino acid sequence set forth in SEQ ID NO: 25, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 25. Other linker sequences may include portions of immunoglobulin hinge area, CL or CH1 derived from any immunoglobulin heavy or light chain isotype. Exemplary linkers that may be used include any of SEQ ID NOs: 26-56 in Table 1. Additional linkers are described for example in Int. Pat. Publ. No. WO2019/060695, incorporated by reference herein in its entirety.

II. Artificial Cell Death Polypeptide

According to embodiments of the application, an iPSC cell or a derivative cell thereof comprises a second exogenous polynucleotide encoding an artificial cell death polypeptide.

As used herein, the term "artificial cell death polypeptide" refers to an engineered protein designed to prevent potential toxicity or otherwise adverse effects of a cell therapy. The artificial cell death polypeptide could mediate induction of apoptosis, inhibition of protein synthesis, DNA replication, growth arrest, transcriptional and post-transcriptional genetic regulation and/or antibody-mediated depletion. In some instance, the artificial cell death polypeptide is activated by an exogenous molecule, e.g. an antibody, that when activated, triggers apoptosis and/or cell death of a therapeutic cell.

In certain embodiments, an artificial cell death polypeptide comprises an inactivated cell surface receptor that comprises an epitope specifically recognized by an antibody, particularly a monoclonal antibody, which is also referred to herein as a monoclonal antibody-specific epitope. When expressed by iPSCs or derivative cells thereof, the inactivated cell surface receptor is signaling inactive or significantly impaired, but can still be specifically recognized by an antibody. The specific binding of the antibody to the inactivated cell surface receptor enables the elimination of the iPSCs or derivative cells thereof by ADCC and/or ADCP mechanisms, as well as, direct killing with antibody drug conjugates with toxins or radionuclides.

In certain embodiments, the inactivated cell surface receptor comprises an epitope that is selected from epitopes specifically recognized by an antibody, including but not limited to, ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, polatuzumab vedotin, ranibizumab, tocilizumab, trastuzumab, vedolizumab, adalimumab, belimumab, canakinumab, denosumab, golimumab, ipilimumab, ofatumumab, panitumumab, or ustekinumab.

Epidermal growth factor receptor, also known as EGFR, ErbB1 and HER1, is a cell-surface receptor for members of the epidermal growth factor family of extracellular ligands. As used herein, "truncated EGFR," "tEGFR," "short EGFR" or "sEGFR" refers to an inactive EGFR variant that lacks the EGF-binding domains and the intracellular signaling domains of the EGFR. An exemplary tEGFR variant contains residues 322-333 of domain 2, all of domains 3 and 4 and the transmembrane domain of the native EGFR sequence containing the cetuximab binding epitope. Expression of the tEGFR variant on the cell surface enables cell elimination by an antibody that specifically binds to the tEGFR, such as cetuximab (Erbitux®), as needed. Due to the absence of the EGF-binding domains and intracellular signaling domains, tEGFR is inactive when expressed by iPSCs or derivative cell thereof.

An exemplary inactivated cell surface receptor of the application comprises a tEGFR variant. In certain embodiments, expression of the inactivated cell surface receptor in an engineered immune cell expressing a chimeric antigen receptor (CAR) induces cell suicide of the engineered immune cell when the cell is contacted with an anti-EGFR antibody. Methods of using inactivated cell surface receptors are described in WO2019/070856, WO2019/023396, WO2018/058002, the disclosure of which is incorporated herein by reference. For example, a subject who has previously received an engineered immune cell of the present disclosure that comprises a heterologous polynucleotide encoding an inactivated cell surface receptor comprising a tEGFR variant can be administered an anti-EGFR antibody in an amount effective to ablate in the subject the previously administered engineered immune cell.

In certain embodiments, the anti-EGFR antibody is cetuximab, matuzumab, necitumumab or panitumumab, preferably the anti-EGFR antibody is cetuximab.

In certain embodiments, the tEGFR variant comprises or consists of an amino acid sequence at least 90%, such as at least 90%, 91%, 82%, 93%, 94%, 95%, 96%, 97%, 98%, 99% or 100%, identical to SEQ ID NO: 71, preferably the amino acid sequence of SEQ ID NO: 71.

In some embodiments, the inactivated cell surface receptor comprises one or more epitopes of CD79b, such as an epitope specifically recognized by polatuzumab vedotin. In certain embodiments, the CD79b epitope comprises or consists of an amino acid sequence at least 90%, such as at least 90%, 91%, 82%, 93%, 94%, 95%, 96%, 97%, 98%, 99% or 100%, identical to SEQ ID NO: 78, preferably the amino acid sequence of SEQ ID NO: 78.

In some embodiments, the inactivated cell surface receptor comprises one or more epitopes of CD20, such as an epitope specifically recognized by rituximab. In certain embodiments, the CD20 epitope comprises or consists of an amino acid sequence at least 90%, such as at least 90%, 91%, 82%, 93%, 94%, 95%, 96%, 97%, 98%, 99% or 100%, identical to SEQ ID NO: 80, preferably the amino acid sequence of SEQ ID NO: 80.

In some embodiments, the inactivated cell surface receptor comprises one or more epitopes of Her 2 receptor or ErbB, such as an epitope specifically recognized by trastuzumab. In certain embodiments, the monoclonal antibody-specific epitope comprises or consists of an amino acid sequence at least 90%, such as at least 90%, 91%, 82%, 93%, 94%, 95%, 96%, 97%, 98%, 99% or 100%, identical to SEQ ID NO: 82, preferably the amino acid sequence of SEQ ID NO: 82.

In some embodiments the inactivated cell surface receptor further comprises a cytokine, such as interleukin-15 or interleukin-2.

As used herein "Interleukin-15" or "IL-15" refers to a cytokine that regulates T and NK cell activation and proliferation, or a functional portion thereof. A "functional portion" ("biologically active portion") of a cytokine refers to a portion of the cytokine that retains one or more functions of full length or mature cytokine. Such functions for IL-15 include the promotion of NK cell survival, regulation of NK cell and T cell activation and proliferation as well as the support of NK cell development from hematopoietic stem cells. As will be appreciated by those of skill in the art, the sequence of a variety of IL-15 molecules are known in the art. In certain embodiments, the IL-15 is a wild-type IL-15. In certain embodiments, the IL-15 is a human IL-15. In certain embodiments, the IL-15 comprises an amino acid sequence at least 90%, such as at least 90%, 91%, 82%, 93%, 94%, 95%, 96%, 97%, 98%, 99% or 100%, identical to SEQ ID NO: 72, preferably the amino acid sequence of SEQ ID NO: 72.

As used herein "Interleukin-2" refers to a cytokine that regulates T and NK cell activation and proliferation, or a functional portion thereof. In certain embodiments, the IL-2 is a wild-type IL-2. In certain embodiments, the IL-2 is a human IL-2. In certain embodiments, the IL-2 comprises an amino acid sequence at least 90%, such as at least 90%, 91%, 82%, 93%, 94%, 95%, 96%, 97%, 98%, 99% or 100%, identical to SEQ ID NO: 76, preferably the amino acid sequence of SEQ ID NO: 76.

In certain embodiments, an inactivated cell surface receptor comprises a monoclonal antibody-specific epitope operably linked to a cytokine, preferably by an autoprotease peptide. Examples of the autoprotease peptide include, but are not limited to, a peptide sequence selected from the group consisting of porcine teschovirus-1 2A (P2A), a foot-and-mouth disease virus (FMDV) 2A (F2A), an Equine Rhinitis A Virus (ERAV) 2A (E2A), a Thosea asigna virus 2A (T2A), a cytoplasmic polyhedrosis virus 2A (BmCPV2A), a Flacherie Virus 2A (BmIFV2A), and a combination thereof. In one embodiment, the autoprotease peptide comprises or is an autoprotease peptide of a porcine tesehovirus-1 2A (P2A) peptide. In certain embodiments, the autoprotease peptide comprises an amino acid sequence at least 90%, such as at least 90%, 91%, 82%, 93%, 94%, 95%, 96%, 97%, 98%, 99% or 100%, identical to SEQ ID NO: 73, preferably the amino acid sequence of SEQ ID NO: 73.

In certain embodiments, an inactivated cell surface receptor comprises a truncated epithelial growth factor receptor (tEGFR) variant operably linked to an interleukin-15 (IL-15) or IL-2 by an autoprotease peptide. In a particular embodiment, the inactivated cell surface receptor comprises an amino acid sequence at least 90%, such as at least 90%, 91%, 82%, 93%, 94%, 95%, 96%, 97%, 98%, 99% or 100%, identical to SEQ ID NO: 74, preferably the amino acid sequence of SEQ ID NO: 74.

In some embodiments, an inactivated cell surface receptor further comprises a signal sequence. In certain embodiments, the signal sequence comprises an amino acid sequence at least 90%, such as at least 90%, 91%, 82%, 93%, 94%, 95%, 96%, 97%, 98%, 99% or 100%, identical to SEQ ID NO: 77, preferably the amino acid sequence of SEQ ID NO: 77.

In some embodiments, an inactivated cell surface receptor further comprises a hinge domain. In some embodiments, the hinge domain is derived from CD8. In one embodiment, the CD8 hinge domain comprises the amino acid sequence set forth in SEQ ID NO: 21, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 21.

In certain embodiments, an inactivated cell surface receptor further comprises a transmembrane domain. In some embodiments, the transmembrane domain is derived from CD8. In one embodiment, the CD8 transmembrane domain comprises the amino acid sequence set forth in SEQ ID NO: 23, or a variant thereof having at least 50, at least 55, at least 60, at least 65, at least 70, at least 75, at least 80, at least 85, at least 90, at least 95, at least 96, at least 97, at least 98 or at least 99%, sequence identity with SEQ ID NO: 23.

In certain embodiment, an inactivated cell surface receptor comprises one or more epitopes specifically recognized by an antibody in its extracellular domain, a transmembrane region and a cytoplasmic domain. In some embodiments, the inactivated cell surface receptor further comprises a hinge region between the epitope(s) and the transmembrane region. In some embodiments, the inactivated cell surface receptor comprises more than one epitopes specifically recognized by an antibody, the epitopes can have the same or different amino acid sequences, and the epitopes can be linked together via a peptide linker, such as a flexible peptide linker have the sequence of (GGGGS)n, wherein n is an integer of 1-8 (SEQ ID NO: 25). In some embodiments, the inactivated cell surface receptor further comprises a cytokine, such as an IL-15 or IL-2. In certain embodiments, the cytokine is in the cytoplasmic domain of the inactivated cell surface receptor. Preferably, the cytokine is operably linked to the epitope(s) specifically recognized by an antibody, directly or indirectly, via an autoprotease peptide, such as those described herein. In some embodiments, the cytokine is indirectly linked to the epitope(s) by connecting to the transmembrane region via the autoprotease peptide.

Non-limiting exemplary inactivated cell surface receptor regions and sequences are provided in Table 2.

TABLE 2

| Regions | Sequence | SEQ ID NO |
|---|---|---|
| tEGFR-IL15: | | |
| tEGFR | MRPSGTAGAALLALLAALCPASRAGVRKCKKCEGPCRK VCNGIGIGEFKDSLSINATNIKHFKNCTSISGDLHILPVAF RGDSFTHTPPLDPQELDILKTVKEITGFLLIQAWPENRTD LHAFENLEIIRGRTKQHGQFSLAVVSLNITSLGLRSLKEIS DGDVIISGNKNLCYANTINWKKLFGTSGQKTKIISNRGE NSCKATGQVCHALCSPEGCWGPEPRDCVSCRNVSRGRE CVDKCNLLEGEPREFVENSECIQCHPECLPQAMNITCTG RGPDNCIQCAHYIDGPHCVKTCPAGVMGENNTLVWKY | 71 |

TABLE 2-continued

| Regions | Sequence | SEQ ID NO |
|---|---|---|
| | ADAGHVCHLCHPNCTYGCTGPGLEGCPTNGPKIPSIATG MVGALLLLLVVALGIGLFM | |
| P2A | ATNFSLLKQAGDVEENPGP | 73 |
| IL-15 | MRISKPHLRSISIQCYLCLLLNSHFLTEAGIHVFILGCFSA GLPKTEANWVNISDLKKIEDLIQSMHIDATLYTESDVH PSCKVTAMKCFLLELQVISLESGDASIHDTVENLIILANN SLSSNGNVTESGCKECEELEEKNIKEFLQSFVHIVQMFIN TS | 72 |
| CD79b-IL15: | | |
| Signal Sequence | MEFGLSWVFLVALFRGVQC | 77 |
| CD79b epitope | ARSEDRYRNPKGSACSRIWQS | 78 |
| CD8 (AA 136-182) | TTTPAPRPPTPAPTIASQPLSLRPEACRPAAGGAVHTRGL DFACDIY | 21 |
| CD8 (AA 183-203) | IYIWAPLAGTCGVLLLSLVIT | 23 |
| P2A | ATNFSLLKQAGDVEENPGP | 73 |
| IL-15 | MRISKPHLRSISIQCYLCLLLNSHFLTEAGIHVFILGCFSA GLPKTEANWVNISDLKKIEDLIQSMHIDATLYTESDVH PSCKVTAMKCFLLELQVISLESGDASIHDTVENLIILANN SLSSNGNVTESGCKECEELEEKNIKEFLQSFVHIVQMFIN TS | 72 |
| CD20 mimitope-IL15: | | |
| Signal Sequence | MEFGLSWVFLVALFRGVQC | 77 |
| CD20 mimitope | ACPYANPSLC | 80 |
| Linker | GGGSGGGS | 27 |
| CD8 (AA 136-182) | TTTPAPRPPTPAPTIASQPLSLRPEACRPAAGGAVHTRGL DFACDIY | 21 |
| CD8 (AA 183-203) | IYIWAPLAGTCGVLLLSLVIT | 23 |
| P2A | ATNFSLLKQAGDVEENPGP | 73 |
| IL-15 | MRISKPHLRSISIQCYLCLLLNSHFLTEAGIHVFILGCFSA GLPKTEANWVNISDLKKIEDLIQSMHIDATLYTESDVH PSCKVTAMKCFLLELQVISLESGDASIHDTVENLIILANN SLSSNGNVTESGCKECEELEEKNIKEFLQSFVHIVQMFIN TS | 72 |
| ErbB epitope-IL15: | | |
| Signal Sequence | MEFGLSWVFLVALFRGVQC | 77 |
| ErbB epitope | EGLACHQLCARGHCWGPGPTQCVNCSQFLRGQECVEE CRVLQGLPREYVNARHCLPCHPECQPQNGSVTCFGPEA DQCVACAHYKDPPFCVARCPSGVKPDLSYMPIWKFPDE EGACQPCPINCTHSCVDLDDKGCPAEQRASPLTSIISAVV GILLVVVLGVVFGILIGGGGSGG | 82 |
| P2A | ATNFSLLKQAGDVEENPGP | 73 |
| IL-15 | MRISKPHLRSISIQCYLCLLLNSHFLTEAGIHVFILGCFSA GLPKTEANWVNISDLKKIEDLIQSMHIDATLYTESDVH PSCKVTAMKCFLLELQVISLESGDASIHDTVENLIILANN SLSSNGNVTESGCKECEELEEKNIKEFLQSFVHIVQMFIN TS | 72 |

In a particular embodiment, the inactivated cell surface receptor comprises an amino acid sequence at least 90%, such as at least 90%, 91%, 82%, 93%, 94%, 95%, 96%, 97%, 98%, 99% or 100%, identical to SEQ ID NO: 79, preferably the amino acid sequence of SEQ ID NO: 79.

In a particular embodiment, the inactivated cell surface receptor comprises an amino acid sequence at least 90%, such as at least 90%, 91%, 82%, 93%, 94%, 95%, 96%, 97%, 98%, 99% or 100%, identical to SEQ ID NO: 81, preferably the amino acid sequence of SEQ ID NO: 81.

In a particular embodiment, the inactivated cell surface receptor comprises an amino acid sequence at least 90%, such as at least 90%, 91%, 82%, 93%, 94%, 95%, 96%, 97%, 98%, 99% or 100%, identical to SEQ ID NO: 83, preferably the amino acid sequence of SEQ ID NO: 83.

III. HLA Expression

In certain embodiments, an iPSC or derivative cell thereof of the application can be further modified by introducing a third exogenous polynucleotide encoding one or more proteins related to immune evasion, such as non-classical HLA class I proteins (e.g., HLA-E and HLA-G). In particular, disruption of the B2M gene eliminates surface expression of all MHC class I molecules, leaving cells vulnerable to lysis by NK cells through the "missing self" response. Exogenous HLA-E expression can lead to resistance to NK-mediated lysis (Gornalusse et al., Nat Biotechnol. 2017 August; 35(8): 765-772).

In certain embodiments, the iPSC or derivative cell thereof comprises a third exogenous polypeptide encoding at least one of a human leukocyte antigen E (HLA-E) and human leukocyte antigen G (HLA-G). In a particular embodiment, the HLA-E comprises an amino acid sequence at least 90%, such as at least 90%, 91%, 82%, 93%, 94%, 95%, 96%, 97%, 98%, 99% or 100%, identical to SEQ ID NO: 65, preferably the amino acid sequence of SEQ ID NO: 65. In a particular embodiment, the HLA-G comprises an amino acid sequence at least 90%, such as at least 90%, 91%, 92%, 93%, 94%, 95%, 96%, 97%, 98%, 99% or 100%, identical to SEQ ID NO: 68, preferably SEQ ID NO: 68.

In certain embodiments, the third exogenous polynucleotide encodes a polypeptide comprising a signal peptide operably linked to a mature B2M protein that is fused to an HLA-E via a linker. In a particular embodiment, the third exogenous polypeptide comprises an amino acid sequence at least sequence at least 90%, such as at least 90%, 91%, 82%, 93%, 94%, 95%, 96%, 97%, 98%, 99% or 100%, identical to SEQ ID NO: 66.

In other embodiments, the third exogenous polynucleotide encodes a polypeptide comprising a signal peptide operably linked to a mature B2M protein that is fused to an HLA-G via a linker. In a particular embodiment, the third exogenous polypeptide comprises an amino acid sequence at least sequence at least 90%, such as at least 90%, 91%, 82%, 93%, 94%, 95%, 96%, 97%, 98%, 99% or 100%, identical to SEQ ID NO: 69.

IV. Other Optional Genome Edits

In one embodiment of the above described cell, the genomic editing at one or more selected sites may comprise insertions of one or more exogenous polynucleotides encoding other additional artificial cell death polypeptides, targeting modalities, receptors, signaling molecules, transcription factors, pharmaceutically active proteins and peptides, drug target candidates, or proteins promoting engraftment, trafficking, homing, viability, self-renewal, persistence, and/or survival of the genome-engineered iPSCs or derivative cells thereof.

In some embodiments, the exogenous polynucleotides for insertion are operatively linked to (1) one or more exogenous promoters comprising CMV, EF1α, PGK, CAG, UBC, or other constitutive, inducible, temporal-, tissue-, or cell type-specific promoters; or (2) one or more endogenous promoters comprised in the selected sites comprising AAVS1, CCR5, ROSA26, collagen, HTRP, Hll, beta-2 microglobulin, GAPDH, TCR or RUNX1, or other locus meeting the criteria of a genome safe harbor. In some embodiments, the genome-engineered iPSCs generated using the above method comprise one or more different exogenous polynucleotides encoding proteins comprising caspase, thymidine kinase, cytosine deaminase, B-cell CD20, ErbB2 or CD79b wherein when the genome-engineered iPSCs comprise two or more suicide genes, the suicide genes are integrated in different safe harbor locus comprising AAVSl, CCR5, ROSA26, collagen, HTRP, H11, H11, beta-2 microglobulin, GAPDH, TCR or RUNX1. Other exogenous polynucleotides encoding proteins may include those encoding PET reporters, homeostatic cytokines, and inhibitory checkpoint inhibitory proteins such as PD1, PD-L1, and CTLA4 as well as proteins that target the CD47/signal regulatory protein alpha (SIRPα) axis. In some other embodiments, the genome-engineered iPSCs generated using the method provided herein comprise in/del at one or more endogenous genes associated with targeting modality, receptors, signaling molecules, transcription factors, drug target candidates, immune response regulation and modulation, or proteins suppressing engraftment, trafficking, homing, viability, self-renewal, persistence, and/or survival of the iPSCs or derivative cells thereof.

V. Targeted Genome Editing at Selected Locus in iPSCs

According to embodiments of the application, one or more of the exogenous polynucleotides are integrated at one or more loci on the chromosome of an iPSC.

Genome editing, or genomic editing, or genetic editing, as used interchangeably herein, is a type of genetic engineering in which DNA is inserted, deleted, and/or replaced in the genome of a targeted cell. Targeted genome editing (interchangeable with "targeted genomic editing" or "targeted genetic editing") enables insertion, deletion, and/or substitution at pre-selected sites in the genome. When an endogenous sequence is deleted or disrupted at the insertion site during targeted editing, an endogenous gene comprising the affected sequence can be knocked-out or knocked-down due to the sequence deletion or disruption. Therefore, targeted editing can also be used to disrupt endogenous gene expression with precision. Similarly used herein is the term "targeted integration," referring to a process involving insertion of one or more exogenous sequences at pre-selected sites in the genome, with or without deletion of an endogenous sequence at the insertion site.

Targeted editing can be achieved either through a nuclease-independent approach, or through a nuclease-dependent approach. In the nuclease-independent targeted editing approach, homologous recombination is guided by homologous sequences flanking an exogenous polynucleotide to be inserted, through the enzymatic machinery of the host cell.

Alternatively, targeted editing could be achieved with higher frequency through specific introduction of double strand breaks (DSBs) by specific rare-cutting endonucleases. Such nuclease-dependent targeted editing utilizes DNA repair mechanisms including non-homologous end joining (NHEJ), which occurs in response to DSBs. Without a donor vector containing exogenous genetic material, the NHEJ often leads to random insertions or deletions (in/dels) of a small number of endogenous nucleotides. In comparison, when a donor vector containing exogenous genetic material flanked by a pair of homology arms is present, the exogenous genetic material can be introduced into the genome during homology directed repair (HDR) by homologous recombination, resulting in a "targeted integration."

Available endonucleases capable of introducing specific and targeted DSBs include, but not limited to, zinc-finger nucleases (ZFN), transcription activator-like effector nucleases (TALEN), RNA-guided CRISPR (Clustered Regular Interspaced Short Palindromic Repeats) systems. Additionally, DICE (dual integrase cassette exchange) system utilizing phiC31 and Bxbl integrases is also a promising tool for targeted integration.

ZFNs are targeted nucleases comprising a nuclease fused to a zinc finger DNA binding domain. By a "zinc finger DNA binding domain" or "ZFBD" it is meant a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include, but not limited to, C2H2 zinc fingers, C3H zinc fingers, and C4 zinc fingers. A "designed" zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A "selected" zinc finger domain is a domain not found in nature whose production results primarily from an empirical process such as phage display, interaction trap or hybrid selection. ZFNs are described in greater detail in U.S. Pat. Nos. 7,888,121 and 7,972,854, the complete disclosures of which are incorporated herein by reference. The most recognized example of a ZFN in the art is a fusion of the Fokl nuclease with a zinc finger DNA binding domain.

A TALEN is a targeted nuclease comprising a nuclease fused to a TAL effector DNA binding domain. By "transcription activator-like effector DNA binding domain", "TAL effector DNA binding domain", or "TALE DNA binding domain" it is meant the polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in U.S. Patent Application No. 2011/0145940, which is herein incorporated by reference. The most recognized example of a TALEN in the art is a fusion polypeptide of the Fold nuclease to a TAL effector DNA binding domain.

Another example of a targeted nuclease that finds use in the subject methods is a targeted Spoll nuclease, a polypeptide comprising a Spo1 1 polypeptide having nuclease activity fused to a DNA binding domain, e.g. a zinc finger DNA binding domain, a TAL effector DNA binding domain, etc. that has specificity for a DNA sequence of interest. See, for example, U.S. Application No. 61/555,857, the disclosure of which is incorporated herein by reference.

Additional examples of targeted nucleases suitable for the present application include, but not limited to Bxbl, phiC3 1, R4, PhiBT1, and Wp/SPBc/TP901-1, whether used individually or in combination.

Other non-limiting examples of targeted nucleases include naturally occurring and recombinant nucleases; CRISPR related nucleases from families including cas, cpf, cse, csy, csn, csd, cst, csh, csa, csm, and cmr; restriction endonucleases; meganucleases; homing endonucleases, and the like. As an example, CRISPR/Cas9 requires two major components: (1) a Cas9 endonuclease and (2) the crRNA-tracrRNA complex. When co-expressed, the two components form a complex that is recruited to a target DNA sequence comprising PAM and a seeding region near PAM. The crRNA and tracrRNA can be combined to form a chimeric guide RNA (gRNA) to guide Cas9 to target selected sequences. These two components can then be delivered to mammalian cells via transfection or transduction. As another example, CRISPR/Cpf1 comprises two major components: (1) a CPf1 endonuclease and (2) a crRNA. When co-expressed, the two components form a ribonucleoprotein (RNP) complex that is recruited to a target DNA sequence comprising PAM and a seeding region near PAM. The crRNA can be combined to form a chimeric guide RNA (gRNA) to guide Cpf1 to target selected sequences. These two components can then be delivered to mammalian cells via transfection or transduction.

MAD7 is an engineered Cas12a variant originating from the bacterium *Eubacterium rectale* that has a preference for 5'-TTTN-3' and 5'-CTTN-3' PAM sites and does not require a tracrRNA. See, for example, PCT Publication No. 2018/236548, the disclosure of which is incorporated herein by reference.

DICE mediated insertion uses a pair of recombinases, for example, phiC31 and Bxbl, to provide unidirectional integration of an exogenous DNA that is tightly restricted to each enzymes' own small attB and attP recognition sites. Because these target att sites are not naturally present in mammalian genomes, they must be first introduced into the genome, at the desired integration site. See, for example, U.S. Application Publication No. 2015/0140665, the disclosure of which is incorporated herein by reference.

One aspect of the present application provides a construct comprising one or more exogenous polynucleotides for targeted genome integration. In one embodiment, the construct further comprises a pair of homologous arm specific to a desired integration site, and the method of targeted integration comprises introducing the construct to cells to enable site specific homologous recombination by the cell host enzymatic machinery. In another embodiment, the method of targeted integration in a cell comprises introducing a construct comprising one or more exogenous polynucleotides to the cell, and introducing a ZFN expression cassette comprising a DNA-binding domain specific to a desired integration site to the cell to enable a ZFN-mediated insertion. In yet another embodiment, the method of targeted integration in a cell comprises introducing a construct comprising one or more exogenous polynucleotides to the cell, and introducing a TALEN expression cassette comprising a DNA-binding domain specific to a desired integration site to the cell to enable a TALEN-mediated insertion. In another embodiment, the method of targeted integration in a cell comprises introducing a construct comprising one or more exogenous polynucleotides to the cell, introducing a Cpf1 expression cassette, and a gRNA comprising a guide sequence specific to a desired integration site to the cell to enable a Cpf1-mediated insertion. In another embodiment, the method of targeted integration in a cell comprises introducing a construct comprising one or more exogenous polynucleotides to the cell, introducing a Cas9 expression cassette, and a gRNA comprising a guide sequence specific to a desired integration site to the cell to enable a Cas9-mediated insertion. In still another embodiment, the method of targeted integration in a cell comprises introducing a construct comprising one or more att sites of a pair of DICE recombinases to a desired integration site in the cell, introducing a construct comprising one or more exogenous polynucleotides to the cell, and introducing an expression cassette for DICE recombinases, to enable DICE-mediated targeted integration.

Sites for targeted integration include, but are not limited to, genomic safe harbors, which are intragenic or extragenic regions of the human genome that, theoretically, are able to accommodate predictable expression of newly integrated DNA without adverse effects on the host cell or organism. In certain embodiments, the genome safe harbor for the targeted integration is one or more loci of genes selected from the group consisting of AAVS1, CCR5, ROSA26, collagen, HTRP, Hll, GAPDH, TCR and RUNX1 genes.

In other embodiments, the site for targeted integration is selected for deletion or reduced expression of an endogenous gene at the insertion site. As used herein, the term "deletion" with respect to expression of a gene refers to any genetic modification that abolishes the expression of the gene. Examples of "deletion" of expression of a gene include, e.g., a removal or deletion of a DNA sequence of the gene, an insertion of an exogenous polynucleotide sequence at a locus of the gene, and one or more substitutions within the gene, which abolishes the expression of the gene.

Genes for target deletion include, but are not limited to, genes of major histocompatibility complex (MHC) class I and MHC class II proteins. Multiple MHC class I and class II proteins must be matched for histocompatibility in allogeneic recipients to avoid allogeneic rejection problems. "MHC deficient", including MHC-class I deficient, or MHC-class II deficient, or both, refers to cells that either lack, or no longer maintain, or have reduced level of surface expression of a complete MHC complex comprising a MHC class I protein heterodimer and/or a MHC class II heterodimer, such that the diminished or reduced level is less than the level naturally detectable by other cells or by synthetic methods. MHC class I deficiency can be achieved by functional deletion of any region of the MHC class I locus (chromosome 6p21), or deletion or reducing the expression level of one or more MHC class-I associated genes including, not being limited to, beta-2 microglobulin (B2M) gene, TAP 1 gene, TAP 2 gene and Tapasin genes. For example, the B2M gene encodes a common subunit essential for cell surface expression of all MHC class I heterodimers. B2M null cells are MHC-I deficient. MHC class II deficiency can be achieved by functional deletion or reduction of MHC-II associated genes including, not being limited to, RFXANK, CIITA, RFX5 and RFXAP. CIITA is a transcriptional coactivator, functioning through activation of the transcription factor RFX5 required for class II protein expression. CIITA null cells are MHC-II deficient. In certain embodiments, one or more of the exogenous polynucleotides are integrated at one or more loci of genes selected from the group consisting of B2M, TAP 1, TAP 2, Tapasin, RFXANK, CIITA, RFX5 and RFXAP genes to thereby delete or reduce the expression of the gene(s) with the integration.

In certain embodiments, the exogenous polynucleotides are integrated at one or more loci on the chromosome of the cell, preferably the one or more loci are of genes selected from the group consisting of AAVS1, CCR5, ROSA26, collagen, HTRP, HI 1, GAPDH, RUNX1, B2M, TAPI, TAP2, Tapasin, NLRC5, CIITA, RFXANK, CIITA, RFX5, RFXAP, TCR a or b constant region, NKG2A, NKG2D, CD38, CIS, CBL-B, SOCS2, PD1, CTLA4, LAG3, TIM3, or TIGIT genes, provided at least one of the one or more loci is of a MHC gene, such as a gene selected from the group consisting of B2M, TAP 1, TAP 2, Tapasin, RFXANK, CIITA, RFX5 and RFXAP genes. Preferably, the one or more exogenous polynucleotides are integrated at a locus of an MHC class-I associated gene, such as a beta-2 microglobulin (B2M) gene, TAP 1 gene, TAP 2 gene or Tapasin gene; and at a locus of an MHC-II associated gene, such as a RFXANK, CIITA, RFX5, RFXAP, or CIITA gene; and optionally further at a locus of a safe harbor gene selected from the group consisting of AAVS1, CCR5, ROSA26, collagen, HTRP, H11, GAPDH, TCR and RUNX1 genes. More preferably, the one or more of the exogenous polynucleotides are integrated at the loci of CIITA, AAVS1 and B2M genes.

In certain embodiments, (i) the first exogenous polynucleotide is integrated at a locus of AAVS1 gene; (ii) the second exogenous polypeptide is integrated at a locus of CIITA gene; and (iii) the third exogenous polypeptide is integrated at a locus of B2M gene; wherein integrations of the exogenous polynucleotides delete or reduce expression of CIITA and B2M genes.

In certain embodiments, (i) the first exogenous polynucleotide comprises the polynucleotide sequence having at least 90%, 91%, 92%, 93%, 94%, 95%, 96%, 97%, 98%, 99% or 100% sequence identity to SEQ ID NO: 62; (ii) the second exogenous polynucleotide comprises the polynucleotide sequence having at least 90%, 91%, 92%, 93%, 94%, 95%, 96%, 97%, 98%, 99% or 100% sequence identity to SEQ ID NO: 75; and (iii) the third exogenous polynucleotide comprises the polynucleotide sequence having at least 90%, 91%, 92%, 93%, 94%, 95%, 96%, 97%, 98%, 99% or 100% sequence identity to SEQ ID NO: 67.

In certain embodiments, (i) the first exogenous polynucleotide comprises the polynucleotide sequence of SEQ ID NO: 62; (ii) the second exogenous polynucleotide comprises the polynucleotide sequence of SEQ ID NO: 75; and (iii) the third exogenous polynucleotide comprises the polynucleotide sequence of SEQ ID NO: 67.

Derivative Cells

In another aspect, the invention relates to a cell derived from differentiation of an iPSC, a derivative cell. As described above, the genomic edits introduced into the iPSC cell are retained in the derivative cell. In certain embodiments of the derivative cell obtained from iPSC differentiation, the derivative cell is a hematopoietic cell, including, but not limited to, HSCs (hematopoietic stem and progenitor cells), hematopoietic multipotent progenitor cells, T cell progenitors, NK cell progenitors, T cells, NKT cells, NK cells, B cells, antigen presenting cells (APC), monocytes and macrophages. In certain embodiments, the derivative cell is an immune effector cell, such as a NK cell or a T cell.

In certain embodiments, the application provides a natural killer (NK) cell or a T cell comprising: (i) a first exogenous polynucleotide encoding a chimeric antigen receptor (CAR); (ii) a second exogenous polynucleotide encoding a truncated epithelial growth factor receptor (tEGFR) variant and an interleukin 15 (IL-15), wherein the tEGFR variant and IL-15 are operably linked by an autoprotease peptide, such as an autoprotease peptide of a porcine tesehovirus-1 2A (P2A) peptide; and (iii) a deletion or reduced expression of an MHC class I associated gene and an MHC class II associated gene, such as an MHC class-I associated gene selected from the group consisting of a B2M gene, TAP 1 gene, TAP 2 gene and Tapasin gene, and an MHC-II associated gene selected from the group consisting of a RFXANK gene, CIITA gene, RFX5 gene, RFXAP gene, and CIITA gene, preferably the B2M gene and CIITA gene.

In certain embodiments, the NK cell or T cell further comprises a third exogenous polynucleotide encoding at least one of a human leukocyte antigen E (HLA-E) and a human leukocyte antigen G (HLA-G).

Also provided is a NK cell or a T cell comprising: (i) a first exogenous polynucleotide encoding a chimeric antigen receptor (CAR) having the amino acid sequence of SEQ ID NO: 61; (ii) a second exogenous polynucleotide encoding a truncated epithelial growth factor receptor (tEGFR) variant having the amino acid sequence of SEQ ID NO: 71, an autoprotease peptide having the amino acid sequence of SEQ ID NO: 73, and interleukin 15 (IL-15) having the amino acid sequence of SEQ ID NO: 72; and (iii) a third exogenous polynucleotide encoding a human leukocyte antigen E (HLA-E) having the amino acid sequence of SEQ ID NO: 66; wherein the first, second and third exogenous polynucleotides are integrated at loci of AAVS1, CIITA and B2M genes, respectively, to thereby delete or reduce expression of CIITA and B2M.

In certain embodiments, the first exogenous polynucleotide comprises the polynucleotide sequence of SEQ ID NO: 62; the second exogenous polynucleotide comprises the polynucleotide sequence of SEQ ID NO: 75; and the third exogenous polynucleotide comprises the polynucleotide sequence of SEQ ID NO: 67.

Also provided is a CD34+ hematopoietic progenitor cell (HPC) derived from an induced pluripotent stem cell (iPSC) comprising: (i) a first exogenous polynucleotide encoding a chimeric antigen receptor (CAR); (ii) a second exogenous polynucleotide encoding an inactivated cell surface receptor that comprises a monoclonal antibody-specific epitope and an interleukin 15 (IL-15), wherein the inactivated cell surface receptor and the IL-15 are operably linked by an autoprotease peptide; and (iii) a deletion or reduced expression of one or more of B2M, TAP 1, TAP 2, Tapasin, RFXANK, CIITA, RFX5 and RFXAP genes.

In certain embodiments, the CD34+ HPC further comprises a third exogenous polynucleotide encoding a human leukocyte antigen E (HLA-E) and/or human leukocyte antigen G (HLA-G).

In certain embodiments, the CAR comprises (i) a signal peptide; (ii) an extracellular domain comprising a binding domain that specifically binds the CD19 antigen; (iii) a hinge region; (iv) a transmembrane domain; (v) an intracellular signaling domain; and (vi) a co-stimulatory domain, such as a co-stimulatory domain comprising a CD28 signaling domain.

Also provided is a method of manufacturing the derivative cell. The method comprises differentiating the iPSC under conditions for cell differentiation to thereby obtain the derivative cell.

An iPSC of the application can be differentiated by any method known in the art. Exemplary methods are described in U.S. Pat. Nos. 8,846,395, 8,945,922, 8,318,491, WO2010/099539, WO2012/109208, WO2017/070333, WO2017/179720, WO2016/010148, WO2018/048828 and WO2019/157597, each of which are herein incorporated by reference in its entirety. The differentiation protocol may use feeder cells or may be feeder-free. As used herein, "feeder cells" or "feeders" are terms describing cells of one type that are co-cultured with cells of a second type to provide an environment in which the cells of the second type can grow, expand, or differentiate, as the feeder cells provide stimulation, growth factors and nutrients for the support of the second cell type.

Figure 5A:
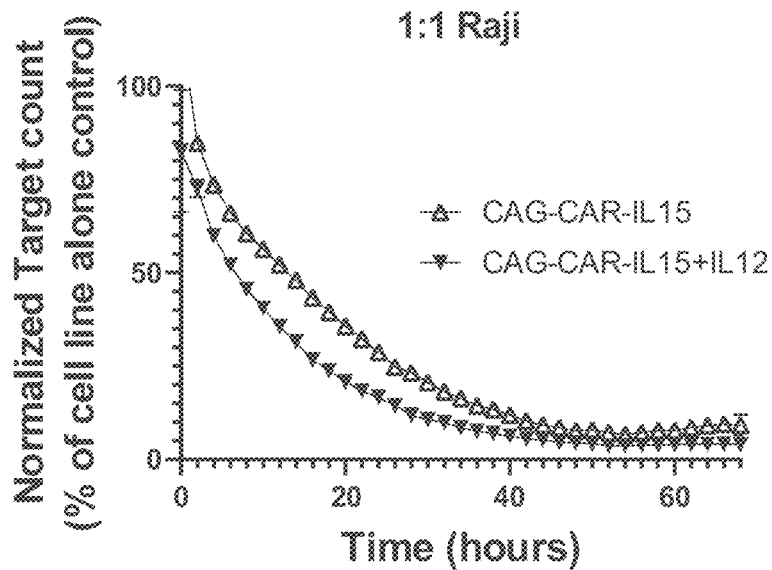
FIGS. 5A-5B show cytotoxicity of CAG-CAR-IL15 expressing iNK cells with and without human recombinant IL12.
Figure 5B:
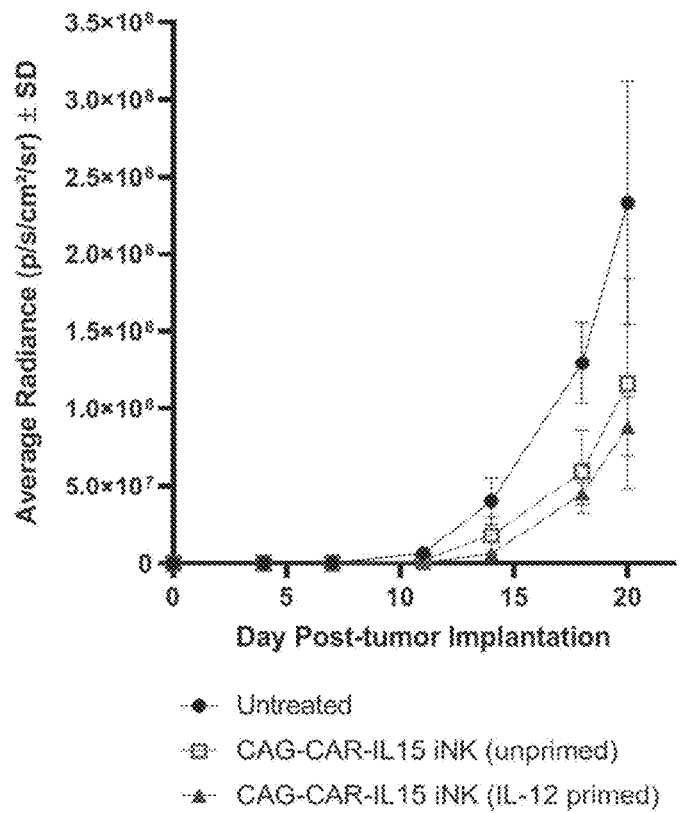

In another embodiment of the invention, the iPSC derivative cells of the invention are NK cells which are prepared by a method of differentiating an iPSC cell into an NK cell by subjecting the cells to a differentiation protocol including the addition of recombinant human IL-12p70 for the final 24 hours of culture. By including the IL-12 in the differentiation protocol, cells that are primed with IL-12 demonstrate more rapid cell killing compared to those that are differentiated in the absence of IL-12 (FIG. 5A). In addition, the cells differentiated using the IL-12 conditions demonstrate improved cancer cell growth inhibition (FIG. 5B).

Polynucleotides, Vectors, and Host Cells (1) Nucleic Acids Encoding a CAR

In another general aspect, the invention relates to an isolated nucleic acid encoding a chimeric antigen receptor (CAR) useful for an invention according to embodiments of the application. It will be appreciated by those skilled in the art that the coding sequence of a CAR can be changed (e.g., replaced, deleted, inserted, etc.) without changing the amino acid sequence of the protein. Accordingly, it will be understood by those skilled in the art that nucleic acid sequences encoding CARs of the application can be altered without changing the amino acid sequences of the proteins.

In certain embodiments, the isolated nucleic acid encodes a CAR targeting CD19. In a particular embodiment, the isolated nucleic acid encoding the CAR comprises a polynucleotide sequence at least 90%, such as at least 90%, 91%, 92%, 93%, 94%, 95%, 96%, 97%, 98% or 100%, identical to SEQ ID NO: 62, preferably the polynucleotide sequence of SEQ ID NO: 62.

In another general aspect, the application provides a vector comprising a polynucleotide sequence encoding a CAR useful for an invention according to embodiments of the application. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible, or repressible promoter. A number of expression vectors capable of delivering nucleic acids to a cell are known in the art and can be used herein for production of a CAR in the cell. Conventional cloning techniques or artificial gene synthesis can be used to generate a recombinant expression vector according to embodiments of the application.

In a particular aspect, the application provides vectors for targeted integration of a CAR useful for an invention according to embodiments of the application. In certain embodiments, the vector comprises an exogenous polynucleotide having, in the 5' to 3' order, (a) a promoter; (b) a polynucleotide sequence encoding a CAR according to an embodiment of the application; and (c) a terminator/polyadenylation signal.

In certain embodiments, the promoter is a CAG promoter. In certain embodiments, the CAG promoter comprises the polynucleotide sequence at least 90%, such as at least 90%, 91%, 92%, 93%, 94%, 95%, 96%, 97%, 98% or 100%, identical to SEQ ID NO: 63. Other promoters can also be used, examples of which include, but are not limited to, EF1α, UBC, CMV, SV40, PGK1, and human beta actin.

In certain embodiments, the terminator/polyadenylation signal is a SV40 signal. In certain embodiments, the SV40 signal comprises the polynucleotide sequence at least 90%, such as at least 90%, 91%, 92%, 93%, 94%, 95%, 96%, 97%, 98% or 100%, identical to SEQ ID NO: 64. Other terminator sequences can also be used, examples of which include, but are not limited to, BGH, hGH, and PGK.

In certain embodiments, the polynucleotide sequence encoding a CAR comprises the polynucleotide sequence at least 90%, such as at least 90%, 91%, 92%, 93%, 94%, 95%, 96%, 97%, 98% or 100%, identical to SEQ ID NO: 62.

In some embodiment, the vector further comprises a left homology arm and a right homology arm flanking the exogenous polynucleotide. As used herein, "left homology arm" and "right homology arm" refers to a pair of nucleic acid sequences that flank an exogenous polynucleotide and facilitate the integration of the exogenous polynucleotide into a specified chromosomal locus. Sequences of the left and right arm homology arms can be designed based on the integration site of interest. In some embodiment, the left or right arm homology arm is homologous to the left or right side sequence of the integration site.

In certain embodiments, the left homology arm comprises the polynucleotide sequence at least 90%, such as at least 90%, 91%, 92%, 93%, 94%, 95%, 96%, 97%, 98% or 100%, identical to SEQ ID NO: 90. In certain embodiments, the right homology arm comprises the polynucleotide sequence at least 90%, such as at least 90%, 91%, 92%, 93%, 94%, 95%, 96%, 97%, 98% or 100%, identical to SEQ ID NO: 91.

In a particular embodiment, the vector comprises a polynucleotide sequence at least 85%, such as at least 85%, 86%, 87%, 88%, 89%, 90%, 91%, 92%, 93%, 94%, 95%, 96%, 97%, 98% or 100%, identical to SEQ ID NO: 92, preferably the polynucleotide sequence of SEQ ID NO: 92.

(2) Nucleic Acids Encoding an Inactivated Cell Surface Receptor

In another general aspect, the invention relates to an isolated nucleic acid encoding an inactivated cell surface receptor useful for an invention according to embodiments of the application. It will be appreciated by those skilled in the art that the coding sequence of an inactivated cell surface receptor can be changed (e.g., replaced, deleted, inserted, etc.) without changing the amino acid sequence of the protein. Accordingly, it will be understood by those skilled in the art that nucleic acid sequences encoding an inactivated cell surface receptor of the application can be altered without changing the amino acid sequences of the proteins.

In certain embodiments, an isolated nucleic acid encodes any inactivated cell surface receptor described herein, such as that comprises a monoclonal antibody-specific epitope, and a cytokine, such as an IL-15 or IL-2, wherein the monoclonal antibody-specific epitope and the cytokine are operably linked by an autoprotease peptide.

In some embodiments, the isolated nucleic acid encodes an inactivated cell surface receptor comprising an epitope specifically recognized by an antibody, such as ibritumomab, tiuxetan, muromonab-CD3, tositumomab, abciximab, basiliximab, brentuximab vedotin, cetuximab, infliximab, rituximab, alemtuzumab, bevacizumab, certolizumab pegol, daclizumab, eculizumab, efalizumab, gemtuzumab, natalizumab, omalizumab, palivizumab, polatuzumab vedotin, ranibizumab, tocilizumab, trastuzumab, vedolizumab, adalimumab, belimumab, canakinumab, denosumab, golimumab, ipilimumab, ofatumumab, panitumumab, or ustekinumab.

In certain embodiments, the isolated nucleic acid encodes an inactivated cell surface receptor having a truncated epithelial growth factor receptor (tEGFR) variant. Preferably, the inactivated cell surface receptor comprises an epitope specifically recognized by cetuximab, matuzumab, necitumumab or panitumumab, preferably cetuximab.

In certain embodiments, the isolated nucleic acid encodes an inactivated cell surface receptor having one or more epitopes of CD79b, such as an epitope specifically recognized by polatuzumab vedotin.

In certain embodiments, the isolated nucleic acid encodes an inactivated cell surface receptor having one or more epitopes of CD20, such as an epitope specifically recognized by rituximab.

In certain embodiments, the isolated nucleic acid encodes an inactivated cell surface receptor having one or more epitopes of Her 2 receptor, such as an epitope specifically recognized by trastuzumab In certain embodiments, the autoprotease peptide comprises or is a porcine tesehovirus-1 2A (P2A) peptide.

In certain embodiments, the truncated epithelial growth factor receptor (tEGFR) variant consists of an amino acid sequence having at least 90%, 91%, 92%, 93%, 94%, 95%, 96%, 97%, 98%, 99% or 100% sequence identity to the amino acid sequence of SEQ ID NO: 71.

In certain embodiments, the monoclonal antibody-specific epitope specifically recognized by polatuzumab vedotin consists of an amino acid sequence at least 90%, such as at least 90%, 91%, 82%, 93%, 94%, 95%, 96%, 97%, 98%, 99% or 100%, identical to SEQ ID NO: 78.

In certain embodiments, the monoclonal antibody-specific epitope specifically recognized by rituximab consists of an amino acid sequence at least 90%, such as at least 90%, 91%, 82%, 93%, 94%, 95%, 96%, 97%, 98%, 99% or 100%, identical to SEQ ID NO: 80.

In certain embodiments, the monoclonal antibody-specific epitope specifically recognized by trastuzumab consists of an amino acid sequence at least 90%, such as at least 90%, 91%, 82%, 93%, 94%, 95%, 96%, 97%, 98%, 99% or 100%, identical to SEQ ID NO: 82.

In certain embodiments, the IL-15 comprises an amino acid sequence having at least 90%, 91%, 92%, 93%, 94%, 95%, 96%, 97%, 98%, 99% or 100% sequence identity to the amino acid sequence of SEQ ID NO: 72.

In certain embodiments, the autoprotease peptide has an amino acid sequence having at least 90%, 91%, 92%, 93%, 94%, 95%, 96%, 97%, 98%, 99% or 100% sequence identity to the amino acid sequence of SEQ ID NO: 73.

In certain embodiments, the polynucleotide sequence encodes a polypeptide comprising an amino acid sequence having at least 90%, 91%, 92%, 93%, 94%, 95%, 96%, 97%, 98%, 99% or 100% sequence identity to the amino acid sequence of SEQ ID NO: 74.

In a particular embodiment, the isolated nucleic acid encoding the inactivated cell surface receptor comprises a polynucleotide sequence at least 90%, such as at least 90%, 91%, 92%, 93%, 94%, 95%, 96%, 97%, 98% or 100%, identical to SEQ ID NO: 75, preferably the polynucleotide sequence of SEQ ID NO: 75.

In certain embodiments, the polynucleotide sequence encodes a polypeptide comprising an amino acid sequence having at least 90%, 91%, 92%, 93%, 94%, 95%, 96%, 97%, 98%, 99% or 100% sequence identity to the amino acid sequence of SEQ ID NO: 79.

In another general aspect, the application provides a vector comprising a polynucleotide sequence encoding an inactivated cell surface receptor useful for an invention according to embodiments of the application. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible, or repressible promoter. A number of expression vectors capable of delivering nucleic acids to a cell are known in the art and can be used herein for production of a inactivated cell surface receptor in the cell. Conventional cloning techniques or artificial gene synthesis can be used to generate a recombinant expression vector according to embodiments of the application.

In a particular aspect, the application provides a vector for targeted integration of an inactivated cell surface receptor useful for an invention according to embodiments of the application. In certain embodiments, the vector comprises an exogenous polynucleotide having, in the 5' to 3' order, (a) a promoter; (b) a polynucleotide sequence encoding an inactivated cell surface receptor, such as an inactivated cell surface receptor comprising a truncated epithelial growth factor receptor (tEGFR) variant and an interleukin 15 (IL-15), wherein the tEGFR variant and the IL-15 are operably linked by an autoprotease peptide, such as a porcine teschovirus-1 2A (P2A) peptide, and (c) a terminator/polyadenylation signal.

In certain embodiments, the promoter is a CAG promoter. In certain embodiments, the CAG promoter comprises the polynucleotide sequence at least 90%, such as at least 90%, 91%, 92%, 93%, 94%, 95%, 96%, 97%, 98% or 100%, identical to SEQ ID NO: 63. Other promoters can also be used, examples of which include, but are not limited to, EF1α, UBC, CMV, SV40, PGK1, and human beta actin.

In certain embodiments, the terminator/polyadenylation signal is a SV40 signal. In certain embodiments, the SV40 signal comprises the polynucleotide sequence at least 90%, such as at least 90%, 91%, 92%, 93%, 94%, 95%, 96%, 97%, 98% or 100%, identical to SEQ ID NO: 64. Other terminator sequences can also be used, examples of which include, but are not limited to BGH, hGH, and PGK.

In certain embodiments, the polynucleotide sequence encoding an inactivated cell surface receptor comprises the polynucleotide sequence at least 90%, such as at least 90%, 91%, 92%, 93%, 94%, 95%, 96%, 97%, 98% or 100%, identical to SEQ ID NO: 75.

In some embodiment, the vector further comprises a left homology arm and a right homology arm flanking the exogenous polynucleotide.

In certain embodiments, the left homology arm comprises the polynucleotide sequence at least 90%, such as at least 90%, 91%, 92%, 93%, 94%, 95%, 96%, 97%, 98% or 100%, identical to SEQ ID NO: 84. In certain embodiments, the right homology arm comprises the polynucleotide sequence at least 90%, such as at least 90%, 91%, 92%, 93%, 94%, 95%, 96%, 97%, 98% or 100%, identical to SEQ ID NO: 85

In a particular embodiment, the vector comprises a polynucleotide sequence at least 85%, such as at least 85%, 86%, 87%, 88%, 89%, 90%, 91%, 92%, 93%, 94%, 95%, 96%, 97%, 98% or 100%, identical to SEQ ID NO: 86, preferably the polynucleotide sequence of SEQ ID NO: 86.

(3) Nucleic Acids Encoding an HLA Construct

In another general aspect, the invention relates to an isolated nucleic acid encoding an HLA construct useful for an invention according to embodiments of the application. It will be appreciated by those skilled in the art that the coding sequence of an HLA construct can be changed (e.g., replaced, deleted, inserted, etc.) without changing the amino acid sequence of the protein. Accordingly, it will be understood by those skilled in the art that nucleic acid sequences encoding an HLA construct of the application can be altered without changing the amino acid sequences of the proteins.

In certain embodiments, the isolated nucleic acid encodes an HLA construct comprising a signal peptide, such as an HLA-G signal peptide, operably linked to an HLA coding sequence, such as a coding sequence of a mature B2M, and/or a mature HLA-E. In some embodiments, the HLA coding sequence encodes the HLA-G and B2M, which are operably linked by a 4×GGGGS linker, and/or the B2M and HLA-E, which are operably linked by a 3×GGGGS linker. In a particular embodiment, the isolated nucleic acid encoding the HLA construct comprises a polynucleotide sequence at least 90%, such as at least 90%, 91%, 92%, 93%, 94%, 95%, 96%, 97%, 98% or 100%, identical to SEQ ID NO: 67, preferably the polynucleotide sequence of SEQ ID NO: 67. In another embodiment, the isolated nucleic acid encoding the HLA construct comprises a polynucleotide sequence at least 90%, such as at least 90%, 91%, 92%, 93%, 94%, 95%, 96%, 97%, 98% or 100%, identical to SEQ ID NO: 70, preferably the polynucleotide sequence of SEQ ID NO: 70.

In another general aspect, the application provides a vector comprising a polynucleotide sequence encoding a HLA construct useful for an invention according to embodiments of the application. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible, or repressible promoter. A number of expression vectors capable of delivering nucleic acids to a cell are known in the art and can be used herein for production of a HLA construct in the cell. Conventional cloning techniques or artificial gene synthesis can be used to generate a recombinant expression vector according to embodiments of the application.

In a particular aspect, the application provides vectors for targeted integration of a HLA construct useful for an invention according to embodiments of the application. In certain embodiments, the vector comprises an exogenous polynucleotide having, in the 5' to 3' order, (a) a promoter; (b) a polynucleotide sequence encoding an HLA construct; and (c) a terminator/polyadenylation signal.

In certain embodiments, the promoter is a CAG promoter. In certain embodiments, the CAG promoter comprises the polynucleotide sequence at least 90%, such as at least 90%, 91%, 92%, 93%, 94%, 95%, 96%, 97%, 98% or 100%, identical to SEQ ID NO: 63. Other promoters can also be used, examples of which include, but are not limited to, EF1α, UBC, CMV, SV40, PGK1, and human beta actin.

In certain embodiments, the terminator/polyadenylation signal is a SV40 signal. In certain embodiments, the SV40 signal comprises the polynucleotide sequence at least 90%, such as at least 90%, 91%, 92%, 93%, 94%, 95%, 96%, 97%, 98% or 100%, identical to SEQ ID NO: 64. Other terminator sequences can also be used, examples of which include, but are not limited to BGH, hGH, and PGK.

In certain embodiments, a polynucleotide sequence encoding a HLA construct comprises a signal peptide, such as a HLA-G signal peptide, a mature B2M, and a mature HLA-E, wherein the HLA-G and B2M are operably linked by a 4×GGGGS linker (SEQ ID NO: 31) and the B2M transgene and HLA-E are operably linked by a 3×GGGGS linker (SEQ ID NO: 25). In particular embodiments, the HLA construct comprises the polynucleotide sequence at least 90%, such as at least 90%, 91%, 92%, 93%, 94%, 95%, 96%, 97%, 98% or 100%, identical to SEQ ID NO: 67, preferably the polynucleotide sequence of SEQ ID NO: 67. In another embodiment, the HLA construct comprises the polynucleotide sequence at least 90%, such as at least 90%, 91%, 92%, 93%, 94%, 95%, 96%, 97%, 98% or 100%, identical to SEQ ID NO: 70, preferably the polynucleotide sequence of SEQ ID NO: 70.

In some embodiment, the vector further comprises a left homology arm and a right homology arm flanking the exogenous polynucleotide.

In certain embodiments, the left homology arm comprises the polynucleotide sequence at least 90%, such as at least 90%, 91%, 92%, 93%, 94%, 95%, 96%, 97%, 98% or 100%, identical to SEQ ID NO: 87. In certain embodiments, the right homology arm comprises the polynucleotide sequence at least 90%, such as at least 90%, 91%, 92%, 93%, 94%, 95%, 96%, 97%, 98% or 100%, identical to SEQ ID NO: 88.

In a particular embodiment, the vector comprises a polynucleotide sequence at least 85%, such as at least 85%, 86%, 87%, 88%, 89%, 90%, 91%, 92%, 93%, 94%, 95%, 96%, 97%, 98% or 100%, identical to SEQ ID NO: 89, preferably the polynucleotide sequence of SEQ ID NO: 89.

(4) Host Cells

In another general aspect, the application provides a host cell comprising a vector of the application and/or an isolated nucleic acid encoding a construct of the application. Any host cell known to those skilled in the art in view of the present disclosure can be used for recombinant expression of exogenous polynucleotides of the application. According to particular embodiments, the recombinant expression vector is transformed into host cells by conventional methods such as chemical transfection, heat shock, or electroporation, where it is stably integrated into the host cell genome such that the recombinant nucleic acid is effectively expressed.

Examples of host cells include, for example, recombinant cells containing a vector or isolated nucleic acid of the application useful for the production of a vector or construct of interest; or an engineered iPSC or derivative cell thereof containing one or more isolated nucleic acids of the application, preferably integrated at one or more chromosomal loci. A host cell of an isolated nucleic acid of the application can also be an immune effector cell, such as a T cell or NK cell, comprising the one or more isolated nucleic acids of the application. The immune effector cell can be obtained by differentiation of an engineered iPSC of the application. Any suitable method in the art can be used for the differentiation in view of the present disclosure. The immune effector cell can also be obtained transfecting an immune effector cell with one or more isolated nucleic acids of the application.

Compositions

In another general aspect, the application provides a composition comprising an isolated polynucleotide of the application, a host cell and/or an iPSC or derivative cell thereof of the application.

In certain embodiments, the composition further comprises one or more therapeutic agents selected from the group consisting of a peptide, a cytokine, a checkpoint inhibitor, a mitogen, a growth factor, a small RNA, a dsRNA (double stranded RNA), siRNA, oligonucleotide, mononuclear blood cells, a vector comprising one or more polynucleic acids of interest, an antibody, a chemotherapeutic agent or a radioactive moiety, or an immunomodulatory drug (IMiD).

In certain embodiments, the composition is a pharmaceutical composition comprising an isolated polynucleotide of the application, a host cell and/or an iPSC or derivative cell thereof of the application and a pharmaceutically acceptable carrier. The term "pharmaceutical composition" as used herein means a product comprising an isolated polynucleotide of the application, an isolated polypeptide of the application, a host cell of the application, and/or an iPSC or derivative cell thereof of the application together with a pharmaceutically acceptable carrier. Polynucleotides, polypeptides, host cells, and/or iPSCs or derivative cells thereof of the application and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition described herein or the biological activity of a composition described herein. According to particular embodiments, in view of the present disclosure, any pharmaceutically acceptable carrier suitable for use in a polynucleotide, polypeptide, host cell, and/or iPSC or derivative cell thereof can be used.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier may be used in formulating the pharmaceutical compositions of the application.

Methods of Use

In another general aspect, the application provides a method of treating a disease or a condition in a subject in need thereof. The methods comprise administering to the subject in need thereof a therapeutically effective amount of cells of the application and/or a composition of the application. In certain embodiments, the disease or condition is cancer. The cancer can, for example, be a solid or a liquid cancer. The cancer, can, for example, be selected from the group consisting of a lung cancer, a gastric cancer, a colon cancer, a liver cancer, a renal cell carcinoma, a bladder urothelial carcinoma, a metastatic melanoma, a breast cancer, an ovarian cancer, a cervical cancer, a head and neck cancer, a pancreatic cancer, an endometrial cancer, a prostate cancer, a thyroid cancer, a glioma, a glioblastoma, and other solid tumors, and a non-Hodgkin's lymphoma (NHL), Hodgkin's lymphoma/disease (HD), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors. In a preferred embodiment, the cancer is a non-Hodgkin's lymphoma (NHL).

According to embodiments of the application, the composition comprises a therapeutically effective amount of an isolated polynucleotide, an isolated polypeptide, a host cell, and/or an iPSC or derivative cell thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to a cell of the application and/or a pharmaceutical composition of the application a therapeutically effective amount means an amount of the cells and/or the pharmaceutical composition that modulates an immune response in a subject in need thereof.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

The cells of the application and/or the pharmaceutical compositions of the application can be administered in any convenient manner known to those skilled in the art. For example, the cells of the application can be administered to the subject by aerosol inhalation, injection, ingestion, transfusion, implantation, and/or transplantation. The compositions comprising the cells of the application can be administered transarterially, subcutaneously, intradermally, intratumorally, intranodally, intramedullary, intramuscularly, intrapleurally, by intravenous (i.v.) injection, or intraperitoneally. In certain embodiments, the cells of the application can be administered with or without lymphodepletion of the subject.

The pharmaceutical compositions comprising cells of the application can be provided in sterile liquid preparations, typically isotonic aqueous solutions with cell suspensions, or optionally as emulsions, dispersions, or the like, which are typically buffered to a selected pH. The compositions can comprise carriers, for example, water, saline, phosphate buffered saline, and the like, suitable for the integrity and viability of the cells, and for administration of a cell composition.

Sterile injectable solutions can be prepared by incorporating cells of the application in a suitable amount of the appropriate solvent with various other ingredients, as desired. Such compositions can include a pharmaceutically acceptable carrier, diluent, or excipient such as sterile water, physiological saline, glucose, dextrose, or the like, that are suitable for use with a cell composition and for administration to a subject, such as a human. Suitable buffers for providing a cell composition are well known in the art. Any vehicle, diluent, or additive used is compatible with preserving the integrity and viability of the cells of the application.

The cells of the application and/or the pharmaceutical compositions of the application can be administered in any physiologically acceptable vehicle. A cell population comprising cells of the application can comprise a purified population of cells. Those skilled in the art can readily determine the cells in a cell population using various well known methods. The ranges in purity in cell populations comprising genetically modified cells of the application can be from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or from about 95% to about 100%. Dosages can be readily adjusted by those skilled in the art, for example, a decrease in purity could require an increase in dosage.

The cells of the application are generally administered as a dose based on cells per kilogram (cells/kg) of body weight of the subject to which the cells and/or pharmaceutical compositions comprising the cells are administered. Generally, the cell doses are in the range of about $10^4$ to about $10^{10}$ cells/kg of body weight, for example, about $10^5$ to about $10^9$, about $10^5$ to about $10^8$, about $10^5$ to about $10^7$, or about $10^5$ to about $10^6$, depending on the mode and location of administration. In general, in the case of systemic administration, a higher dose is used than in regional administration, where the immune cells of the application are administered in the region of a tumor and/or cancer. Exemplary dose ranges include, but are not limited to, $1\times10^4$ to $1\times10^8$, $2\times10^4$ to $1\times10^8$, $3\times10^4$ to $1\times10^8$, $4\times10^4$ to $1\times10^8$, $5\times10^4$ to $6\times10^8$, $7\times10^4$ to $1\times10^8$, $8\times10^4$ to $1\times10^8$, $9\times10^4$ to $1\times10^8$, $1\times10^5$ to $1\times10^8$, $1\times10^5$ to $9\times10^7$, $1\times10^5$ to $8\times10^7$, $1\times10^5$ to $7\times10^7$, $1\times10^5$ to $6\times10^7$, $1\times10^5$ to $5\times10^7$, $1\times10^5$ to $4\times10^7$, $1\times10^5$ to $4\times10^7$, $1\times10^5$ to $3\times10^7$, $1\times10^5$ to $2\times10^7$, $1\times10^5$ to $1\times10^7$, $1\times10^5$ to $9\times10^6$, $1\times10^5$ to $8\times10^6$, $1\times10^5$ to $7\times10^6$, $1\times10^5$ to $6\times10^6$, $1\times10^5$ to $5\times10^6$, $1\times10^5$ to $4\times10^6$, $1\times10^5$ to $4\times10^6$, $1\times10^5$ to $3\times10^6$, $1\times10^5$ to $2\times10^6$, $1\times10^5$ to $1\times10^6$, $2\times10^5$ to $9\times10^7$, $2\times10^5$ to $8\times10^7$, $2\times10^5$ to $7\times10^7$, $2\times10^5$ to $6\times10^7$, $2\times10^5$ to $5\times10^7$, $2\times10^5$ to $4\times10^7$, $2\times10^5$ to $4\times10^7$, $2\times10^5$ to $3\times10^7$, $2\times10^5$ to $2\times10^7$, $2\times10^5$ to $1\times10^7$, $2\times10^5$ to $9\times10^6$, $2\times10^5$ to $8\times10^6$, $2\times10^5$ to $7\times10^6$, $2\times10^5$ to $6\times10^6$, $2\times10^5$ to $5\times10^6$, $2\times10^5$ to $4\times10^6$, $2\times10^5$ to $4\times10^6$, $2\times10^5$ to $3\times10^6$, $2\times10^5$ to $2\times10^6$, $2\times10^5$ to $1\times10^6$, $3\times10^5$ to $3\times10^6$ cells/kg, and the like. Additionally, the dose can be adjusted to account for whether a single dose is being administered or whether multiple doses are being administered. The precise determination of what would be considered an effective dose can be based on factors individual to each subject.

As used herein, the terms "treat," "treating," and "treatment" are all intended to refer to an amelioration or reversal of at least one measurable physical parameter related to a cancer, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

The cells of the application and/or the pharmaceutical compositions of the application can be administered in combination with one or more additional therapeutic agents. In certain embodiments the one or more therapeutic agents are selected from the group consisting of a peptide, a cytokine, a checkpoint inhibitor, a mitogen, a growth factor, a small RNA, a dsRNA (double stranded RNA), siRNA, oligonucleotide, mononuclear blood cells, a vector comprising one or more polynucleic acids of interest, an antibody, a chemotherapeutic agent or a radioactive moiety, or an immunomodulatory drug (IMiD).

EXAMPLES

| Abbreviations | |
|---|---|
| ABC | Antibodies Bound Per Cell |
| ADCC | Antibody Dependent Cellular Cytotoxicity |
| ALL | Acute Lymphoblastic Leukemia |
| ANOVA | Analysis Of Variance |
| APC | Allophycocyanin |
| ATCC | American Type Culture Collection |
| b2M | Beta-2 Microglobulin |
| BRC | Baby Rabbit Complement |
| BSA | Bovine Serum Albumin |
| BUV | Brilliant Ultra Violet |
| BV | Brilliant Violet |
| C | Celsius |
| CAR | Chimeric Antigen Receptor |
| CD | Cluster Of Differentiation |
| CDC | Complement-Mediated Cytotoxicity |
| CTL | Cytotoxic Lymphocyte |
| CTV | Celltrace Violet |
| DMEM | Dulbecco's Modified Eagle Medium |
| E:T | Effector To Target Ratio |
| $EC_{50}$ | Half Maximal Effective Concentration |
| EGFR | Epidermal Growth Factor |
| FACS | Fluorescence Activated Cell Sorting |
| FBS | Fetal Bovine Serum |
| Fc | Fragment Crystallizable |
| FcR | Fc Receptor |
| FMO | Fluorescence Minus One |
| FSC-A | Forward Scatter Area |
| FSC-H | Forward Scatter Height |
| GRex | Gas Permeable Rapid Expansion |
| MOI | Multiplicity Of Infection |
| N | Number Of Animals |
| NCI | National Cancer Institute |
| ng | Nanogram |

| Abbreviations -continued | |
|---|---|
| NIR | Near-IR |
| NK | Natural Killer |
| NKCM | Nk Culture Media |
| NKG2A | Natural Killer Group 2 Member A |
| NLR | Nuclight Red |
| NSCLC | Non-Small Cell Lung Carcinoma |
| NSG | Nod-Scid-Gamma |
| p | Probability Value |
| PBMC | Peripheral Blood Mononuclear Cell |
| PB-NK | Peripheral Blood Derived Natural Killer Cell |
| PBS | Phosphate-Buffered Saline |
| HC | Hemacare |
| HLA | Human Leukocyte Antigen |
| HLA-E | Human Leukocyte Antigen Class I, E |
| HP-β-CD | 2-Hydroxypropyl-Beta-Cyclodextrin |
| hr | Hour |
| HSA | Human Serum Albumin |
| Ig | Immunoglobulin |
| IL- | Interleukin |
| IMDM | Iscove Modified Dulbecco Media |
| iNK | Ipsc Derived Natural Killer Cell |
| iNK | Ipsc-Derived Natural Killer |
| IP | Intraperitoneal |
| iPSC | Induced Pluripotent Stem Cell |
| IR | Infrared |
| IU | International Units |
| IV | Intravenous |
| K | Thousand |
| kg | Kilogram |
| KO | Genetic Knockout |
| LLOD | Lower Limit Of Detection |
| mAb | Monoclonal Antibody |
| mg | Microgram |
| mg | Milligram |
| MHC | Major Histocompatibility Complex |
| min | Minute |
| mL | Milliliter |
| mM | Micromolar |
| mm | Millimeter |
| PE | Phycoerythrin |
| perCP-Cy5.5 | Peridinin Chlorophyll Protein Complex-Cyanin 5.5 |
| pg | Picograms |
| PR | R-Phycoerythrin |
| RCU | Red Calibrated Unit |
| rhIL-2 | Recombinant Human Interleukin-2 |
| RO | Reverse Osmosis |
| RT | Room Temperature |
| SD | Standard Deviation |
| SEM | Standard Error Of The Mean |
| SSC-A | Side Scatter Area |
| TGI | Tumor Growth Inhibition |
| WT | Wild Type |
| xG | Times Gravity |

Example 1. Cell Line Development iPSC Development

Induced pluripotent stem cell (iPSC) parental cell lines were generated from peripheral blood mononuclear cells (PBMCs) using an episomal plasmid-based process as previously described in U.S. Pat. Nos. 8,546,140; 9,644,184; 9,328,332; and 8,765,470, the complete disclosures of which are incorporated herein by reference.

Vector (Plasmid) Production

Gene fragments (gBlocks) encoding the transgene of interest, with the promoter, terminator, and homology arms were designed and synthesized by chemical synthesis at IDT, Inc. The gBlock gene fragments were assembled into a pUC19 plasmid using the In-Fusion® Cloning HD Plus kit (Takara Bio; Shiga, Japan) according to manufacturer's protocol. Reaction products from In-Fusion Cloning, i.e. expression constructs, were transformed into Stbl3 bacterial cells (Thermo Fisher; Waltham, Mass.) for amplification according to manufacturer's protocol. Vector (plasmid) from the amplified expression construct was purified from bacterial cell culture using the HiSpeed Plasmid Maxi Prep kit (Qiagen; Hilden, Germany) according to the manufacturer's protocol. Research grade sequencing was performed on purified plasmid DNA and evaluated by restriction digestion to confirm transgene sequence. The concentration of purified plasmid DNA was measured by absorbance. Additionally, the absorbance ratio at A260/A280 nm and A260/A230 nm were measured to evaluate residual RNA and protein levels, respectively.

CIITA Targeting Plasmid

The CIITA targeting plasmid contains a CAG promoter (SEQ ID NO: 63), SV40 terminator/polyadenylation (SEQ ID NO: 64), and tEGFR-IL15 coding sequence. The tEGFR-IL15 transgene encodes tEGFR-IL15, which contains residues 322-333 of domain 2, all of domains 3 and 4 and the transmembrane domain of the native EGFR sequence (SEQ ID NO: 71). The tEGFR-IL15 transgene is followed by an in frame P2A peptide sequence (SEQ ID NO: 73) and then the full-length IL-15 sequence (SEQ ID NO: 72). A schematic of the CIITA targeting transgene plasmid is shown in FIG. 1A.

AAVS1 Targeting Plasmid

Figure 1B:
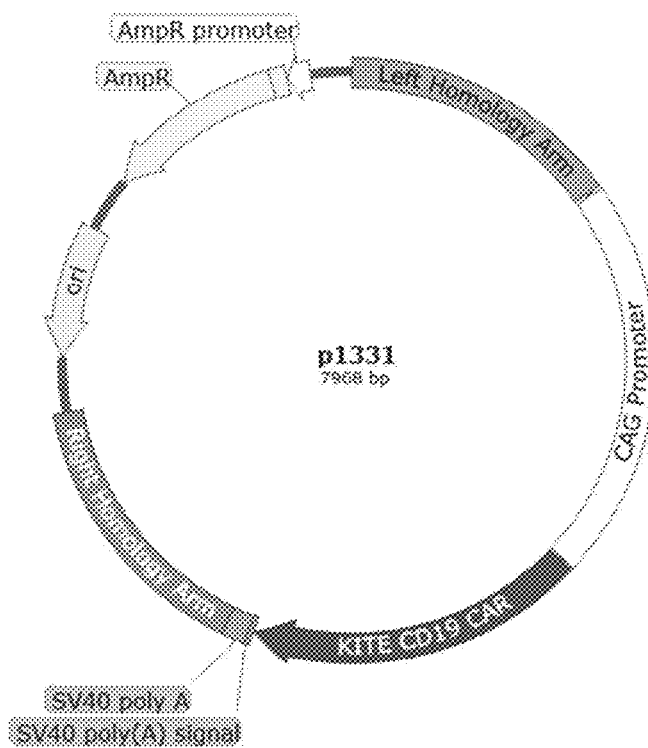

The AAVS1 targeting plasmid contains a CAG promoter (SEQ ID NO: 63), SV40 terminator/polyadenylation (SEQ ID NO: 64), and anti-CD19 scFv chimeric antigen receptor (CAR) sequence (SEQ ID NO: 62). The encoded CAR contains the GMCSFR signal peptide connected to the FMC63 scFv followed by residues 114 to 220 of CD28 and residues 52 to 163 of CD3zeta isoform 3. A schematic of the AAVS1 targeting transgene plasmid is shown in FIG. 1B.

B2M Targeting Plasmid

Figure 1C:
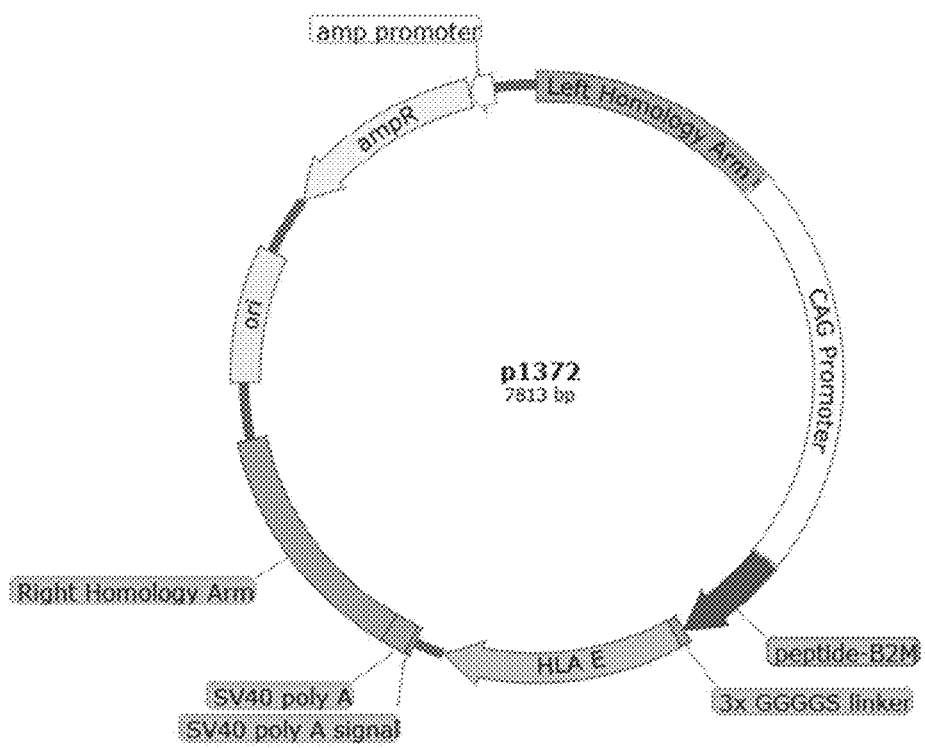

The B2M targeting plasmid contains a CAG promoter (SEQ ID NO: 63), SV40 terminator/polyadenylation (SEQ ID NO: 64), and Peptide-B2M-HLA-E coding sequence (SEQ ID NO: 67). The B2M-transgene encoded protein (SEQ ID NO: 66) contains the signal peptide from HLA-G followed by the nine amino acid peptide VMAPRTLIL connected to a 4×GGGGS linker, the mature B2M sequence connected to a 3×GGGGS linker and then the mature HLA-E sequence (SEQ ID NO: 65). A schematic of the B2M targeting transgene plasmid is shown in FIG. 1C.

Transgene insertion into the B2M (exon 2) and CIITA (exon 1) results in disruption of the coding sequences and prevents translation of the full-length sequence. Loss of expression of B2M will prevent proper MHC Class I assembly and disrupt expression. Loss of CIITA will prevent HLA II gene transcription and prevent MHC Class II expression. Insertion of the transgene into intron 1 of the AAVS1 locus does not result in any coding sequence alterations. Homology arm sequences were designed to sit on the 5' and 3' sides of a Cpf1 genome nuclease cut site and include from 500-1200 bp of target locus-specific sequence.

CAR-Engineered iPSC Cell Line Establishment

Cell line establishment consisted of transfection, electroporation, CAR-Engineered iPSC expansion, cell sorting, and cell cloning steps. Three serial rounds of transfection and electroporation were performed with the associated purified plasmid DNA and recombinant Cpf1 ultra/guide RNA Ribonucleoprotein (RNP) complexes that are specific to a single target locus (either B2M, CIITA, or AAVS1).

Guide RNAs (gRNAs) were selected using the Benchling™ software design tool, with all off-target sites scoring less than 2 (0-100) (Table 3). The vast majority of potential off-target sites were intergenic.

TABLE 3

Guide RNAs

| SEQ ID NO: | gRNA target | Sequence |
|---|---|---|
| 93 | B2M | TTTACTCACGTCATCCAGCAGAGA |
| 94 | AAVS1 | TTTATCTGTCCCCTCCACCCCACA |
| 95 | CIITA | TTTACCTTGGGGCTCTGACAGGTA |

Briefly, a vial of iPSC cells from the parental cell line was thawed into Complete Essential 8™ medium (Thermo Fisher) with H1152 Rho Kinase Inhibitor, pelleted, and resuspended in Complete Essential 8 medium. The cell suspension was then transferred to the wells of a Vitronectin-coated, 6-well plate containing Complete Essential 8 medium with H1152 and incubated at 37° C., 5% $CO_2$, low $O_2$. Cells from one well were expanded into a T-75 flask. When the flask reached 60-70% confluency, it was propagated into another T-75 flask. When this flask became 60-70% confluent, the cells were used for transfection. H1152 was added to a T-75 flask containing iPSC cells and the cells were incubated at 37° C., 5% $CO_2$, low $O_2$.

Following incubation, cells were washed with DPBS, dissociated from the flask, and resuspended in Complete Essential 8 medium. Cells were counted and seeded into a T-75 flask, which had been pre-coated with Vitronectin, containing Complete Essential 8 medium with H1152, at an appropriate cell density for transfection. Lipofectamine Stem reagent (Thermo Fisher) and purified plasmid DNA were prepared in Opti-MEM (Thermo Fisher) and incubated. The transfection mix containing purified plasmid DNA was added to the cells and then incubated at 37° C., 5% $CO_2$, low $O_2$.

After transfection, cells were washed with DPBS, dissociated from the flask, and resuspended in Complete Essential 8 medium. The cells were then washed with Opti-MEM, counted, washed with additional Opti-MEM, and resuspended in Opti-MEM at an appropriate cell density for electroporation. Ribonucleoprotein (RNP) complex was generated by combining Alt-R® CRISPR-Cpf1 crRNA and Alt-R® Cpf1 Ultra Nuclease (IDT; Coralville, Iowa). RNP complex and Cpf1 electroporation enhancer were added to the transfected cells and were electroporated. Electroporated cells were then added to the wells of a pre-warmed, Vitronectin-coated, 24-well plate containing Complete Essential 8 medium and NU7026 and were incubated at 37° C., 5% $CO_2$, low $O_2$.

Cells were cultured for a minimum of 10 days in Complete Essential 8 medium on Vitronectin-coated plates for homology directed repair to occur. Once cells on the 24-well plate were 60-70% confluent, they were dissociated and propagated into one well of a 6-well plate. After reaching confluency, one well of a 6-well plate was propagated into a T-75 flask. Cells were maintained in culture for the minimum 10-day duration, after which the culture was analyzed for the presence of inserted transgenes and/or absence of deleted endogenous genes by flow cytometry. Cells were then subjected to flow cytometry sorting to isolate the modified population.

After each round of transfection and electroporation, the expanded, engineered cells were sorted for stable integrants by Fluorescence Activated Cell Sorting (FACS) using transgene-specific antibodies. Sorting after each round of engineering included markers from the previous rounds and may require multiple rounds of sorting to sufficiently enrich the population for all the respective markers. Sorting was performed on a MacsQuant Tyto cell sorter (Miltenyi Biotech; Bergisch Gladbach, Germany) using fluorescently labeled antibodies to human HLA-E, human EGFR and a fusion protein of human CD19-Fc.

After completion of all three engineering steps and necessary rounds of sorting, single cell clones were isolated by limited dilution cloning. Cells were washed once with DPBS and dissociated from the plate. Cells were resuspended in Complete Essential 8 medium, filtered through a 70-μm cell strainer, counted, and diluted to a final density of 1000 cells/mL in Complete Essential 8 medium. The cells were then transferred in 200-μL aliquots to 9 mL StemFit® (Amsbio; Abington, United Kingdom) with 1 mL CloneR™ supplement (StemCell Technologies; Vancouver, Canada), plated at 100 μL/well, and rested for 24 hours. After resting, medium was changed every 48 hours until colonies were approximately 2 mm in diameter, at which time wells with single colonies were identified by visual inspection and were split to duplicate Vitronectin-coated plates containing Complete Essential 8 medium. Medium was changed every day until cells reach greater than 50% confluency. One of the plates was used for expanding single-cell lines into 6-well plates for use in the process and the other was used for characterization.

Hematopoietic Progenitor Cell (HPC) Differentiation iPSC cells thawed from cryopreserved cell banks were grown on plates coated with Vitronectin in E8 medium supplemented with H1152 Rho Kinase Inhibitor. The iPSC cells were passaged twice through dissociation with TrypLE™ (Thermo Fisher), and re-seeding on to Vitronectin plates with E8 media+H1152. After two passages through dissociation TrypLE treatment, the iPSC cells were once more treated with TrypLE and the cells were resuspended in an optimized concentration in HDM-I media plus H1152. HDM media contains IMDM medium, Ham's F12 medium, CTS B27 minus Vitamin A supplement, Non Essential Amino Acids, Ascorbic Acid Mg 2-phosphate, Monothioglycerol, and Heparin. HDM-I media contains HDM+ CHIR99021 GSK3 inhibitor, FGF2, and VEGF. The resuspended cells were then seeded into the appropriate vessels depending on scale. The next day (D1), 80% of the medium was replaced with Fresh HDM-I medium. At days 2, 3, and 4, 80% of the medium was removed and replaced with HDM-II medium (HDM media+BMP4, FGF2, and VEGF). At day 5, HPCs may start to appear in the cultures, budding off of the cell aggregates. Once the HPCs started to appear, they were harvested 2 days later, but no earlier than day 8. Starting at day 5; every day 80% of the medium was removed, and any HPCs in the removed media are collected by centrifugation and the cells resuspended in HDM-III (HDM+BMP4, SCF, TPO, FLT3L, and IL3) and added back to the culture. HPCs were then harvested at day 8 or day 9 (depending on day of initial appearance of the HPCs)

Natural Killer (NK) Cell and T Cell Differentiation and Activation

The HPCs were differentiated to generate NK or T cells. Cells were thawed, washed, and seeded into retronectin/DLL4-coated G-Rex bioreactors. Notch signaling, specific cytokines, and growth factors were used for differentiation into lymphoid lineage and subsequent NK or T cell maturation and activation. During harvest, the culture was concentrated and washed, formulated using a defined cryopreservation medium, and filled into AT vials using an M1 filling station. Vials were visually inspected, cryopreserved in a controlled rate freezer, and stored in the vapor phase of a LN2 freezer.

NK and T cells can also be differentiated using feeder cells. Briefly, K562 myelogenous leukemia cells engineered to express class I molecules, CD64, 4-1BBL and transmembrane are cultured with the HCPs for a sufficient time to promote differentiation of NK or T cells.

Example 2. CD19 Targeted Cytotoxicity Assay

Figure 2:
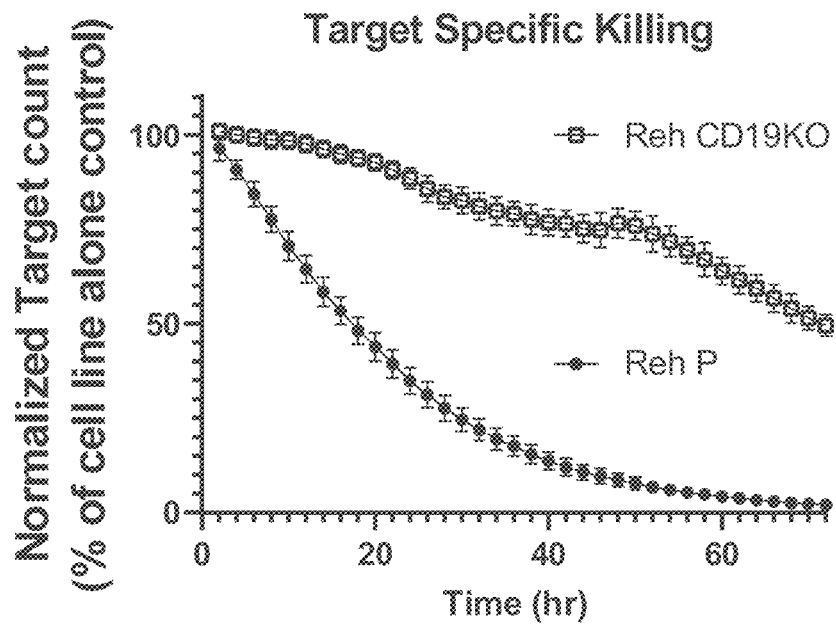
FIG. 2 shows a graph demonstrating CAR-iNK cell-mediated target cell cytotoxicity over time in Reh cells and CD19 knockout (CD19KO) Reh cells.

To demonstrate CD19-specific target cell killing, cytotoxicity was measured using an IncuCyte® assay (Essen Bioscience Inc.; Ann Arbor, Mich.). A CD19-knockout Reh B leukemia cell line was established. Cells were also transduced with NucLightRed using lentivirus from Essen Biosciences (Sartorious) for use in Incucyte assay. Next, parental and CD19-knockout Reh B cell leukemia cells were co-cultured with iNK cells expressing FMC63 CD28z CAR (anti-CD19) at a 1:1 effector-to-target cell ratio. Target cell death was measured over 72 hours. CAR iNK cells effectively kill CD19-positive target cells (FIG. 2).

Example 3. CAR/IL-15 iNK Assays

Figure 3A:
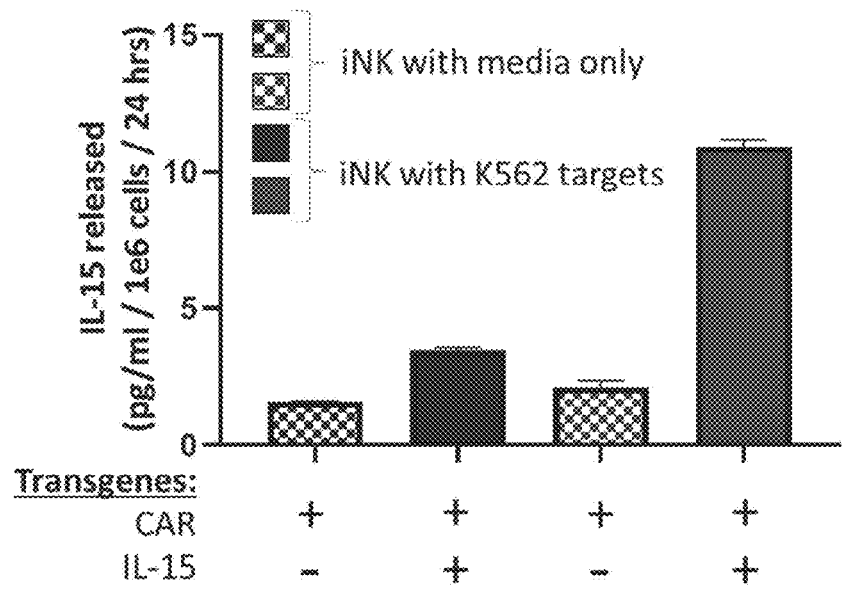
FIGS. 3A-C show functionality of iNK cell expressing CAR-IL15 compared to iNK cells expressing CAR alone.

In order to test the ability of iNK cells engineered to express the IL-15 transgene (CAR/IL-15 iNK) to release IL-15, CAR iNK or CAR/IL-15 iNK cells were cultured in media alone or co-cultured with K562 myelogenous leukemia cells (ATCC) at a 1:1 effector to target ratio. Supernatants were collected after incubating for 24, 28, 72 or 96 hours and assayed for IL-15 concentration using an MSD immunoassay (Cat #K151URK-4) according to manufacturer's protocol (Meso Scale Diagnostic; Rockville, Md.). In both media only and with K562 targets, iNK cells engineered to express the IL-15 transgene demonstrated superior IL-15 release into the culture media (FIG. 3A).

Figure 3B:
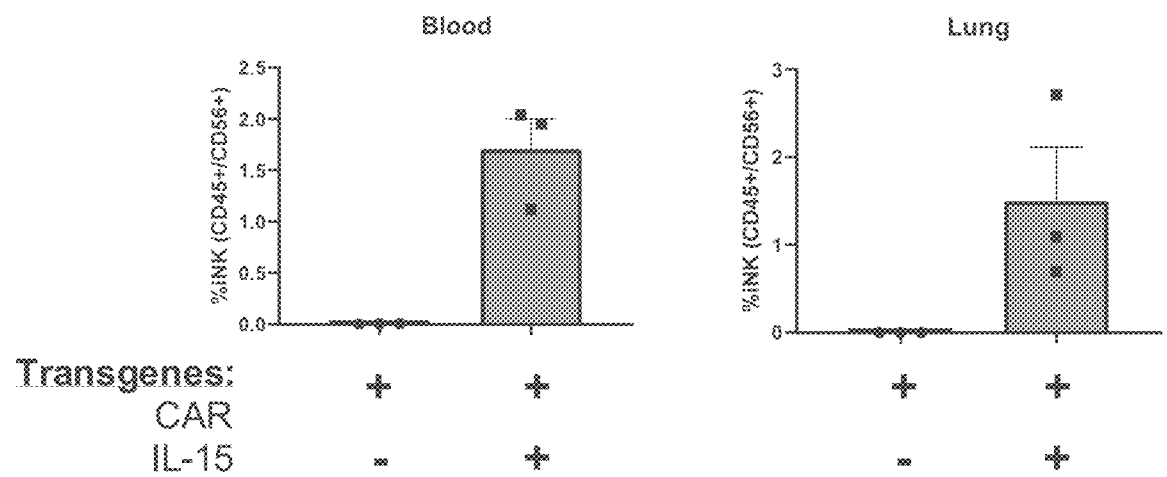

To test the in vivo persistence of the CAR/EL-15 iNK cells, CAR iNK or CAR/IL-15 iNK cells (10E6 cells) were injected intravenously into immunodeficient NSG™ mice (The Jackson Laboratory; Bar Harbor, Me.) on Day 0. On Day 20 post-injection, blood and lungs were analyzed for the presence of human $CD45^+$ $CD56^+$ cells (infused iNK cells) using Fluorescence-activated Cell Sorting (FACS). Only when infused cells carried the human IL-15 transgene were they detectable after 20 days (FIG. 3B).

Figure 3C:
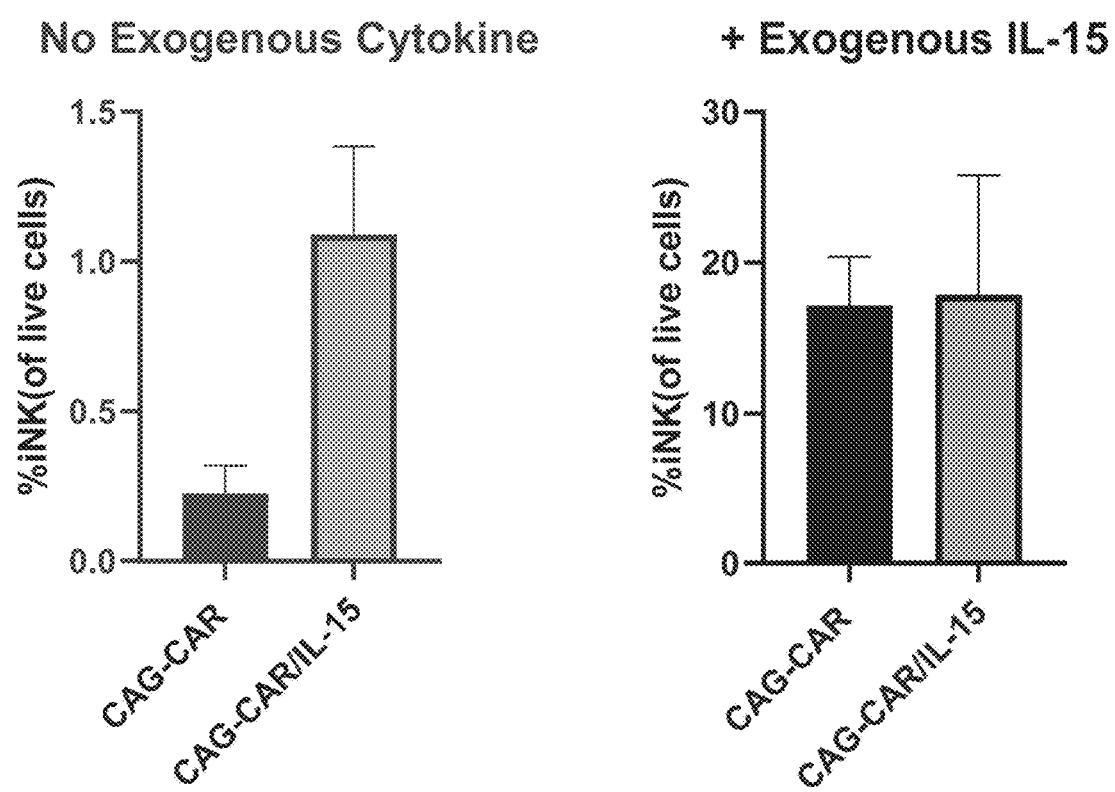

To further test the impact of the IL-15 transgene on the persistence of CAG-CAR/IL-15 cells in vivo, mice were intravenously infused with $1\times10^7$ CAG-CAR or CAG-CAR/IL-15 cells on study Day 1. Half of the mice were supplemented with exogenous recombinant human IL-15 (1 μg/mouse daily, intraperitoneal) for the duration of the study. On study day 8 lungs were harvested and processed for flow cytometry analysis. Samples were stained with Fixable LiveDead NearIR (Thermo fisher), anti-huCD45, anti-huCD56. During analysis iNK cells were defined as CD56/CD45 double positive cells and recorded as a percentage of the live cell population (FIG. 3C).

Figure 4A:
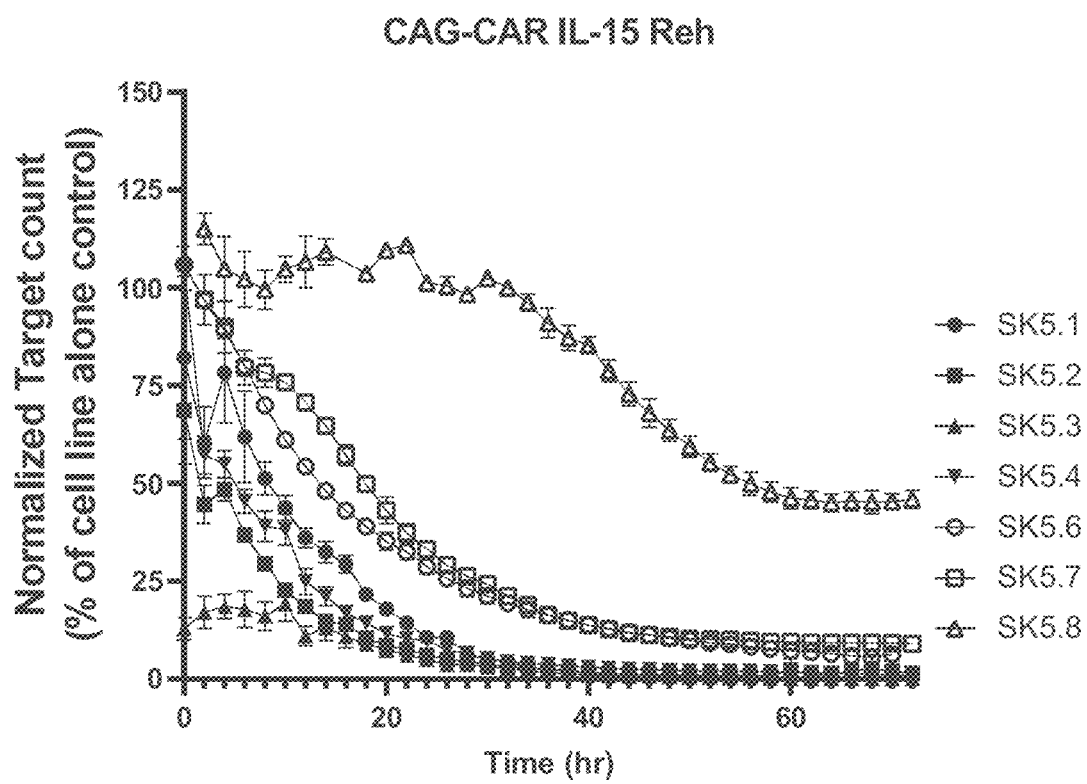
FIGS. 4A-C show the proliferation and serial killing of CAG-CAR-IL-15 iNK cells.

To test the ability of the CAR/IL-15 iNK cells to kill over multiple rounds of target challenge, a serial killing assay was set up with a bulk culture, for repeated stimulation, in parallel to Incucyte assays for quantification of cytolytic activity at each round. CAR/IL-15 iNK cells were cultured at a 1:1 effector to target ratio (E:T) with Irradiated Reh cells (2Gy) for 3-4 days. Results showed that CAR/IL-15-iNK cells perform serial killing for seven rounds before exhausting (FIG. 4A). At the end of the bulk culture no Reh target cells were detectable. CAR/IL-15 iNK cells were counted on the ViCell Blue to track expansion and allow for setting up subsequent bulk culture and Incucyte assays. Incucyte based killing assays were set up in parallel to each bulk culture, using the cells harvested from the prior bulk culture as the effector population with multiple E:Ts 5:1, 1:1, 1:5.

Figure 4B:
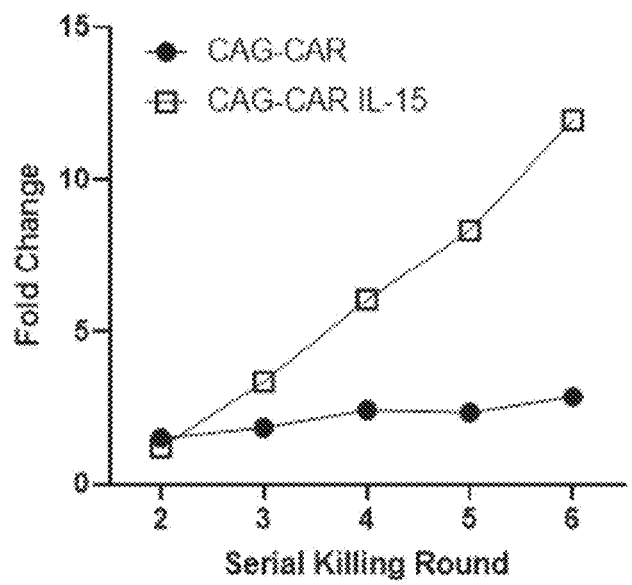
Figure 4C:
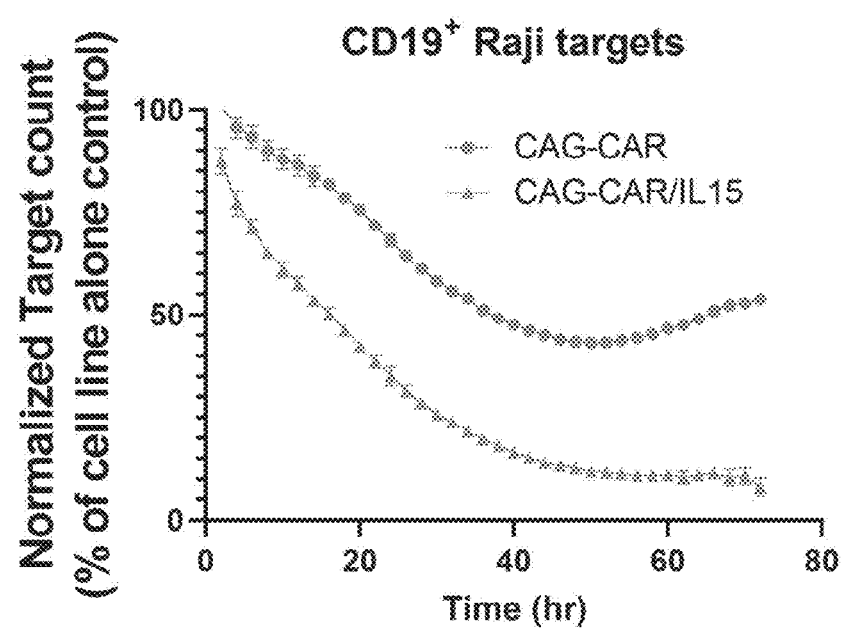

Next, the CAR/IL-15-iNK cells were compared to CAR-iNK cells not expressing IL-15. The CAR/IL-15-iNK cells showed superior proliferation compared to CAR-iNK cells (FIG. 4B). The CAR/IL-15-iNK cells also showed superior serial killing of Raji cells compared to CAR-iNK cells (FIG. 4C).

Example 4. Cytokine Enhanced Cytotoxicity Assays

Interleukin-12 is a cytokine that stimulates the production of interferon-gamma (IFN-γ) and tumor necrosis factor-alpha (TNF-α) from T cells and natural killer (NK) cells. To determine whether IL-12 had an effect on the target cytotoxicity of CAR/IL-15 iNK cells, iNK cells were differentiated in the standard protocol (no IL-12) or with inclusion of 10 ng/ml recombinant human IL-12p70 (PeproTech; Rocky Hill, N.J.) for the final 24 hours of culture. iNK cells were used in an Incucyte killing assay to determine efficacy for killing the Raji CD19+ B cell leukemia cell line (ATCC; Manassas, Va.). Cells that were primed with IL-12 demonstrated more rapid killing of Raji cells compared to those that were differentiated in the absence of IL-12 (FIG. 5A).

IL-12 primed iNK cells were further tested for effects on tumorigenesis in vivo. Luciferase-labeled Burkitt's lymphoma cell line Raji, was intravenously (iv) implanted in female NSG™ mice on study Day 0. Mice were intravenously infused with $1 \times 10^7$ unprimed or IL12-primed CAG-CAR-IL15 iNK cells on study days 1, 4, and 7. Mice were supplemented with intraperitoneal recombinant human IL-2 (100,000 IU, PeproTech #200-02) three times weekly for the duration of the study, beginning on day 1. An untreated group served as the control. Mice were injected with Luciferin (VivoGlo™, Promega) prior to imaging using the IVIS SpectrumCT (Perkin Elmer). The reaction of the luciferin substrate with the firefly luciferase enzyme produced by the Raji tumor cells, produces light measured as bioluminescent signal. Data are represented as mean whole body bioluminescent average radiance±SD. 50% and 62% tumor growth inhibition was observed with unprimed and IL-12 primed iNK treatment, respectively, at study termination on Day 20 (*p<0.05, **p<0.01) (FIG. 5B).

Example 5. Elimination Assay

Figure 6A:
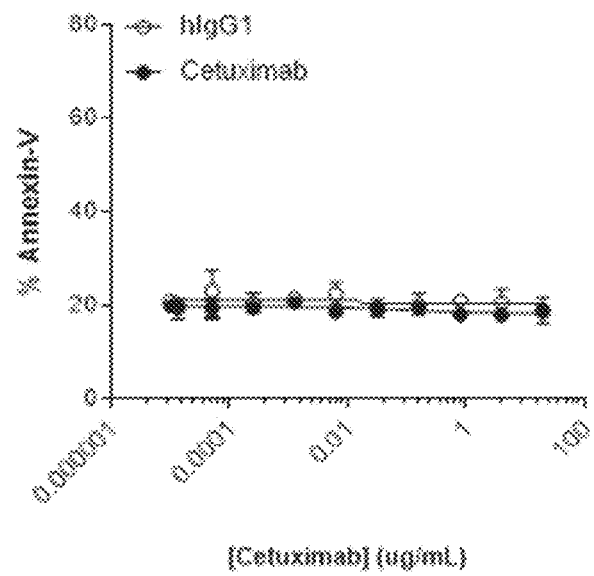
FIGS. 6A-6B show Cetuximab-induced cell elimination in CAG-CAR expressing iNK cells and CAG-CAR-IL15-tEGFR expressing iNK cells.
Figure 6B:
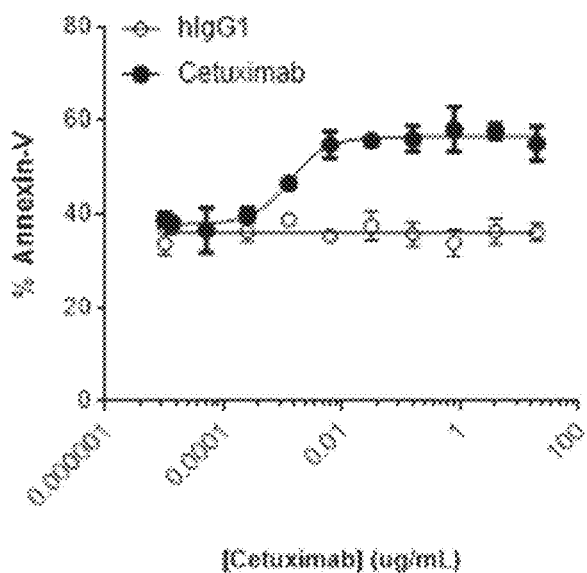

CAR/IL15 iNK cells were engineered to express tEGFR as an elimination feature, intended to operate as the target of antibody-dependent cell-mediated cytotoxicity (ADCC) and antibody-dependent cellular phagocytosis (ADCP) through dosing with Cetuximab, an EGFR inhibitor. iNK cells with or without EGFR expressed from a transgene were co-cultured with human PBMCs. Increasing doses of Cetuximab were added to facilitate ADCC and cells were incubated for 3 hours. Control cells were treated with human IgG1. Results are shown in FIGS. 6A-6B. Only EGFR-expressing iNK cells showed dose-dependent cell death (Annexin V staining) in the ADCC assay. This data demonstrates that the CAR/IL15/tEGFR iNK cells can be efficiently eliminated using Cetuximab.

Example 6. MHC Class I and Class II Deletion

The plasmid constructs described in the present application are designed to target integration of exogenous polypeptides useful for the invention of the application and simultaneously delete or reduce expression of MHC class I and class II genes. Genomic engineering of IPSCs using the B2M and CIITA targeting plasmids is done as described above. After differentiation to an NK cell, confirmation of MHC class I and II expression is confirmed using flow cytometry using antibodies specific for HLA I (alpha chain) and HLA II (alpha or beta chain).

Example 7. Non-Classical HLA Expression iNK cells of application are engineered to further express non-classical HLA proteins, HLA-E or HLA-G. Expression is confirmed at all stages by flow cytometry using antibodies specific for HLA-E or HLA-G.

Example 8. iNK Mediated Lysis of K562 Cells

To demonstrate the ability iNK cells to elicit basic NK cell functionality, iNK clone iNK1248-iPSC611 and primary peripheral blood NK (PB-NK) cells from 3 PBMC donors were assessed for the ability to kill K562 cells using the Incucyte live imaging platform. The Incucyte platform allows for real-time quantification of fluorescently labeled target cells, depletion of which serves as a measurement of target lysis.

K562 Cell Line Generation and Propagation

The chronic myelogenous leukemia (CML) cell K562 cell line was obtained from ATCC. K562 cells were transduced with NucLight Red lentivirus following the standard Sartorius protocol. Transduced cells were selected and cultured in IMDM culture media containing 1 ug/mL of puromycin. Cells were cultured spitting every 2-3 days keeping cell density between 1e5 cells/mL and 1e6 cells/mL.

NK Isolation

PBMCs from 3 donors were thawed in a 37 C and centrifuged for 3 min at 300G. Supernatant was aspirated and cells were resuspended in RPMI+10% FBS 10 ng/mL Il-15 and rested overnight. NK cells were isolated from rested PBMCs using CD56 MicroBeads, human (Miltenyi, part 130-050-401) according to manufacturers recommended protocol.

NK Purity Check

CAR-iNK clones and PB-NK donors were plated at 100K cells per well in 96 well U-bottom plate (BD falcon 353077). All wash steps were carried out by centrifugation at 300×G for 3 min and flicking supernatants into the sink. Cells were washed 2× in PBS and stained with 100 ul of a 1:1000 dilution (in PBS) of LIVE/DEAD™ Fixable Near-IR viability dye (thermo Fisher) for 15 min at room temperature (RT). Cells were washed 2× in BD FACS stain buffer BSA (BD). TrustainFcX, human Fc receptor block, was diluted 1:100 in BD FACS stain and 50 ul of dilution was added to each well incubating for 30 min at 4 C. Cells were washed 2× in BD FACS stain buffer BSA (BD). A staining cocktail was made by diluting the mAbs for CD16, CD4, CD19, CD45, CD3, CD56, CD14 and 1:100 in BD FACS Stain buffer. Cells were stained with 50 ul of staining cocktail and incubated for 30 min at 4 C protected from light. Cells were washed 2× using BD FACS Stain buffer fixed in 100 ul of BD Stabilizing fixative. All samples were run with the same voltage on the BD Symphony A3 Lite. Flow cytometry data was analyzed using FlowJo 10.7.2.

TABLE 4

Flow Reagents

| | Clone | Fluorophore | Supplier | catalog # | lot # | Dilution |
|---|---|---|---|---|---|---|
| near-IR fluorescent reactive dye | — | near-IR | Thermo Fisher | L34976A | 2298176 | 1:1,000 |
| Human TruStain FcX | — | — | BioLegend | 422302 | B328706 | 1:100 |
| CD16 | 3G8 | BV 421 | BioLegend | 302038 | B303711 | 1:100 |
| CD4 | OKT4 | BV 605 | BioLegend | 317438 | B310529 | 1:100 |
| CD19 | HIB19 | BV 650 | BioLegend | 302238 | B300887 | 1:100 |
| CD45 | HI30 | BV785 | BioLegend | 304048 | B284678 | 1:100 |
| CD3 | HIT3a | Alexa Fluor 488 | BioLegend | 300320 | B278330 | 1:100 |
| CD56 | 5.1H11 | PE | BioLegend | 362508 | B316093 | 1:100 |
| CD14 | M5E2 | PE/Cy7 | BioLegend | 301814 | B272337 | 1:100 |
| CD8 | SK1 | APC | BioLegend | 344722 | B304311 | 1:100 |

Incucyte Assay Setup

CAR-iNK and PB-NK effector cell clones were added to wells of a 96-well flat-bottom plate (BD catalog #353072) in 100 µL of NKCM media with final effector number of $4\times10^5$/well for 20:1 E:T wells, $2\times10^5$/well for 10:1 E:T wells and $2\times10^4$/well for the 1:1 E:T well. NKCM assay media is made up of 500 mL of IMDM and 500 mL Ham's F-12 Nutrient Mix as base media. Base media is supplemented with 2%, CTS B-27 Supplement, XenoFree, w/o Vitamin A, 1% MEM Non-Essential Amino Acids Solution, 250 µM Ascorbic acid Mg 2-phosphate, 100 µM Mono-Thio-Glycerol, 1% GlutaMax and 2 mM Nicotinamide.

Subsequently $2\times10^4$ K562-NLR cells was added to each well in 100 µL of NKCM media. Assay was conducted in triplicate wells for each CAR-iNK effector cell. Assay plates were rested at room temperature for 15 minutes to allow cells to settle. Plates were placed in Incucyte S3 Instrument in a 37° C. incubator with 5% CO2. Instrument scan type was set to whole well read, with image phase, and red channel with a red acquisition time of 400 ms. Instrument scan frequency was set to read every 3 hours for 72 hours. Whole Well Analysis parameter was selected for the Incucyte assay. RCU threshold was set to 2.0, and radius was set to 100 µm, with Edge Split On.

Analysis

NLR Count Per Well data was exported from Incucyte 2020A software for all wells at all timepoints, and pasted to Microsoft Excel. Each triplicate value was divided by the average (N=3) of the appropriate Target Cell Only wells for each target cell line, and this value was multiplied by 100 to calculate values for Normalized Target Count as a percentage of the average of NLR count in target cell only wells. Data were graphically represented with GraphPad Prism software (Version 8.) Triplicate Normalized NLR Target Count values were graphed on Y axis for each timepoint on X axis.

Figure 7A:
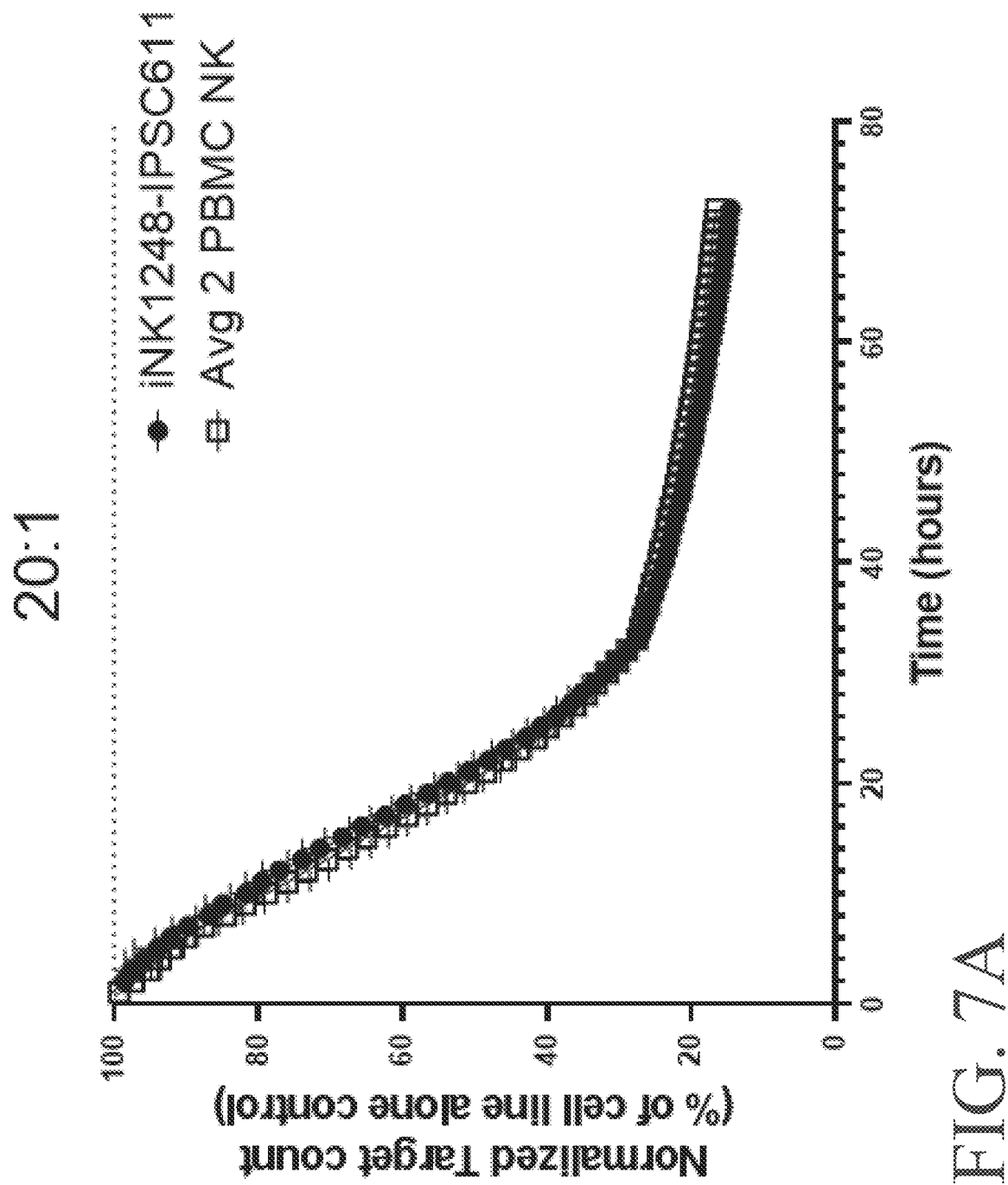
FIG. 7A shows an Incucyte based assay measuring the loss of Nuclight Red K562 cells over time with an effector to target ratio of 20:1. Normalized target cell count as a percentage of target cell only count for four iNK1248-iPSC611 and the average of 3 PB-NKs. Each data point is the average of 3 replicates and error bars represent standard error of the mean.
Figure 7B:
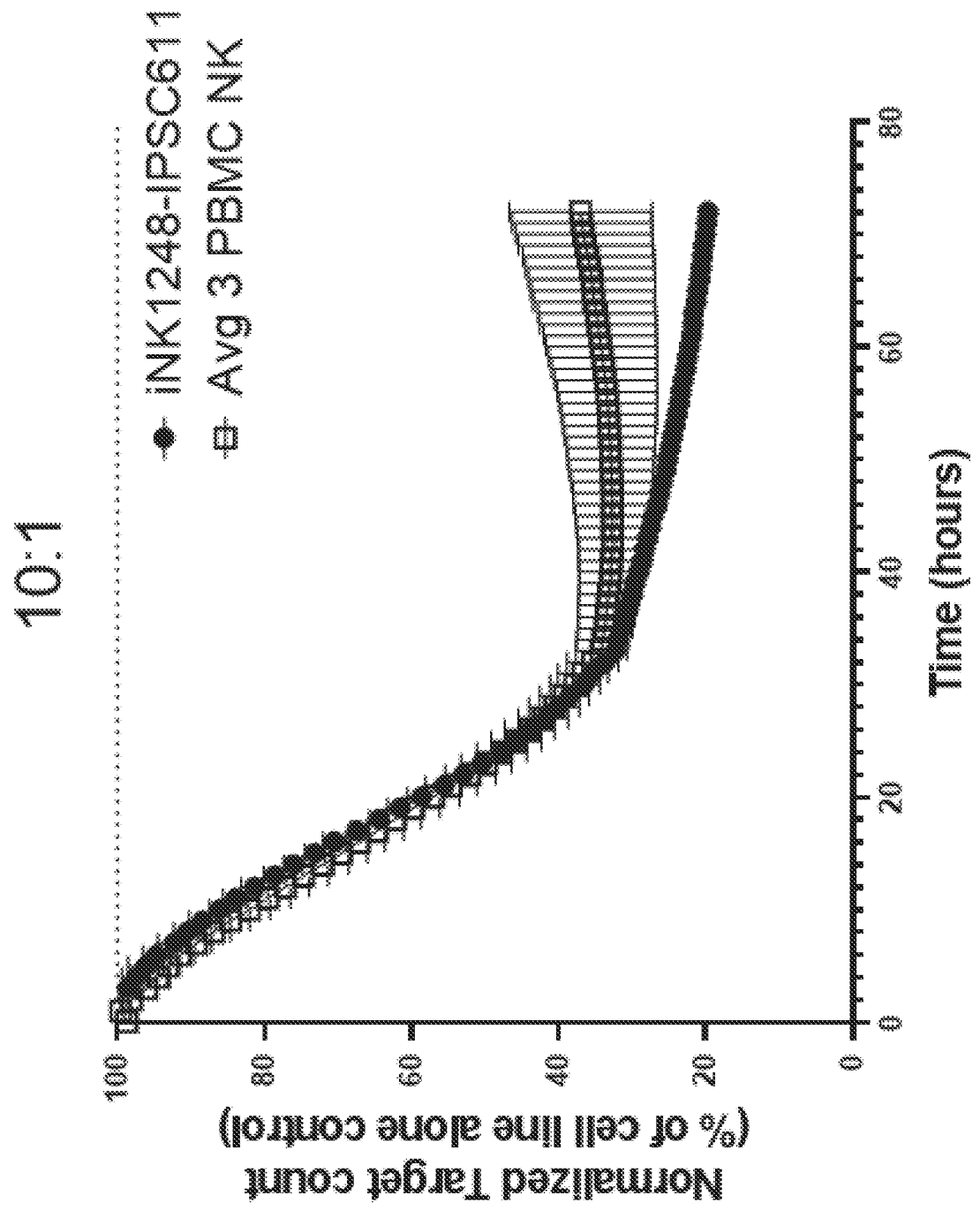
FIG. 7B shows an Incucyte based assay measuring the loss of Nuclight Red K562 cells over time with an effector to target ratio of 10:1. Normalized target cell count as a percentage of target cell only count for four iNK1248-iPSC611 and the average of 3 PB-NKs. Each data point is the average of 3 replicates and error bars represent standard error of the mean.
Figure 7C:
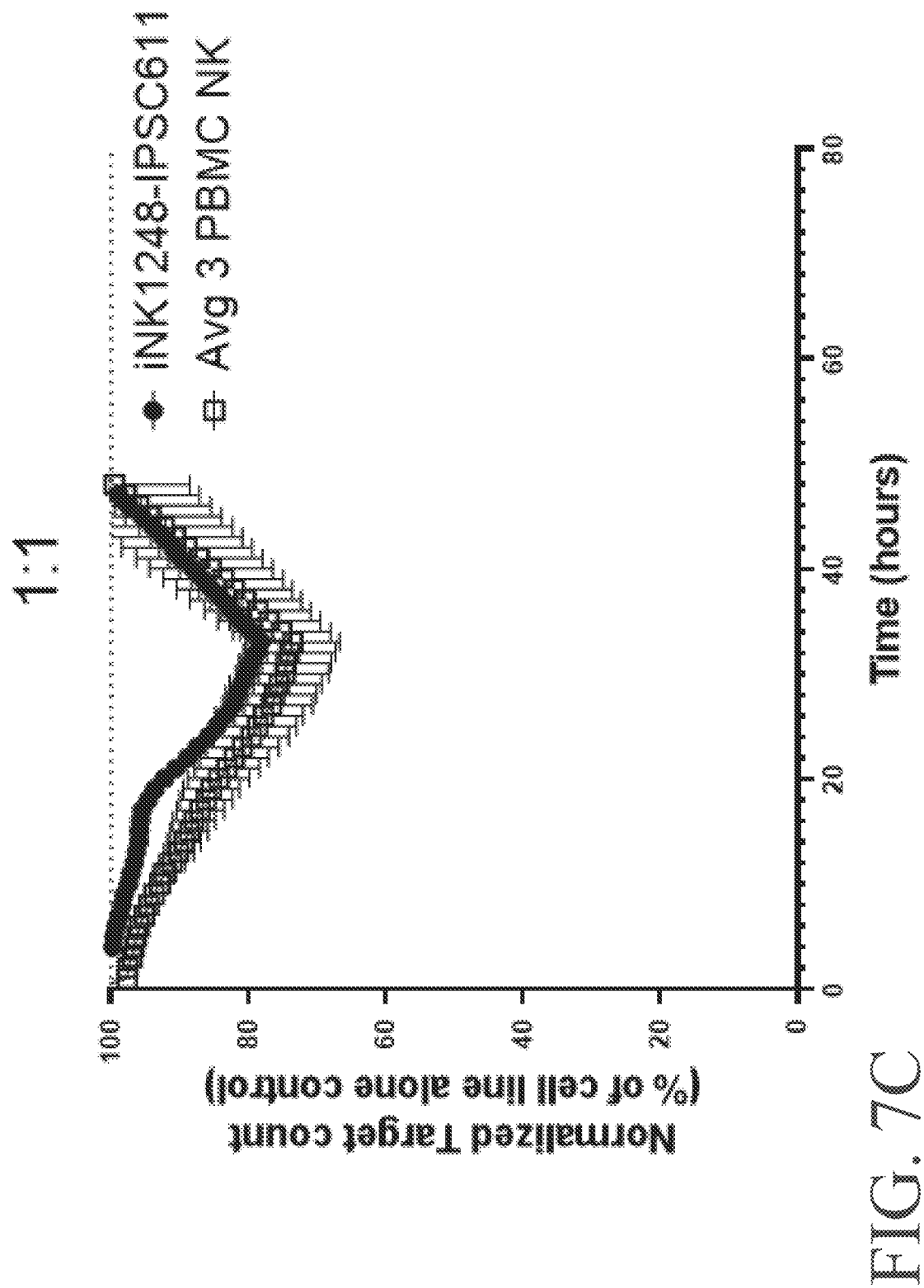
FIG. 7C shows an Incucyte based assay measuring the loss of Nuclight Red K562 cells over time with an effector to target ratio of 1:1. Normalized target cell count as a percentage of target cell only count for four iNK1248-iPSC611 and the average of 3 PB-NKs. Each data point is the average of 3 replicates and error bars represent standard error of the mean.

Results iNK1248-iPSC611 and PB-NK cells showed ability to kill K562 cells at effector to target ratios of 20:1, 10:1 and 1:1. As shown in FIGS. 7A-C, the Incucyte based assay measured the loss of Nuclight Red K562 cells over time with effector to target ratios of (A) 20:1, (B) 10:1, and (C) 1:1. Normalized target cell count as a percentage of target cell only count for four iNK1248-iPSC611 and the average of 3 PB-NKs.

Figure 8:
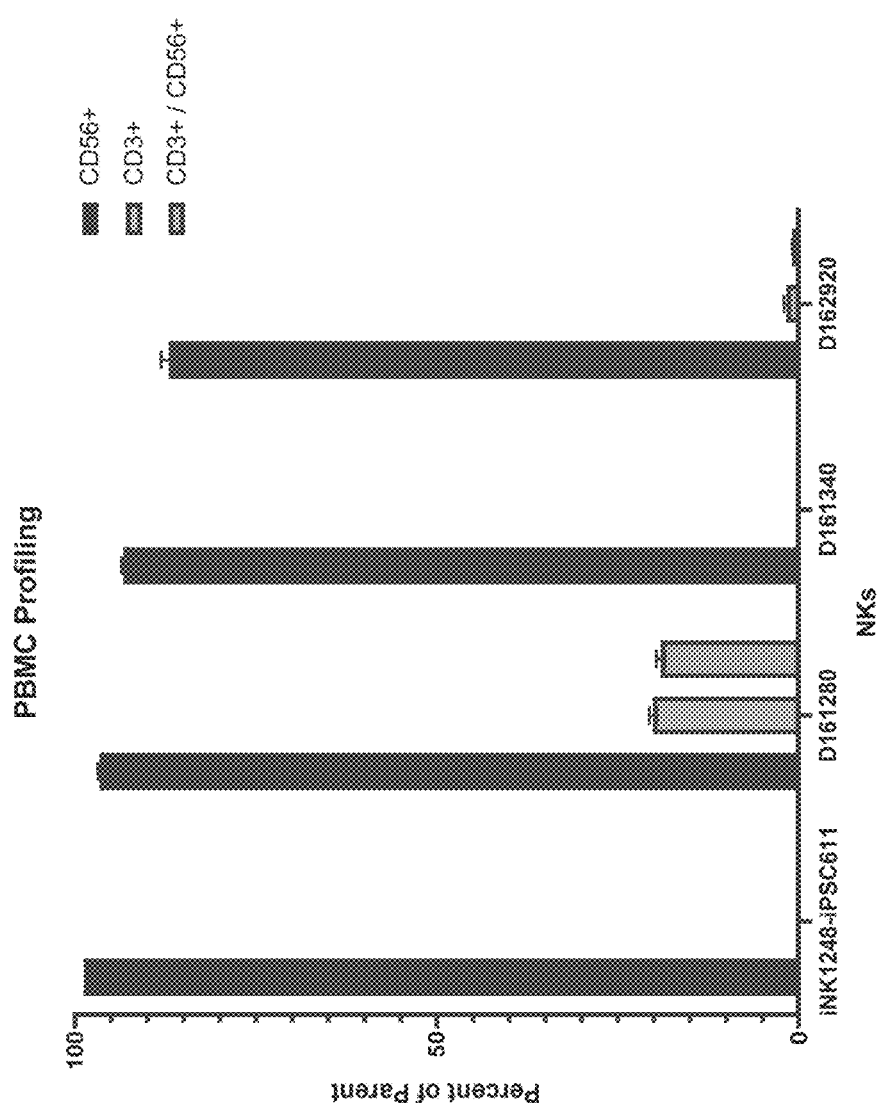
FIG. 8 shows a flow-based NK purity check of PB-NKs isolated from three PBMC donors and iNK1248-iPSC611.
Figure 9A:
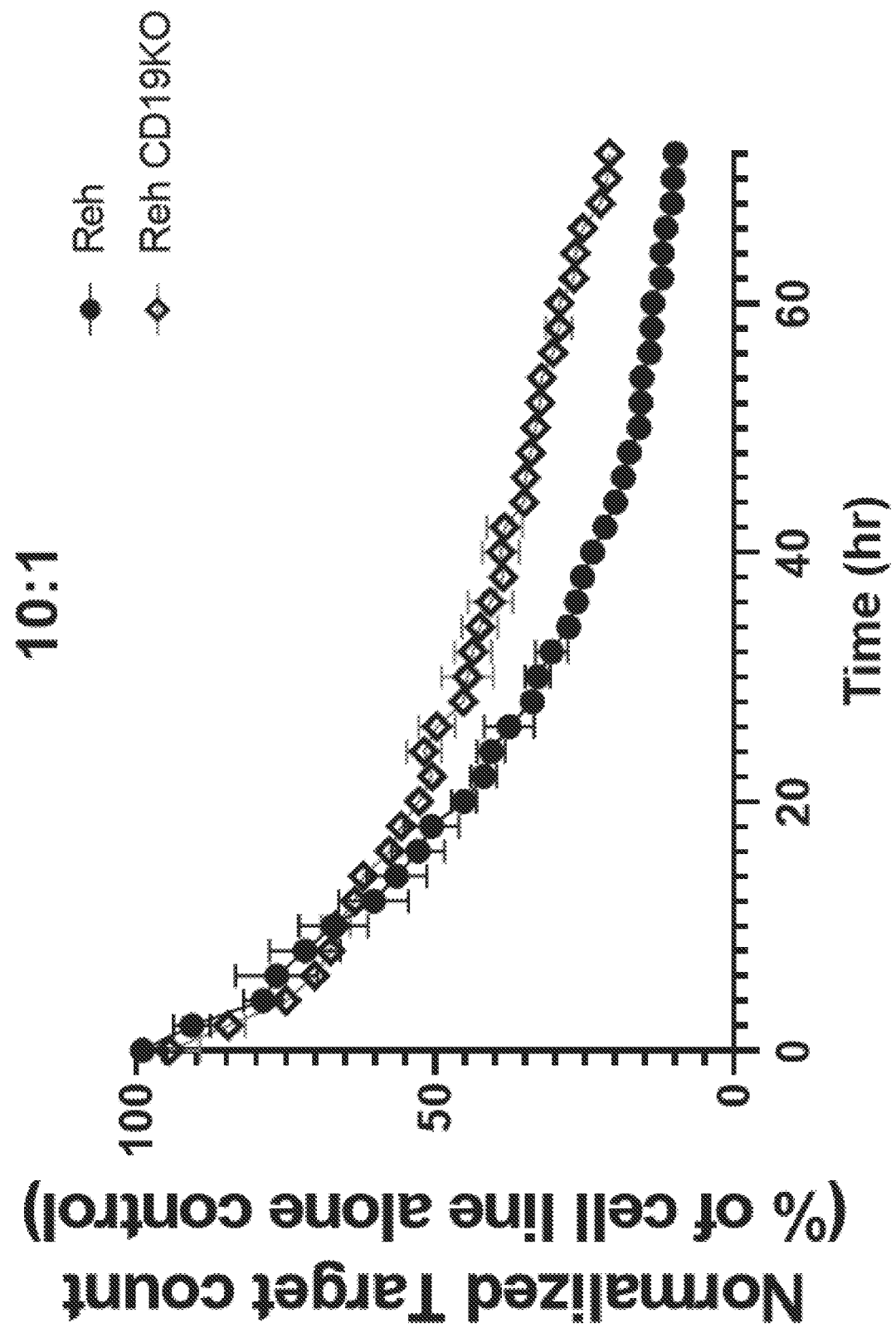
FIG. 9A shows an Incucyte based assay measuring the loss of Nuclight Red target cells over time with an effector to target ratio of 10:1. Normalized target cell count in Reh and Reh-CD19KO co-cultured with iNK1248-iPSC611 at an effector to target ratio of 10:1 as a percentage of target cell only counts. Each data point is the average of 3 replicates and error bars represent standard error of the mean.
Figure 9B:
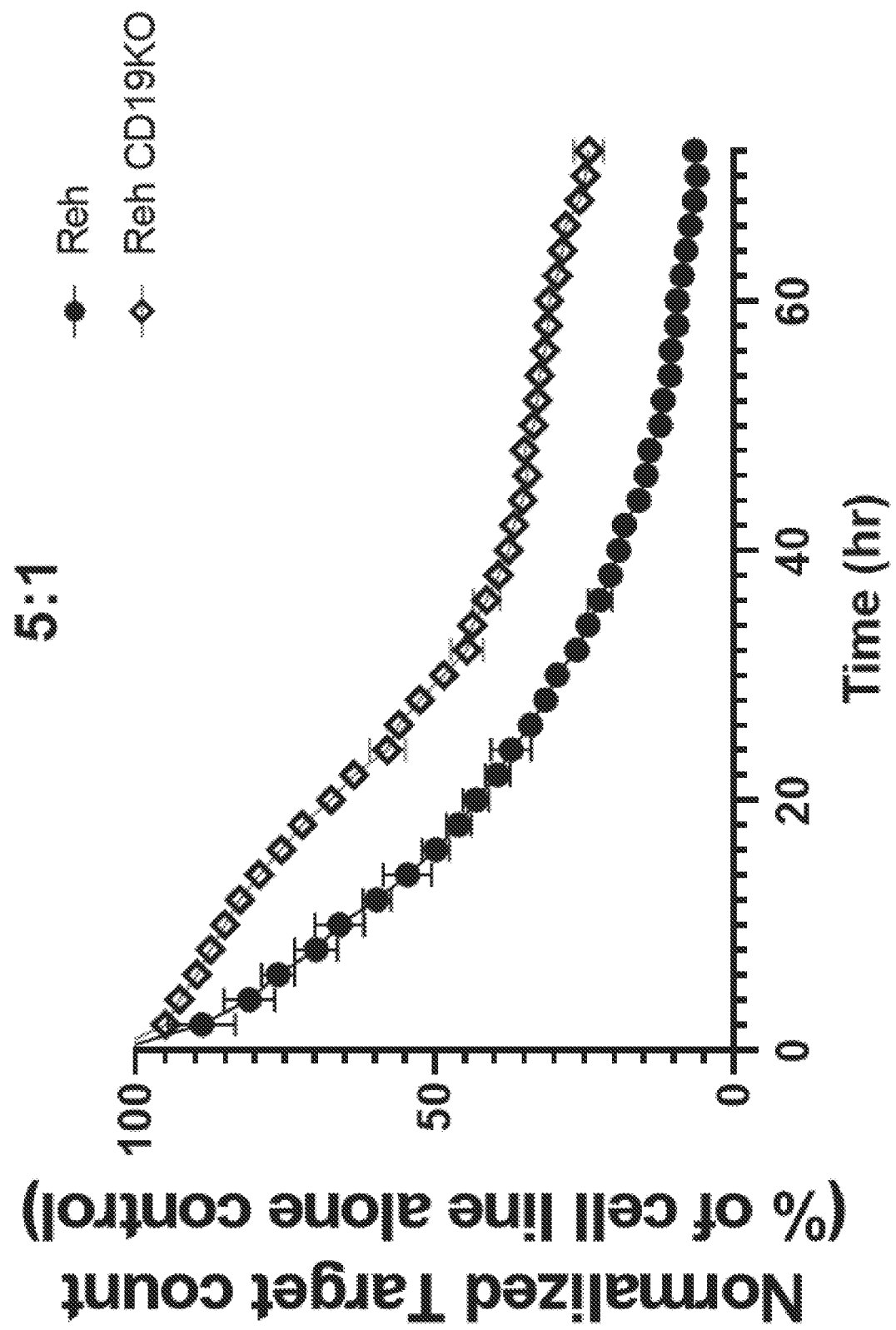
FIG. 9B shows an Incucyte based assay measuring the loss of Nuclight Red target cells over time with an effector to target ratio of 5:1. Normalized target cell count in Reh and Reh-CD19KO co-cultured with iNK1248-iPSC611 at an effector to target ratio of 5:1 as a percentage of target cell only counts. Each data point is the average of 3 replicates and error bars represent standard error of the mean.
Figure 9C:
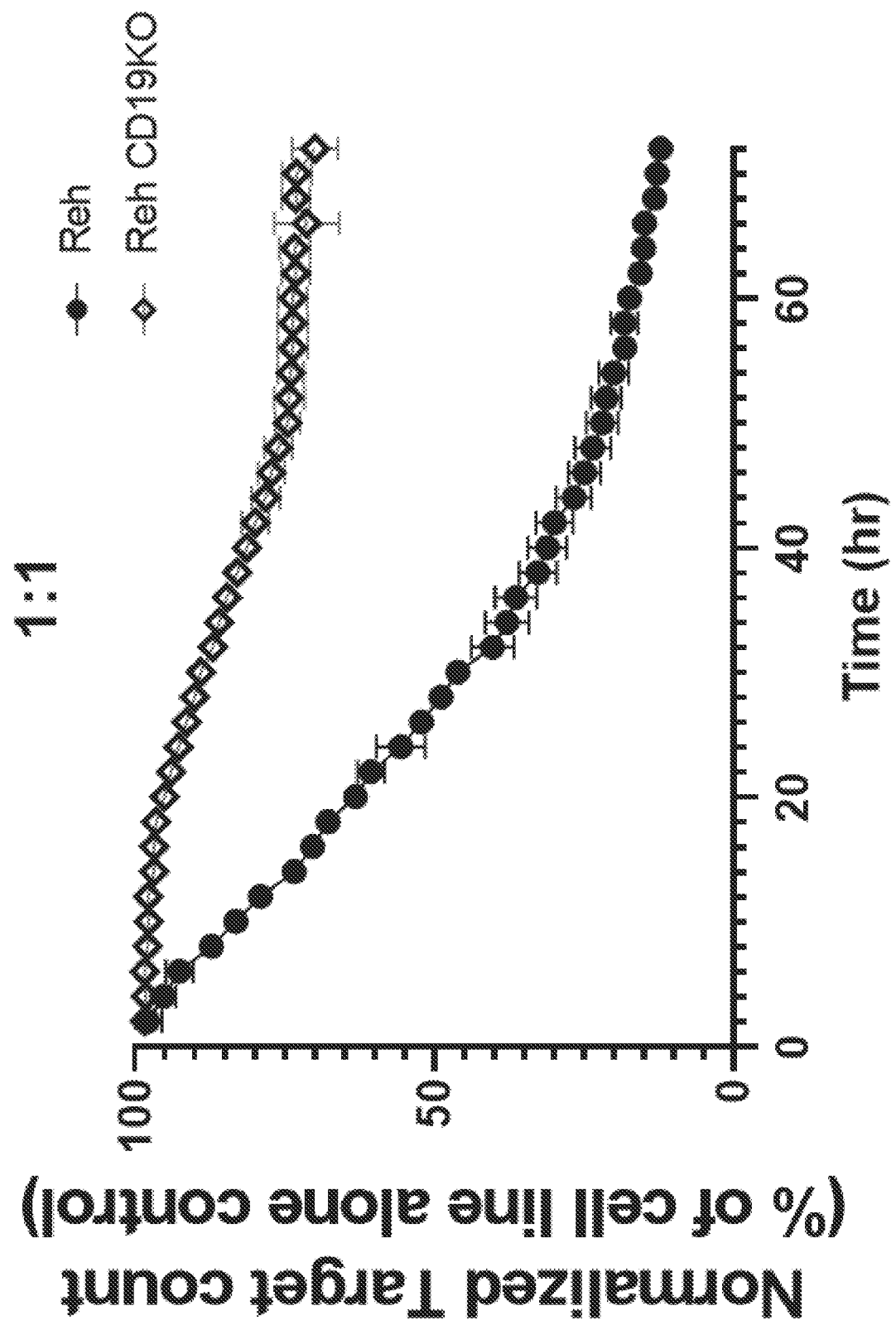
FIG. 9C shows an Incucyte based assay measuring the loss of Nuclight Red target cells over time with an effector to target ratio of 1:1. Normalized target cell count in Reh and Reh-CD19KO co-cultured with iNK1248-iPSC611 at an effector to target ratio of 1:1 as a percentage of target cell only counts. Each data point is the average of 3 replicates and error bars represent standard error of the mean.
Figure 9D:
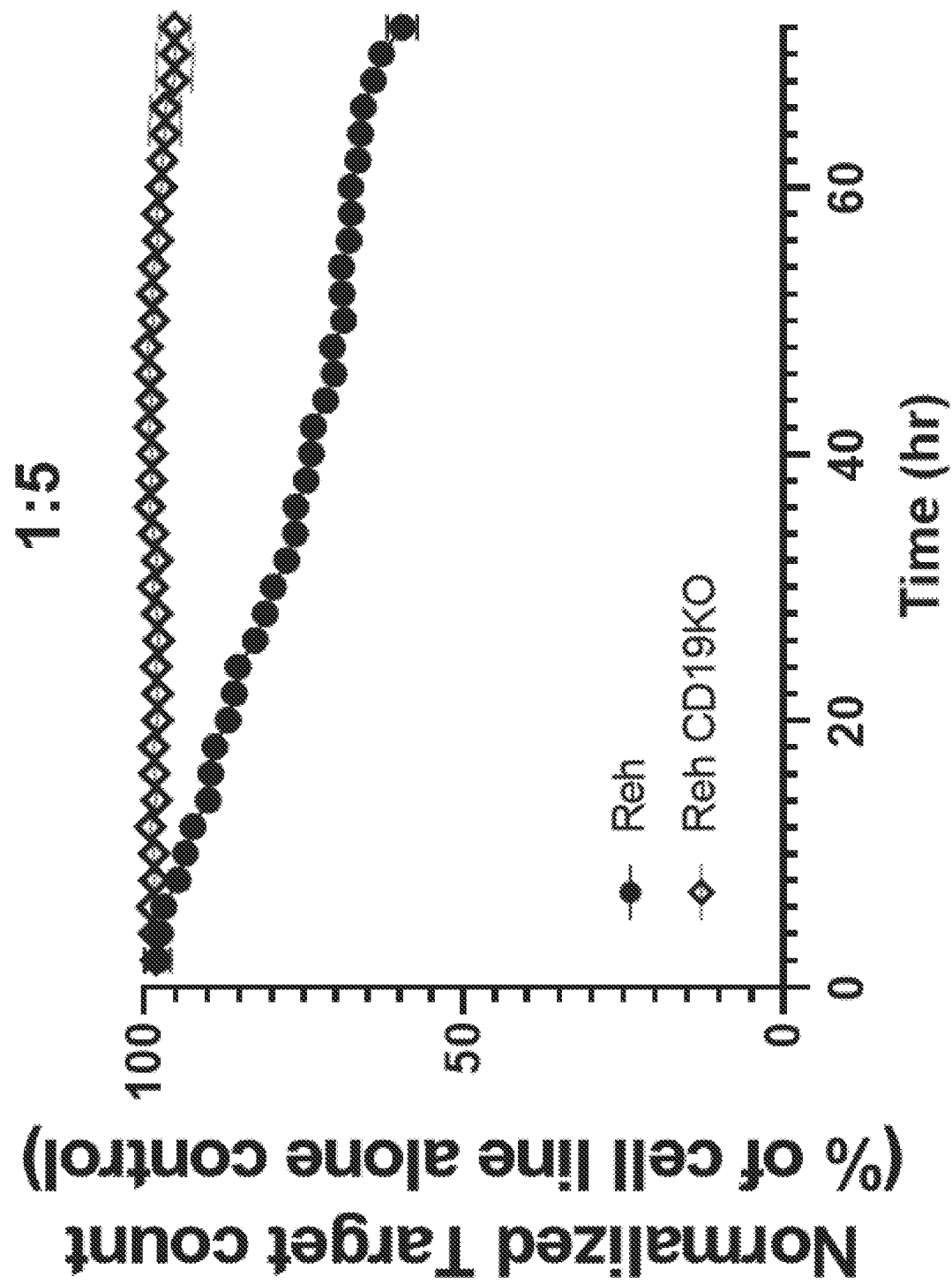
FIG. 9D shows an Incucyte based assay measuring the loss of Nuclight Red target cells over time with an effector to target ratio of 1:5. Normalized target cell count in Reh and Reh-CD19KO co-cultured with iNK1248-iPSC611 at an effector to target ratio of 1:5 as a percentage of target cell only counts. Each data point is the average of 3 replicates and error bars represent standard error of the mean.
Figure 10A:
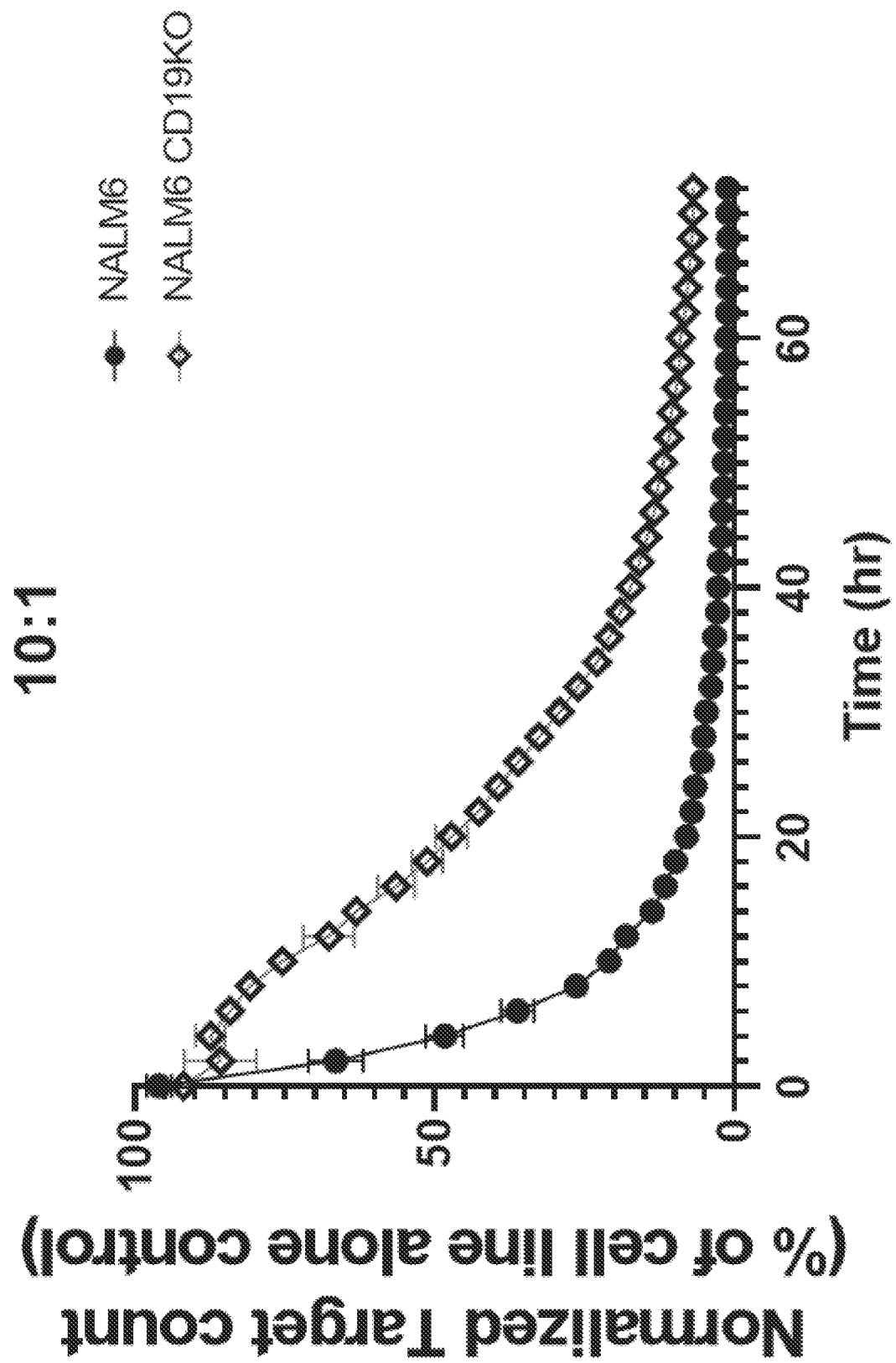
FIG. 10A shows an Incucyte based assay measuring the loss of Nuclight Red target cells over time with an effector to target ratio of 10:1. Normalized target cell count in NALM6 and NALM6-CD19K0 co-cultured with iNK1248-iPSC611 at an effector to target ratio of 10:1 as a percentage of target cell only counts. Each data point is the average of 3 replicates and error bars represent standard error of the mean.
Figure 10B:
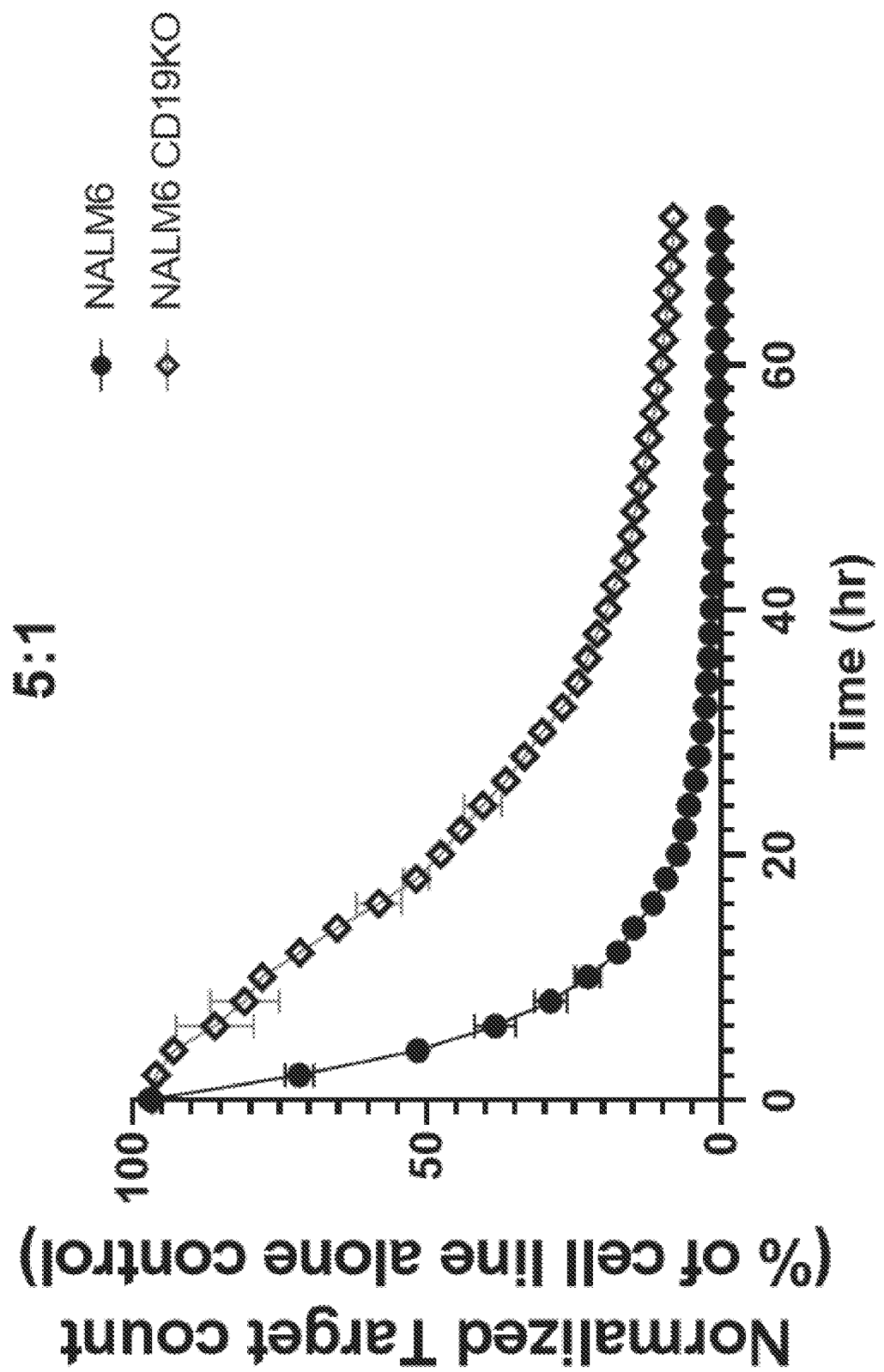
FIG. 10B shows an Incucyte based assay measuring the loss of Nuclight Red target cells over time with an effector to target ratio of 5:1. Normalized target cell count in NALM6 and NALM6-CD19KO co-cultured with iNK1248-iPSC611 at an effector to target ratio of 5:1 as a percentage of target cell only counts. Each data point is the average of 3 replicates and error bars represent standard error of the mean.
Figure 10C:
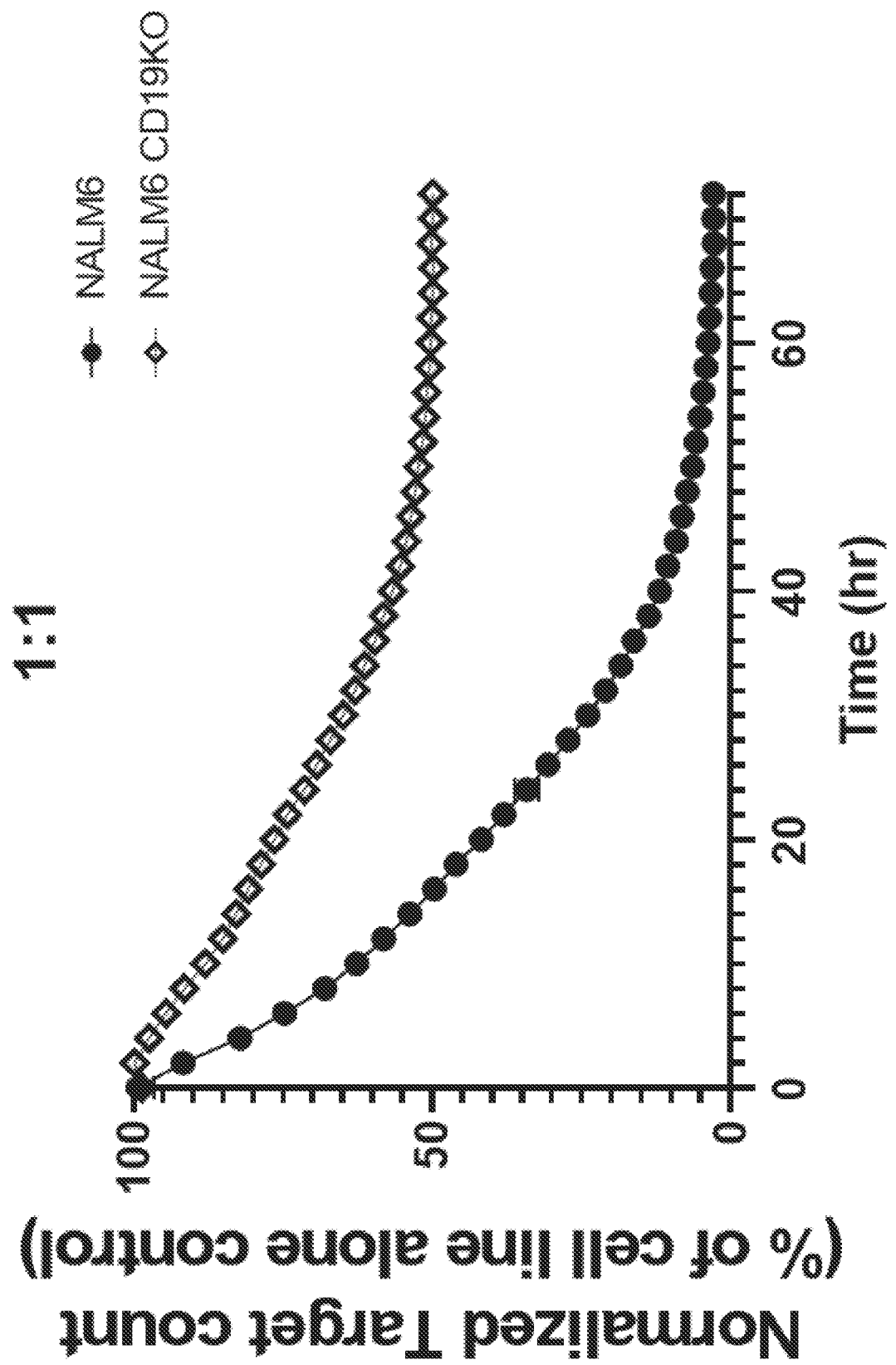
FIG. 10C shows an Incucyte based assay measuring the loss of Nuclight Red target cells over time with an effector to target ratio of 1:1. Normalized target cell count in NALM6 and NALM6-CD19KO co-cultured with iNK1248-iPSC611 at an effector to target ratio of 1:1 as a percentage of target cell only counts. Each data point is the average of 3 replicates and error bars represent standard error of the mean.
Figure 10D:
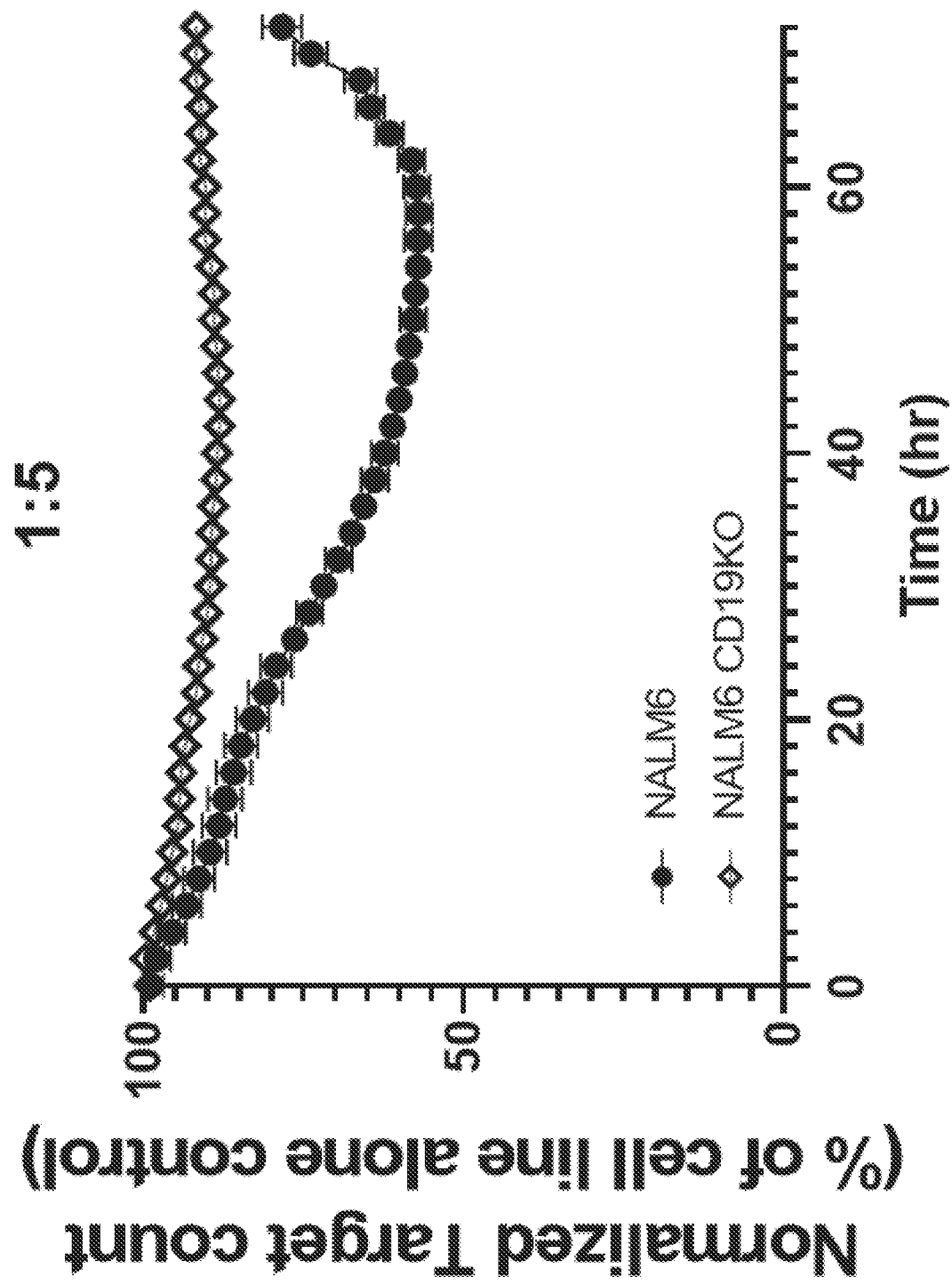
FIG. 10D shows an Incucyte based assay measuring the loss of Nuclight Red target cells over time with an effector to target ratio of 1:5. Normalized target cell count in NALM6 and NALM6-CD19KO co-cultured with iNK1248-iPSC611 at an effector to target ratio of 1:5 as a percentage of target cell only counts. Each data point is the average of 3 replicates and error bars represent standard error of the mean.

With respect to purity, the PB-NK cells were between 87% and 96% CD45+/CD56+ post isolation. iNK1248-iPSC611 was 98.8% CD45+/CD56+. PB-NK cells were between 20.15% and 0.195% CD3+ and between 19.1% and 0.075% CD3+/CD56+. iNK1248-iPSC611 was 0.08% Cd3+ and 0.048% CD3+ CD56+ (FIG. 8).

Example 9. In Vitro Elimination of CD19+ Cells Using CAR-iNK Cells

CAR-iNK clone, iNK1248-iPSC611, has have been engineered to express anti-CD19 chimeric antigen receptor (CAR) to target CD19+ cancers. The Incucyte live cell imaging platform was used to demonstrate the cytolytic activity of iNK1248-iPSC611 at multiple effector to target ratios (E:T) through real-time quantification of fluorescently labeled target cells, depletion of which serves as a measurement of efficacy of effector target cell killing. Isogenic pairs of Reh and NALM6 cell lines, naively expressing CD19 or CD19 knock out (KO), were used to demonstrate CAR mediated lysis of CD19+ target cells.

NucLight Red Transduction of Target Cell Lines

Reh and NALM6 cells were obtained from ATCC. Cell lines were transduced with Incucyte NucLightRed Lentivirus Reagent (EF1α Promoter, Puromycin Selection) according to manufacturer's protocol at MOI of 3, in cell culture media with 8 µg/mL Polybrene. NLR-transduced cells were selected and cell lines were cultured in RPMI with 10% FBS and 1 µg/mL Puromycin.

Generation of Reh-CD19KO and NALM6-CD19KO Target Lines

Reh-CD19KO and NALM6-CD19KO were generated using the Lonza CRISPR-Cas-9 system on parental Reh and NALM6 cells (previously NucLight Red transduced) according to manufacturer's protocol for Amaxa 4-D Nucleofector. Target sequence for custom CD19KO crRNA used was: GCTGTGCTGCAGTGCCTCAA. CD19+ cells were removed using Human CD19 Positive Selection Kit II according to manufacturer's protocol, and CD19 expression was assayed via flow cytometry. Cell lines were cultured in RPMI-10% FBS, 1 µg/mL puromycin.

TABLE 5

CD19KO Reagents

| Material | Supplier | Part# |
|---|---|---|
| Puromycin Dihydrochloride | Gibco | A11138-03 |
| SF Cell Line 4D-Nucleofector X Kit L | Lonza | V4XC-2012 |
| Alt-R CRISPR-Cas9 tracrRNA | IDT | 1072532 |
| Alt-R S.p. HiFi Cas9 Nuclease V3 | IDT | 1081061 |
| Alt-R CRISPR-Cas9 CrRNA | IDT | Custom order# 17424545 |
| EasySep Human CD19 Positive Selection Kit II | Stem Cell Technologies | 17854 |

Incucyte CAR-iNK Killing Assay Setup $2 \times 10^5$ (10:1), $1 \times 10^5$ (5:1), $2 \times 10^4$ (1:1), or $4 \times 10^3$ (1:5) of each CAR-iNK effector cell clone were added to wells of a 96-well flat-bottom plate (BD catalog #353072) in 100 µL of NKCM media, followed by $2 \times 10^4$ Reh-NLR, Reh-CD19KO-NLR, NALM6-NLR, or NALM6-CD19KO-NLR cells in 100 µL of NKCM media. Assay was conducted in triplicate wells for each CAR-iNK effector cell. Assay plates were rested at room temperature for 15 minutes to allow cells to settle. Plates were placed in Incucyte S3 Instrument in a 37° C. incubator with 5% CO2. Instrument scan type was set to whole well read, with image phase, and red channel with a red acquisition time of 400 ms. Instrument scan frequency was set to read every 2 hours for 72 hours. Whole Well Analysis parameter was selected for the Incucyte assay. RCU threshold was set to 2.0, and radius was set to 100 with Edge Split On.

Analysis

NLR Count Per Well data was exported from Incucyte 2020A software for all wells at all timepoints, and pasted to Microsoft Excel. Each triplicate value was divided by the average (N=3) of the appropriate Target Cell Only wells for each target cell line, and this value was multiplied by 100 to calculate values for Normalized Target Count as a percentage of the average of NLR count in target cell only wells. Data were graphically represented with GraphPad Prism software (Version 8.) Triplicate Normalized NLR Target Count values were graphed on Y axis for each timepoint on X axis.

Results

Antigen specific lysis of both Reh and NALM6 cells by iNK1248-iPSC611 cells was exhibited across a range of effector to target ratios. At each E:T ratios tested CD19+ cells were killed quicker and more completely than the matched CD19KO lines.

Four E:T ratios showed a range of cytolytic activity against Reh cells (FIG. 9). Less cytolytic activity observed in Reh CD19KO cells as compared to parental Reh cells. FIG. 9 shows the results of an Incucyte based assay measuring the loss of Nuclight Red target cells over time with four effector to target ratios. Normalized target cell count in Reh and Reh-CD19KO co-cultured with iNK1248-iPSC611 at E:T ratios of (A) 10:1, (B) 5:1, (C) 1:1, and (D) 1:5 as a percentage of target cell only counts. FIG. 10 shows the results of an Incucyte based assay measuring the loss of Nuclight Red target cells over time with four effector to target ratios. Normalized target cell count in NALM6 and NALM6-CD19KO co-cultured with iNK1248-iPSC611 at E:T ratios of (A) 10:1, (B) 5:1, (C) 1:1, (D) and 1:5 as a percentage of target cell only counts.

Example 10. In Vitro Persistence of iNK Cells

The single cell iNK clone iNK1248-iPSC611 was engineered to secrete the NK homeostatic cytokine IL-15. In a 21-day persistence assay, in the presence of varying levels of IL-2 (10 nM-0 nM), the in-vitro persistence of iNK1248-iPSC611 was compared to that of a bulk non engineered "wild type" (WT) iNK iNK1487-iPSC005 cell and the NK cell leukemia line KHYG-1. Every 3-4 days cells were harvested counted on a ViCell Blue and re-seeded in fresh media. Cumulative fold expansion was calculated using viable cell counts collected from the ViCell Blu.

21-Day Persistence Assay $1.5 \times 10^6$ of iNK1248-iPSC611, WT iNK1487-iPSC005 or KHYG-1 immortalized NK cells were added to individual wells of a 24 well plate at 0.5e6/mL in a total of 3 mL of NKCM containing six different concentrations of IL2. $1.5 \times 10^6$ KHYG-1 immortalized NK cells were also added to individual wells of a 24 well plate at 0.5e6/mL in a total of 3 mL of RPMI+10% HI FBS+1×Pen Strep containing six different concentrations of IL2. Both plates were transferred to an incubator set at 37° C. with 5% CO2.

Every 72 or 96 hours, cells were harvested and transferred into individual 15 mL conical tubes. Cells were centrifuged at 300 g for 10 minutes. Supernatants were aspirated, and cell pellets were resuspended in 3 mL of basal RPMI assay media. Two hundred microliters of cells were removed to count on the ViCell Blu.

After counting, the cells were centrifuged again at 300 g for 10 minutes. Supernatants were aspirated and cells were resuspended in NKCM assay media or RPMI assay media containing the corresponding concentration of IL2 at 0.5e6 cells/mL. Cells were replated at 0.5e6 cells/mL in 3 mL per well. If cells were resuspended at 0.5e6 cells/mL in a volume less than 3 mL, the total volume was plated. If resuspension volume fell below 200 uL, the cell line was not re-plated. At the end of 14 days, the assay was terminated and the cells were discarded.

Analysis

Cell counts and cell viabilities were taken using the ViCell Blu. The population used to calculate fold change was viable cells per mL. Data were graphically represented with GraphPad Prism software (Version 8.4.3).

Results

Figure 11:
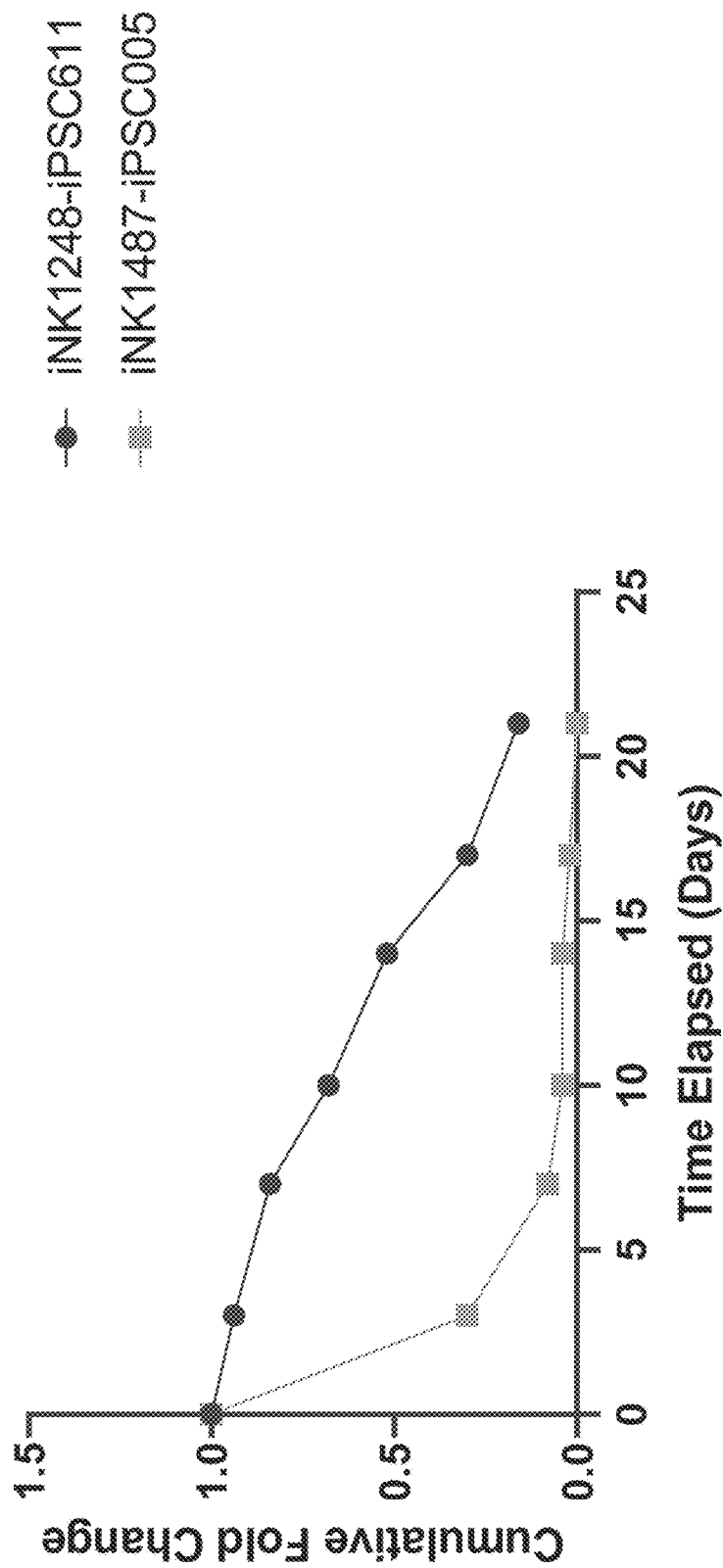
FIG. 11 shows cumulative fold expansion of iNK1248-iPSC611 and WT iNK1487-iPSC005 over a 21-day persistence assay without exogenous IL2 support. Cells were cultured in basal NKCM for 14 days at 37° C. with 5% $CO_2$. Every 3-4 days, all conditions were harvested, counted on the ViCell Blu, resuspended at 0.5e6/mL in appropriate media and then replated. After 21 days, cumulative fold change was calculated.
Figure 12A:
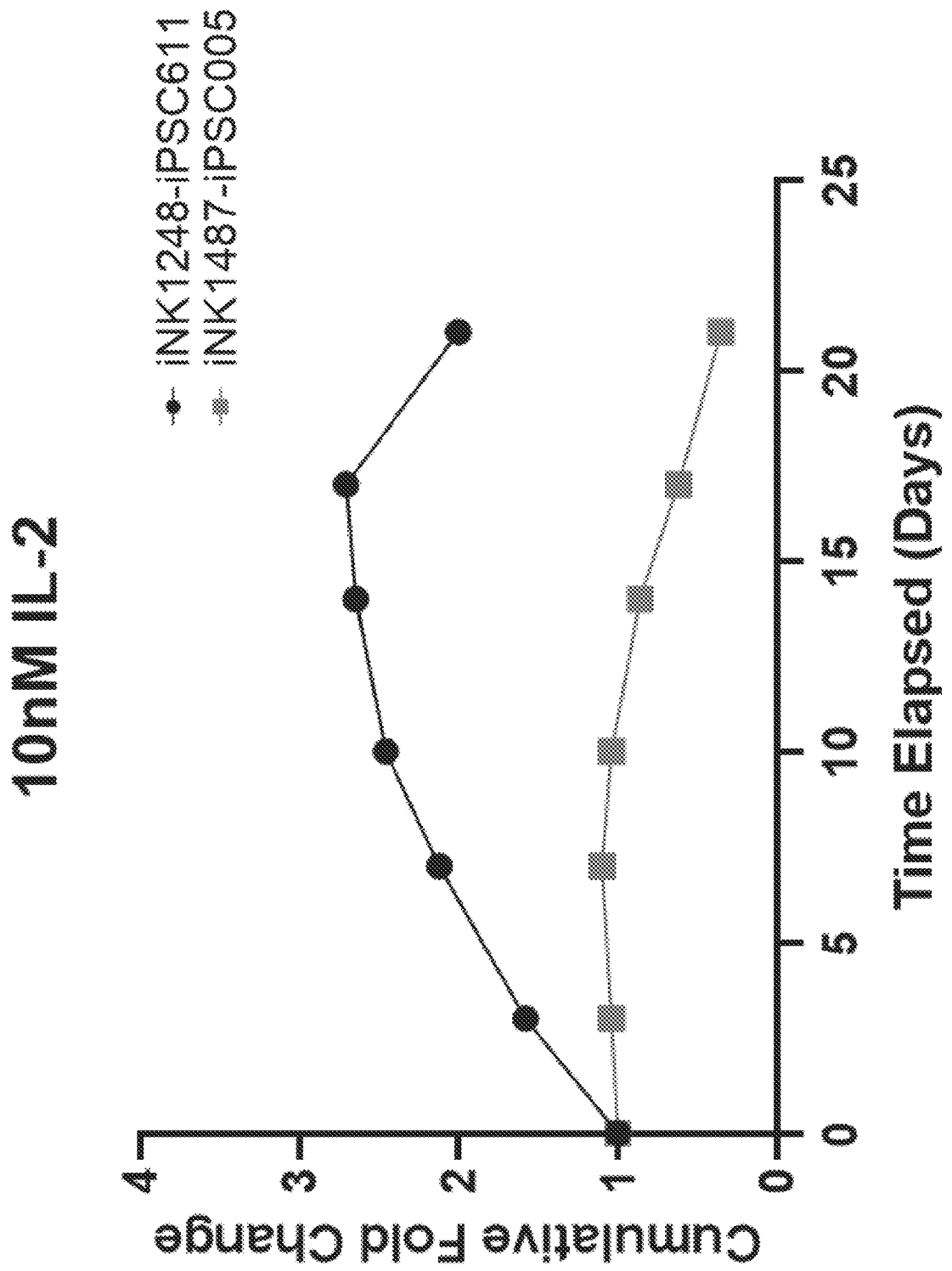
FIG. 12A shows cumulative fold expansion of iNK1248-iPSC611 and WT iNK1487-iPSC005 over a 21-day persistence assay. Cells were cultured in NKCM containing one of six IL2 concentrations: 10 nM for 21 days at 37° C. with 5% $CO_2$. Every 3-4 days, all conditions were harvested, counted on the ViCell Blu, resuspended at 0.5e6/mL in appropriate media and then replated. After 21 days, cumulative fold change was calculated.
Figure 12B:
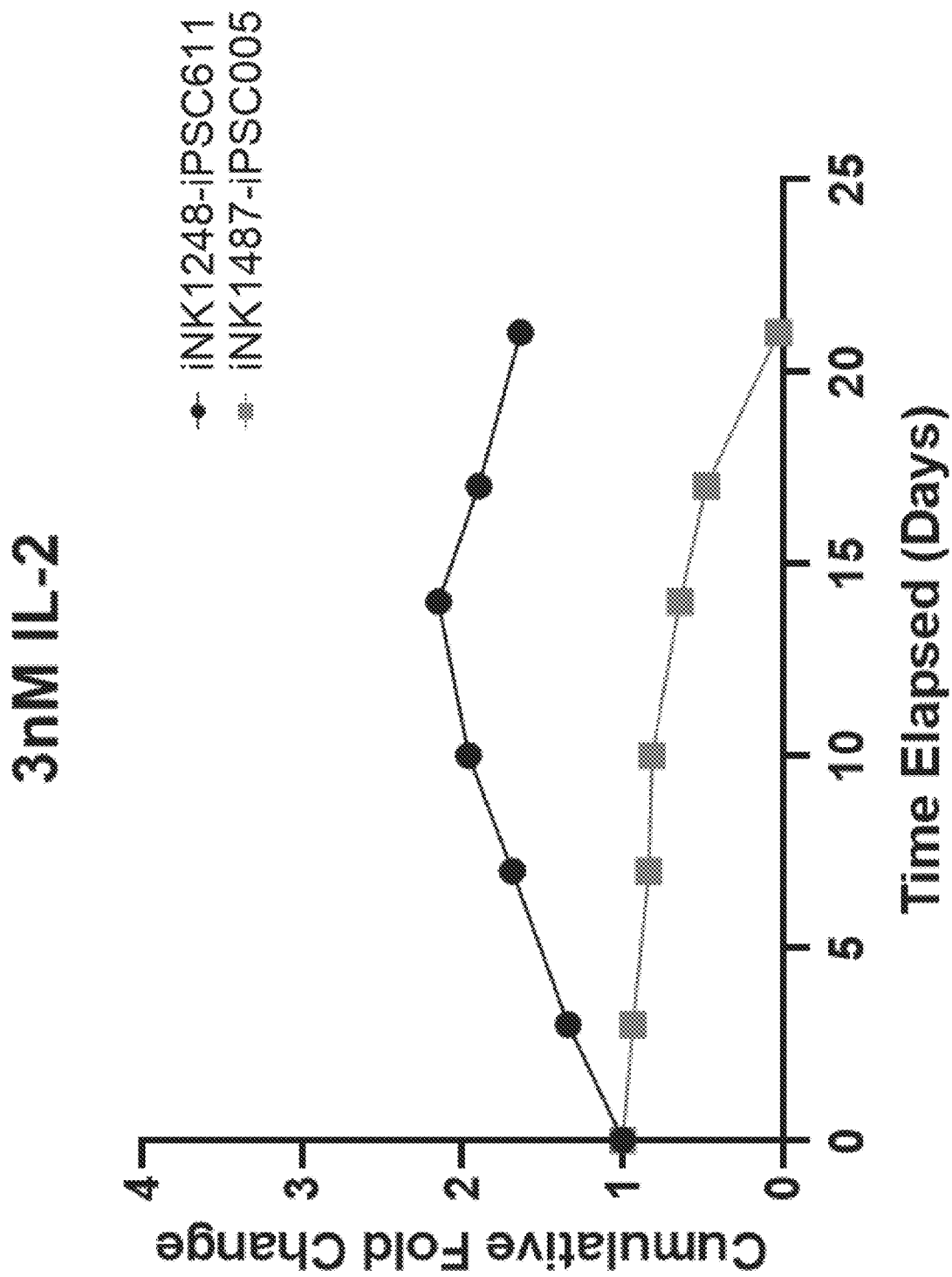
FIG. 12B shows cumulative fold expansion of iNK1248-iPSC611 and WT iNK1487-iPSC005 over a 21-day persistence assay. Cells were cultured in NKCM containing one of six IL2 concentrations: 3 nM for 21 days at 37° C. with 5% $CO_2$. Every 3-4 days, all conditions were harvested, counted on the ViCell Blu, resuspended at 0.5e6/mL in appropriate media and then replated. After 21 days, cumulative fold change was calculated.
Figure 12C:
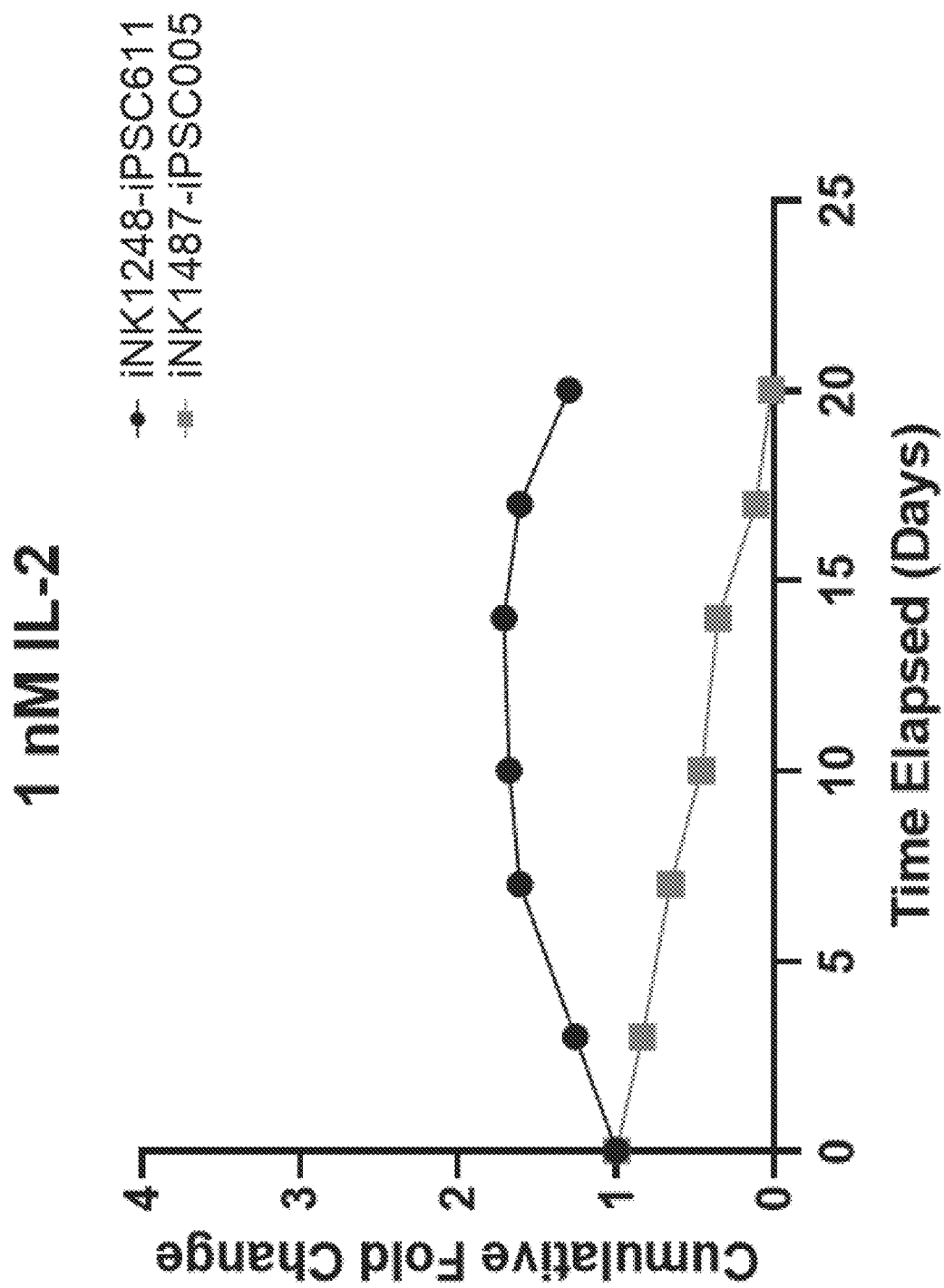
FIG. 12C shows cumulative fold expansion of iNK1248-iPSC611 and WT iNK1487-iPSC005 over a 21-day persistence assay. Cells were cultured in NKCM containing one of six IL2 concentrations: 1 nM for 21 days at 37° C. with 5% $CO_2$. Every 3-4 days, all conditions were harvested, counted on the ViCell Blu, resuspended at 0.5e6/mL in appropriate media and then replated. After 21 days, cumulative fold change was calculated.
Figure 12D:
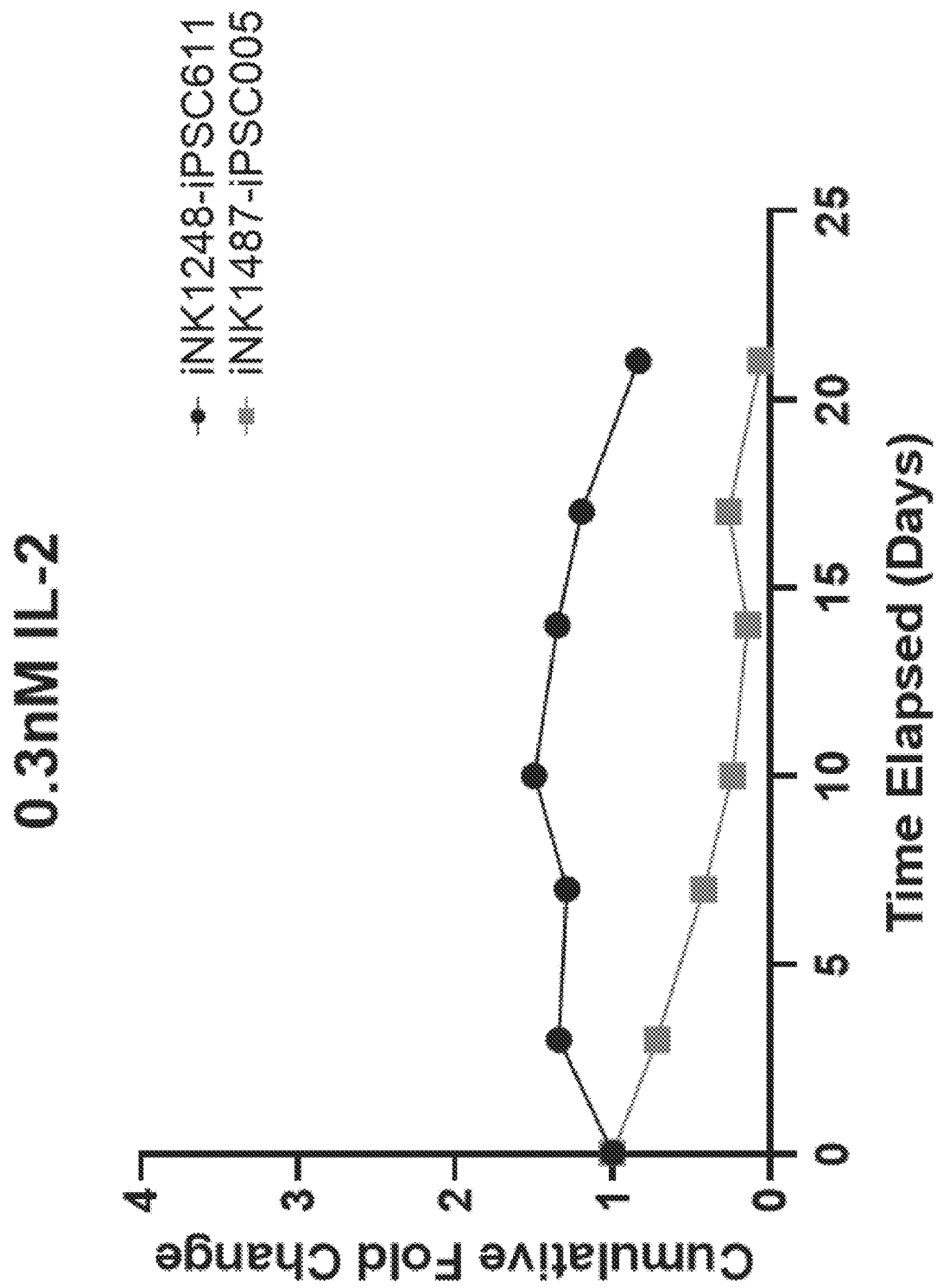
FIG. 12D shows cumulative fold expansion of iNK1248-iPSC611 and WT iNK1487-iPSC005 over a 21-day persistence assay. Cells were cultured in NKCM containing one of six IL2 concentrations: 0.3 nM for 21 days at 37° C. with 5% $CO_2$. Every 3-4 days, all conditions were harvested, counted on the ViCell Blu, resuspended at 0.5e6/mL in appropriate media and then replated. After 21 days, cumulative fold change was calculated.
Figure 12E:
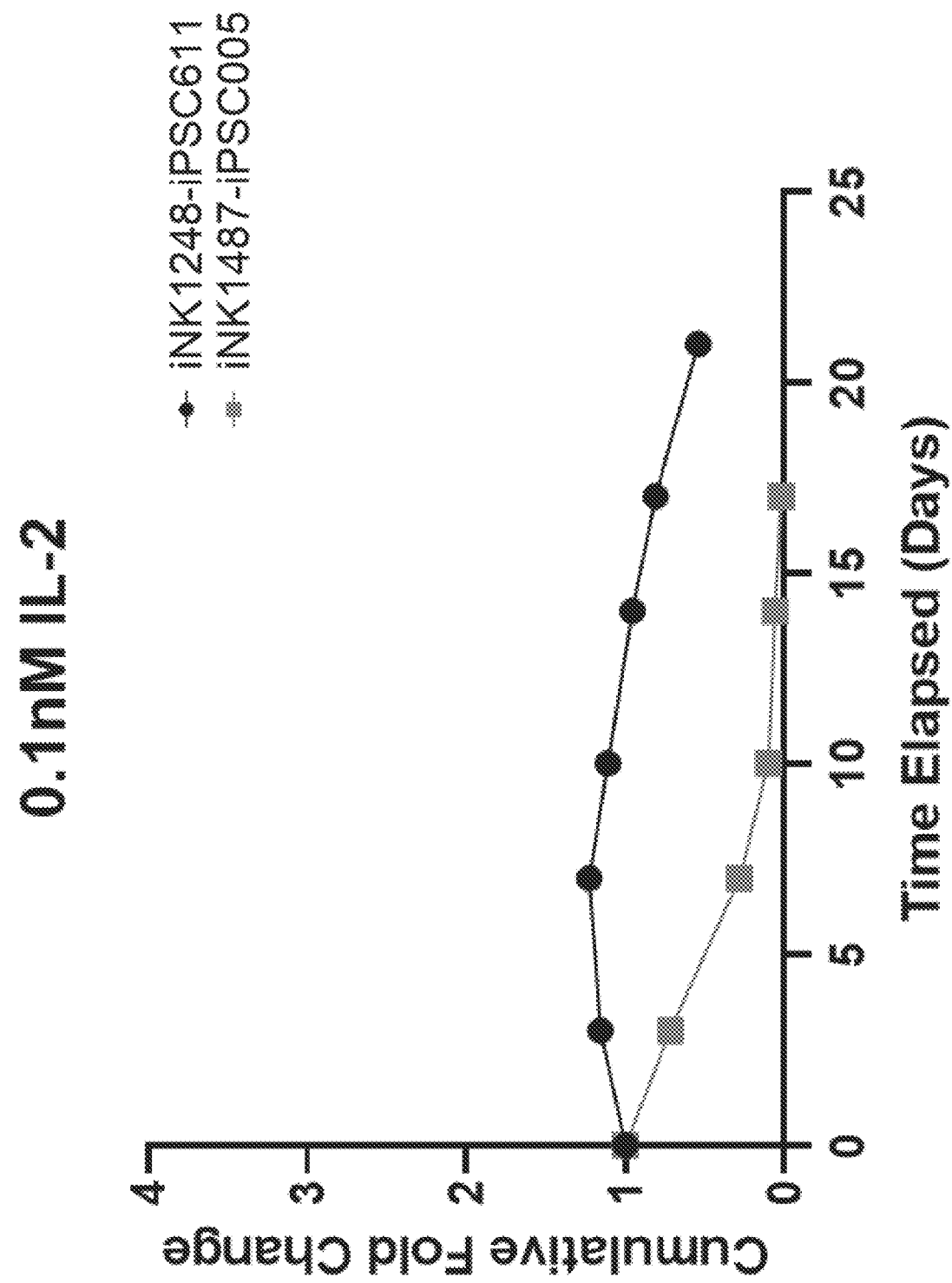
FIG. 12E shows cumulative fold expansion of iNK1248-iPSC611 and WT iNK1487-iPSC005 over a 21-day persistence assay. Cells were cultured in NKCM containing one of six IL2 concentrations: 0.1 nM for 21 days at 37° C. with 5% $CO_2$. Every 3-4 days, all conditions were harvested, counted on the ViCell Blu, resuspended at 0.5e6/mL in appropriate media and then replated. After 21 days, cumulative fold change was calculated.
Figure 12F:
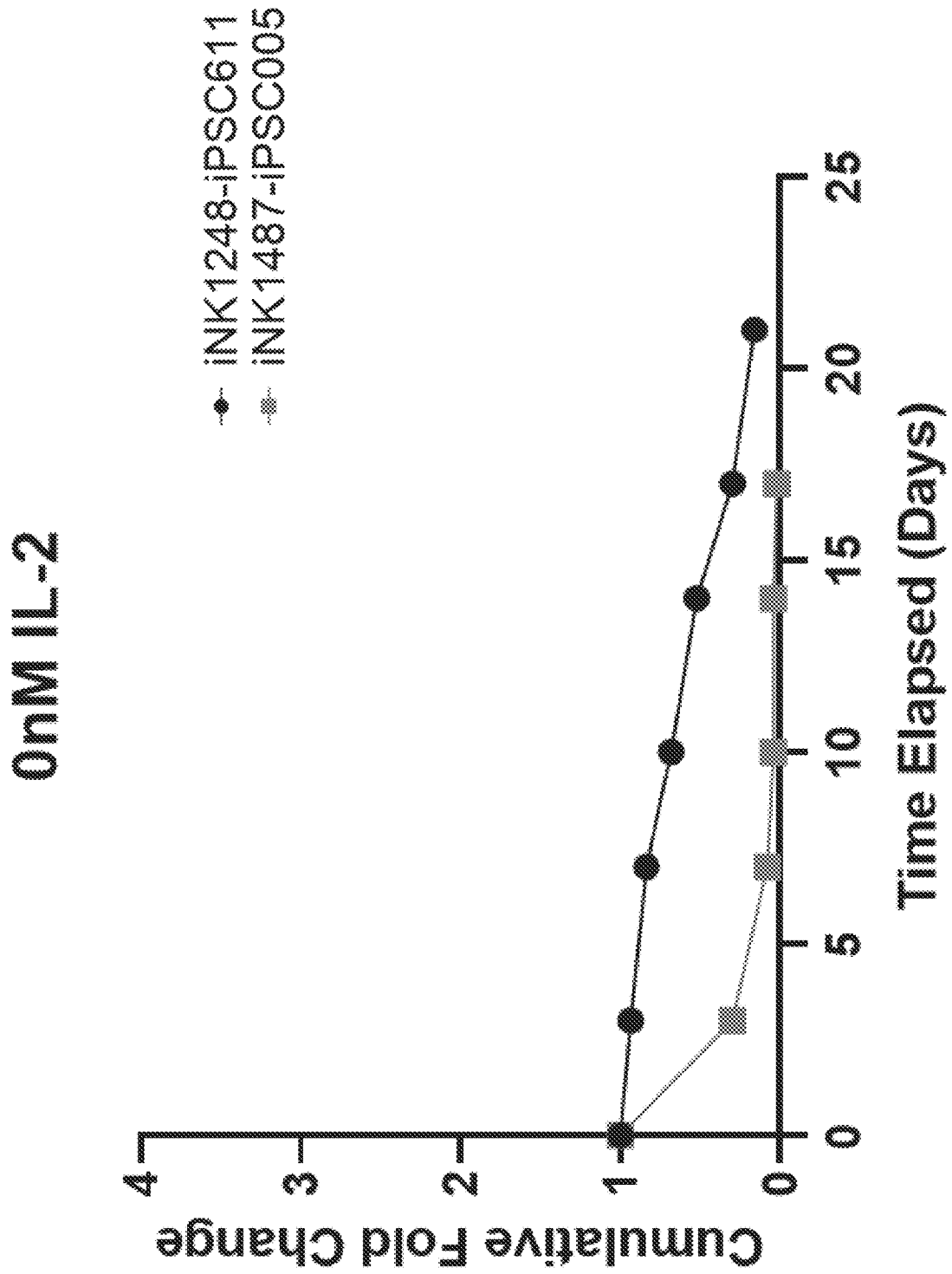
FIG. 12F shows cumulative fold expansion of iNK1248-iPSC611 and WT iNK1487-iPSC005 over a 21-day persistence assay. Cells were cultured in NKCM containing one of six IL2 concentrations: 0 nM for 21 days at 37° C. with 5% $CO_2$. Every 3-4 days, all conditions were harvested, counted on the ViCell Blu, resuspended at 0.5e6/mL in appropriate media and then replated. After 21 days, cumulative fold change was calculated.

The single cell clone iNK1248-IPSC611 persisted in-vitro longer than the WT iNK1487-iPSC005 in the absence of exogenous IL-2 (FIG. 11). Cells were cultured in basal NKCM for 14 days at 37° C. with 5% CO2. Every 3-4 days, all conditions were harvested, counted on the ViCell Blu, resuspended at 0.5e6/mL in appropriate media and then replated. After 21 days, cumulative fold change was calculated. The single cell clone iNK1248-IPSC611 persisted in-vitro longer than the WT iNK1487-iPSC005 in the absence of exogenous IL-2 indicating that the IL-15 transgene is functional and exhibits the intended mode of action, namely enhanced persistence. The IL-15 released by iNK1248-IPSC611 is adequate to support homeostatic survival of the cells but not sufficient to cause mitogenic expansion.

Exogenous IL-2 support increased the persistence of both iNK1248-iPSC611 and WT iNK1487-iPSC005 (FIG. 12A-F). Cells were cultured in NKCM containing one of six IL2 concentrations: 10 nM (FIG. 12A), 3 nM (FIG. 12B), 1 nM (FIG. 12C), 0.3 nM (FIG. 12D), 0.1 nM (FIG. 12E), 0 nM (FIG. 12F) for 21 days at 37° C. with 5% CO2. Every 3-4 days, all conditions were harvested, counted on the ViCell Blu, resuspended at 0.5e6/mL in appropriate media and then replated. After 21 days, cumulative fold change was calculated. Exogenous IL-2 support increased the persistence of both iNK1248-iPSC611 and WT iNK1487-iPSC005 indicating that additional homeostatic cytokine is required to enable limited mitogenic expansion of iNK1248-IPSC611. To determine if a combination of engineered M-15 and exogenous IL-2 elicit uncontrolled proliferation of therapeutic iNK, culture of the cells for two weeks in the presence of IL-2 was performed and iNK1248-IPSC611 was compared to the IL-2-dependent NK leukemia line KHYG-1. KHYG-1 but not iNK1248-IPSC611 exhibited logarithmic growth over two weeks of culture.

Example 11. In Vitro Elimination of Therapeutic iNK Cells with Cetuximab

Antibody-dependent cellular cytotoxicity (ADCC) is a mechanism of cell immune defense whereby a target cell which has been coated with antibodies recognizing cell surface antigens is lysed by an effector cell bearing Fc receptors. ADCC can be mediated by a variety of immune cells, including natural killer (NK) cells, neutrophils, macrophages, and eosinophils by recognition of bound immunoglobulin via their Fc receptors, particularly CD16 (FcγRIII).

Cetuximab is a chimeric mouse-human antibody targeted against the extracellular domain of epidermal growth factor receptor (EGFR). It has been demonstrated to mediate ADCC against EGFR-expressing tumor cell lines via its human IgG1 Fc region (Kurai, 2007)

The following experiment was conducted to assess whether the iPSC-derived NK (iNK) development candidate 611 (e.g., therapeutic iNK) expresses EGFR and is susceptible to ADCC mediated by Cetuximab compared with an isotype control antibody when cultured with interleukin (IL)-2 activated peripheral blood mononuclear cells (PBMC).

Primary Effector Cell Isolation & Culture

Peripheral mononuclear blood cells (PBMC) were collected from buffy coats of consented healthy adult donors (Bloodworks Northwest) by centrifugation over a Ficoll-Hypaque density gradient. Cells were cultured overnight at $1\times10^6$/mL in RPMI (Life Technologies) supplemented with 10% fetal bovine serum (FBS, Hyclone) and 55 mM b-mercaptoethanol (Life Technologies) in the presence of 10 ng/mL IL-2 (Peprotech) before use in experiments.

ADCC Assays iNK cells were labeled with 2.5 mM CTV (Life Technologies) and $2.5\times10^4$ cells plated/well as targets in a 96 well flat bottom plate (Corning) in triplicate. Cetuximab (Selleckchem) or a human IgG1 isotype control (Invivogen) were pre-incubated with therapeutic iNK targets at concentrations of 10 pg/mL-10 mg/mL for 30' prior to addition of effector cells. IL-2 activated effector PBMCs were added at an effector:target (E:T) ratio of 25:1 in triplicate wells/condition and cultures incubated for 16 hours in a 5% CO2, 37% C° incubator. Dead cells were identified by flow cytometry using LIVE/DEAD™ Fixable Near-IR Dead Cell Stain (ThermoFisher) according to manufacturer's protocol. Samples were acquired on a Symphony A3 (BD Biosciences) and analyzed on FlowJo version 10.7.1 software.

Flow Cytometry

For determination of antibodies bound per cell (ABC), $2\times10^5$ therapeutic iNK cells were labeled with EGFR-PE (Novus Biologicals) for 15' at RT in the dark, washed with Cell Staining Buffer (BioLegend), and fixed for 10' at RT in the dark with Fixation Buffer (BioLegend). A single tube of BD Quantibrite beads (BD Biosciences) was reconstituted with 500 mL PBS per manufacturer's protocol. Labeled therapeutic iNK cells and a BD Quantibrite PE tube were acquired on a Symphony A3 (BD Biosciences) using the same voltages and settings, and all samples were analyzed on FlowJo version 10.7.1 software. By using known ratios of PE to antibodies, PE molecules can be converted per cell to antibodies per cell. Quantibrite beads were gated on by FSC-A vs SSC-A. Subsequently the PE fluorescence was visualized as a histogram and gates were drawn for each of the 4 distinct peaks. Geometric mean fluorescence was exported for each PE peak and used for ABC calculations.

For analysis of ADCC assays, cells were transferred to a 96 well round bottom plate (Falcon), washed in 1×PBS pH 7.2 (Life Technologies) and resuspended in PBS containing LIVE/DEAD™ Fixable Near-IR Dead Cell Stain (ThermoFisher) according to manufacturer's protocol. Non-specific binding to Fc receptors (FcR) was blocked using Human TruStain FcX Fc receptor blocking solution (BioLegend) prior to addition of antibodies. Cells were incubated with antibodies against CD56 and CD16 for 20' at RT and washed three times with Cell Staining Buffer (BioLegend) before fixation with Fixation Buffer (BioLegend). Samples were collected on a Symphony A3 (BD Biosciences) and all FCS files analyzed on FlowJo version 10.7.1 software.

Figure 13:
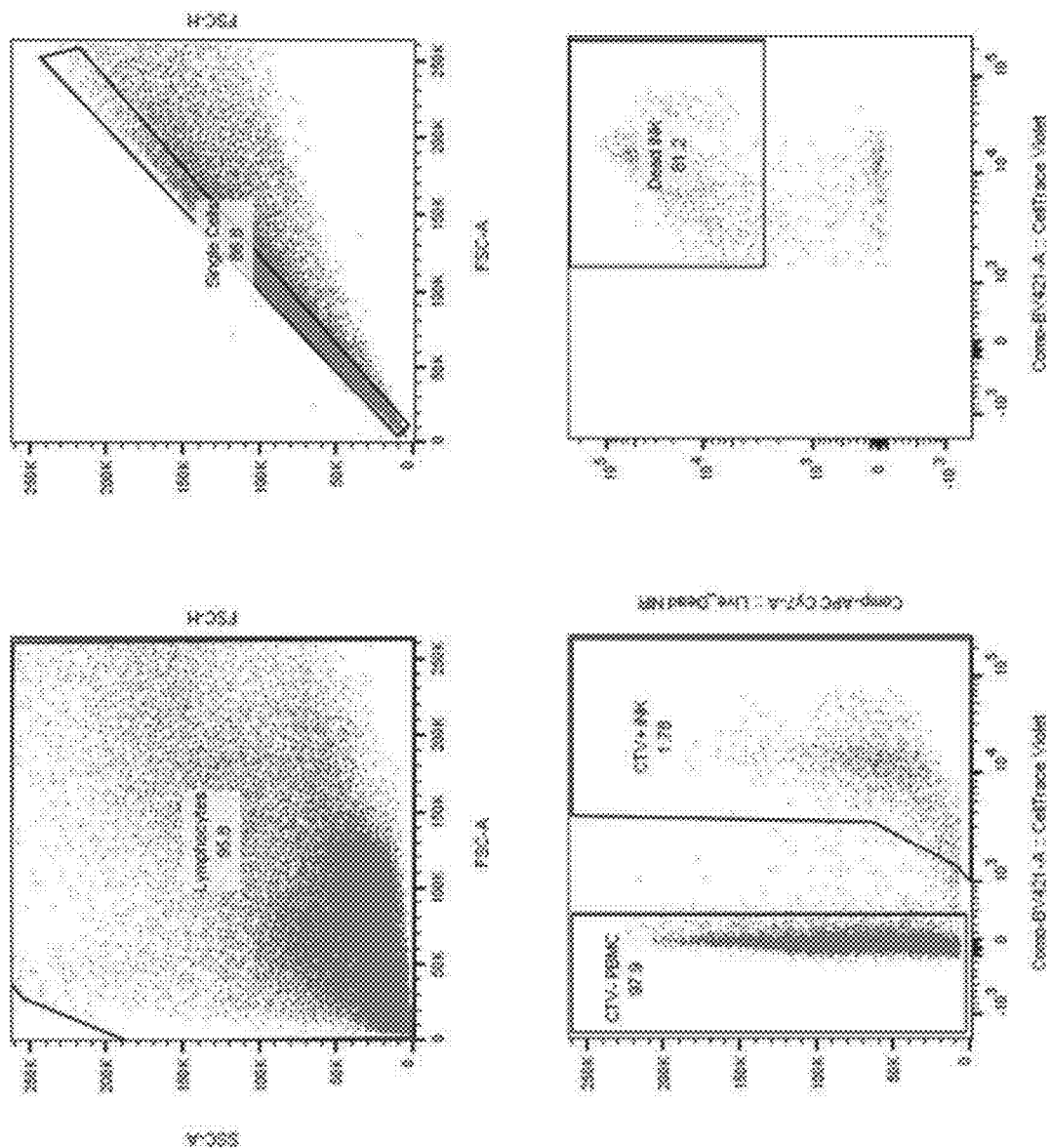
FIG. 13 shows a gating strategy for ADCC assays. Cells were gated on lymphocytes, followed by exclusion of doublets, followed by gating on CellTrace Violet (CTV)+ iNK, and finally on LIVE/DEAD™ Near-IR+ to determine % of dead therapeutic iNK targets. FSC-A=forward scatter area, SSC-A=side scatter area, FSC-H=forward scatter height, CTV=CellTrace Violet, NIR=Near-IR.

Lymphocytes were gated on based on forward scatter area (FSC-A) and side scatter area (SSC-A). Singlets were excluded based on forward scatter area (FSC-A) vs forward scatter height (FSC-H) gate. Gates were drawn on CTV$^+$ therapeutic iNK targets or CTV$^-$ effector cells, and a subsequent gate drawn on CTV$^+$ therapeutic iNK cells that labeled positive for LIVE/DEAD Fixable Near-IR. As shown in FIG. 13, cells were gated on lymphocytes, followed by exclusion of doublets, followed by gating on CellTrace Violet (CTV)+ iNK, and finally on LIVE/DEAD™ Near-IR+ to determine % of dead therapeutic iNK targets. FSC-A=forward scatter area, SSC-A=side scatter area, FSC-H=forward scatter height, CTV=CellTrace Violet, NIR=Near-IR.

Analysis

To calculate antibodies bound per cell (ABC), a linear regression was plotted of Log10 PE molecules per bead against Log10 geometric mean-PE, using the following equation: y=mx+c where y equals Log10 fluorescence and x equals Log10 PE molecules per bead. For each sample the number of antibodies bound per cells was determined by using the equation above and interpolating the ABC value based on the geometric mean fluorescence value for each sample.

Percent specific cell lysis for ADCC assays was calculated as in (Kim, 2007) using the following equation where LIVE/DEAD NIR$^+$CTV$^+$ targets are considered dead iNK and the percent of spontaneous iNK cell death is determined by iNK cells cultured without addition of effector cells (0:1 E:T):

Results

Figure 14:
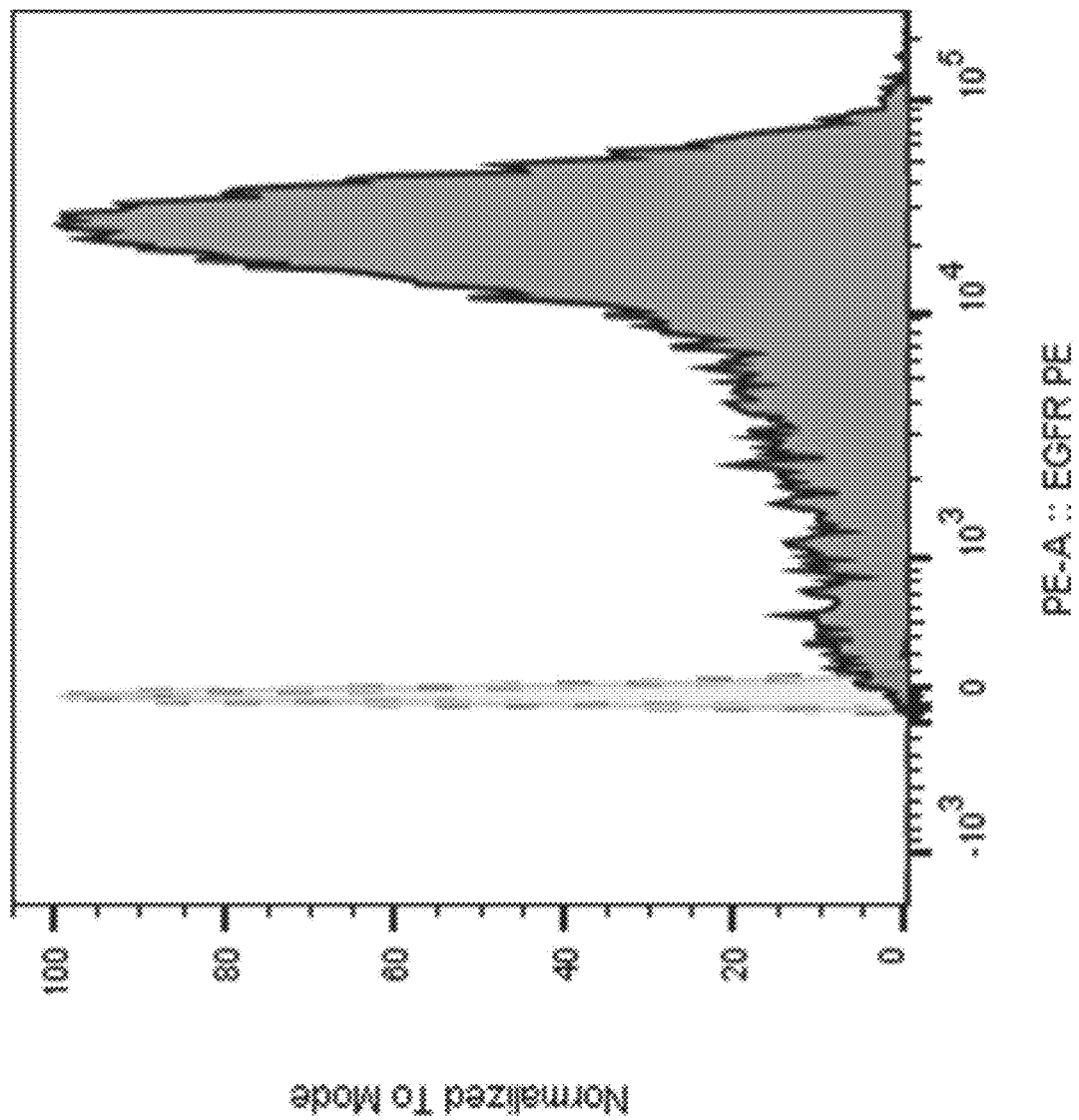
FIG. 14 shows EGFR staining on therapeutic iNK cells. EGFR PE levels on therapeutic iNK stained with EGFR (black histogram) compared with unstained therapeutic iNK (gray histogram) or an unedited WT iNK (dashed line).

ABC value for therapeutic iNK was calculated to be 7,341 by Quantibrite bead technology using geometric mean fluorescent intensity values. (FIG. 14 and Table 6). FIG. 14 shows EGFR PE levels on therapeutic iNK stained with EGFR (black histogram) compared with unstained therapeutic iNK (gray histogram) or an unedited WT iNK (dashed line). EGFR expression was observed on therapeutic iNK cells by flow cytometry with values of 7,341 ABC. This level of EGFR was sufficient to observe ADCC activity mediated by Cetuximab with an EC50 of 2.0 ng/mL in co-cultures of iNK with IL-2 activated PBMC.

TABLE 6

EGFR antibodies bound per cell

| iNK | Geometric Mean | Geometric mean-background | ABC |
|---|---|---|---|
| Therapeutic iNK unstained (background) | 63.1 | 0 | 0 |
| Therapeutic iNK EGFR | 11,214 | 11,150 | 7,341 |

Figure 15:
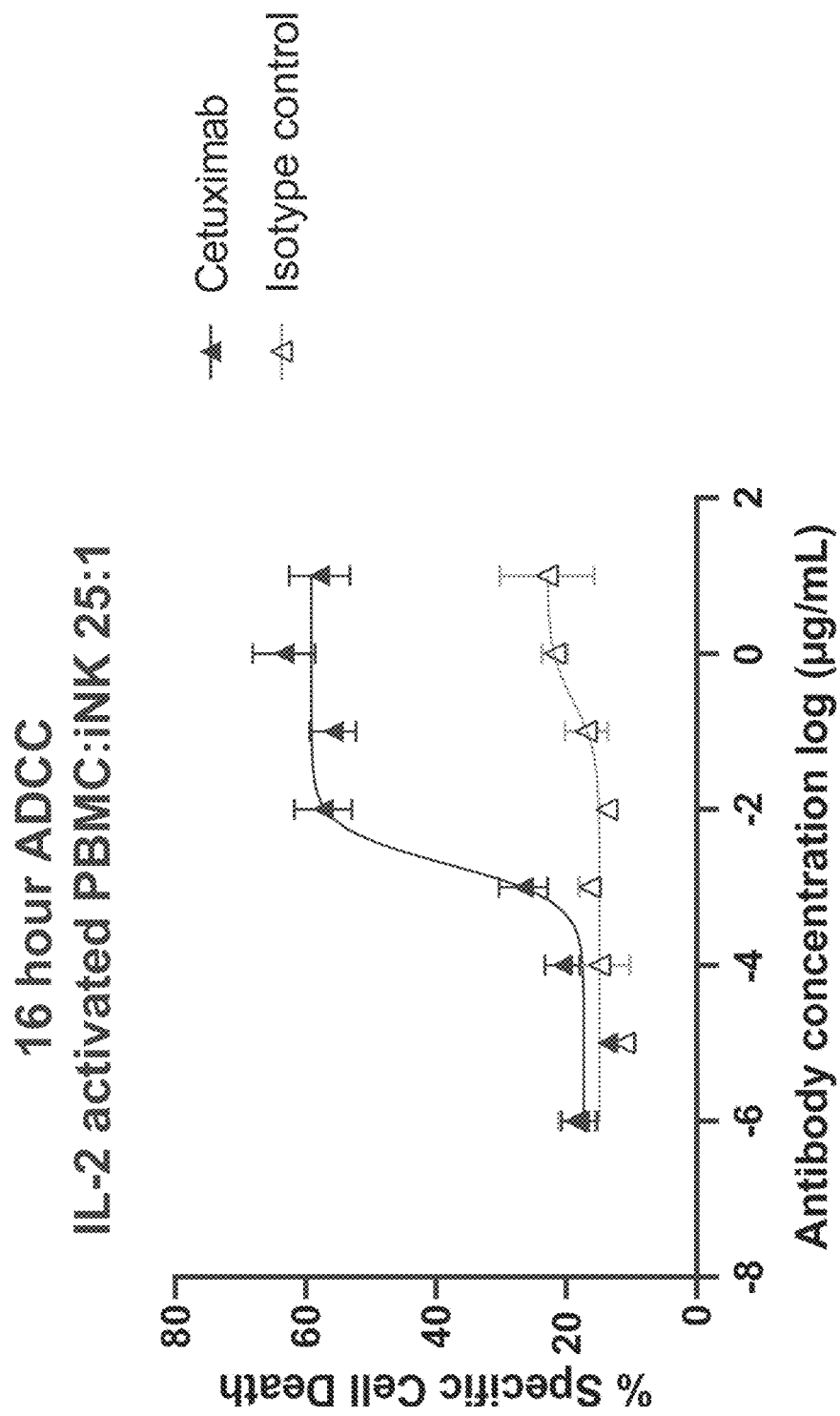
FIG. 15 shows cetuximab-mediated ADCC of therapeutic iNK cells. Percent specific cell lysis of therapeutic iNK cells mediated by Cetuximab (black triangles) compared with human IgG1 isotype control (open triangles). IL-2 activated PBMC were co-cultured with therapeutic iNK at a 25:1 E:T ratio for 16 hours and percent specific cell death of iNK determined. Each data point is a mean of triplicate wells, error bars±standard deviation.

Addition of Cetuximab to co-cultures of IL-2 activated PBMC and iNK cells mediated ADCC of therapeutic iNK targets in a concentration-dependent fashion, with an $EC_{50}$ of 2.0 ng/mL (FIG. 15). FIG. 15 shows the percent specific cell lysis of therapeutic iNK cells mediated by Cetuximab (black triangles) compared with human IgG1 isotype control (open triangles). IL-2 activated PBMC were co-cultured with therapeutic iNK at a 25:1 E:T ratio for 16 hours and percent specific cell death of iNK determined. Each data point is a mean of triplicate wells, error bars±standard deviation. Addition of human IgG1 isotype control did not mediate ADCC of therapeutic iNK targets, although some background killing was observed at the highest concentration of antibody.

Example 12. Antibody and Complement Evasion Using B2M Knockout

Allogeneic cell therapy products derived from induced pluripotent stem cells (iPSC) have the potential to be used as an off-the-shelf treatment for many diseases but may generate a vigorous immune response by the host due to incompatibilities in human leukocyte antigen (HLA) genes. In addition to an immune response mediated by CD8 T cells to HLA Class I molecules, some patients may have pre-existing antibodies (Ab) to these polymorphic proteins (1, 2). If Abs to HLA Class I molecules do exist, there is the potential for complement-mediated cytotoxicity (CDC) of the effector cells. A strategy to eliminate binding by Abs to HLA Class I molecules is by deletion of beta-2 microglobulin (b2M), which encodes a subunit common to HLA Class I protein and is required for cell surface expression.

The CDC assay is a simple method to measure how well an Ab induces the killing of cells in the presence of complement proteins (3). Plasma, as well as serum contains the full spectrum of complement proteins, which is referred to as the complement cascade. However, these molecules are labile and as such, collected serum samples must be quickly frozen before use in CDC assays. As an alternative, rabbit complement can be used as a reagent in assays to substitute for human complement. Using a common pan-HLA-ABC Ab to model a potential HLA Class I titer from a patient (4), iNK cells were tested to demonstrate the sensitivity of wild-type (WT) HLA Class I expressing iNK cells and protection of B2M knock out (KO) Clone 611 iNK cells from CDC.

Complement-Mediated Cytotoxicity Assay iNK cells, WT 005 and Clone 611, were diluted to 4×10e6/mL in RPMI-1640 basal media. iNK cells were seeded at 200K cells/well in a polypropylene, U-well, 96-well plate (50 uL/well). Samples were seeded in triplicate. Abs were diluted in RPMI-1640 at 40 ug/mL and dispensed at 50 uL/well (10 ug/mL final). Baby rabbit complement (BRC) was thawed just prior to use, then diluted 1:5 in RPMI-1640 and dispensed at 100 uL/well (10% BRC final). Final volumes for each well was 200 uL. For both iNK cell types there were 4 conditions: A, No add (RPMI-1640 alone); B, Isotype Ab+BRC; C, anti-HLA-ABC Ab+BRC; and D, anti-CD52 Ab+BRC. Cells were then incubated for 1 hr at 37 C, 5% CO2.

After the incubation period, the plate was centrifuged at 1200 RPM for 1 minute and decanted to remove the RPMI-1640 with BRC and replaced with 200 uL/well RPMI-1640+ 10% heat-inactivated FBS. Cells were then counted using Trypan Blue to score both live and dead cells.

Analysis

Cellular viability was graphically represented and statistically analyzed using GraphPad Prism software. Statistical significance for differences in viability was evaluated using Student's T test. Differences between samples were considered significant when the probability value (p) was ≤0.05.

Results

Upon thaw and centrifugation, cells were resuspended in 1 mL Easysep buffer and counted for viability using Trypan Blue. Cells were found to have high viability before use in the CDC assay. WT 005: 24.6×10e6/mL, 95% viability. Clone 611 iNK cells: 22.6×10e6/mL, 93% viability.

Figure 16:
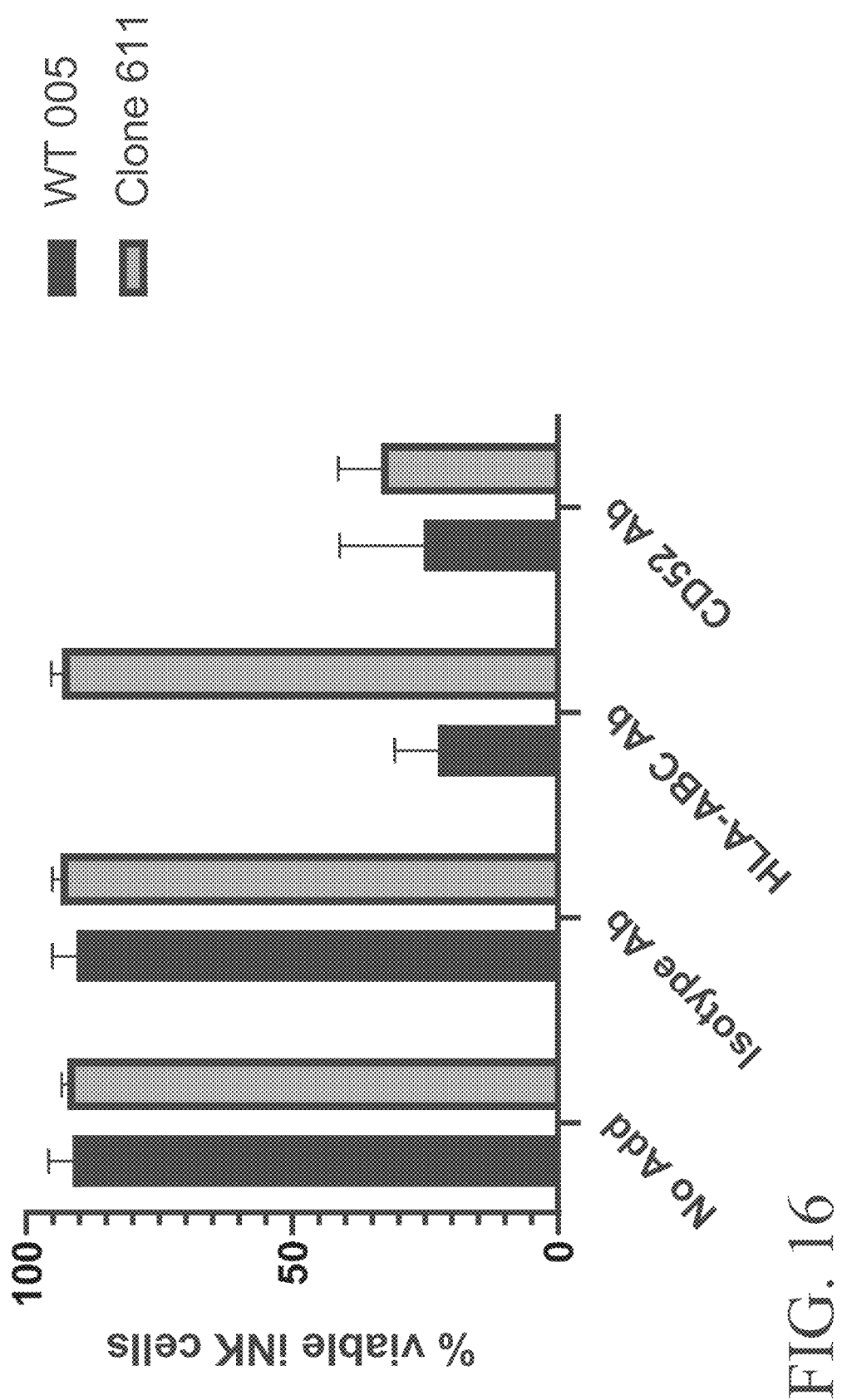
FIG. 16 shows select sensitivity of WT iNK cells to anti-HLA-ABC Ab-mediated complement cytotoxicity.

Elimination of B2M from iNK cells protects from complement-mediated cytotoxicity in the presence of Abs to HLA-ABC molecules and complement. As shown in FIG. 16, both freshly thawed WT 005 and Clone 611 iNK cells were found to maintain high viability when cultured for 1 hr in RPMI-1640 alone or with the isotype Ab plus BRC. In contrast, only the WT 005 iNK cells were killed in the presence of the HLA-ABC Ab plus BRC with no effect on clone 611 iNK cells. To prove Clone 611 iNK cells were still sensitive to complement-mediated killing, we included an Ab to CD52. Addition of the anti-CD52 Ab plus BRC resulted in the killing of both iNK cells.

Example 13. Comparison of CTL Activation and iNK Cell Lysis Between β2M-Deficient, iPSC-Derived NK Cells and β2M-Expressing, Wild-Type iNK Cells Allogeneic cell therapy products derived from induced pluripotent stem cells (iPSC) have the potential to be used as an off-the-shelf treatment for many diseases, but may generate a vigorous immune response by the host due to incompatibilities in human leukocyte antigen (HLA) genes (Lanza, et al. Nat Rev Immunol. 2019 December; 19(12): 723-733). Notably, direct lysis of mismatched class I HLA-bearing cells occurs via activation of host CD8+ T cells that interact with the class I HLA molecules (Felix, et al. Nat Rev Immunol. 2007 December; 7(12):942-53). Activation of host CD8 T cells is thwarted by deletion of beta-2 microglobulin (β2M), which encodes a subunit common to all class I HLA genes and is required for their surface expression (Krangel, et al. Cell. 1979 December; 18(4):979-91; and Zijlstra, et al. Nature. 1989 Nov. 23; 342(6248):435-8).

Here iPSC-derived NK (iNK) which are genetically edited to be β2M-deficient (KO) are cultured with CD8+ cytotoxic lymphocytes (CTL) derived from peripheral blood mononuclear cells (PBMC) from multiple donors to determine whether they induce CTL activation and lysis of iNK cells compared with wild-type iNK which express (32M.

Generation of Effector Cytotoxic Lymphocytes (CTL)

Isolated cryopreserved peripheral mononuclear blood cells (PBMC) from consented healthy adult donors were purchased (StemCell Technologies) and stored in liquid nitrogen until use. CTLs with specific reactivity to the parental iPSC line were generated. Briefly, T cells were isolated from $5 \times 10^7$ PBMC with Human T cell Isolation kit (StemCell Technologies) according to manufacturer's instructions and primed three times by co-culture with parental iPSC-derived iNK cells in media with IL2, followed by another round of T cell isolation, and then expanded with Immunocult anti-CD2/CD3/CD28 stimulation reagent (StemCell Technologies) in media with IL2, IL7 and IL15. Expanded cells were cryopreserved in CS-10 (StemCell Technologies) buffer at 107 cells/ml.

Allo-Evasion Cytotoxicity and CTL Activation Assays iNK cells were labeled with 5 μM CTV (Life Technologies) according to manufacturer's instructions and $5 \times 10^4$ cells plated/well as targets in a 96-well U-bottom plate (Falcon) in duplicate. Cryopreserved CTLs were thawed and added at an effector:target (E:T) ratio of 5:1 in triplicate wells/condition and cultures incubated for 48 hours in a 5% CO2, 37% Co incubator.

Flow Cytometry

Cells were washed in 1×PBS pH 7.2 (Life Technologies) and resuspended in PBS containing LIVE/DEAD™ Fixable Near-IR Dead Cell Stain (ThermoFisher) according to manufacturer's protocol. Non-specific binding to Fc receptors (FcR) was blocked using Human TruStain FcX Fc receptor blocking solution (BioLegend) prior to addition of antibodies. Cells were incubated with antibodies against TCRab, CD4, CD8 and CD25 for 20' at RT and washed three times with Cell Staining Buffer (BioLegend) before fixation with Fixation Buffer (BioLegend). Samples were collected on a Symphony A3 (BD Biosciences) and all FCS files analyzed on FlowJo version 10.7.1 software.

Figure 17:
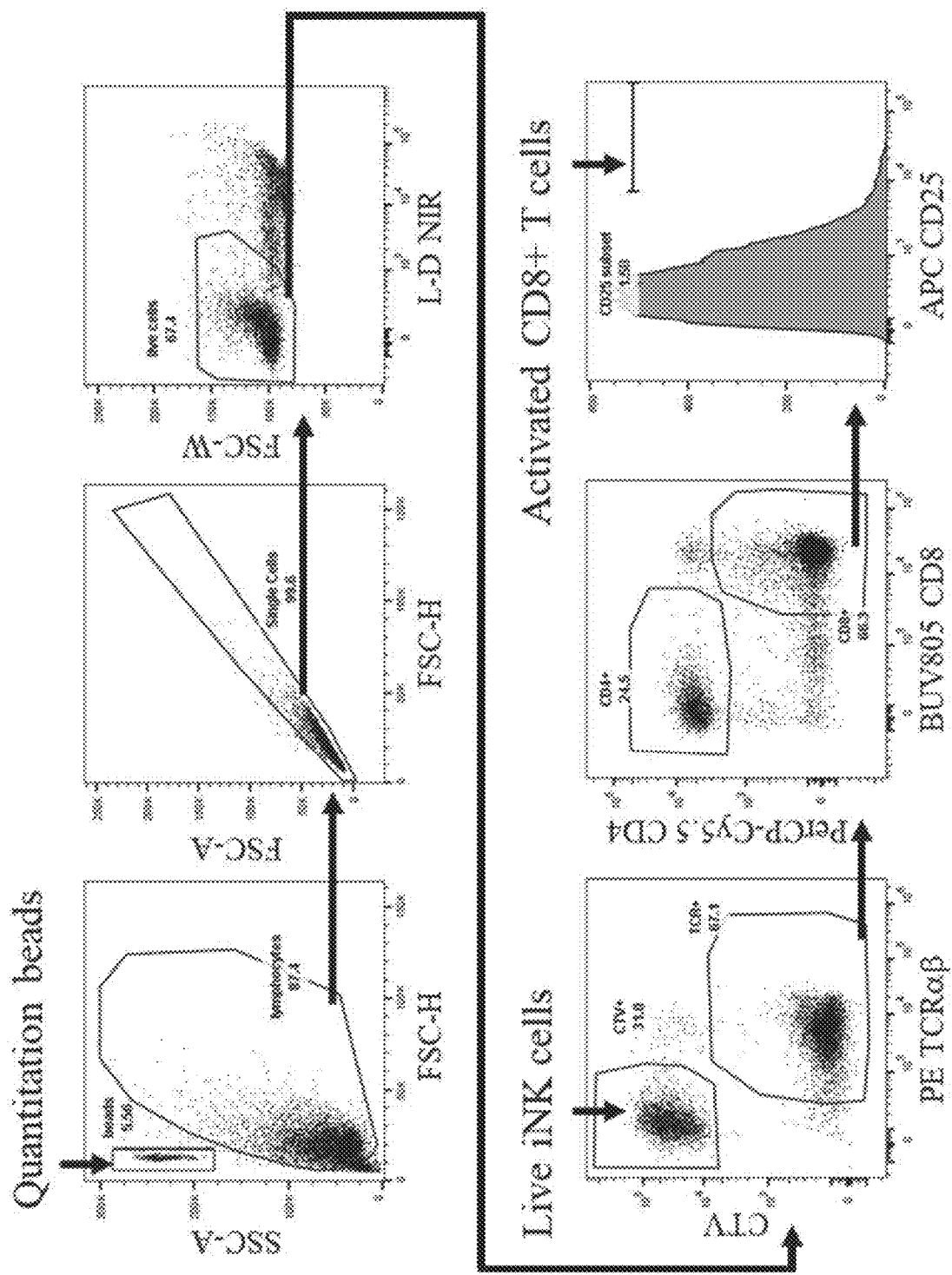
FIG. 17 shows a gating strategy for allo-evasion CTL cytotoxicity and activation assays. Cells were gated on quantitation beads and lymphocytes. Within lymphocytes exclusion of doublets, followed by gating on LIVE/DEAD™ Near-IR negative, followed by CTV to identify iNK cells and TCRαβ to identify T cells. Within T cells, CD4-negative, CD8-positive cells, followed by CD25 to identify activated CD8+ T cells. Key assay parameters Quantitation beads, live iNK cells and activated CD8+ T cells are indicated. FSC-A=forward scatter area, SSC-A=side scatter area, FSC-H=forward scatter height, FSC-W=forward scatter width, L-D=LIVE/DEAD™ Near-IR, CTV=CellTrace Violet.

Lymphocytes and quantitation beads were gated based on forward scatter height (FSC-H) and side scatter area (SSC-A). Singlets were excluded based on forward scatter area (FSC-A) vs forward scatter height (FSC-H) gate. Live cells were gated as negative for LIVE/DEAD NIR staining. Based on CTV and TCRαβ, T cells (TCRαβ positive, CTV negative) and iNK cells (CTV positive and TCRαβ negative) were gated. Within the T cell gate, CD8 positive and CD4 negative cells were selected. Within the CD8+ T cell population, expression of CD25 was assessed, the CD25-positive gate determined to capture minimal positive background events among T cells cultured alone without targets (FIG. 17). As shown in FIG. 17, cells were gated on quantitation beads and lymphocytes. Within lymphocytes exclusion of doublets, followed by gating on LIVE/DEAD™ Near-IR negative, followed by CTV to identify iNK cells and TCRαβ to identify T cells. Within T cells, CD4-negative, CD8-positive cells, followed by CD25 to identify activated CD8+ T cells. Key assay parameters Quantitation beads, live iNK cells and activated CD8+ T cells are indicated. FSC-A=forward scatter area, SSC-A=side scatter area, FSC-H=forward scatter height, FSC-W=forward scatter width, L-D=LIVE/DEAD™ Near-IR, CTV=CellTrace Violet.

Analysis

The live iNK number for each well was normalized by dividing the acquired CTV+ gate event count by the event count from the quantitation bead gate. Average of duplicate wells for each donor condition was used for calculated values. Specific lysis of iNK cells by CTL was determined by the following calculation:

Where $iNK_a$ is the normalized CTV+ event count in the given iNK:CTL co-culture condition; and $iNK_a$ is the normalized CTV+ event count in the corresponding control iNK alone condition. To determine significance of assay outcomes, p-values were determined by unpaired student's t-test of assay values, n=3 individual donors.

Results

Figure 18A:
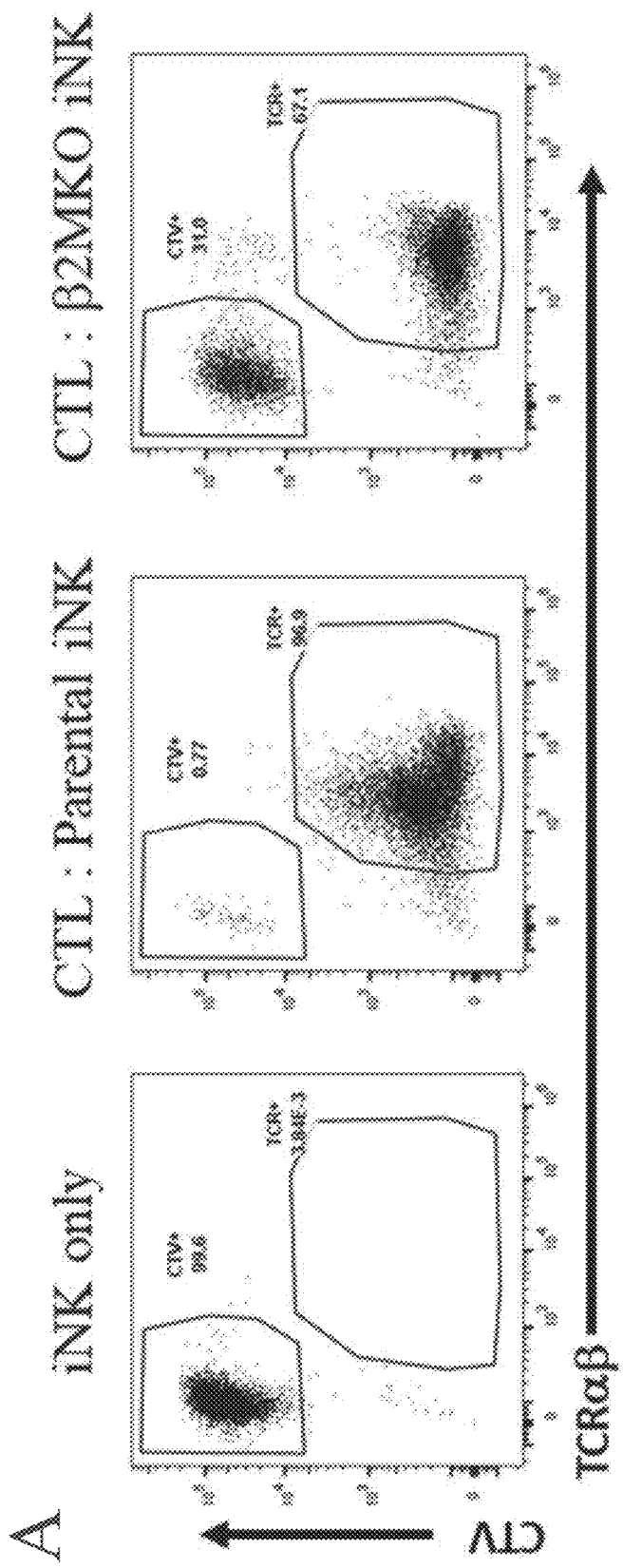
FIGS. 18A-B show CTL-mediated lysis of iNK cells. Assessment of specific iNK lysis by FACS.
Figure 18B:
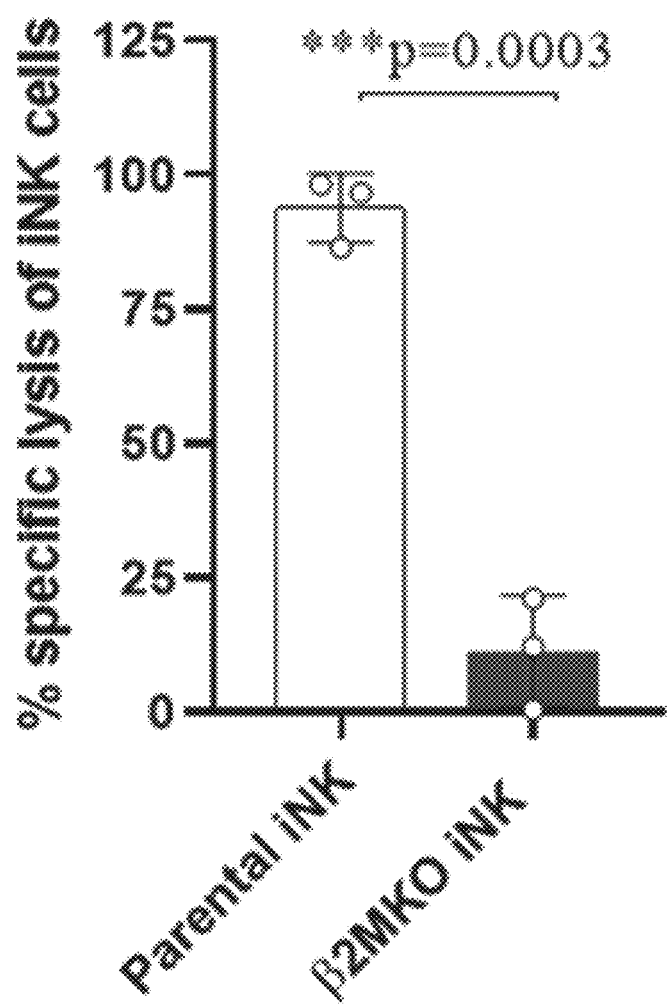

Specific killing of parental iNK cells was observed at 86-98%, corresponding to 64-84% activation of CTL when co-cultured with the parental iNK cells. 0.5-21% specific killing was observed among edited β2MKO iNK, corresponding to 1-3% activation of CTL in co-culture with β2MKO iNK cells. Both iNK killing and CTL activation were significantly reduced when β2MKO iNK cells were used as targets.

iNK cells were incubated alone or with CTL at a 5:1 CTL:iNK ratio for 48 hours, then live iNK cells were measured by flow cytometry (FIG. 18A). Parental iNK exhibited 86-98% specific lysis, while β2MKO iNK exhibited 0.5-21% specific lysis (FIG. 18B).

Figure 19A:
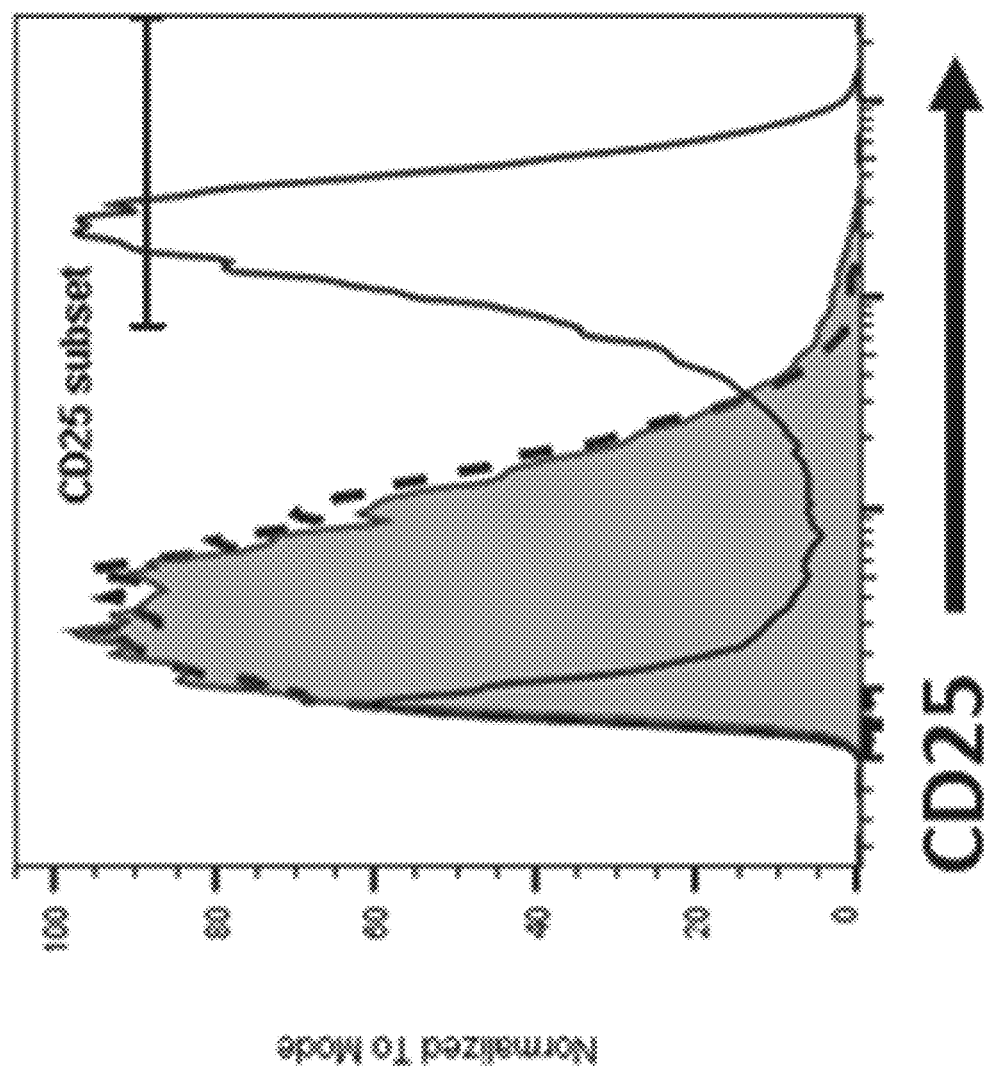
FIG. 19A shows activation of iNK-specific CTL in co-cultures.
Figure 19B:
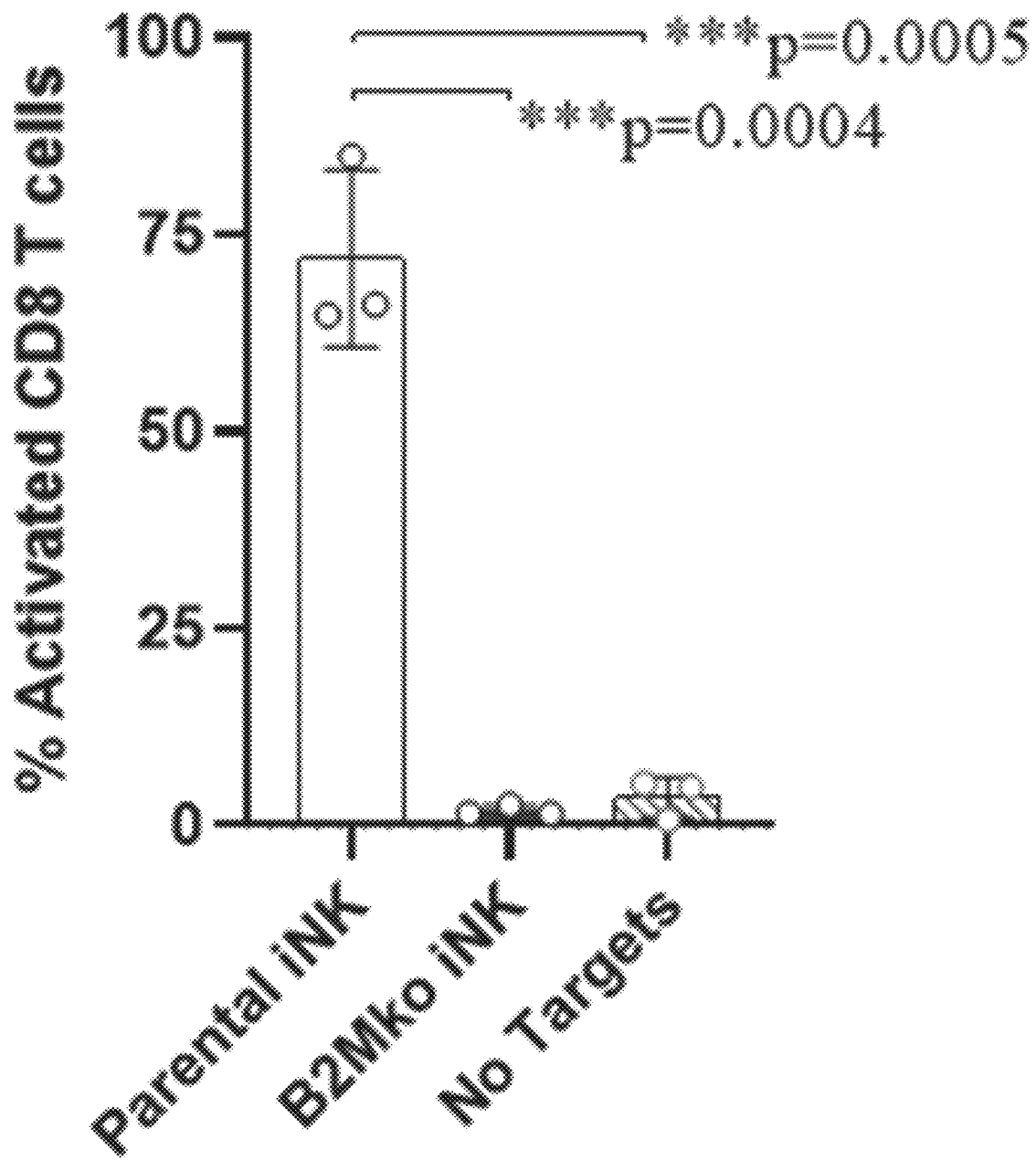
FIG. 19B show activation of iNK-specific CTL in co-cultures.

CTL were incubated alone or with iNK at a 5:1 CTL:iNK ratio for 48 hours, then activation of CD8+ T cells by CD25 expression was measured by flow cytometry (FIG. 19A). 64-84% of CTL were activated by the parental wild-type iNK, while 1-3% were activated by β2MKO iNK, and 0.5-5% activated without target cells present (FIG. 19B).

Example 14. PBMC-Mediated Killing of β2M$^{-/-}$/HLA-E$^+$ iNK Cells

Allogeneic cell therapy products derived from induced pluripotent stem cells (iPSC) have the potential to be used as an off-the-shelf treatment for many diseases, but may generate a vigorous immune response by the host due to incompatibilities in human leukocyte antigen (HLA) genes. A strategy to eliminate activation of host CD8 T cells is by deletion of beta-2 microglobulin (β2M), which encodes a subunit common to class I major histocompatibility complex (MHC) and is required for surface expression of MHC class I (Krangel, et al. Cell. 1979 December; 18(4):979-91; and Zijlstra, et al. Nature. 1989 Nov. 23; 342(6248):435-8).

A limitation of this approach, however, is that while rejection of engineered iPSC cell products by CD8 may be abrogated, these MHC class I-negative cells may be lysed by natural killer (NK) cells due to "missing self" (Bix, et al. Nature 349, 329-331 (1991); Liao, et al. Science 253, 199-202 (1991)).

An approach to limit lysis by host NK cells is by overexpression of HLA-E on the surface of iPSC-derived cell products (Gornalusse, et al. Nat Biotechnol. 2017 August; 35(8):765-772; Hoerster, et al. Front Immunol. 2021 Jan. 29; 11:586168). HLA-E is a minimally polymorphic ligand which presents peptides derived from signal sequences of other HLA class I molecules and binds the inhibitory NK receptor complex CD94/NKG2A (Braud, et al. Nature 349, 329-331 (1991); Miller, et al. J Immunol. 2003 Aug. 1; 171(3):1369-75).

Here iPSC-derived NK (iNK) which are edited to be β2M$^{-/-}$ but express HLA-E (e.g., therapeutic iNK) are cultured with peripheral blood mononuclear cells (PBMC) to determine whether they are less susceptible to killing by PBMC compared with iNK which lack PM and do not express HLA-E.

Primary Effector Cell Isolation and Culture

Peripheral mononuclear blood cells (PBMC) were collected from buffy coats of consented healthy adult donors (Bloodworks Northwest) by centrifugation over a Ficoll-Hypaque density gradient and cryopreserved in Cryostor CS10.

Allo-Evasion Cytoxicity Assays iNK cells were labeled with 2.5 µM CTV (Life Technologies) according to manufacturer's instructions and $2.5 \times 10^4$ cells plated/well as targets in a 96 well flat bottom plate (Corning) in triplicate. Cryopreserved PBMCs were thawed and added at an effector:target (E:T) ratio of 25:1 in triplicate wells/condition and cultures incubated for 72 hours in a 5% CO2, 37% Co incubator. Dead cells were identified by flow cytometry using LIVE/DEAD™ Fixable Near-IR Dead Cell Stain (ThermoFisher) according to manufacturer's protocol. Samples were acquired on a Symphony A3 (BD Biosciences) and analyzed on FlowJo version 10.7.1 software.

Flow Cytometry

For determination of antibodies bound per cell (ABC), $1 \times 10^5$ iNK cells were labeled with mouse IgG1 PE isotype control (BioLegend) or HLA-E PE (BioLegend) for 15' at RT in the dark, washed with Cell Staining Buffer (BioLegend), and fixed for 10' at RT in the dark with Fixation Buffer (BioLegend). A single tube of BD Quantibrite beads (BD Biosciences) was reconstituted with 500 mL PBS per manufacturer's protocol. Labeled iNK cells and a BD Quantibrite PE tube were acquired on a Symphony A3 (BD Biosciences) using the same voltages and settings, and all samples were analyzed on FlowJo version 10.7.1 software. By using known ratios of PE to antibodies, PE molecules can be converted per cell to antibodies per cell. Quantibrite beads were gated on by FSC-A vs SSC-A. Subsequently the PE fluorescence was visualized as a histogram and gates were drawn for each of the 4 distinct peaks. Geometric mean fluorescence was exported for each PE peak and used for ABC calculations.

For NK cell phenotyping, cells were transferred to a 96 well round bottom plate (Falcon), washed in 1×PBS pH 7.2 (Life Technologies) and resuspended in PBS containing LIVE/DEAD' Fixable Near-IR Dead Cell Stain (ThermoFisher) according to manufacturer's protocol. Non-specific binding to Fc receptors (FcR) was blocked using Human TruStain FcX Fc receptor blocking solution (BioLegend) prior to addition of antibodies. Cells were incubated with antibodies against CD3, CD56, and CD16 for 20' at RT and washed three times with Cell Staining Buffer (BioLegend) before fixation with Fixation Buffer (BioLegend). Samples were collected on a Symphony A3 (BD Biosciences) and all FCS files analyzed on FlowJo version 10.7.1 software.

For analysis of allo-evasion cytotoxicity assays, cells were transferred to a 96 well round bottom plate (Falcon), washed in 1×PBS pH 7.2 (Life Technologies) and resuspended in PBS containing LIVE/DEAD™ Fixable Near-IR Dead Cell Stain (ThermoFisher) according to manufacturer's protocol. Non-specific binding to Fc receptors (FcR) was blocked using Human TruStain FcX Fc receptor blocking solution (BioLegend) prior to addition of antibodies. Cells were incubated with antibodies against CD56 and CD16 for 20' at RT and washed three times with Cell Staining Buffer (BioLegend) before fixation with Fixation Buffer (BioLegend). Samples were collected on a Symphony A3 (BD Biosciences) and all FCS files analyzed on FlowJo version 10.7.1 software.

Figure 20:
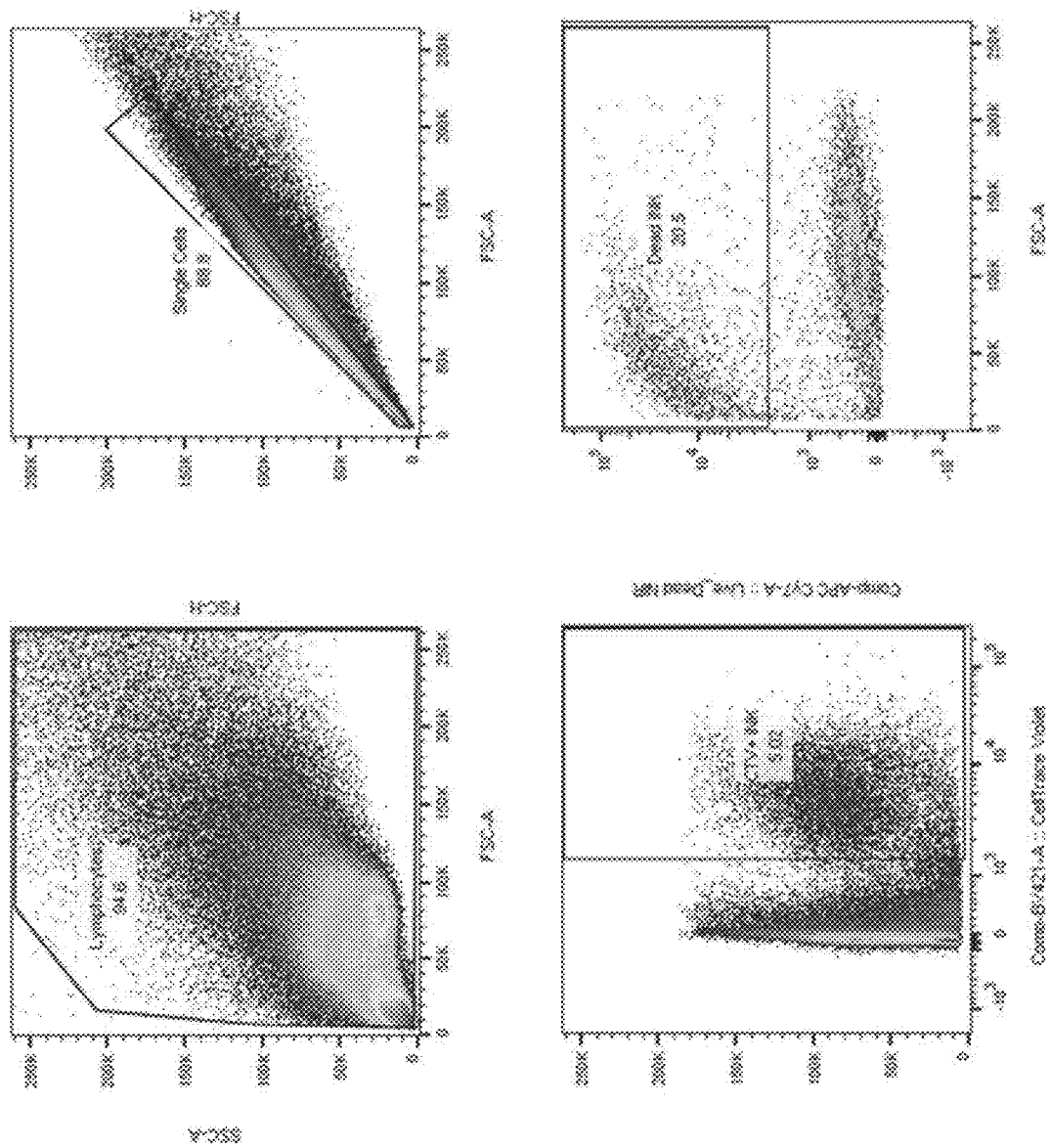
FIG. 20 shows a gating strategy for all-evasion cytotoxicity assays. Cells were gated on lymphocytes, followed by exclusion of doublets, followed by gating on CellTrace Violet (CTV)+ iNK, and finally on LIVE/DEAD™ Near-IR+ to determine % of dead iNK targets. FSC-A=forward scatter area, SSC-A=side scatter area, FSC-H=forward scatter height, CTV=CellTrace Violet, NIR=Near-IR.

Lymphocytes were gated on based on forward scatter area (FSC-A) and side scatter area (SSC-A). Singlets were excluded based on forward scatter area (FSC-A) vs forward scatter height (FSC-H) gate. Gates were drawn on $CTV^+$ iNK targets or $CTV^-$ effector cells, and a subsequent gate drawn on $CTV^+$ iNK cells that labeled positive for LIVE/DEAD Fixable Near-IR (FIG. 20). Cells were gated on lymphocytes, followed by exclusion of doublets, followed by gating on CellTrace Violet (CTV)+ iNK, and finally on LIVE/DEAD™ Near-IR+ to determine % of dead iNK targets. FSC-A=forward scatter area, SSC-A=side scatter area, FSC-H=forward scatter height, CTV=CellTrace Violet, NIR=Near-IR.

Analysis

To calculate antibodies bound per cell (ABC), a linear regression was plotted of Log10 PE molecules per bead against Log10 geometric mean-PE, using the following equation: y=mx+c where y equals Log10 fluorescence and x equals Log10 PE molecules per bead. For each sample the number of antibodies bound per cells was determined by using the equation above and interpolating the ABC value based on the geometric mean fluorescence value for each sample after subtraction of isotype control background values.

Cell death for allo-evasion assays was calculated by determining the mean percent of LIVE/DEAD $NIR^+CTV^+$ targets (dead iNK) for each iNK group and dividing by the mean percent of LIVE/DEAD NIR+CTV+WT iNK targets. Results are presented as "Cell death relative to WT iNK".

Results

HLA-E expression was measured on edited iNK cells from line 004 by flow cytometry with a value of 3.625 ABC. Expression of HLA-E on therapeutic iNK cells was sufficient to observe a reduction in cell death when cultured with PBMC compared with HLA-E negative, β2M KO iNK.

Figure 21:
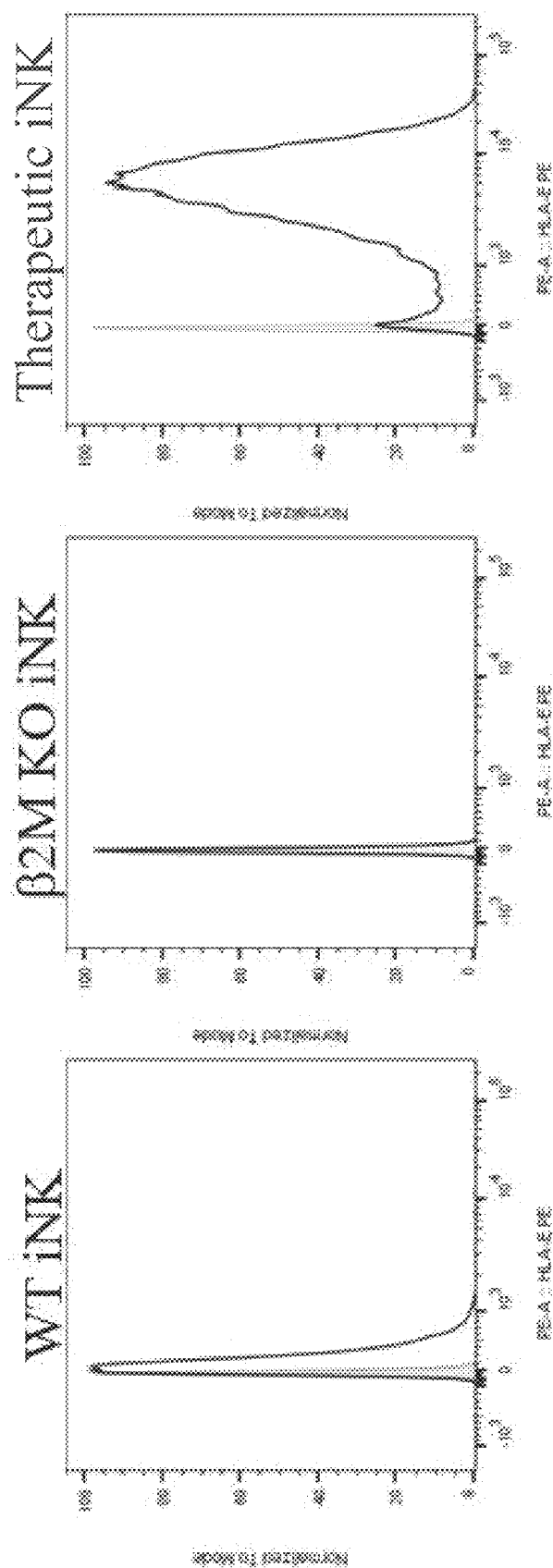
FIG. 21 shows HLA-E staining on therapeutic iNK cells. HLA-E=open histogram, mouse IgG1 isotype control=gray filled histogram.

ABC value for HLA-E expressing therapeutic iNK cells was calculated to be 3,625 by Quantibrite using geometric mean fluorescent intensity values. (FIG. 21; HLA-E=open histogram, mouse IgG1 isotype control=gray filled histogram).

Figure 22:
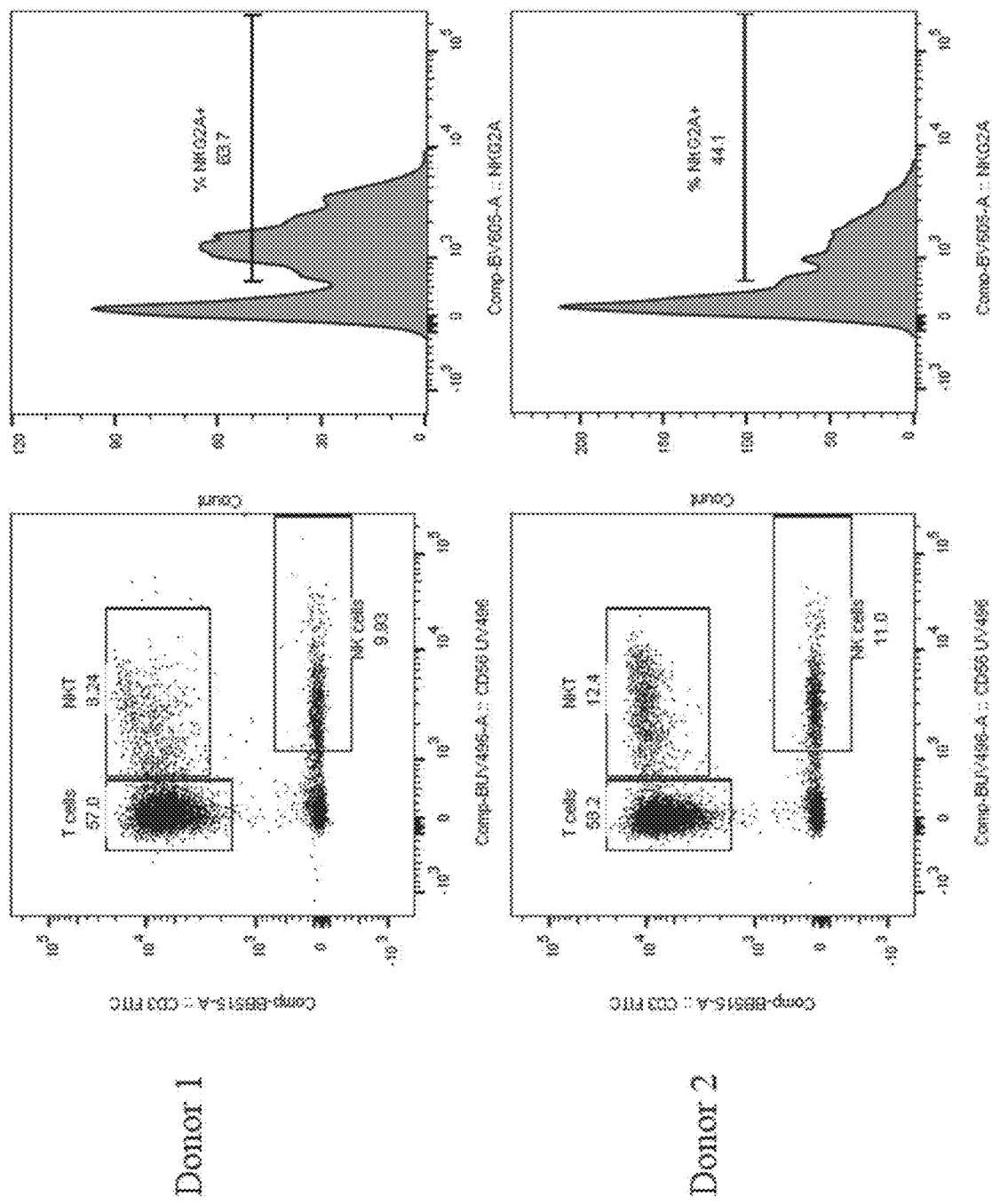
FIG. 22 shows NKG2A staining on PBMCs. PBMC samples were gated on viable lymphocytes (data not shown), followed by a gate on CD3-CD56+ cells ("NK cells"). Frequencies of NKG2A-expressing NK cells were then determined based on an FMO.

HLA-E binds the heterodimer CD94/NKG2A, an inhibitory receptor which is expressed on NK cells. Because CD94 can also pair with NKG2C to form an activating receptor, it was not assessed here. Frequency of NKG2A-expressing NK cells within a PBMC milieu was measured on two donors. Cryopreserved PBMC were thawed and stained for cells expressing NK cell markers ($CD3^-CD56^-CD16^{+/-}$) and frequencies of NKG2A-expressing NK cells assessed. In donor 1, 63.7% of NK cells expressed NKG2A while donor 2 contained 44.1% $NKG2A^+$ NK cells. (FIG. 22). PBMC samples were gated on viable lymphocytes, followed by a gate on CD3-CD56+ cells ("NK cells"). Frequencies of NKG2A-expressing NK cells were then determined based on an FMO.

Figure 23:
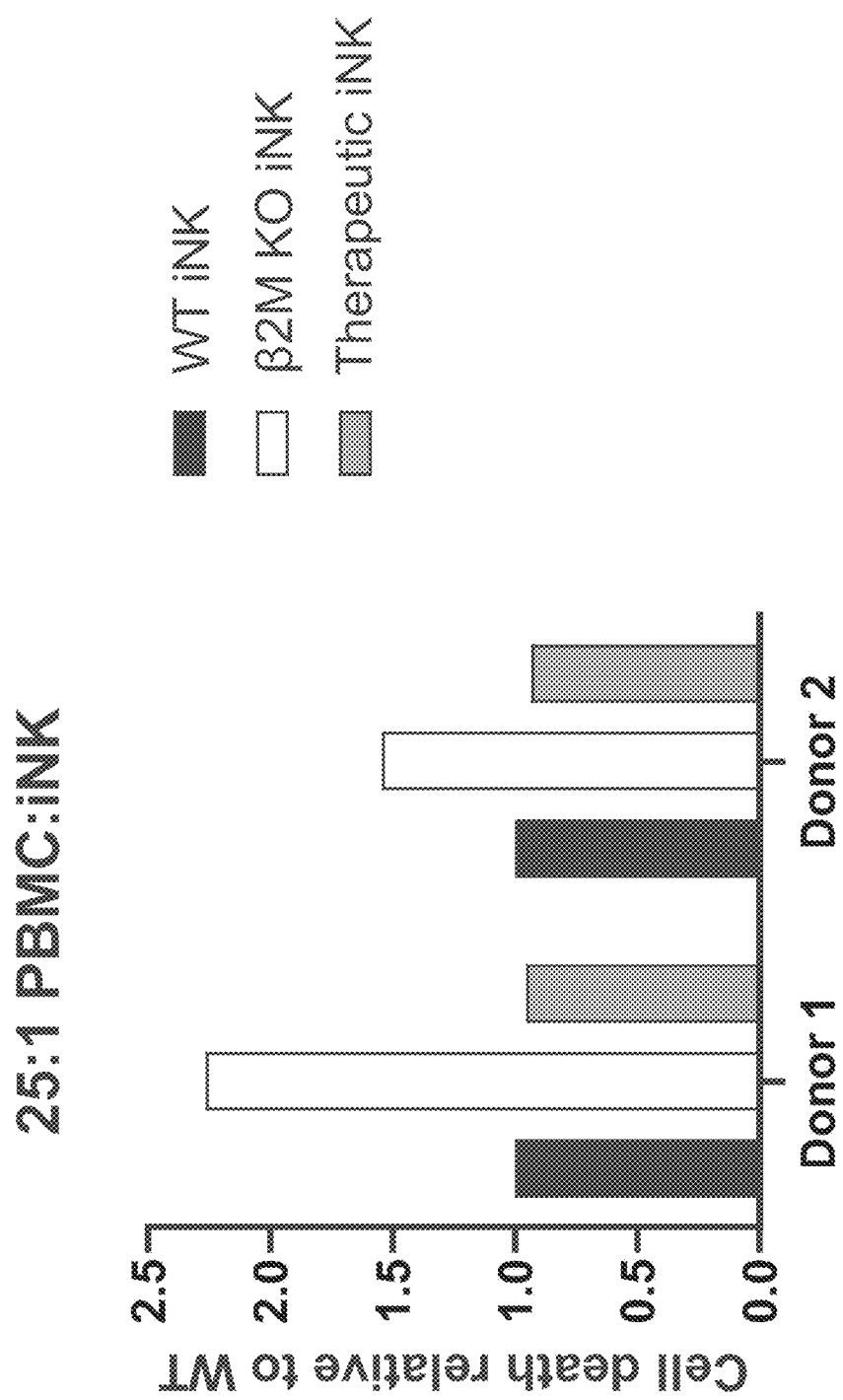
FIG. 23 shows cell death of therapeutic iNK cells (gray bars) relative to WT (black bars) compared with iNK lacking β2M (white bars). Freshly thawed PBMC were co-cultured with therapeutic iNK at a 25:1 E:T ratio in the presence of 10 ng/mL IL-15 for 72 hours and cell death of edited iNK relative to WT determined. Each data point is a mean of triplicate wells.

Donor mis-matched PBMC and edited iNK cells were incubated at a 25:1 E:T ratio for 72 hours, and iNK cell viability measured by flow cytometry. iNK cells lacking surface HLA (b2M KO, white bars) exhibited an approximate 2.25 and 1.5-fold increase in cell death relative to WT (black bars) in PBMC co-cultures with donors 1 and 2, respectively. Therapeutic iNK cells, which express HLA-E, reduced cell death to the level of WT iNK (gray bars) (FIG. 23 and Table 7). Freshly thawed PBMC were co-cultured with therapeutic iNK at a 25:1 E:T ratio in the presence of 10 ng/mL IL-15 for 72 hours and cell death of edited iNK relative to WT determined as described in methods. Each data point is a mean of triplicate wells.

TABLE 7

Percent cell death in PBMC: Therapeutic iNK co-cultures

|         | WT iNK       | b2M KO iNK   | Therapeutic iNK |
|---------|--------------|--------------|-----------------|
| Donor 1 | 19.63 ± 0.91 | 44.47 ± 2.1  | 18.8 ± 4.6      |
| Donor 2 | 25.67 ± 0.67 | 39.67 ± 2.1  | 24.0 ± 0.95     |

Mean cell death ± standard deviation

Example 15. In Vivo Evaluation of Anti-Tumor Efficacy of iNK Cells

The purpose of this study is to evaluate the in vivo anti-tumor efficacy of cryopreserved iPSC611 CD19iNK cells. A secondary purpose of this study is to evaluate single-dose 7-day persistence of cryopreserved iPSC611 CD19iNK.

Animals

For this study, female NSG (NOD·Cg-Prkdc$^{scid}$ Il2rg$^{tm1Wjl}$/SzJ) mice (Jackson Labs, Bar Harbor, Me., USA), were used. At study initiation, mice were 7-9 weeks of age, and initial body weight was an average of 23 grams. Animals were acclimated for one week prior to any experimental procedures being performed.

Autoclaved water and irradiated food (Laboratory Autoclavable Rodent Diet 5010, Lab Diet) were provided ad libitum, and the animals were maintained on a 12-hour light and dark cycle. Cages, bedding, and water bottles were autoclaved before use and changed biweekly. The experiment was carried out in accordance with The Guide for the Care and Use of Laboratory Animals.

Tumors

NALM6-Fluc-Puro (ALL) tumor cells (Imanis Life Sciences, CL151) were maintained in RPMI 1640 medium with 10 mM HEPES, 2.5 µg/mL Puromycin, and 10% (v/v) HI FBS. Each mouse received $1\times10^5$ NALM6-Fluc-Puro cells in serum-free RPMI 1640 medium in a total volume of 0.2 mL.

Efficacy Study Design & Treatment

The tumor cell implant day was designated as Study Day 0. NALM6-Fluc-Puro tumor cells were intravenously implanted, and mice randomized into treatment groups of N=10 by bioluminescent signal (range 64,120-141,400 p/s/cm$^2$/sr; mean=92,649±19,925 p/s/cm$^2$/sr).

On Days 1, 8, and 15 following i.v. NALM6-Fluc-Puro tumor cell implantation, mice were intravenously injected with $10\times10^6$ or $15\times10^6$ cryopreserved iPSC611 therapeutic iNK cells thawed and resuspended in Lactated Ringer's/5% Human Serum Albumin (Groups 2, 3), in a volume of 0.2 mL. Group 1 remained as an untreated control (Table 8, Efficacy Study Design).

TABLE 8

Efficacy Study Design

| Group | N  | Treatment | Dose Level (cells/mouse) | Preparation |
|-------|----|-----------|--------------------------|-------------|
| 1     | 10 | N/A       | 0                        | N/A         |
| 2     | 10 | iPSC611   | $10\times10^6$           | Cryogenic   |
| 3     | 10 |           | $15\times10^6$           |             |

All mice received intraperitoneal recombinant human IL-2 (PeproTech® 200-02) on Days 1, 2, 4, 7, 8, 10, 12, 15, 17, 19, 21, 23, 25, and 28, at a dose of 100,000 international units (IU) per mouse in 0.2 mL. Briefly, lyophilized rhIL-2 (1 mg) is centrifuged at 2000 g for 1 minute, resuspended and solubilized in 1 mL 100 mM acetic acid, then mixed with 4 mL 0.1% BSA in PBS. 1 mL aliquots are frozen at −80° C. until use, at which point the aliquot is thawed at ambient temperature and mixed with 3 mL PBS for a final concentration of 500,000 IU/mL.

Tumor burden was assessed by bioluminescent imaging using an IVIS Lumina S5 (Perkin Elmer®). Briefly, mice were injected i.p. with 150 mg/kg D-Luciferin (VivoGlo™ Luciferin, Promega™), anesthetized via 2.5-3.5% vaporized isoflurane in oxygen, and imaged on automatic exposure ventrally and dorsally 20 minutes post-luciferin injection. Total whole-body bioluminescence is calculated by adding the average radiance of ventral and dorsal images.

Animal body weight and bioluminescence were monitored twice weekly. Animals were monitored daily for clinical signs. Individual animals were removed from the study and humanely euthanized when in moribund condition, or when an animal lost ≥20% of the original body weight for three consecutive measurements.

In some instances, supportive nutrition and hydration was provided, to ensure wellness of the mice on study. All mice were provided with HydroGel® ad libitum on the day of treatment (Days 1, 8, and 15).

Persistence Study

An additional cohort of satellite animals was designated for tissue sampling to evaluate single dose persistence of iPSC611 cells. 10 female NSG mice were intravenously implanted with NALM6-Fluc-Puro cells as described previously, on Day 0. On Day 1, mice received a single intravenous injection of $15\times10^6$ cryogenic iPSC611 cells (Group 3). Group 1 remained as an untreated control Table 9, Persistence Study Design). All animals received recombinant human IL-2, dosed as described previously, on Days 1, 3, 5, and 7.

TABLE 9

Persistence Study Design

| Group* | N | Treatment | Dose Level (cells/mouse) | Preparation |
|--------|---|-----------|--------------------------|-------------|
| 1      | 5 | N/A       | 0                        | N/A         |
| 3      | 5 | iPSC611   | $15\times10^6$           | Cryogenic   |

*Groups numbered to match those of efficacy study

On Day 8, all mice on study plus one naïve age-matched mouse, were humanely euthanized and sampled. Whole blood was collected via cardiac puncture into lithium heparin-coated tubes (BD 365965). Lungs were flushed with PBS through the right ventricle in situ, trimmed, and placed into 2.4 mL 1× Buffer S (Miltenyi Biotech GmbH, 130-095-927) on wet ice until processing. Cervical lymph nodes were harvested and placed into 2.4 mL 1× Buffer S on wet ice until processing.

Blood was processed by transferring to a 96 well 2 mL deep well plate containing 1.5 mL of PBS. The plate was centrifuged for 5 min at 300 g and supernatant was decanted. The cell pellets were resuspended in 750 µL of ACK lysis solution and incubated at room temp for 5 min, at which point 750 µL of PBS was added to each well. The plate was centrifuged for centrifuged for 5 min at 300 g and supernatant was decanted. ACK lysis was repeated 2× as described above. After completion of ACK lysis the resulting Cell pellets were resuspended in 1500 of PBS and transferred to a 96 well U bottom plate for FACS staining and analysis.

TABLE 10

FACS Reagents

| | Clone | Fluorophore | Supplier | catalog # | lot # | Dilution |
|---|---|---|---|---|---|---|
| LIVE/DEAD ™ Fixable Near-IR viability dye | | Near-IR | | L34976A | | 1:1000 |
| Fc Receptor Blocker | | | Innovex | NB309 | | 1:2 |
| CD45 | HI30 | BV421 | Biolegend | 304032 | B286533 | 1:20 |
| CD56 | 5.1H11 | BV786 | Biolegend | 362550 | B303958 | 1:20 |

Tissues were processed using the Miltenyi Biotech GmbH Lung Dissociation Kit. Briefly, 1× Buffer S was prepared by mixing 1 mL 20× Buffer S with 19 mL sterile water. Enzyme D was reconstituted with 3 mL 1× Buffer S, using gentle inversion every minute until solubilized. Enzyme A was reconstituted with 1 mL 1× Buffer S, using gentle inversion every minute until solubilized. Tissues were individually collected into 1× Buffer S in gentleMACS C Tubes. Immediately prior to processing, 100 μL of Enzyme D and 15 μL of Enzyme A were added to each tube. Tubes were placed on the gentleMACS Dissociator on program "m_lung_01." The tubes were then placed in incubation at 37 C on the MACS-mix Tube Rotator for 30 minutes, followed by further mechanical dissociation using the gentleMACS Dissociator on program "m_lung_02." Samples were then filtered through a MACS SmartStrainer (70 μm) placed on a 50 mL tube and washed with 10 mL PBS. The suspension was centrifuged at 300×g for 10 minutes, supernatant aspirated, and cell pellet resuspended in PBS at $10 \times 10^6$ cells/mL for plating, staining, and FACS analysis.

Cell suspensions from blood, lung and cervical lymph nodes were plated at approximately 1e6 cells per well in a 96-well U-bottom plate (BD falcon 353077). All wash steps carried out by centrifugation at 300×G for 3 min and flicking supernatants into the sink. Cells were washed 2× in PBS and stained with 50 μl of a 1:1000 dilution (in PBS) of LIVE/DEAD™ Fixable Near-IR viability dye (thermo Fisher) for 15 min at room temperature (RT). 500 of Fc Receptor Blocker (Innovex NB309) was added to each well and incubated for 20 minutes at 4° C. Cells were washed 2× in BD FACS stain buffer BSA (BD). A staining cocktail were made by diluting the mAbs for CD45 and CD56 1:20 in BD FACS Stain buffer. Cells were stained with 500 of staining cocktail and incubated for 30 min at 4 C protected from light. Cells were washed 2× using BD FACS Stain buffer fixed in 100 μl of BD Stabilizing fixative. All samples were run with the same voltage on the BD Symphony A3 Lite collecting all events. Flow cytometry data was analyzed using FlowJo 10.7.2.

iNK cells were defined as live singlets that were CD45+ and CD56+ and represented as #iNK cells per 100K live lymphocytes. The lower limit of detection (LLOD) was defined as maximum+1 standard deviation (SD) of the control group that received no iNK treatment. Samples above the LLOD were plotted in graph pad Prism.

Analysis

Body weights are graphically represented as percent change in mean group body weight, using the formula: where 'W' represents mean body weight of the treated group on a particular day, and '$W_0$' represents mean body weight of the same treated group at initiation of treatment.

Percent tumor growth inhibition (TGI) is defined as the difference between whole body average radiance of the treated and control groups, calculated as % TGI=(I−T/C) 100 where T is the average radiance of the treatment group and C is the average radiance of the control group.

For survival assessment, results are plotted as the percentage survival against days post-tumor implantation. Adverse clinical signs indicating excessive tumor burden (such as ruffled/matted fur, hunched posture, inactivity, or hind limb weakness) are used as a surrogate endpoint for death. Median survival is determined utilizing Kaplan Meier survival analysis.

The percent increased lifespan (ILS) is calculated as % ILS=$S_T/S_C$, where $S_T$ is the median survival day of the treatment group and $S_C$ is the median survival day of the control group. Animals failing to reach the surrogate endpoint due to adverse clinical signs or death unrelated to treatment or tumor burden, are censored for the survival assessment.

Tumor bioluminescent data, body weight, survival, and persistence were graphically represented and statistically analyzed utilizing GraphPad Prism software (Version 9.0.1). Statistical significance for tumor bioluminescence was evaluated using an ordinary two-way analysis of variance (ANOVA) and Tukey multiple comparisons, with a 95% confidence interval. Differences between groups were considered significant when the probability value (p) was ≤0.05. Statistical significance for probability of survival was evaluated using a Mantel-Cox test with a Gehan-Breslow-Wilcoxon test. Statistical significance for persistence was evaluated using an ordinary one-way analysis of variance (ANOVA) and Tukey multiple comparisons, with a 95% confidence interval. Differences between groups were considered significant when the probability value was ≤0.05.

Results

Cryogenic iPSC611 cells were well-tolerated as determined by body weight and clinical observations. iPSC611 demonstrated significant anti-tumor efficacy at both dose levels. Enhanced increased life span was observed in mice treated with iPSC611 cells. Cryogenic iPSC611 had limited in vivo persistence one week post-injection.

Figure 24:
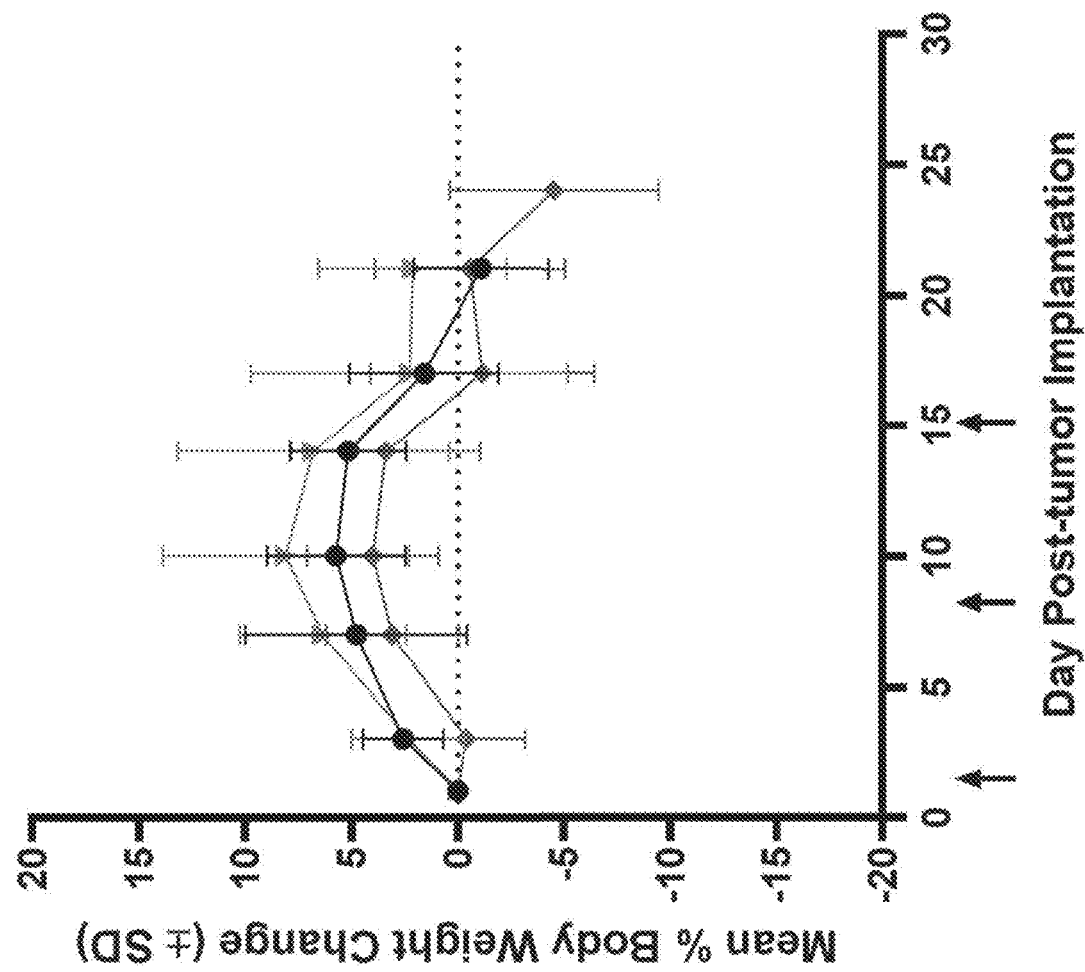
FIG. 24 shows mean percent body weight change of untreated mice (•), or mice treated intravenously with iPSC611 at $10\times10^6$ (▼) and $15\times10^6$ (♦) (cryogenic) cells. Means are plotted where ≥50% of the treatment group are present. Arrows represent dosing days.

Group mean body weight changes of NALM6-Fluc-Puro tumor-bearing mice treated with iPSC611 cells or tumor alone control, are graphically represented in FIG. 24 (Mean percent body weight change of untreated mice (•), or mice treated intravenously with iPSC611 at $10 \times 10^6$ (▼) and $15 \times 10^6$ (♦) (cryogenic) cells). Means are plotted where ≥50% of the treatment group are present. Arrows represent dosing days. No significant body weight loss (>10% loss from the start of treatment) was observed in any group receiving iPSC611 cells or in the tumor alone control.

Figure 25:
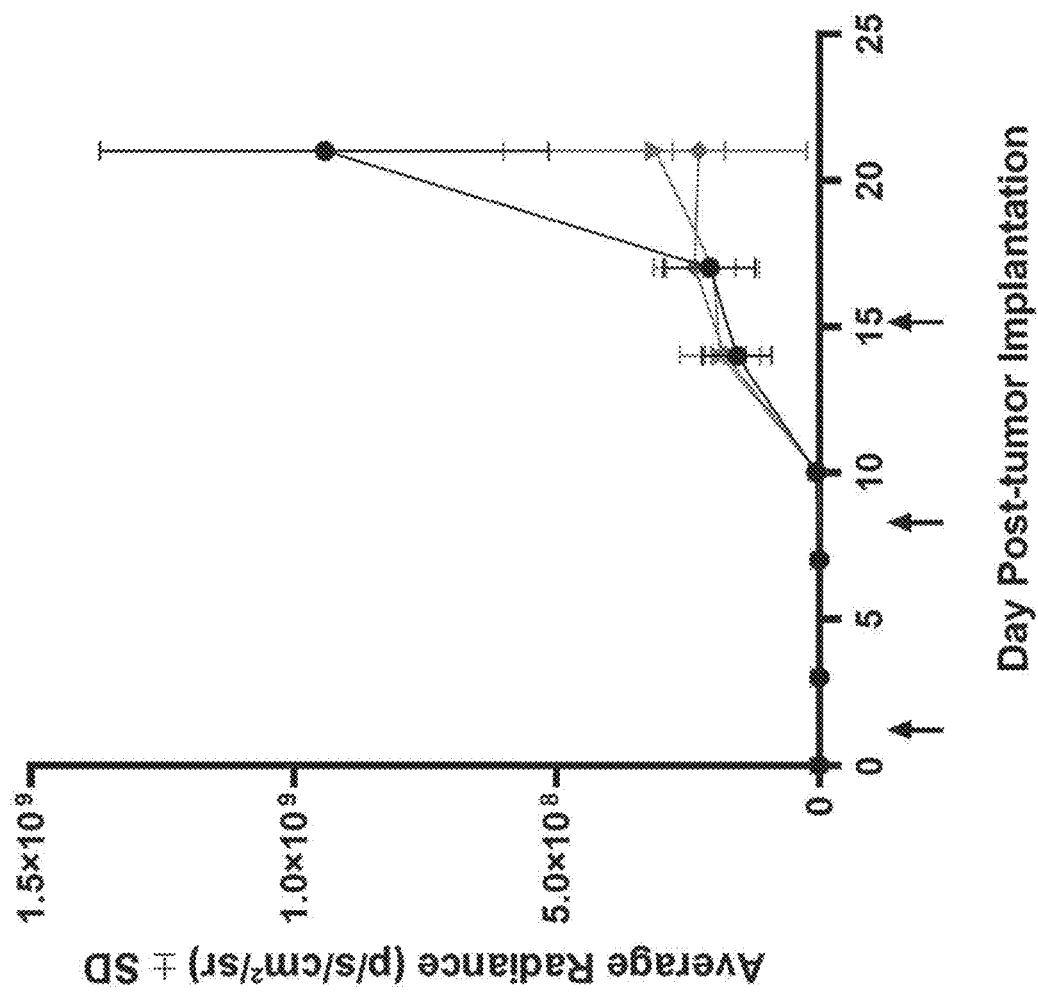
FIG. 25 shows mean whole body average radiance of untreated mice (•), and mice treated intravenously weekly for three doses with iPSC611 at $10\times10^6$ (▼) and $15\times10^6$ (♦) (cryogenic) cells. Groups are plotted until Day 21, the last imaging timepoint where the untreated control group remained and the timepoint at which % TGI was calculated. Arrows represent dosing days.

Statistically significant anti-tumor activity was observed with iPSC611 at $10 \times 10^6$ and $15 \times 10^6$ cryogenic cells (Table 11). Tumor growth is represented in FIG. 25 (Mean whole body average radiance of untreated mice (•), and mice treated intravenously weekly for three doses with iPSC611 at $10 \times 10^6$ (▼) and $15 \times 10^6$ (♦) (cryogenic) cells). Groups are plotted until Day 21, the last imaging timepoint where the untreated control group remained and the timepoint at which % TGI was calculated. Arrows represent dosing days.

TABLE 11

Tumor Growth Inhibition of iPSC611 in the Intravenous NALM6 Xenograft Model

| Treatment | $10 \times 10^6$ cryogenic cells/mouse | | $15 \times 10^6$ cryogenic cells/mouse | |
|---|---|---|---|---|
| | p-value | TGI (%) | p-value | TGI (%) |
| iPSC611 | 0.0230 | 66.7 | 0.0089 | 75.6 |

$^a$ Only p-values ≤ 0.05 (significant with 95% confidence interval) are reported.
NS = not significant;
TGI = tumor growth inhibition.

Figure 26:
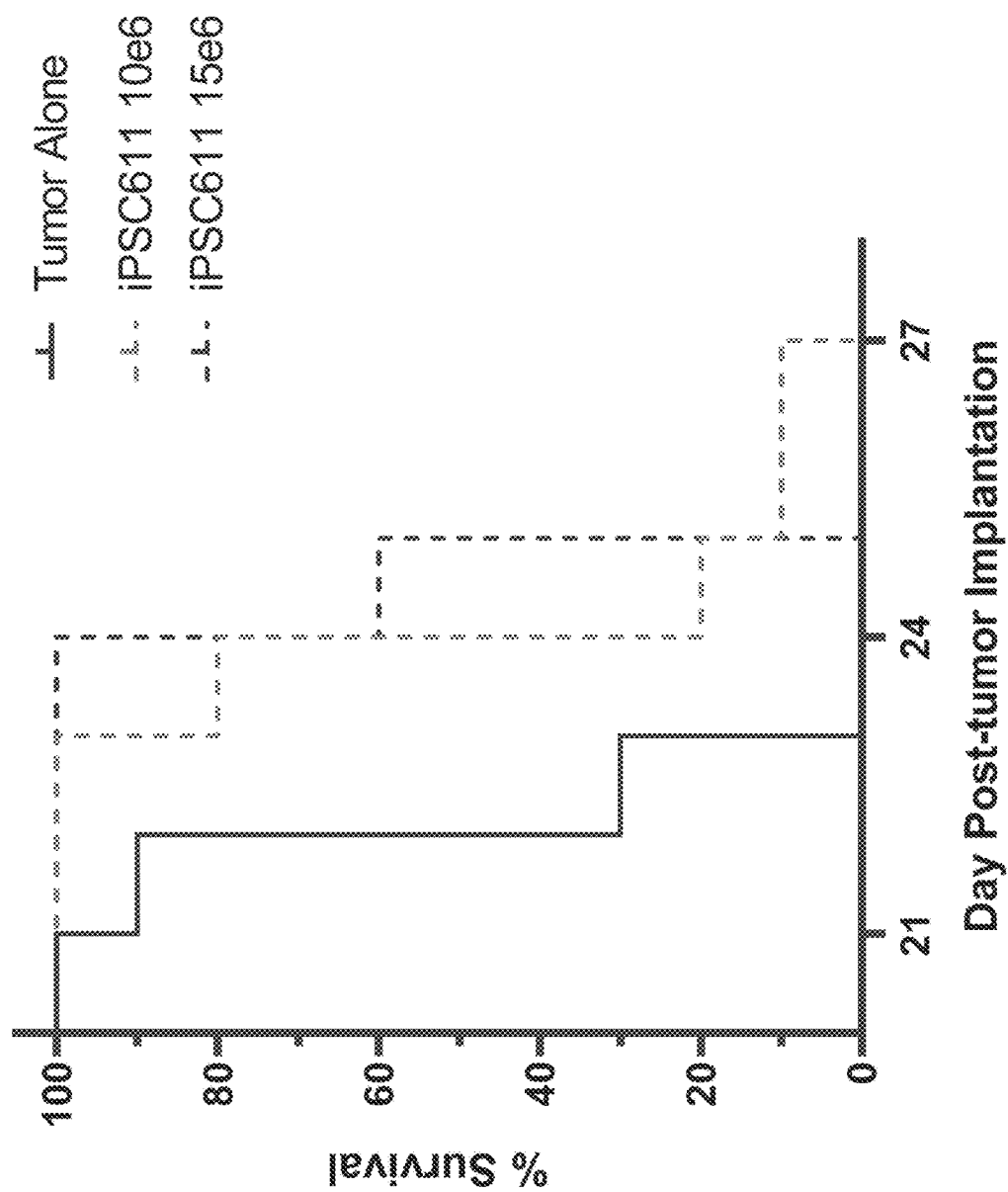
FIG. 26 shows percent survival of NALM6-bearing mice treated with iPSC611. Mice were left untreated, or treated intravenously weekly for three doses with iPSC611 at $10\times10^6$ and $15\times10^6$ cryogenic cells. Mice were humanely euthanized when in moribund condition and exhibiting signs of excessive tumor burden, as a surrogate for survival.

Percent Increased Life Span (% ILS) was calculated for all treatment groups. Enhanced survival over tumor alone control was observed for groups receiving iPSC611 at $10 \times 10^6$ and $15 \times 10^6$ cryogenic cells (Table 12, FIG. 26).

TABLE 12

Percent Increased Life Span for NALM6-bearing mice treated with iPSC611

| Treatment | Condition | Dose | % ILS |
|---|---|---|---|
| iPSC611 | Cryogenic | $10 \times 10^6$ | 109.1 |
| | | $15 \times 10^6$ | 113.6 |

Persistence of fresh and cryogenic iPSC611 was evaluated in blood and tissue, one week following injection of iNK into NALM6 tumor-bearing mice. Poor recovery of live cells was observed for cervical lymph node samples. Therefore, these were not analyzed.

Figure 27:
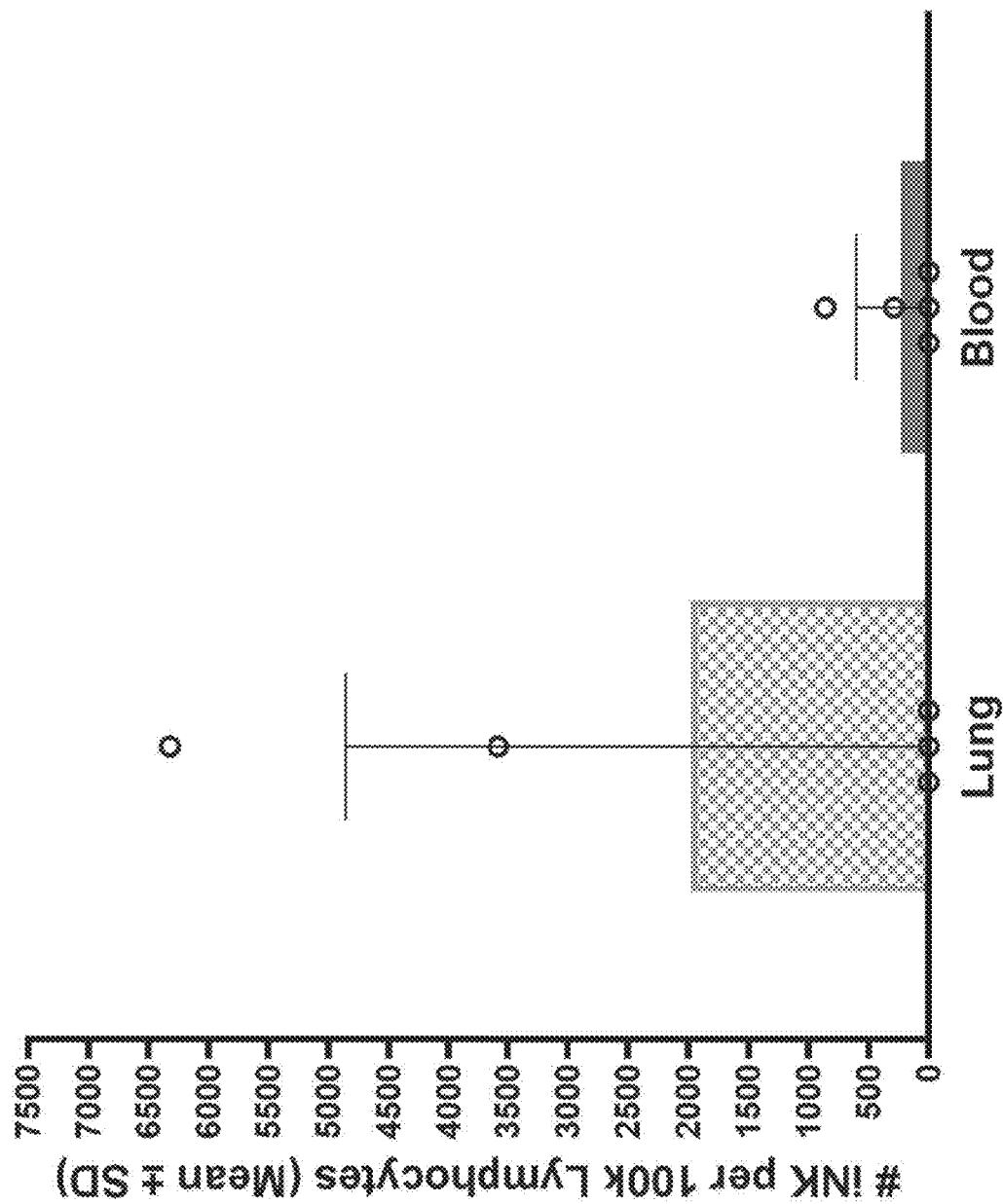
FIG. 27 shows persistence of iPSC611 in lungs and blood of NALM6-bearing mice. Mice were left untreated, or received a single intravenous dose of iPSC611 at $15\times10^6$ cryogenic cells. One-week post-injection, lungs and blood were harvested for FACS analysis. Number of iNK per 100,000 lymphocytes is plotted for individual mice (o), and average per group represented by bars.

FACS analysis of lungs and blood indicated limited persistence of cryogenic iPSC611 (FIG. 27). Mice were left untreated, or received a single intravenous dose of iPSC611 at $15 \times 10^6$ cryogenic cells. One-week post-injection, lungs and blood were harvested for FACS analysis. Number of iNK per 100,000 lymphocytes is plotted for individual mice (o), and average per group represented by bars. iNK were detected in lungs and blood of two of the five mice injected with iPSC611, one week post-injection.

Example 16. In Vivo Evaluation of Elimination of iNK Cells

The purpose of this study is to evaluate the in vivo elimination of cryopreserved iPSC611 CD19iNK cells, using Erbitux (cetuximab).
Animals
For this study, female NSG (NOD.Cg-Prkdc$^{scid}$ Il2rg$^{tm1Wjl}$/SzJ) mice (Jackson Labs, Bar Harbor, Me., USA), were used. At study initiation, mice were 10-12 weeks of age, and initial body weight was an average of 24.3 grams. Animals were acclimated for one week prior to any experimental procedures being performed.

Autoclaved water and irradiated food (Laboratory Autoclavable Rodent Diet 5010, Lab Diet) were provided ad libitum, and the animals were maintained on a 12-hour light and dark cycle. Cages, bedding, and water bottles were autoclaved before use and changed biweekly. The experiment was carried out in accordance with The Guide for the Care and Use of Laboratory Animals.
Study Design and Treatment Mice were randomized into groups of N=5 by body weight (range 23.1-25.7 grams; mean=24.3±0.85 grams) (Table 13, Study Design).

The iPSC611 cell implant day was designated as Study Day 1. On Day 1, mice were intravenously injected with $15 \times 10^6$ cryopreserved iPSC611 cells thawed and resuspended in Lactated Ringer's/5% Human Serum Albumin (Groups 2, 3), in a volume of 0.2 mL. Group 1 remained as an untreated control.

All mice in Groups 1, 2, and 3 received intraperitoneal recombinant human IL-2 (PeproTech® 200-02) on Days 1 and 3, at a dose of 100,000 international units (IU) per mouse in 0.2 mL. Briefly, lyophilized rhIL-2 (1 mg) is centrifuged at 2000 g for 1 minute, resuspended and solubilized in 1 mL 100 mM acetic acid, then mixed with 4 mL 0.1% BSA in PBS. 1 mL aliquots are frozen at −80° C. until use, at which point the aliquot is thawed at ambient temperature and mixed with 3 mL PBS for a final concentration of 500,000 IU/mL.

On Days 2 and 3, mice received intraperitoneal antibody therapy. Group 2 was dosed with 20 mL/kg PBS, IP. Group 3 was dosed with 40 mg/kg cetuximab in a volume of 20 mL/kg, IP.

Animal body weight was recorded daily. Animals were monitored daily for clinical signs.

TABLE 13

Study Design

| | | Day 1 | Day 2 and 3 Treatment (IP) | | |
|---|---|---|---|---|---|
| Group | N | CD19iNK (IV) | Agent | Dose Level (mg/kg) | rhIL-2 (IP) |
| 1 | 2 | N/A | N/A | N/A | + |
| 2 | 5 | iPSC611 | PBS | 0 | + |
| 3 | 5 | $15 \times 10^6$ cells/mouse | cetuximab | 40 | + |

IV = intravenous
IP = intraperitoneal
+ = dosed

Sampling

On Day 5, all mice on study were humanely euthanized and sampled. Blood was collected via cardiac puncture into Lithium Heparin coated tubes (BD Microtainer 365965). Lungs were flushed with PBS through the right ventricle in situ, trimmed, and placed into PBS+2% FBS on wet ice until processing.

Blood was processed through 2 rounds of ACK lysis following the following protocol. Blood was transferred to a 2 ml deep well plate and tubes rinsed with 1 ml of PBS. Deep well was centrifuged for 3 min at 300×G. The supernatant was removed and 1 mL of ACK added to each well. The plate was incubated for 2 minutes and then 1 mL of PBS was added to stop osmotic lysis. The plate was centrifuged for 3 minutes at 300×G and supernatant was removed. ACK lysis was repeated 1-2 more times as needed. Samples were resuspended in 200 µL of BD FACS stain buffer and transferred to a 96 well U-bottom plate for staining Lungs were processed to a single-cell suspension using mechanical dissociation and gentle enzymatic digestion. Briefly, lung tissue was transferred into a dish without medium, and minced into a homogenous paste (<1 mm in size) using a razor blade or scalpel. Minced tissue was transferred to 2 mL digestion medium containing 10% Collagenase/Hyaluronidase, 15% DNase I Solution (1 mg/mL), and 75% RPMI 1640 Medium, and incubated at 37° C. for 20 minutes on a shaking platform. The tissue was then passed through a 70 µm nylon mesh strainer over a 50 mL conical tube using the rubber end of a syringe plunger to obtain a cell suspension. The suspension was passed through a new 70 µm nylon mesh strainer over a 50 mL conical tube to filter, and rinsed with 10 mL RPMI. The cell suspension was transferred into a 15 mL conical tube and centrifuge at 500×G for 10 minutes at room temperature with the brake on low. Supernatant was removed and discarded. Cells were resuspended in 10 mL of PBS and counted, adjusted to $10 \times 10^6$ cells/mL, and underwent one ACK lysis step before plating, staining, and FACS analysis.

TABLE 14

FACS Reagents

| | Clone | Fluorophore | Supplier | catalog # | lot # | Dilution |
|---|---|---|---|---|---|---|
| LIVE/DEAD ™ Fixable Near-IR viability dye | | Near-IR | | L34976A | | 1:1000 |
| Fc Receptor Blocker | | | Innovex | NB309 | | 1:2 |
| CD45 | HI30 | BV421 | Biolegend | 304032 | B286533 | 1:20 |
| CD56 | 5.1H11 | BV786 | Biolegend | 362550 | B303958 | 1:20 |

Cell suspensions from lung were plated at approximately 1e6 cells per well in a 96-well U-bottom plate (BD falcon 353077). All wash steps carried out by centrifugation at 300×G for 3 minutes and flicking supernatants into the sink. Cells were washed 2× in PBS and stained with 50 µl of a 1:1000 dilution (in PBS) of LIVE/DEAD™ Fixable Near-IR viability dye (thermo Fisher) for 15 minutes at room temperature (RT). 50 µl of Fc Receptor Blocker (Innovex NB309) was added to each well and incubated for 20 minutes at 4° C. Cells were washed 2× in BD FACS stain buffer BSA (BD). A staining cocktail were made by diluting the mAbs for CD45 and CD56 1:20 in BD FACS Stain buffer. Cells were stained with 50 µl of staining cocktail and incubated for 30 minutes at 4° C. protected from light. Cells were washed 2× using BD FACS Stain buffer fixed in 100 µl of BD Stabilizing fixative. All samples were run with the same voltage on the BD Symphony A3 Lite collecting all events. Flow cytometry data was analyzed using FlowJo 10.7.2.

iNK cells were defined as live singlets that were CD45+ and CD56+ and represented as #iNK cells per 100K live lymphocytes. The lower limit of detection (LLOD) was defined as maximum+1 standard deviation (SD) of the control group that received no iNK treatment. Samples above the LLOD were plotted in graph pad Prism.

Analysis

Body weights are graphically represented as percent change in mean group body weight, using the formula: where 'W' represents mean body weight of the treated group on a particular day, and '$W_0$' represents mean body weight of the same treated group at initiation of treatment.

Body weight and persistence were graphically represented and statistically analyzed utilizing GraphPad Prism software (Version 9.0.1). Statistical significance for elimination was evaluated using an unpaired one-tailed t-test with Welch's correction, with a 95% confidence interval. Differences between groups were considered significant when the probability value was ≤0.05.

Figure 28:
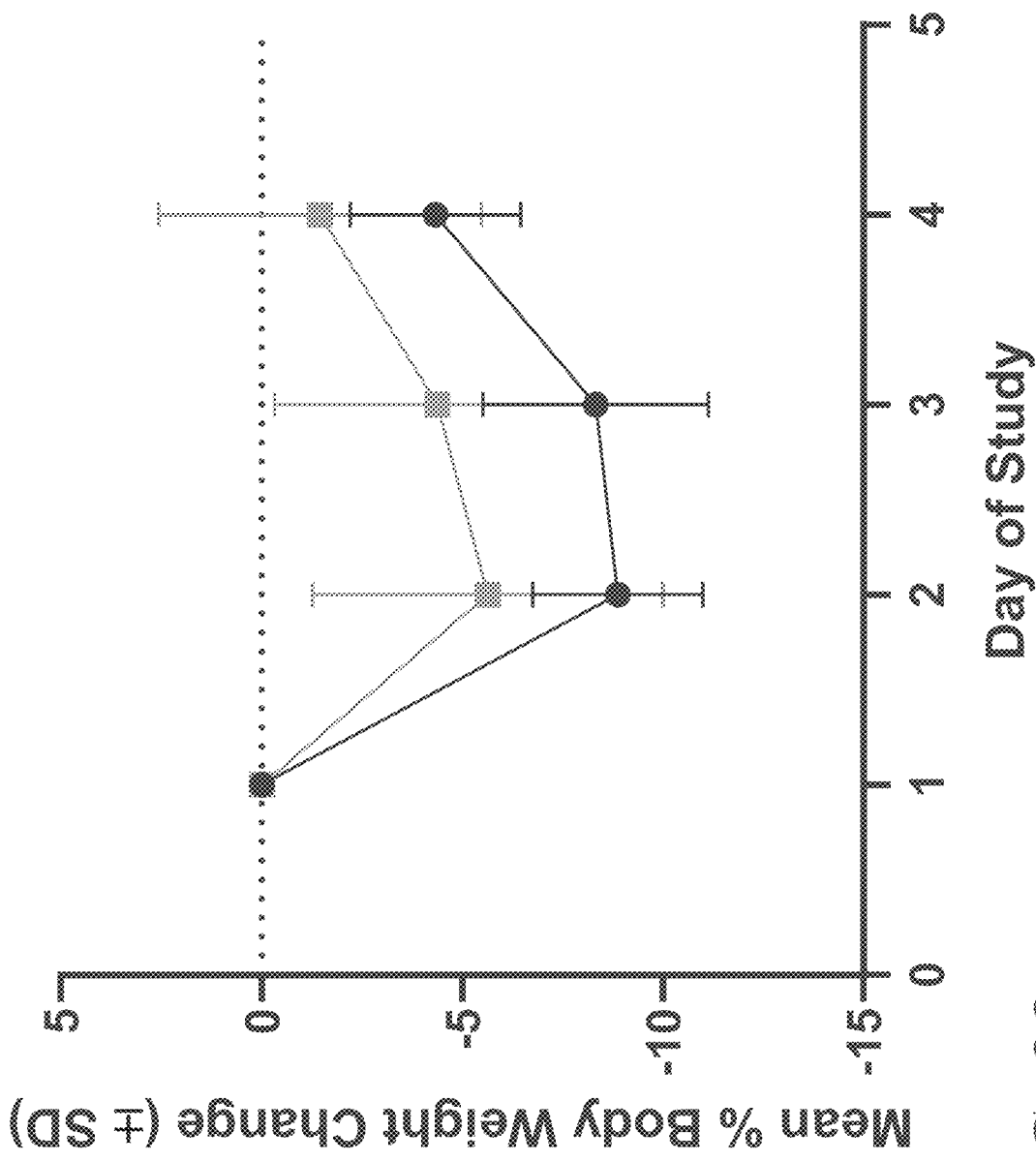
FIG. 28 shows mean percent body weight change of mice treated intravenously with iPSC611 at $15\times10^6$ cells receiving IP PBS (•), or cetuximab at 40 mg/kg (■).

Results iPSC611 cells were significantly reduced in the lungs and blood of mice that received cetuximab treatment. Group mean body weight changes of mice are graphically represented in FIG. 28 (mean percent body weight change of mice treated intravenously with iPSC611 at $15 \times 10^6$ cells receiving IP PBS (•), or cetuximab at 40 mg/kg (■)). No significant body weight loss (>10% loss from the start of treatment) was observed in any group receiving iPSC611 cells and antibody.

Figure 29:
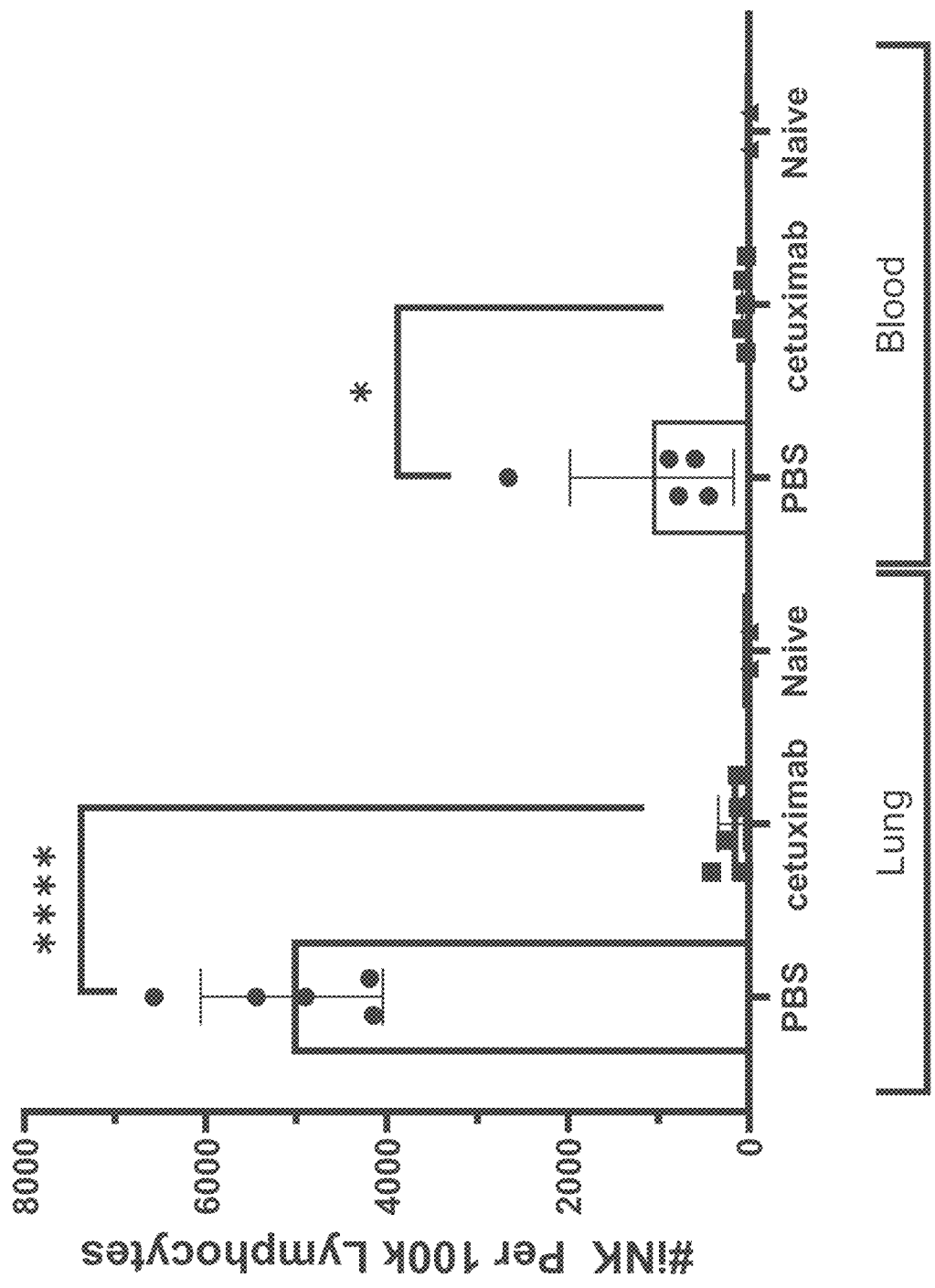
FIG. 29 shows presence of iPSC611 in lungs and blood of NSG mice. Mice were left untreated (naïve), or received a single intravenous dose of iPSC611 at $15\times10^6$ cells on Day 1. On Days 2 and 3, mice were treated IP with 20 mL/kg PBS (•), or 40 mg/kg cetuximab (■). All mice received rhIL-2 on Days 1 and 3. On Day 5, lungs and blood were sampled and processed for FACS analysis and detection of iPSC611. There was a significant 96% reduction of iNK in lungs (p=0.0002) and 95% reduction of iNK in the blood (p=0.0321) of cetuximab-treated mice. Data is represented as the Number of iNK per 100,000 lymphocytes per mouse, with mean±SD plotted.

The presence of iNK was evaluated in blood and lungs, four days following injection of iPSC611 into NSG mice. FACS analysis of lungs indicated a significant 96% reduction in number of iNK in the lungs of mice that received cetuximab versus PBS-treated mice (p=0.0002). As shown in FIG. 29, FACS analysis of blood indicated a significant 95% reduction in number of iNK in the blood of mice that received cetuximab versus PBS-treated mice (p=0.0321).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. A polynucleotide encoding an inactivated cell surface receptor that comprises a truncated epithelial growth factor receptor (tEGFR) variant comprising an amino acid sequence having at least 90% sequence identity to SEQ ID NO: 71 and an interleukin 15 (IL-15) comprising an amino acid sequence having at least 90% sequence identity to SEQ ID NO: 72, wherein the tEGFR variant and the IL-15 are operably linked by an autoprotease peptide comprising the amino acid sequence of SEQ ID NO: 73.

2. The polynucleotide according to claim 1, wherein the tEGFR variant consists of the amino acid sequence of SEQ ID NO: 71.

3. The polynucleotide according to claim 1, wherein the IL-15 consists of the amino acid sequence of SEQ ID NO: 72.

4. The polynucleotide according to claim 1, wherein the autoprotease peptide consists of the amino acid sequence of SEQ ID NO: 73.

5. The polynucleotide according to claim 1 consisting of operably linked polynucleotides encoding the tEGFR variant having the amino acid sequence of SEQ ID NO: 71, the autoprotease peptide having the amino acid sequence of SEQ ID NO: 73, and the IL-15 having the amino acid sequence of SEQ ID NO: 72.

6. The polynucleotide of claim 1, wherein the inactivated cell surface receptor comprises the amino acid sequence of SEQ ID NO: 74.

7. A protein encoded by the polynucleotide according to claim 1.

8. An induced pluripotent stem cell (iPSC) or a derivative cell thereof comprising the polynucleotide of claim 1.

9. A vector comprising the polynucleotide according to claim 1.

10. The vector according to claim 9, wherein the vector further comprises:
   (i) a promoter;
   (ii) a terminator and/or a polyadenylation signal sequence;
   (iii) a left homology sequence comprising a polynucleotide sequence having at least 90% sequence identity to the polynucleotide sequence of SEQ ID NO: 84; and
   (iv) a right homology sequence comprising a polynucleotide sequence having at least 90% sequence identity to the polynucleotide sequence of SEQ ID NO: 85.

11. The vector according to claim 10, wherein the vector comprises a polynucleotide sequence having at least 90% sequence identity to SEQ ID NO: 86.

* * * * *

SEQUENCE LISTING

<160> NUMBER OF SEQ ID NOS: 95

<210> SEQ ID NO 1
<211> LENGTH: 22
<212> TYPE: PRT
<213> ORGANISM: Homo sapiens

<400> SEQUENCE: 1

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 2
<211> LENGTH: 120
<212> TYPE: PRT
<213> ORGANISM: Artificial Sequence
<220> FEATURE:
<223> OTHER INFORMATION: FMC63 VH

<400> SEQUENCE: 2

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 3
<211> LENGTH: 18
<212> TYPE: PRT
<213> ORGANISM: Artificial Sequence
<220> FEATURE:
<223> OTHER INFORMATION: Whitlow Linker

<400> SEQUENCE: 3

Gly Ser Thr Ser Gly Ser Gly Lys Pro Gly Ser Gly Glu Gly Ser Thr
1               5                   10                  15

Lys Gly

<210> SEQ ID NO 4
<211> LENGTH: 107
<212> TYPE: PRT
<213> ORGANISM: Artificial Sequence
<220> FEATURE:
<223> OTHER INFORMATION: FMC63 VL

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr

```
                20                  25                  30
Leu Asn Trp Tyr Gln Gln Lys Pro Asp Gly Thr Val Lys Leu Leu Ile
         35                  40                  45

Tyr His Thr Ser Arg Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr
                100                 105

<210> SEQ ID NO 5
<211> LENGTH: 107
<212> TYPE: PRT
<213> ORGANISM: Homo sapiens

<400> SEQUENCE: 5

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
             20                  25                  30

Phe Pro Gly Pro Ser Lys Pro Phe Trp Val Leu Val Val Val Gly Gly
         35                  40                  45

Val Leu Ala Cys Tyr Ser Leu Leu Val Thr Val Ala Phe Ile Ile Phe
     50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                 85                  90                  95

Ala Pro Pro Arg Asp Phe Ala Ala Tyr Arg Ser
                100                 105

<210> SEQ ID NO 6
<211> LENGTH: 112
<212> TYPE: PRT
<213> ORGANISM: Homo sapiens

<400> SEQUENCE: 6

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
             20                  25                  30

Asp Val Leu Asp Lys Arg Arg Gly Arg Asp Pro Glu Met Gly Gly Lys
         35                  40                  45

Pro Arg Arg Lys Asn Pro Gln Glu Gly Leu Tyr Asn Glu Leu Gln Lys
     50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
                100                 105                 110

<210> SEQ ID NO 7
<211> LENGTH: 245
<212> TYPE: PRT
```

```
<213> ORGANISM: Artificial Sequence
<220> FEATURE:
<223> OTHER INFORMATION: FMC63 scFV

<400> SEQUENCE: 7

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser Gly Ser Thr Ser Gly Ser Gly Lys
        115                 120                 125

Pro Gly Ser Gly Glu Gly Ser Thr Lys Gly Asp Ile Gln Met Thr Gln
    130                 135                 140

Thr Thr Ser Ser Leu Ser Ala Ser Leu Gly Asp Arg Val Thr Ile Ser
145                 150                 155                 160

Cys Arg Ala Ser Gln Asp Ile Ser Lys Tyr Leu Asn Trp Tyr Gln Gln
                165                 170                 175

Lys Pro Asp Gly Thr Val Lys Leu Leu Ile Tyr His Thr Ser Arg Leu
            180                 185                 190

His Ser Gly Val Pro Ser Arg Phe Ser Gly Ser Gly Ser Gly Thr Asp
        195                 200                 205

Tyr Ser Leu Thr Ile Ser Asn Leu Glu Gln Glu Asp Ile Ala Thr Tyr
    210                 215                 220

Phe Cys Gln Gln Gly Asn Thr Leu Pro Tyr Thr Phe Gly Gly Gly Thr
225                 230                 235                 240

Lys Leu Glu Ile Thr
                245

<210> SEQ ID NO 8
<211> LENGTH: 42
<212> TYPE: PRT
<213> ORGANISM: Homo sapiens

<400> SEQUENCE: 8

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 9
<211> LENGTH: 94
<212> TYPE: PRT
<213> ORGANISM: Homo sapiens

<400> SEQUENCE: 9
```

```
Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
            35                  40                  45

Ser Pro Gly Gly Leu Ala Pro Glu Ile Ser Pro Leu Glu Val Leu Glu
    50                  55                  60

Arg Asp Lys Val Thr Gln Leu Leu Pro Leu Asn Thr Asp Ala Tyr Leu
65                  70                  75                  80

Ser Leu Gln Glu Leu Gln Gly Gln Asp Pro Thr His Leu Val
                85                  90
```

```
<210> SEQ ID NO 10
<211> LENGTH: 62
<212> TYPE: PRT
<213> ORGANISM: Homo sapiens

<400> SEQUENCE: 10

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
            35                  40                  45

Glu Asp Gly Lys Glu Ser Arg Ile Ser Val Gln Glu Arg Gln
    50                  55                  60
```

```
<210> SEQ ID NO 11
<211> LENGTH: 42
<212> TYPE: PRT
<213> ORGANISM: Homo sapiens

<400> SEQUENCE: 11

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
            35                  40
```

```
<210> SEQ ID NO 12
<211> LENGTH: 25
<212> TYPE: PRT
<213> ORGANISM: Homo sapiens

<400> SEQUENCE: 12

Thr Tyr Cys Phe Ala Pro Arg Cys Arg Glu Arg Arg Asn Glu Arg
1               5                   10                  15

Leu Arg Arg Glu Ser Val Arg Pro Val
            20                  25
```

```
<210> SEQ ID NO 13
<211> LENGTH: 61
<212> TYPE: PRT
<213> ORGANISM: Homo sapiens

<400> SEQUENCE: 13

Lys Trp Lys Lys Lys Arg Pro Arg Asn Ser Tyr Lys Cys Gly Thr
1               5                   10                  15
```

```
Asn Thr Met Glu Arg Glu Glu Ser Glu Gln Thr Lys Lys Arg Glu Lys
                20                  25                  30

Ile His Ile Pro Glu Arg Ser Asp Glu Ala Gln Arg Val Phe Lys Ser
            35                  40                  45

Ser Lys Thr Ser Ser Cys Asp Lys Ser Asp Thr Cys Phe
    50                  55                  60
```

<210> SEQ ID NO 14
<211> LENGTH: 48
<212> TYPE: PRT
<213> ORGANISM: Homo sapiens

<400> SEQUENCE: 14

```
Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
                20                  25                  30

Ile Pro Ile Gln Glu Asp Tyr Arg Lys Pro Glu Pro Ala Cys Ser Pro
            35                  40                  45
```

<210> SEQ ID NO 15
<211> LENGTH: 38
<212> TYPE: PRT
<213> ORGANISM: Homo sapiens

<400> SEQUENCE: 15

```
Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
                20                  25                  30

Leu Thr Asp Val Thr Leu
            35
```

<210> SEQ ID NO 16
<211> LENGTH: 51
<212> TYPE: PRT
<213> ORGANISM: Homo sapiens

<400> SEQUENCE: 16

```
Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
                20                  25                  30

Arg Trp Gln Lys Gln Arg Cys Pro Val Val Lys Ser Lys Cys Arg Glu
            35                  40                  45

Asn Ala Ser
    50
```

<210> SEQ ID NO 17
<211> LENGTH: 24
<212> TYPE: PRT
<213> ORGANISM: Homo sapiens

<400> SEQUENCE: 17

```
Leu Cys Ala Arg Pro Arg Arg Ser Pro Ala Gln Glu Asp Gly Lys Val
1               5                   10                  15

Tyr Ile Asn Met Pro Gly Arg Gly
            20
```

<210> SEQ ID NO 18
<211> LENGTH: 52
<212> TYPE: PRT
<213> ORGANISM: Homo sapiens

<400> SEQUENCE: 18

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50

<210> SEQ ID NO 19
<211> LENGTH: 120
<212> TYPE: PRT
<213> ORGANISM: Homo sapiens

<400> SEQUENCE: 19

Trp Arg Arg Lys Arg Lys Glu Lys Gln Ser Glu Thr Ser Pro Lys Glu
1               5                   10                  15

Phe Leu Thr Ile Tyr Glu Asp Val Lys Asp Leu Lys Thr Arg Arg Asn
            20                  25                  30

His Glu Gln Glu Gln Thr Phe Pro Gly Gly Gly Ser Thr Ile Tyr Ser
        35                  40                  45

Met Ile Gln Ser Gln Ser Ser Ala Pro Thr Ser Gln Glu Pro Ala Tyr
    50                  55                  60

Thr Leu Tyr Ser Leu Ile Gln Pro Ser Arg Lys Ser Gly Ser Arg Lys
65                  70                  75                  80

Arg Asn His Ser Pro Ser Phe Asn Ser Thr Ile Tyr Glu Val Ile Gly
                85                  90                  95

Lys Ser Gln Pro Lys Ala Gln Asn Pro Ala Arg Leu Ser Arg Lys Glu
            100                 105                 110

Leu Glu Asn Phe Asp Val Tyr Ser
        115                 120

<210> SEQ ID NO 20
<211> LENGTH: 41
<212> TYPE: PRT
<213> ORGANISM: Homo sapiens

<400> SEQUENCE: 20

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 21
<211> LENGTH: 47
<212> TYPE: PRT
<213> ORGANISM: Homo sapiens

<400> SEQUENCE: 21

Thr Thr Thr Pro Ala Pro Arg Pro Pro Thr Pro Ala Pro Thr Ile Ala
1               5                   10                  15

```
Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45
```

<210> SEQ ID NO 22
<211> LENGTH: 39
<212> TYPE: PRT
<213> ORGANISM: Homo sapiens

<400> SEQUENCE: 22

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35
```

<210> SEQ ID NO 23
<211> LENGTH: 21
<212> TYPE: PRT
<213> ORGANISM: Homo sapiens

<400> SEQUENCE: 23

```
Ile Tyr Ile Trp Ala Pro Leu Ala Gly Thr Cys Gly Val Leu Leu Leu
1               5                   10                  15

Ser Leu Val Ile Thr
            20
```

<210> SEQ ID NO 24
<211> LENGTH: 27
<212> TYPE: PRT
<213> ORGANISM: Homo sapiens

<400> SEQUENCE: 24

```
Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25
```

<210> SEQ ID NO 25
<211> LENGTH: 15
<212> TYPE: PRT
<213> ORGANISM: Artificial Sequence
<220> FEATURE:
<223> OTHER INFORMATION: (GGGGS)3

<400> SEQUENCE: 25

```
Gly Gly Gly Gly Ser Gly Gly Gly Gly Ser Gly Gly Gly Gly Ser
1               5                   10                  15
```

<210> SEQ ID NO 26
<211> LENGTH: 20
<212> TYPE: PRT
<213> ORGANISM: Artificial Sequence
<220> FEATURE:
<223> OTHER INFORMATION: Linker 3

<400> SEQUENCE: 26

```
Gly Gly Ser Glu Gly Lys Ser Ser Gly Ser Gly Ser Glu Ser Lys Ser
1               5                   10                  15

Thr Gly Gly Ser
            20
```

<210> SEQ ID NO 27
<211> LENGTH: 8
<212> TYPE: PRT
<213> ORGANISM: Artificial Sequence
<220> FEATURE:
<223> OTHER INFORMATION: Linker 4

<400> SEQUENCE: 27

Gly Gly Gly Ser Gly Gly Gly Ser
1               5

<210> SEQ ID NO 28
<211> LENGTH: 12
<212> TYPE: PRT
<213> ORGANISM: Artificial Sequence
<220> FEATURE:
<223> OTHER INFORMATION: Linker 5

<400> SEQUENCE: 28

Gly Gly Gly Ser Gly Gly Gly Ser Gly Gly Gly Ser
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Linker 6

<400> SEQUENCE: 29

Gly Gly Gly Ser Gly Gly Gly Ser Gly Gly Gly Ser Gly Gly Gly Ser
1               5                   10                  15

<210> SEQ ID NO 30
<211> LENGTH: 20
<212> TYPE: PRT
<213> ORGANISM: Artificial Sequence
<220> FEATURE:
<223> OTHER INFORMATION: Linker 7

<400> SEQUENCE: 30

Gly Gly Gly Ser Gly Gly Gly Ser Gly Gly Gly Ser Gly Gly Gly Ser
1               5                   10                  15

Gly Gly Gly Ser
            20

<210> SEQ ID NO 31
<211> LENGTH: 20
<212> TYPE: PRT
<213> ORGANISM: Artificial Sequence
<220> FEATURE:
<223> OTHER INFORMATION: Linker 8

<400> SEQUENCE: 31

Gly Gly Gly Gly Ser Gly Gly Gly Gly Ser Gly Gly Gly Gly Ser Gly
1               5                   10                  15

Gly Gly Gly Ser
            20

<210> SEQ ID NO 32
<211> LENGTH: 25
<212> TYPE: PRT
<213> ORGANISM: Artificial Sequence
<220> FEATURE:
<223> OTHER INFORMATION: Linker 9

```
<400> SEQUENCE: 32

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 33
<211> LENGTH: 14
<212> TYPE: PRT
<213> ORGANISM: Artificial Sequence
<220> FEATURE:
<223> OTHER INFORMATION: Linker 10

<400> SEQUENCE: 33

Ile Arg Pro Arg Ala Ile Gly Gly Ser Lys Pro Arg Val Ala
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Linker 11

<400> SEQUENCE: 34

Gly Lys Gly Gly Ser Gly Lys Gly Gly Ser Gly Lys Gly Gly Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Linker 12

<400> SEQUENCE: 35

Gly Gly Lys Gly Ser Gly Gly Lys Gly Ser Gly Gly Lys Gly Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Linker 13

<400> SEQUENCE: 36

Gly Gly Gly Lys Ser Gly Gly Gly Lys Ser Gly Gly Gly Lys Ser
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Linker 14

<400> SEQUENCE: 37

Gly Lys Gly Lys Ser Gly Lys Gly Lys Ser Gly Lys Gly Lys Ser
1               5                   10                  15

<210> SEQ ID NO 38
<211> LENGTH: 15
<212> TYPE: PRT
<213> ORGANISM: Artificial Sequence
```

```
<220> FEATURE:
<223> OTHER INFORMATION: Linker 15

<400> SEQUENCE: 38

Gly Gly Gly Lys Ser Gly Gly Lys Ser Gly Lys Gly Gly Ser
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Linker 16

<400> SEQUENCE: 39

Gly Lys Pro Gly Ser Gly Lys Pro Gly Ser Gly Lys Pro Gly Ser
1               5                   10                  15

<210> SEQ ID NO 40
<211> LENGTH: 20
<212> TYPE: PRT
<213> ORGANISM: Artificial Sequence
<220> FEATURE:
<223> OTHER INFORMATION: Linker 17

<400> SEQUENCE: 40

Gly Lys Pro Gly Ser Gly Lys Pro Gly Ser Gly Lys Pro Gly Ser Gly
1               5                   10                  15

Lys Pro Gly Ser
            20

<210> SEQ ID NO 41
<211> LENGTH: 20
<212> TYPE: PRT
<213> ORGANISM: Artificial Sequence
<220> FEATURE:
<223> OTHER INFORMATION: Linker 18

<400> SEQUENCE: 41

Gly Lys Gly Lys Ser Gly Lys Gly Lys Ser Gly Lys Gly Lys Ser Gly
1               5                   10                  15

Lys Gly Lys Ser
            20

<210> SEQ ID NO 42
<211> LENGTH: 14
<212> TYPE: PRT
<213> ORGANISM: Artificial Sequence
<220> FEATURE:
<223> OTHER INFORMATION: Linker 19

<400> SEQUENCE: 42

Ser Thr Ala Gly Asp Thr His Leu Gly Gly Glu Asp Phe Asp
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Linker 20

<400> SEQUENCE: 43

Gly Glu Gly Gly Ser Gly Glu Gly Gly Ser Gly Glu Gly Gly Ser
1               5                   10                  15
```

<210> SEQ ID NO 44
<211> LENGTH: 15
<212> TYPE: PRT
<213> ORGANISM: Artificial Sequence
<220> FEATURE:
<223> OTHER INFORMATION: Linker 21

<400> SEQUENCE: 44

Gly Gly Glu Gly Ser Gly Gly Glu Gly Ser Gly Gly Glu Gly Ser
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Linker 22

<400> SEQUENCE: 45

Gly Glu Gly Glu Ser Gly Glu Gly Glu Ser Gly Glu Gly Glu Ser
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Linker 23

<400> SEQUENCE: 46

Gly Gly Gly Glu Ser Gly Gly Glu Gly Ser Gly Glu Gly Gly Ser
1               5                   10                  15

<210> SEQ ID NO 47
<211> LENGTH: 20
<212> TYPE: PRT
<213> ORGANISM: Artificial Sequence
<220> FEATURE:
<223> OTHER INFORMATION: Linker 24

<400> SEQUENCE: 47

Gly Glu Gly Glu Ser Gly Glu Gly Glu Ser Gly Glu Gly Glu Ser Gly
1               5                   10                  15

Glu Gly Glu Ser
            20

<210> SEQ ID NO 48
<211> LENGTH: 18
<212> TYPE: PRT
<213> ORGANISM: Artificial Sequence
<220> FEATURE:
<223> OTHER INFORMATION: Linker 25

<400> SEQUENCE: 48

Gly Ser Thr Ser Gly Ser Gly Lys Pro Gly Ser Gly Glu Gly Ser Thr
1               5                   10                  15

Lys Gly

<210> SEQ ID NO 49
<211> LENGTH: 19
<212> TYPE: PRT
<213> ORGANISM: Artificial Sequence
<220> FEATURE:
<223> OTHER INFORMATION: Linker 26

<400> SEQUENCE: 49

Pro Arg Gly Ala Ser Lys Ser Gly Ser Ala Ser Gln Thr Gly Ser Ala
1               5                   10                  15

Pro Gly Ser

<210> SEQ ID NO 50
<211> LENGTH: 19
<212> TYPE: PRT
<213> ORGANISM: Artificial Sequence
<220> FEATURE:
<223> OTHER INFORMATION: Linker 27

<400> SEQUENCE: 50

Gly Thr Ala Ala Ala Gly Ala Gly Ala Ala Gly Gly Ala Ala Ala Gly
1               5                   10                  15

Ala Ala Gly

<210> SEQ ID NO 51
<211> LENGTH: 19
<212> TYPE: PRT
<213> ORGANISM: Artificial Sequence
<220> FEATURE:
<223> OTHER INFORMATION: Linker 28

<400> SEQUENCE: 51

Gly Thr Ser Gly Ser Ser Gly Ser Gly Ser Gly Gly Ser Gly Ser Gly
1               5                   10                  15

Gly Gly Gly

<210> SEQ ID NO 52
<211> LENGTH: 20
<212> TYPE: PRT
<213> ORGANISM: Artificial Sequence
<220> FEATURE:
<223> OTHER INFORMATION: Linker 29

<400> SEQUENCE: 52

Gly Lys Pro Gly Ser Gly Lys Pro Gly Ser Gly Lys Pro Gly Ser Gly
1               5                   10                  15

Lys Pro Gly Ser
            20

<210> SEQ ID NO 53
<211> LENGTH: 4
<212> TYPE: PRT
<213> ORGANISM: Artificial Sequence
<220> FEATURE:
<223> OTHER INFORMATION: Linker 30

<400> SEQUENCE: 53

Gly Ser Gly Ser
1

<210> SEQ ID NO 54
<211> LENGTH: 10
<212> TYPE: PRT
<213> ORGANISM: Artificial Sequence
<220> FEATURE:
<223> OTHER INFORMATION: Linker 31

<400> SEQUENCE: 54

Ala Pro Ala Pro Ala Pro Ala Pro Ala Pro
1               5                   10

```
<210> SEQ ID NO 55
<211> LENGTH: 20
<212> TYPE: PRT
<213> ORGANISM: Artificial Sequence
<220> FEATURE:
<223> OTHER INFORMATION: Linker 32

<400> SEQUENCE: 55

Ala Pro Ala Pro Ala Pro Ala Pro Ala Pro Ala Pro Ala Pro Ala Pro
1               5                   10                  15

Ala Pro Ala Pro
            20

<210> SEQ ID NO 56
<211> LENGTH: 32
<212> TYPE: PRT
<213> ORGANISM: Artificial Sequence
<220> FEATURE:
<223> OTHER INFORMATION: Linker 33

<400> SEQUENCE: 56

Ala Glu Ala Ala Ala Lys Glu Ala Ala Ala Lys Glu Ala Ala Ala Ala
1               5                   10                  15

Lys Glu Ala Ala Ala Lys Glu Ala Ala Ala Lys Ala Ala Ala
            20                  25                  30

<210> SEQ ID NO 57
<211> LENGTH: 15
<212> TYPE: PRT
<213> ORGANISM: Homo sapiens

<400> SEQUENCE: 57

Glu Pro Lys Ser Cys Asp Lys Thr His Thr Cys Pro Pro Cys Pro
1               5                   10                  15

<210> SEQ ID NO 58
<211> LENGTH: 12
<212> TYPE: PRT
<213> ORGANISM: Homo sapiens

<400> SEQUENCE: 58

Glu Arg Lys Cys Cys Val Glu Cys Pro Pro Cys Pro
1               5                   10

<210> SEQ ID NO 59
<211> LENGTH: 62
<212> TYPE: PRT
<213> ORGANISM: Homo sapiens

<400> SEQUENCE: 59

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro
    50                  55                  60

<210> SEQ ID NO 60
<211> LENGTH: 12
<212> TYPE: PRT
<213> ORGANISM: Homo sapiens
```

```
<400> SEQUENCE: 60

Glu Ser Lys Tyr Gly Pro Pro Cys Pro Ser Cys Pro
1               5                   10

<210> SEQ ID NO 61
<211> LENGTH: 486
<212> TYPE: PRT
<213> ORGANISM: Artificial Sequence
<220> FEATURE:
<223> OTHER INFORMATION: anti-CD19 scFv CAR

<400> SEQUENCE: 61

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
        50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ile Glu Val Met Tyr
            260                 265                 270

Pro Pro Pro Tyr Leu Asp Asn Glu Lys Ser Asn Gly Thr Ile Ile His
        275                 280                 285

Val Lys Gly Lys His Leu Cys Pro Ser Pro Leu Phe Pro Gly Pro Ser
    290                 295                 300

Lys Pro Phe Trp Val Leu Val Val Val Gly Gly Val Leu Ala Cys Tyr
305                 310                 315                 320

Ser Leu Leu Val Thr Val Ala Phe Ile Ile Phe Trp Val Arg Ser Lys
                325                 330                 335

Arg Ser Arg Leu Leu His Ser Asp Tyr Met Asn Met Thr Pro Arg Arg
```

```
               340                 345                 350
Pro Gly Pro Thr Arg Lys His Tyr Gln Pro Tyr Ala Pro Pro Arg Asp
            355                 360                 365

Phe Ala Ala Tyr Arg Ser Arg Val Lys Phe Ser Arg Ser Ala Asp Ala
        370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 62
<211> LENGTH: 1461
<212> TYPE: DNA
<213> ORGANISM: Artificial Sequence
<220> FEATURE:
<223> OTHER INFORMATION: anti-CD19 scFv CAR

<400> SEQUENCE: 62
atgctgctgc tggtcacatc tctgctgctg tgcgagctgc ccatcctgc ctttctgctg      60 atccccgaca tccagatgac ccagaccaca agcagcctgt ctgccagcct gggcgataga     120
gtgaccatca gctgtagagc cagccaggac atcagcaagt acctgaactg gtatcagcaa     180
aagcccgacg gcaccgtgaa gctgctgatc taccacacca gcagactgca cagcggcgtg     240
ccaagcagat ttctggcag cggctctggg accgactaca gcctgacaat cagcaacctg     300
gaacaagagg atatcgctac ctacttctgc cagcaaggca caccctgcc ttacaccttt     360 ggcggaggca ccaagctgga aatcaccggc tctacaagcg gcagcggcaa acctggatct     420
ggcgagggat ctaccaaggg cgaagtgaaa ctgcaagagt ctggccctgg actggtggcc     480
ccatctcagt ctctgagcgt gacctgtaca gtcagcggag tgtccctgcc tgattacggc     540
gtgtcctgga tcagacagcc tcctcggaaa ggctggaat ggctgggagt gatctggggc     600
agcgagacaa cctactacaa cagcgccctg aagtcccggc tgaccatcat caaggacaac     660
tccaagagcc aggtgttcct gaagatgaac agcctgcaga ccgacgacac cgccatctac     720
tattgcgcca gcactactac ctacggcggc agctacgcca tggattattg gggccagggc     780
accagcgtga ccgtgtctag catcgaagtg atgtaccctc caccttacct ggacaacgag     840
aagtccaacg gcaccatcat ccacgtgaag ggcaagcacc tgtgtccttc tccactgttc     900
cccggaccta gcaagccttt ctgggtgctc gttgttgttg cggcgtgct ggcctgttac     960 agcctgctgg ttaccgtggc cttcatcatc tttgggtcc gaagcaagcg gagccggctg    1020
ctgcactccg actacatgaa catgaccct agacggcccg gaccaaccag aaagcactac    1080
cagccttacg ctcctcctag agacttcgcc gctaccggt ccagagtgaa gttcagcaga    1140
tccgccgatg ctccccgccta tcagcagggc caaaaccagc tgtacaacga gctgaacctg    1200
```

```
gggagaagag   aagagtacga   cgtgctggac   aagcggagag   gcagagatcc   tgaaatgggc      1260
ggcaagccca   gacggaagaa   tcctcaagag   ggcctgtata   atgagctgca   gaaagacaag      1320
atggccgagg   cctacagcga   gatcggaatg   aagggcgagc   gcagaagagg   caagggacac      1380
gatggactgt   accagggact   gagcaccgcc   accaaggata   cctatgacgc   cctgcacatg      1440
caggccctgc   ctccaagatg   a                                                     1461

<210> SEQ ID NO 63
<211> LENGTH: 1724
<212> TYPE: DNA
<213> ORGANISM: Artificial Sequence
<220> FEATURE:
<223> OTHER INFORMATION: CAG Promoter

<400> SEQUENCE: 63
attgattatt   gactagttat   taatagtaat   caattacggg   gtcattagtt   catagcccat        60
atatggagtt   ccgcgttaca   taacttacgg   taaatggccc   gcctggctga   ccgcccaacg       120
acccccgccc   attgacgtca   ataatgacgt   atgttcccat   agtaacgcca   atagggactt       180
tccattgacg   tcaatgggtg   gactatttac   ggtaaactgc   ccacttggca   gtacatcaag       240
tgtatcatat   gccaagtacg   ccccctattg   acgtcaatga   cggtaaatgg   cccgcctggc       300
attatgccca   gtacatgacc   ttatgggact   ttcctacttg   gcagtacatc   tacgtattag       360
tcatcgctat   taccatgggt   cgaggtgagc   cccacgttct   gcttcactct   ccccatctcc       420
cccccctccc   cacccccaat   tttgtattta   tttattttttt   aattattttg   tgcagcgatg       480
ggggcggggg   ggggggggc   gcgcgccagg   cggggcgggg   cggggcgagg   ggcggggcgg       540
ggcgaggcgg   agaggtgcgg   cggcagccaa   tcagagcggc   gcgctccgaa   agtttccttt       600
tatggcgagg   cggcggcggc   ggcggcccta   taaaaagcga   agcgcgcggc   gggcgggagt       660
cgctgcgttg   ccttcgcccc   gtgccccgct   ccgccgccgc   ctcgcgccgc   cgccccggct       720
ctgactgacc   gcgttactcc   cacaggtgag   cgggcgggac   ggcccttctc   ctccgggctg       780
taattagcgc   ttggtttaat   gacggctcgt   ttcttttctg   tggctgcgtg   aaagccttaa       840
agggctccgg   gagggccctt   tgtgcggggg   ggagcggctc   gggggggtgcg   tgcgtgtgtg       900 tgtgcgtggg   gagcgccgcg   tgcggcccgc   gctgcccggc   ggctgtgagc   gctgcgggcg       960
cggcgcgggg   ctttgtgcgc   tccgcgtgtg   cgcgagggga   gcgcggccgg   gggcggtgcc      1020
ccgcggtgcg   gggggggctgc   gaggggaaca   aaggctgcgt   gcggggtgtg   tgcgtggggg      1080
ggtgagcagg   gggtgtgggc   gcggcggtcg   ggctgtaacc   ccccctgca   ccccctccc      1140 cgagttgctg   agcacggccc   ggcttcgggt   gcggggctcc   gtgcggggcg   tggcgcgggg      1200
ctcgccgtgc   cggcggggg   gtggcggcag   gtggggtgc   cggcggggc   ggggccgcct      1260 cgggccgggg   agggctcggg   ggaggggcgc   ggcggccccg   gagcgccggc   ggctgtcgag      1320
gcgcggcgag   ccgcagccat   tgccttttat   ggtaatcgtg   cgagagggcg   cagggacttc      1380
ctttgtccca   aatctggcgg   agccgaaatc   tgggaggcgc   cgccgcaccc   cctctagcgg      1440
gcgcgggcga   agcggtgcgg   cgccggcagg   aaggaaatgg   gcggggaggg   ccttcgtgcg      1500
tcgccgcgcc   gccgtcccct   tctccatctc   cagcctcggg   gctgccgcag   gggacggct      1560 gccttcgggg   gggacggggc   agggcggggt   tcggcttctg   gcgtgtgacc   ggcgggatat      1620
ctacgaagcg   gccgccctct   gctaaccatg   ttcatgcctt   cttctttttc   ctacagctcc      1680
tgggcaacgt   gctggttatt   gtgctgtctc   atcattttgg   caaa                        1724
```

<210> SEQ ID NO 64
<211> LENGTH: 121
<212> TYPE: DNA
<213> ORGANISM: Artificial Sequence
<220> FEATURE:
<223> OTHER INFORMATION: SV40 terminator/polyadenylation

<400> SEQUENCE: 64

```
aacttgttta ttgcagctta taatggttac aaataaagca atagcatcac aaatttcaca      60
aataaagcat ttttttcact gcattctagt tgtggtttgt ccaaactcat caatgtatct     120
t                                                                     121
```

<210> SEQ ID NO 65
<211> LENGTH: 335
<212> TYPE: PRT
<213> ORGANISM: Homo sapiens

<400> SEQUENCE: 65

```
His Ser Leu Lys Tyr Phe His Thr Ser Val Ser Arg Pro Gly Arg Gly
 1               5                  10                  15

Glu Pro Arg Phe Ile Ser Val Gly Tyr Val Asp Asp Thr Gln Phe Val
            20                  25                  30

Arg Phe Asp Asn Asp Ala Ala Ser Pro Arg Met Val Pro Arg Ala Pro
        35                  40                  45

Trp Met Glu Gln Glu Gly Ser Glu Tyr Trp Asp Arg Glu Thr Arg Ser
    50                  55                  60

Ala Arg Asp Thr Ala Gln Ile Phe Arg Val Asn Leu Arg Thr Leu Arg
65                  70                  75                  80

Gly Tyr Tyr Asn Gln Ser Glu Ala Gly Ser His Thr Leu Gln Trp Met
                85                  90                  95

His Gly Cys Glu Leu Gly Pro Asp Gly Arg Phe Leu Arg Gly Tyr Glu
            100                 105                 110

Gln Phe Ala Tyr Asp Gly Lys Asp Tyr Leu Thr Leu Asn Glu Asp Leu
        115                 120                 125

Arg Ser Trp Thr Ala Val Asp Thr Ala Ala Gln Ile Ser Glu Gln Lys
    130                 135                 140

Ser Asn Asp Ala Ser Glu Ala Glu His Gln Arg Ala Tyr Leu Glu Asp
145                 150                 155                 160

Thr Cys Val Glu Trp Leu His Lys Tyr Leu Glu Lys Gly Lys Glu Thr
                165                 170                 175

Leu Leu His Leu Glu Pro Pro Lys Thr His Val Thr His His Pro Ile
            180                 185                 190

Ser Asp His Glu Ala Thr Leu Arg Cys Trp Ala Leu Gly Phe Tyr Pro
        195                 200                 205

Ala Glu Ile Thr Leu Thr Trp Gln Gln Asp Gly Glu Gly His Thr Gln
    210                 215                 220

Asp Thr Glu Leu Val Glu Thr Arg Pro Ala Gly Asp Gly Thr Phe Gln
225                 230                 235                 240

Lys Trp Ala Ala Val Val Pro Ser Gly Glu Glu Gln Arg Tyr Thr
                245                 250                 255

Cys His Val Gln His Glu Gly Leu Pro Glu Pro Val Thr Leu Arg Trp
            260                 265                 270

Lys Pro Ala Ser Gln Pro Thr Ile Pro Ile Val Gly Ile Ile Ala Gly
        275                 280                 285

Leu Val Leu Leu Gly Ser Val Val Ser Gly Ala Val Val Ala Ala Val
    290                 295                 300
```

Ile Trp Arg Lys Ser Ser Gly Lys Gly Ser Tyr Ser Lys
305 310 315 320

Ala Glu Trp Ser Asp Ser Ala Gln Gly Ser Glu Ser His Ser Leu
325 330 335

<210> SEQ ID NO 66
<211> LENGTH: 504
<212> TYPE: PRT
<213> ORGANISM: Artificial Sequence
<220> FEATURE:
<223> OTHER INFORMATION: HLA-G signal-Peptide-B2M-HLA-E

<400> SEQUENCE: 66

Met Val Val Met Ala Pro Arg Thr Leu Phe Leu Leu Ser Gly Ala
1 5 10 15

Leu Thr Leu Thr Glu Thr Trp Ala Val Met Ala Pro Arg Thr Leu Ile
20 25 30

Leu Gly Gly Gly Gly Ser Gly Gly Gly Gly Ser Gly Gly Gly Ser
35 40 45

Gly Gly Gly Gly Ser Ile Gln Arg Thr Pro Lys Ile Gln Val Tyr Ser
50 55 60

Arg His Pro Ala Glu Asn Gly Lys Ser Asn Phe Leu Asn Cys Tyr Val
65 70 75 80

Ser Gly Phe His Pro Ser Asp Ile Glu Val Asp Leu Leu Lys Asn Gly
85 90 95

Glu Arg Ile Glu Lys Val Glu His Ser Asp Leu Ser Phe Ser Lys Asp
100 105 110

Trp Ser Phe Tyr Leu Leu Tyr Tyr Thr Glu Phe Thr Pro Thr Glu Lys
115 120 125

Asp Glu Tyr Ala Cys Arg Val Asn His Val Thr Leu Ser Gln Pro Lys
130 135 140

Ile Val Lys Trp Asp Arg Asp Met Gly Gly Gly Gly Ser Gly Gly Gly
145 150 155 160

Gly Ser Gly Gly Gly Gly Ser Gly Ser His Ser Leu Lys Tyr Phe His
165 170 175

Thr Ser Val Ser Arg Pro Gly Arg Gly Glu Pro Arg Phe Ile Ser Val
180 185 190

Gly Tyr Val Asp Asp Thr Gln Phe Val Arg Phe Asp Asn Asp Ala Ala
195 200 205

Ser Pro Arg Met Val Pro Arg Ala Pro Trp Met Glu Gln Glu Gly Ser
210 215 220

Glu Tyr Trp Asp Arg Glu Thr Arg Ser Ala Arg Asp Thr Ala Gln Ile
225 230 235 240

Phe Arg Val Asn Leu Arg Thr Leu Arg Gly Tyr Tyr Asn Gln Ser Glu
245 250 255

Ala Gly Ser His Thr Leu Gln Trp Met His Gly Cys Glu Leu Gly Pro
260 265 270

Asp Gly Arg Phe Leu Arg Gly Tyr Glu Gln Phe Ala Tyr Asp Gly Lys
275 280 285

Asp Tyr Leu Thr Leu Asn Glu Asp Leu Arg Ser Trp Thr Ala Val Asp
290 295 300

Thr Ala Ala Gln Ile Ser Glu Gln Lys Ser Asn Asp Ala Ser Glu Ala
305 310 315 320

Glu His Gln Arg Ala Tyr Leu Glu Asp Thr Cys Val Glu Trp Leu His
325 330 335

```
Lys Tyr Leu Glu Lys Gly Lys Glu Thr Leu Leu His Leu Glu Pro Pro
                340                 345                 350
Lys Thr His Val Thr His His Pro Ile Ser Asp His Glu Ala Thr Leu
            355                 360                 365
Arg Cys Trp Ala Leu Gly Phe Tyr Pro Ala Glu Ile Thr Leu Thr Trp
        370                 375                 380
Gln Gln Asp Gly Glu Gly His Thr Gln Asp Thr Glu Leu Val Glu Thr
385                 390                 395                 400
Arg Pro Ala Gly Asp Gly Thr Phe Gln Lys Trp Ala Ala Val Val Val
                405                 410                 415
Pro Ser Gly Glu Glu Gln Arg Tyr Thr Cys His Val Gln His Glu Gly
            420                 425                 430
Leu Pro Glu Pro Val Thr Leu Arg Trp Lys Pro Ala Ser Gln Pro Thr
        435                 440                 445
Ile Pro Ile Val Gly Ile Ile Ala Gly Leu Val Leu Leu Gly Ser Val
        450                 455                 460
Val Ser Gly Ala Val Val Ala Ala Val Ile Trp Arg Lys Lys Ser Ser
465                 470                 475                 480
Gly Gly Lys Gly Gly Ser Tyr Ser Lys Ala Glu Trp Ser Asp Ser Ala
                485                 490                 495
Gln Gly Ser Glu Ser His Ser Leu
            500
```

<210> SEQ ID NO 67
<211> LENGTH: 1515
<212> TYPE: DNA
<213> ORGANISM: Artificial Sequence
<220> FEATURE:
<223> OTHER INFORMATION: HLA-G signal-Peptide-B2M-HLA-E

<400> SEQUENCE: 67

| | |
|---|---|
| atggtggtca tggcccctag aacactgttc ctgctgctgt ctggcgccct gacactgaca | 60 |
| gagacatggg ccgtgatggc ccccagaacc ctgatcctgg cggcggtgg ttcaggcgga | 120 |
| ggaggttcag aggaggggg tagtggaggt ggtggttcta tccagcggac ccctaagatc | 180 |
| caggtgtaca gcagacaccc cgccgagaac ggcaagagca acttcctgaa ctgctacgtg | 240 |
| tccggctttc accccagcga cattgaggtg acctgctga agaacggcga gcggatcgag | 300 |
| aaggtggaac acagcgatct gagcttcagc aaggactggt ccttctacct gctgtactac | 360 |
| accgagttca cccctaccga gaaggacgag tacgcctgca gagtgaacca cgtgacactg | 420 |
| agccagccta agatcgtgaa gtgggatcgc gatatgggcg gaggcggatc tggtggcgga | 480 |
| ggaagtggcg gcgaggatc tggctcccac tccttgaagt atttccacac ttccgtgtcc | 540 |
| cggcccggcc gcggggagcc ccgcttcatc tctgtgggct acgtggacga cacccagttc | 600 |
| gtgcgcttcg acaacgacgc cgcgagtccg aggatggtgc gcgggcgcc gtggatggag | 660 |
| caggaggggt cagagtattg ggaccgggag acacggagcg ccaggacac cgcacagatt | 720 |
| ttccgagtga atctgcggac gctgcgcggc tactacaatc agagcgaggc cgggtctcac | 780 |
| accctgcagt ggatgcatgg ctgcgagctg gggcccgacg gcgcttcct ccgcgggtat | 840 |
| gaacagttcg cctacgacgg caaggattat ctcaccctga atgaggacct gcgctcctgg | 900 |
| accgcggtgg acacggcggc tcagatctcc gagcaaaagt caaatgatgc ctctgaggcg | 960 |
| gagcaccaga gagcctacct ggaagacaca tgcgtggagt ggctccacaa atacctggag | 1020 |
| aagggggaagg agacgctgct tcacctggag ccccaaaga cacacgtgac tcaccacccc | 1080 |

```
atctctgacc atgaggccac cctgaggtgc tgggccctgg gcttctaccc tgcggagatc    1140
acactgacct ggcagcagga tggggagggc catacccagg acacggagct cgtggagacc    1200
aggcctgcag gggatggaac cttccagaag tgggcagctg tggtggtgcc ttctggagag    1260
gagcagagat acacgtgcca tgtgcagcat gaggggctac ccgagcccgt caccctgaga    1320
tggaagccgg cttcccagcc caccatcccc atcgtgggca tcattgctgg cctggttctc    1380
cttggatctg tggtctctgg agctgtggtt gctgctgtga tatggaggaa gaagagctca    1440
ggtggaaaag gagggagcta ctctaaggct gagtggagcg acagtgccca ggggtctgag    1500
tctcacagct tgtaa                                                     1515
```

<210> SEQ ID NO 68
<211> LENGTH: 312
<212> TYPE: PRT
<213> ORGANISM: Homo sapiens

<400> SEQUENCE: 68

```
His Ser Met Arg Tyr Phe Ser Ala Ala Val Ser Arg Pro Gly Arg Gly
1               5                   10                  15

Glu Pro Arg Phe Ile Ala Met Gly Tyr Val Asp Asp Thr Gln Phe Val
            20                  25                  30

Arg Phe Asp Ser Asp Ser Ala Cys Pro Arg Met Glu Pro Arg Ala Pro
        35                  40                  45

Trp Val Glu Gln Glu Gly Pro Glu Tyr Trp Glu Glu Thr Arg Asn
    50                  55                  60

Thr Lys Ala His Ala Gln Thr Asp Arg Met Asn Leu Gln Thr Leu Arg
65                  70                  75                  80

Gly Tyr Tyr Asn Gln Ser Glu Ala Ser Ser His Thr Leu Gln Trp Met
                85                  90                  95

Ile Gly Cys Asp Leu Gly Ser Asp Gly Arg Leu Leu Arg Gly Tyr Glu
            100                 105                 110

Gln Tyr Ala Tyr Asp Gly Lys Asp Tyr Leu Ala Leu Asn Glu Asp Leu
        115                 120                 125

Arg Ser Trp Thr Ala Ala Asp Thr Ala Ala Gln Ile Ser Lys Arg Lys
    130                 135                 140

Cys Glu Ala Ala Asn Val Ala Glu Gln Arg Arg Ala Tyr Leu Glu Gly
145                 150                 155                 160

Thr Cys Val Glu Trp Leu His Arg Tyr Leu Glu Asn Gly Lys Glu Met
                165                 170                 175

Leu Gln Arg Ala Asp Pro Pro Lys Thr His Val Thr His His Pro Val
            180                 185                 190

Phe Asp Tyr Glu Ala Thr Leu Arg Cys Trp Ala Leu Gly Phe Tyr Pro
        195                 200                 205

Ala Glu Ile Ile Leu Thr Trp Gln Arg Asp Gly Glu Asp Gln Thr Gln
    210                 215                 220

Asp Val Glu Leu Val Glu Thr Arg Pro Ala Gly Asp Gly Thr Phe Gln
225                 230                 235                 240

Lys Trp Ala Ala Val Val Val Pro Ser Gly Glu Glu Gln Arg Tyr Thr
                245                 250                 255

Cys His Val Gln His Glu Gly Leu Pro Glu Pro Leu Met Leu Arg Trp
            260                 265                 270

Lys Gln Ser Ser Leu Pro Thr Ile Pro Ile Met Gly Ile Val Ala Gly
        275                 280                 285
```

-continued

```
Leu Val Val Leu Ala Ala Val Val Thr Gly Ala Ala Val Ala Ala Val
            290                 295                 300
Leu Trp Arg Lys Lys Ser Ser Asp
305                 310

<210> SEQ ID NO 69
<211> LENGTH: 471
<212> TYPE: PRT
<213> ORGANISM: Artificial Sequence
<220> FEATURE:
<223> OTHER INFORMATION: HLA-G signal-Peptide-B2M-HLA-G

<400> SEQUENCE: 69

Met Val Val Met Ala Pro Arg Thr Leu Phe Leu Leu Leu Ser Gly Ala
1               5                   10                  15
Leu Thr Leu Thr Glu Thr Trp Ala Arg Ile Ile Pro Arg His Leu Gln
            20                  25                  30
Leu Gly Gly Gly Gly Ser Gly Gly Gly Gly Ser Ile Gln Arg Thr Pro
        35                  40                  45
Lys Ile Gln Val Tyr Ser Arg His Pro Ala Glu Asn Gly Lys Ser Asn
    50                  55                  60
Phe Leu Asn Cys Tyr Val Ser Gly Phe His Pro Ser Asp Ile Glu Val
65                  70                  75                  80
Asp Leu Leu Lys Asn Gly Glu Arg Ile Glu Lys Val Glu His Ser Asp
                85                  90                  95
Leu Ser Phe Ser Lys Asp Trp Ser Phe Tyr Leu Leu Tyr Tyr Thr Glu
            100                 105                 110
Phe Thr Pro Thr Glu Lys Asp Glu Tyr Ala Cys Arg Val Asn His Val
        115                 120                 125
Thr Leu Ser Gln Pro Lys Ile Val Lys Trp Asp Arg Asp Met Gly Gly
    130                 135                 140
Gly Gly Ser Gly Gly Gly Gly Ser Gly Gly Gly Gly Ser Gly Ser His
145                 150                 155                 160
Ser Met Arg Tyr Phe Ser Ala Ala Val Ser Arg Pro Gly Arg Gly Glu
                165                 170                 175
Pro Arg Phe Ile Ala Met Gly Tyr Val Asp Asp Thr Gln Phe Val Arg
            180                 185                 190
Phe Asp Ser Asp Ser Ala Cys Pro Arg Met Glu Pro Arg Ala Pro Trp
        195                 200                 205
Val Glu Gln Glu Gly Pro Glu Tyr Trp Glu Glu Glu Thr Arg Asn Thr
    210                 215                 220
Lys Ala His Ala Gln Thr Asp Arg Met Asn Leu Gln Thr Leu Arg Gly
225                 230                 235                 240
Tyr Tyr Asn Gln Ser Glu Ala Ser Ser His Thr Leu Gln Trp Met Ile
                245                 250                 255
Gly Cys Asp Leu Gly Ser Asp Gly Arg Leu Leu Arg Gly Tyr Glu Gln
            260                 265                 270
Tyr Ala Tyr Asp Gly Lys Asp Tyr Leu Ala Leu Asn Glu Asp Leu Arg
        275                 280                 285
Ser Trp Thr Ala Ala Asp Thr Ala Ala Gln Ile Ser Lys Arg Lys Cys
    290                 295                 300
Glu Ala Ala Asn Val Ala Glu Gln Arg Arg Ala Tyr Leu Glu Gly Thr
305                 310                 315                 320
Cys Val Glu Trp Leu His Arg Tyr Leu Glu Asn Gly Lys Glu Met Leu
                325                 330                 335
```

```
Gln Arg Ala Asp Pro Pro Lys Thr His Val Thr His His Pro Val Phe
                340                 345                 350
Asp Tyr Glu Ala Thr Leu Arg Cys Trp Ala Leu Gly Phe Tyr Pro Ala
            355                 360                 365
Glu Ile Ile Leu Thr Trp Gln Arg Asp Gly Glu Asp Gln Thr Gln Asp
        370                 375                 380
Val Glu Leu Val Glu Thr Arg Pro Ala Gly Asp Gly Thr Phe Gln Lys
385                 390                 395                 400
Trp Ala Ala Val Val Pro Ser Gly Glu Glu Gln Arg Tyr Thr Cys
                405                 410                 415
His Val Gln His Glu Gly Leu Pro Glu Pro Leu Met Leu Arg Trp Lys
            420                 425                 430
Gln Ser Ser Leu Pro Thr Ile Pro Ile Met Gly Ile Val Ala Gly Leu
        435                 440                 445
Val Val Leu Ala Ala Val Val Thr Gly Ala Ala Val Ala Ala Val Leu
    450                 455                 460
Trp Arg Lys Lys Ser Ser Asp
465                 470

<210> SEQ ID NO 70
<211> LENGTH: 1422
<212> TYPE: DNA
<213> ORGANISM: Artificial Sequence
<220> FEATURE:
<223> OTHER INFORMATION: HLA-G signal-Peptide-B2M-HLA-G

<400> SEQUENCE: 70
gccaccatgg tggtcatggc gccccgaacc ctcttcctgc tgctctcggg ggccctgacc      60
ctgaccgaga cctgggcgcg gatcattccc cgacatctgc aactgggagg cggcggttca    120
ggagggggcg atcgatccaa cgcaccccca aagatccagg tctactccag acacccggcc    180
gaaaacggaa agtcgaactt cctgaactgc tatgtgtcag gattccaccc gtccgacatc    240
gaggtggacc tcctgaagaa cggcgaacgc attgagaagg tcgagcactc cgatctgtcg    300
ttctccaagg actggtcctt ctaccttctc tactataccg aattcacccc gaccgagaag    360
gacgaatacg cctgccgggt caaccacgtg accctgagcc agccaaagat cgtgaaatgg    420
gaccgcgata tgggaggagg aggttccggc ggaggaggaa gcggaggcgg aggttccggc    480
tcccactcca tgaggtattt cagcgccgcc gtgtcccggc ctggccgcgg agagcctcgc    540
ttcatcgcca tgggatacgt ggacgacacc cagttcgtca gattcgacag cgacagcgcc    600
tgtcctcgga tggaacctag agcaccttgg gtcgagcaag agggccctga gtactgggaa    660
gaagagacac ggaacaccaa ggctcacgcc cagaccgaca gaatgaacct gcagaccctg    720
cggggctact acaatcagtc tgaggccagc agccatactc tgcagtggat gatcggctgc    780
gatctgggct ctgatggcag actgctgaga ggctacgagc agtacgccta cgacggcaag    840
gattatctgg ccctgaacga ggacctgcgc tcttggacag ctgccgatac agccgctcag    900
atcagcaaga gaaagtgcga ggccgccaat gtggccgaac agagaagggc ttacctggaa    960
ggcacctgtg tggaatggct gcacagatac ctggaaaacg gcaaagagat gctgcagcgg   1020
gccgatcctc ctaagacaca tgtgacccac catcctgtgt tcgactacga ggccacactg   1080
agatgttggg ccctgggctt ttaccctgcc gagatcatcc tgacctggca gcgagatggc   1140
gaggatcaga cccaggatgt ggaactggtg gaaaccagac tgccggcga cggcaccttt   1200 cagaaatggg ctgctgtggt ggtgcccagc ggagaggaac agagatacac ctgtcacgtg   1260
```

```
cagcacgagg gactgcctga acctctgatg ctgagatgga agcagagcag cctgcctaca    1320
atccccatca tgggaatcgt ggccggactg gtggttctgg ccgctgttgt tacaggtgct    1380
gcagtggctg ccgtgctgtg gcggaagaaa agcagcgact ga                       1422
```

<210> SEQ ID NO 71
<211> LENGTH: 371
<212> TYPE: PRT
<213> ORGANISM: Artificial Sequence
<220> FEATURE:
<223> OTHER INFORMATION: truncated EGFR

<400> SEQUENCE: 71

```
Met Arg Pro Ser Gly Thr Ala Gly Ala Ala Leu Leu Ala Leu Leu Ala
1               5                   10                  15

Ala Leu Cys Pro Ala Ser Arg Ala Gly Val Arg Lys Cys Lys Lys Cys
            20                  25                  30

Glu Gly Pro Cys Arg Lys Val Cys Asn Gly Ile Gly Ile Gly Glu Phe
        35                  40                  45

Lys Asp Ser Leu Ser Ile Asn Ala Thr Asn Ile Lys His Phe Lys Asn
    50                  55                  60

Cys Thr Ser Ile Ser Gly Asp Leu His Ile Leu Pro Val Ala Phe Arg
65                  70                  75                  80

Gly Asp Ser Phe Thr His Thr Pro Pro Leu Asp Pro Gln Glu Leu Asp
                85                  90                  95

Ile Leu Lys Thr Val Lys Glu Ile Thr Gly Phe Leu Leu Ile Gln Ala
            100                 105                 110

Trp Pro Glu Asn Arg Thr Asp Leu His Ala Phe Glu Asn Leu Glu Ile
        115                 120                 125

Ile Arg Gly Arg Thr Lys Gln His Gly Gln Phe Ser Leu Ala Val Val
    130                 135                 140

Ser Leu Asn Ile Thr Ser Leu Gly Leu Arg Ser Leu Lys Glu Ile Ser
145                 150                 155                 160

Asp Gly Asp Val Ile Ile Ser Gly Asn Lys Asn Leu Cys Tyr Ala Asn
                165                 170                 175

Thr Ile Asn Trp Lys Lys Leu Phe Gly Thr Ser Gly Gln Lys Thr Lys
            180                 185                 190

Ile Ile Ser Asn Arg Gly Glu Asn Ser Cys Lys Ala Thr Gly Gln Val
        195                 200                 205

Cys His Ala Leu Cys Ser Pro Glu Gly Cys Trp Gly Pro Glu Pro Arg
    210                 215                 220

Asp Cys Val Ser Cys Arg Asn Val Ser Arg Gly Arg Glu Cys Val Asp
225                 230                 235                 240

Lys Cys Asn Leu Leu Glu Gly Glu Pro Arg Glu Phe Val Glu Asn Ser
                245                 250                 255

Glu Cys Ile Gln Cys His Pro Glu Cys Leu Pro Gln Ala Met Asn Ile
            260                 265                 270

Thr Cys Thr Gly Arg Gly Pro Asp Asn Cys Ile Gln Cys Ala His Tyr
        275                 280                 285

Ile Asp Gly Pro His Cys Val Lys Thr Cys Pro Ala Gly Val Met Gly
    290                 295                 300

Glu Asn Asn Thr Leu Val Trp Lys Tyr Ala Asp Ala Gly His Val Cys
305                 310                 315                 320

His Leu Cys His Pro Asn Cys Thr Tyr Gly Cys Thr Gly Pro Gly Leu
                325                 330                 335
```

```
Glu Gly Cys Pro Thr Asn Gly Pro Lys Ile Pro Ser Ile Ala Thr Gly
            340                 345                 350

Met Val Gly Ala Leu Leu Leu Leu Val Val Ala Leu Gly Ile Gly
            355                 360                 365

Leu Phe Met
    370

<210> SEQ ID NO 72
<211> LENGTH: 162
<212> TYPE: PRT
<213> ORGANISM: Homo sapiens

<400> SEQUENCE: 72

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 73
<211> LENGTH: 19
<212> TYPE: PRT
<213> ORGANISM: Artificial Sequence
<220> FEATURE:
<223> OTHER INFORMATION: P2A

<400> SEQUENCE: 73

Ala Thr Asn Phe Ser Leu Leu Lys Gln Ala Gly Asp Val Glu Glu Asn
1               5                   10                  15

Pro Gly Pro

<210> SEQ ID NO 74
<211> LENGTH: 556
<212> TYPE: PRT
<213> ORGANISM: Artificial Sequence
<220> FEATURE:
<223> OTHER INFORMATION: tEGFR-P2A-IL15

<400> SEQUENCE: 74

Met Arg Pro Ser Gly Thr Ala Gly Ala Ala Leu Leu Ala Leu Leu Ala
1               5                   10                  15

Ala Leu Cys Pro Ala Ser Arg Ala Gly Val Arg Lys Cys Lys Lys Cys
            20                  25                  30
```

```
Glu Gly Pro Cys Arg Lys Val Cys Asn Gly Ile Gly Ile Gly Glu Phe
        35                  40                  45
Lys Asp Ser Leu Ser Ile Asn Ala Thr Asn Ile Lys His Phe Lys Asn
    50                  55                  60
Cys Thr Ser Ile Ser Gly Asp Leu His Ile Leu Pro Val Ala Phe Arg
65                  70                  75                  80
Gly Asp Ser Phe Thr His Thr Pro Leu Asp Pro Gln Glu Leu Asp
                85                  90                  95
Ile Leu Lys Thr Val Lys Glu Ile Thr Gly Phe Leu Leu Ile Gln Ala
            100                 105                 110
Trp Pro Glu Asn Arg Thr Asp Leu His Ala Phe Glu Asn Leu Glu Ile
            115                 120                 125
Ile Arg Gly Arg Thr Lys Gln His Gly Gln Phe Ser Leu Ala Val Val
        130                 135                 140
Ser Leu Asn Ile Thr Ser Leu Gly Leu Arg Ser Leu Lys Glu Ile Ser
145                 150                 155                 160
Asp Gly Asp Val Ile Ile Ser Gly Asn Lys Asn Leu Cys Tyr Ala Asn
                165                 170                 175
Thr Ile Asn Trp Lys Lys Leu Phe Gly Thr Ser Gly Gln Lys Thr Lys
            180                 185                 190
Ile Ile Ser Asn Arg Gly Glu Asn Ser Cys Lys Ala Thr Gly Gln Val
            195                 200                 205
Cys His Ala Leu Cys Ser Pro Glu Gly Cys Trp Gly Pro Glu Pro Arg
        210                 215                 220
Asp Cys Val Ser Cys Arg Asn Val Ser Arg Gly Arg Glu Cys Val Asp
225                 230                 235                 240
Lys Cys Asn Leu Leu Glu Gly Glu Pro Arg Glu Phe Val Glu Asn Ser
                245                 250                 255
Glu Cys Ile Gln Cys His Pro Glu Cys Leu Pro Gln Ala Met Asn Ile
            260                 265                 270
Thr Cys Thr Gly Arg Gly Pro Asp Asn Cys Ile Gln Cys Ala His Tyr
        275                 280                 285
Ile Asp Gly Pro His Cys Val Lys Thr Cys Pro Ala Gly Val Met Gly
        290                 295                 300
Glu Asn Asn Thr Leu Val Trp Lys Tyr Ala Asp Ala Gly His Val Cys
305                 310                 315                 320
His Leu Cys His Pro Asn Cys Thr Tyr Gly Cys Thr Gly Pro Gly Leu
                325                 330                 335
Glu Gly Cys Pro Thr Asn Gly Pro Lys Ile Pro Ser Ile Ala Thr Gly
            340                 345                 350
Met Val Gly Ala Leu Leu Leu Leu Val Val Ala Leu Gly Ile Gly
        355                 360                 365
Leu Phe Met Ser Gly Ser Gly Ala Thr Asn Phe Ser Leu Leu Lys Gln
    370                 375                 380
Ala Gly Asp Val Glu Glu Asn Pro Gly Pro Met Arg Ile Ser Lys Pro
385                 390                 395                 400
His Leu Arg Ser Ile Ser Ile Gln Cys Tyr Leu Cys Leu Leu Leu Asn
                405                 410                 415
Ser His Phe Leu Thr Glu Ala Gly Ile His Val Phe Ile Leu Gly Cys
            420                 425                 430
Phe Ser Ala Gly Leu Pro Lys Thr Glu Ala Asn Trp Val Asn Val Ile
        435                 440                 445
```

| | | | |
|---|---|---|---|
| Ser Asp Leu Lys Lys Ile Glu Asp Leu Ile Gln Ser Met His Ile Asp | | | |
| 450 | | 455 | 460 |

Ala Thr Leu Tyr Thr Glu Ser Asp Val His Pro Ser Cys Lys Val Thr
465                 470                 475                 480

Ala Met Lys Cys Phe Leu Leu Glu Leu Gln Val Ile Ser Leu Glu Ser
                485                 490                 495

Gly Asp Ala Ser Ile His Asp Thr Val Glu Asn Leu Ile Ile Leu Ala
            500                 505                 510

Asn Asn Ser Leu Ser Ser Asn Gly Asn Val Thr Glu Ser Gly Cys Lys
        515                 520                 525

Glu Cys Glu Glu Leu Glu Glu Lys Asn Ile Lys Glu Phe Leu Gln Ser
    530                 535                 540

Phe Val His Ile Val Gln Met Phe Ile Asn Thr Ser
545                 550                 555

```
<210> SEQ ID NO 75
<211> LENGTH: 1668
<212> TYPE: DNA
<213> ORGANISM: Artificial Sequence
<220> FEATURE:
<223> OTHER INFORMATION: tEGFR-P2A-IL15

<400> SEQUENCE: 75
```

| | | | | |
|---|---|---|---|---|
| atgaggccct | caggcactgc | cggggccgcc | ctcctggccc | tgttagccgc tttgtgtcca | 60 |
| gcaagccgcg | ccggagtgcg | gaaatgtaag | aaatgcgaag | accctgccg gaaggtatgc | 120 |
| aacggcattg | ggattggcga | attcaaggac | agcctgagca | ttaatgctac aaacatcaag | 180 |
| cactttaaga | attgcaccag | cattagcggc | gatctgcata | tactgccagt ggctttccga | 240 |
| ggcgactctt | ttactcatac | ccctccgctg | gaccctcaag | agctggacat tctcaagact | 300 |
| gtgaaggaaa | ttacggggtt | tctgctcatt | caggcctggc | ctgaaaaccg cacggatttg | 360 |
| catgcctttg | agaatctgga | aataatcaga | ggccggacga | acagcatgg ccagttcagc | 420 |
| ctcgcggtcg | tctcttttgaa | tattacgtca | ctcggcctca | ggtccctcaa agagatttct | 480 |
| gatggcgatg | tcatcatctc | tggtaataag | aatctgtgtt | acgcaaatac catcaattgg | 540 |
| aagaagctct | ttgggacctc | aggtcaaaag | actaaaatta | tctccaaccg cggcgagaac | 600 |
| agctgtaagg | ctacaggcca | ggtttgccac | gcgctctgct | ccccagaggg ttgctggggg | 660 |
| cctgagccaa | gggattgcgt | tcatgtcgc | aacgtgtctc | ggggcagaga atgcgtggat | 720 |
| aaatgtaacc | tcttagaggg | cgaacctcgc | gagtttgttg | agaactcaga atgtatacag | 780 |
| tgccacccg | aatgtcttcc | tcaggccatg | aatatcacat | gcaccggacg cggaccagac | 840 |
| aactgtatcc | aatgtgctca | ctacattgac | ggacctcatt | gtgtgaaaac atgccccgca | 900 |
| ggagttatgg | gagaaaacaa | caccctcgtt | tggaaatatg | ccgatgcagg tcacgtatgt | 960 |
| cacctgtgcc | acccaaactg | cacttatggg | tgcaccgggc | cgggcctgga ggggtgccct | 1020 |
| acgaatggac | caaaaattcc | cagtattgca | actgggatgg | tcgggcact gttgttgctg | 1080 |
| cttgtggttg | ccctcgggat | aggcctgttt | atgtctggct | ccggcgccac caatttcagc | 1140 |
| ctgctgaaac | aggcaggcga | cgtcgaagaa | aatccaggac | caatgcgaat atcaaaacca | 1200 |
| cacttgcgca | gcatttctat | acagtgctat | ttgtgcttgt | tgctgaactc tcacttcctc | 1260 |
| acagaggctg | ggatacacgt | tttcatactt | ggatgttttt | cagctgggct gccgaagaca | 1320 |
| gaggcgaatt | gggtgaatgt | aatttcagac | ctcaagaaga | tcgaggatct catccagtcc | 1380 |
| atgcacatcg | acgctactct | gtacacagag | agcgatgtcc | accttcttg taaggttacc | 1440 |

```
gccatgaaat gcttcctttt ggaactccaa gtcatctcat tggaatcagg ggatgcgtcc    1500
attcatgaca ccgtggaaaa cctgataata ctggctaaca acagcttgtc aagtaatggg    1560
aatgttactg agtccggttg taaagaatgt gaagagctgg aggagaagaa cattaaggaa    1620
tttttgcaat cttttgtaca tattgttcag atgtttatta acacaagc                 1668
```

<210> SEQ ID NO 76
<211> LENGTH: 153
<212> TYPE: PRT
<213> ORGANISM: Homo sapiens

<400> SEQUENCE: 76

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 77
<211> LENGTH: 19
<212> TYPE: PRT
<213> ORGANISM: Artificial Sequence
<220> FEATURE:
<223> OTHER INFORMATION: Signal Sequence

<400> SEQUENCE: 77

```
Met Glu Phe Gly Leu Ser Trp Val Phe Leu Val Ala Leu Phe Arg Gly
1               5                   10                  15

Val Gln Cys
```

<210> SEQ ID NO 78
<211> LENGTH: 21
<212> TYPE: PRT
<213> ORGANISM: Artificial Sequence
<220> FEATURE:
<223> OTHER INFORMATION: Polivy epitope

<400> SEQUENCE: 78

```
Ala Arg Ser Glu Asp Arg Tyr Arg Asn Pro Lys Gly Ser Ala Cys Ser
1               5                   10                  15

Arg Ile Trp Gln Ser
            20
```

<210> SEQ ID NO 79

<211> LENGTH: 287
<212> TYPE: PRT
<213> ORGANISM: Artificial Sequence
<220> FEATURE:
<223> OTHER INFORMATION: CD79b-P2A-IL15

<400> SEQUENCE: 79

Met Glu Phe Gly Leu Ser Trp Val Phe Leu Val Ala Leu Phe Arg Gly
1               5                   10                  15

Val Gln Cys Ala Arg Ser Glu Asp Arg Tyr Arg Asn Pro Lys Gly Ser
            20                  25                  30

Ala Cys Ser Arg Ile Trp Gln Ser Thr Thr Pro Ala Pro Arg Pro
        35                  40                  45

Pro Thr Pro Ala Pro Thr Ile Ala Ser Gln Pro Leu Ser Leu Arg Pro
    50                  55                  60

Glu Ala Cys Arg Pro Ala Ala Gly Gly Ala Val His Thr Arg Gly Leu
65                  70                  75                  80

Asp Phe Ala Cys Asp Ile Tyr Ile Trp Ala Pro Leu Ala Gly Thr Cys
                85                  90                  95

Gly Val Leu Leu Leu Ser Leu Val Ile Thr Ala Thr Asn Phe Ser Leu
            100                 105                 110

Leu Lys Gln Ala Gly Asp Val Glu Glu Asn Pro Gly Pro Met Arg Ile
        115                 120                 125

Ser Lys Pro His Leu Arg Ser Ile Ser Ile Gln Cys Tyr Leu Cys Leu
    130                 135                 140

Leu Leu Asn Ser His Phe Leu Thr Glu Ala Gly Ile His Val Phe Ile
145                 150                 155                 160

Leu Gly Cys Phe Ser Ala Gly Leu Pro Lys Thr Glu Ala Asn Trp Val
                165                 170                 175

Asn Val Ile Ser Asp Leu Lys Lys Ile Glu Asp Leu Ile Gln Ser Met
            180                 185                 190

His Ile Asp Ala Thr Leu Tyr Thr Glu Ser Asp Val His Pro Ser Cys
        195                 200                 205

Lys Val Thr Ala Met Lys Cys Phe Leu Leu Glu Leu Gln Val Ile Ser
    210                 215                 220

Leu Glu Ser Gly Asp Ala Ser Ile His Asp Thr Val Glu Asn Leu Ile
225                 230                 235                 240

Ile Leu Ala Asn Asn Ser Leu Ser Ser Asn Gly Asn Val Thr Glu Ser
                245                 250                 255

Gly Cys Lys Glu Cys Glu Glu Leu Glu Glu Lys Asn Ile Lys Glu Phe
            260                 265                 270

Leu Gln Ser Phe Val His Ile Val Gln Met Phe Ile Asn Thr Ser
        275                 280                 285

<210> SEQ ID NO 80
<211> LENGTH: 10
<212> TYPE: PRT
<213> ORGANISM: Artificial Sequence
<220> FEATURE:
<223> OTHER INFORMATION: CD20 mimitope

<400> SEQUENCE: 80

Ala Cys Pro Tyr Ala Asn Pro Ser Leu Cys
1               5                   10

<210> SEQ ID NO 81
<211> LENGTH: 296
<212> TYPE: PRT

<213> ORGANISM: Artificial Sequence
<220> FEATURE:
<223> OTHER INFORMATION: CD20 mimitope-P2A-IL15

<400> SEQUENCE: 81

```
Met Glu Phe Gly Leu Ser Trp Val Phe Leu Val Ala Leu Phe Arg Gly
1               5                   10                  15

Val Gln Cys Ala Cys Pro Tyr Ala Asn Pro Ser Leu Cys Gly Gly Gly
            20                  25                  30

Gly Ser Gly Gly Gly Ser Ala Cys Pro Tyr Ala Asn Pro Ser Leu
        35                  40                  45

Cys Thr Thr Pro Ala Pro Arg Pro Pro Thr Pro Ala Pro Thr Ile
50                  55                  60

Ala Ser Gln Pro Leu Ser Leu Arg Pro Glu Ala Cys Arg Pro Ala Ala
65                  70                  75                  80

Gly Gly Ala Val His Thr Arg Gly Leu Asp Phe Ala Cys Asp Ile Tyr
                85                  90                  95

Ile Trp Ala Pro Leu Ala Gly Thr Cys Gly Val Leu Leu Leu Ser Leu
            100                 105                 110

Val Ile Thr Ala Thr Asn Phe Ser Leu Leu Lys Gln Ala Gly Asp Val
        115                 120                 125

Glu Glu Asn Pro Gly Pro Met Arg Ile Ser Lys Pro His Leu Arg Ser
130                 135                 140

Ile Ser Ile Gln Cys Tyr Leu Cys Leu Leu Leu Asn Ser His Phe Leu
145                 150                 155                 160

Thr Glu Ala Gly Ile His Val Phe Ile Leu Gly Cys Phe Ser Ala Gly
                165                 170                 175

Leu Pro Lys Thr Glu Ala Asn Trp Val Asn Val Ile Ser Asp Leu Lys
            180                 185                 190

Lys Ile Glu Asp Leu Ile Gln Ser Met His Ile Asp Ala Thr Leu Tyr
        195                 200                 205

Thr Glu Ser Asp Val His Pro Ser Cys Lys Val Thr Ala Met Lys Cys
210                 215                 220

Phe Leu Leu Glu Leu Gln Val Ile Ser Leu Glu Ser Gly Asp Ala Ser
225                 230                 235                 240

Ile His Asp Thr Val Glu Asn Leu Ile Ile Leu Ala Asn Asn Ser Leu
                245                 250                 255

Ser Ser Asn Gly Asn Val Thr Glu Ser Gly Cys Lys Glu Cys Glu Glu
            260                 265                 270

Leu Glu Glu Lys Asn Ile Lys Glu Phe Leu Gln Ser Phe Val His Ile
        275                 280                 285

Val Gln Met Phe Ile Asn Thr Ser
    290                 295
```

<210> SEQ ID NO 82
<211> LENGTH: 176
<212> TYPE: PRT
<213> ORGANISM: Artificial Sequence
<220> FEATURE:
<223> OTHER INFORMATION: ErbB epitope

<400> SEQUENCE: 82

```
Glu Gly Leu Ala Cys His Gln Leu Cys Ala Arg Gly His Cys Trp Gly
1               5                   10                  15

Pro Gly Pro Thr Gln Cys Val Asn Cys Ser Gln Phe Leu Arg Gly Gln
            20                  25                  30
```

```
Glu Cys Val Glu Glu Cys Arg Val Leu Gln Gly Leu Pro Arg Glu Tyr
            35                  40                  45

Val Asn Ala Arg His Cys Leu Pro Cys His Pro Glu Cys Gln Pro Gln
 50                  55                  60

Asn Gly Ser Val Thr Cys Phe Gly Pro Glu Ala Asp Gln Cys Val Ala
 65                  70                  75                  80

Cys Ala His Tyr Lys Asp Pro Pro Phe Cys Val Ala Arg Cys Pro Ser
                 85                  90                  95

Gly Val Lys Pro Asp Leu Ser Tyr Met Pro Ile Trp Lys Phe Pro Asp
            100                 105                 110

Glu Glu Gly Ala Cys Gln Pro Cys Pro Ile Asn Cys Thr His Ser Cys
            115                 120                 125

Val Asp Leu Asp Asp Lys Gly Cys Pro Ala Glu Gln Arg Ala Ser Pro
130                 135                 140

Leu Thr Ser Ile Ile Ser Ala Val Val Gly Ile Leu Leu Val Val Val
145                 150                 155                 160

Leu Gly Val Val Phe Gly Ile Leu Ile Gly Gly Gly Ser Gly Gly
                165                 170                 175
```

<210> SEQ ID NO 83
<211> LENGTH: 376
<212> TYPE: PRT
<213> ORGANISM: Artificial Sequence
<220> FEATURE:
<223> OTHER INFORMATION: ErbB epitope-P2A-IL15

<400> SEQUENCE: 83

```
Met Glu Phe Gly Leu Ser Trp Val Phe Leu Val Ala Leu Phe Arg Gly
 1               5                  10                  15

Val Gln Cys Glu Gly Leu Ala Cys His Gln Leu Cys Ala Arg Gly His
            20                  25                  30

Cys Trp Gly Pro Gly Pro Thr Gln Cys Val Asn Cys Ser Gln Phe Leu
            35                  40                  45

Arg Gly Gln Glu Cys Val Glu Glu Cys Arg Val Leu Gln Gly Leu Pro
 50                  55                  60

Arg Glu Tyr Val Asn Ala Arg His Cys Leu Pro Cys His Pro Glu Cys
 65                  70                  75                  80

Gln Pro Gln Asn Gly Ser Val Thr Cys Phe Gly Pro Glu Ala Asp Gln
                 85                  90                  95

Cys Val Ala Cys Ala His Tyr Lys Asp Pro Pro Phe Cys Val Ala Arg
            100                 105                 110

Cys Pro Ser Gly Val Lys Pro Asp Leu Ser Tyr Met Pro Ile Trp Lys
            115                 120                 125

Phe Pro Asp Glu Glu Gly Ala Cys Gln Pro Cys Pro Ile Asn Cys Thr
130                 135                 140

His Ser Cys Val Asp Leu Asp Asp Lys Gly Cys Pro Ala Glu Gln Arg
145                 150                 155                 160

Ala Ser Pro Leu Thr Ser Ile Ile Ser Ala Val Val Gly Ile Leu Leu
                165                 170                 175

Val Val Val Leu Gly Val Val Phe Gly Ile Leu Ile Gly Gly Gly Gly
                180                 185                 190

Ser Gly Gly Ala Thr Asn Phe Ser Leu Leu Lys Gln Ala Gly Asp Val
            195                 200                 205

Glu Glu Asn Pro Gly Pro Met Arg Ile Ser Lys Pro His Leu Arg Ser
            210                 215                 220
```

| | | | | | | | | | | | | | | |
|---|---|---|---|---|---|---|---|---|---|---|---|---|---|---|
|Ile|Ser|Ile|Gln|Cys|Tyr|Leu|Cys|Leu|Leu|Asn|Ser|His|Phe|Leu|
|225| | | |230| | | |235| | | |240| | |
|Thr|Glu|Ala|Gly|Ile|His|Val|Phe|Ile|Leu|Gly|Cys|Phe|Ser|Ala|Gly|
| | | | |245| | | |250| | | |255| | |
|Leu|Pro|Lys|Thr|Glu|Ala|Asn|Trp|Val|Asn|Val|Ile|Ser|Asp|Leu|Lys|
| | | |260| | | |265| | | |270| | |
|Lys|Ile|Glu|Asp|Leu|Ile|Gln|Ser|Met|His|Ile|Asp|Ala|Thr|Leu|Tyr|
| | |275| | | | |280| | | |285| | |
|Thr|Glu|Ser|Asp|Val|His|Pro|Ser|Cys|Lys|Val|Thr|Ala|Met|Lys|Cys|
| |290| | | | |295| | | |300| | |
|Phe|Leu|Leu|Glu|Leu|Gln|Val|Ile|Ser|Leu|Glu|Ser|Gly|Asp|Ala|Ser|
|305| | | |310| | | |315| | | |320| | |
|Ile|His|Asp|Thr|Val|Glu|Asn|Leu|Ile|Ile|Leu|Ala|Asn|Asn|Ser|Leu|
| | | |325| | | |330| | | |335| | |
|Ser|Ser|Asn|Gly|Asn|Val|Thr|Glu|Ser|Gly|Cys|Lys|Glu|Cys|Glu|
| | |340| | | |345| | | |350| | |
|Leu|Glu|Glu|Lys|Asn|Ile|Lys|Glu|Phe|Leu|Gln|Ser|Phe|Val|His|Ile|
| | |355| | | |360| | | |365| | |
|Val|Gln|Met|Phe|Ile|Asn|Thr|Ser|
|370| | | |375| | | |

<210> SEQ ID NO 84
<211> LENGTH: 1000
<212> TYPE: DNA
<213> ORGANISM: Artificial Sequence
<220> FEATURE:
<223> OTHER INFORMATION: CIITA targeting left homology arm

<400> SEQUENCE: 84

```
acaggaggta accatttaac aagaaagcag agtgatgtta gattatagca agatactgtt      60
gactgtagaa ggctctgagg ctagagagct gctttctata aaacagagtg atcatatatt     120
agaagaggtg ttaaagacat gttcacacca agctgagact tcctccttga taccaccagg     180
aggatgggca gagactggaa aagacactaa ctttctccct atgggagtca gtattattta     240
gcatcacttt ggcgggtcac cccaaaccat ctgactacaa gggtaccata tttgggttaa     300
cactcttttg gtataatttta tgttttagtc caatgtcttg ggatgaaaat gacaggtggg     360
ccacttatga tctccagaga aattcagggc aatttggtgt gggagtaggc atggtagagg     420
agagcagcat ctaagaagtc cccagcagag gctctcagct tgtcttgagg catctgggcg     480
gagggctatg atactggccc catcctgcag aaggtggcag atattggcag ctggcaccag     540
tgcggttcca ttgtgatcat catttctgaa cgtcagactg ttgaaggttc ccccaacaga     600
ctttctgtgc aactttctgt cttcaccaaa ttcagtccac agtaaggaag tgaaattaat     660
ttcagaggtg tggggagggc ttaagggagt gtggtaaaat tagagggtgt tcagaaacag     720
aaatctgacc gcttgggggcc accttgcagg gagagttttt ttgatgatcc ctcacttgtt     780
tctttgcatg ttggcttagc ttggcgggct cccaactggt gactggttag tgatgaggct     840
agtgatgagg ctgtgtgctt ctgagctggg catccgaagg catccttggg gaagctgagg     900
gcacgaggag gggctgccag actccgggag ctgctgcctg gctgggattc ctacacaatg     960
cgttgcctgg ctccacgccc tgctgggtcc tacctgtcag                          1000
```

<210> SEQ ID NO 85
<211> LENGTH: 1000
<212> TYPE: DNA
<213> ORGANISM: Artificial Sequence
<220> FEATURE:
<223> OTHER INFORMATION: CIITA targeting right homology arm

<400> SEQUENCE: 85

```
agccccaagg taaaaaggcc gggaaagcat cttaatttag cgtgcagtct cagctggtcc        60
tgccattcca gataaacaga gaaccattc tgaattgggg atgggggtga ggatgggaac       120
aggagtctgt gtcctgctgg ggcaggccat tggaagatgt gaaagagttg tctatttcct      180
tccaccggag ggagacttca ggtcagccag gtgtctggag tatgaaccat gtatcagcac      240
cgaaaggttc tagaagtcag actttcgggc agtgtgtcac taactctcag catgctggcc     300
tggctcggcc cacagcaagg tcttctcgcc tcccttggg taaatactga ggggtgcctc       360
tgcaggacgg gacctctgcc agactccact ccatacccag agaagcaggg aaaccaaaat     420
tggagtcagc cttgaggtgt agctgttgag ccctcagcag ctggggagag ctggcggatg    480
ctgccctccc cccagtttcc taatggtgtt gtttaaaaag ggtcagggga cggggaaca       540
gatggtggga agagcacagt gcagacacct ggcaccggct ctgaaggcag catggcagct     600
acaccgttgg ctgggaaggg tgtgcccctg aagaagtcgt ttacattctc gagtcaattt     660
tcctggagta tacaatggac ctgtgggaaa gcctgtatga aagggtaatg atgagggacc   720
tagcacagtg tccaatattt tataggaact ggaattgagc tcataggagc tcaatttat     780
tggcattgct gttgttggat ggttaaaggg gtggtatccc ttttctcaga ctcccctgaa     840
atgtatggtt tgctttgaac ccagagactg atgacaggtc tgccggtgtg gttgggtgca    900
gccttaagtt gctacgggaa agtgttggag ggggagaagt cagaggtaac cttgcccccct  960
ccctcaattc cagatgagga aattcaggcc tgaaaaggga                          1000
```

<210> SEQ ID NO 86
<211> LENGTH: 6604
<212> TYPE: DNA
<213> ORGANISM: Artificial Sequence
<220> FEATURE:
<223> OTHER INFORMATION: CIITA targeting plasmid

<400> SEQUENCE: 86

```
cgcctgacct ctcgaacagg aggtaaccat ttaacaagaa agcagagtga tgttagatta        60
tagcaagata ctgttgactg tagaaggctc tgaggctaga gagctgcttt ctataaaaca      120
gagtgatcat atattagaag aggtgttaaa gacatgttca caccaagctg agacttcctc    180
cttgatacca ccaggaggat gggcagagac tggaaaagac actaactttc tccctatggg  240
agtcagtatt atttagcatc actttggcgg gtcaccccaa accatctgac tacaagggta    300
ccatatttgg gttaacactc ttttggtata atttatgttt tagtccaatg tcttgggatg    360
aaaatgacag gtgggccact tatgatctcc agagaaattc agggcaattt ggtgtgggag   420
taggcatggt agaggagagc agcatctaag aagtccccag cagaggctct cagcttgtct    480
tgaggcatct gggcggaggg ctatgatact ggccccatcc tgcagaaggt ggcagatatt   540
ggcagctggc accagtgcgg ttccattgtg atcatcattt ctgaacgtca gactgttgaa   600
ggttcccca acagactttc tgtgcaactt tctgtcttca ccaaattcag tccacagtaa    660
ggaagtgaaa ttaatttcag aggtgtgggg agggcttaag ggagtgtggt aaaattagag    720
ggtgttcaga aacagaaatc tgaccgcttg gggccacctt gcaggagag ttttttttgat    780
gatccctcac ttgttctttt gcatgttggc ttagcttggc gggctcccaa ctggtgactg   840
gttagtgatg aggctagtga tgaggctgtg tgcttctgag ctgggcatcc gaaggcatcc   900
```

```
ttggggaagc tgagggcacg aggagggct gccagactcc gggagctgct gcctggctgg    960
gattcctaca caatgcgttg cctggctcca cgccctgctg ggtcctacct gtcagtcgag   1020
aaggatctgc gatcgctccg gtgccgtca gtgggcagag cgcacatcgc ccacagtccc    1080
cgagaagttg gggggagggg tcggcaattg aacgggtgcc tagagaaggt ggcgcggggt   1140
aaactgggaa agtgatgtcg tgtactggct ccgcctttt cccgagggtg ggggagaacc    1200
gtatataagt gcagtagtcg ccgtgaacgt tcttttcgc aacgggtttg ccgccagaac    1260
acagctgaag cttcgagggg ctcgcatctc tccttcacgc gcccgccgcc ctacctgagg   1320
ccgccatcca cgccggttga gtcgcgttct gccgcctccc gctgtggtg cctcctgaac    1380
tgcgtccgcc gtctaggtaa gtttaaagct caggtcgaga ccgggccttt gtccggcgct   1440
cccttggagc ctacctagac tcagccggct ctccacgctt tgcctgaccc tgcttgctca   1500
actctacgtc tttgtttcgt tttctgttct gcgccgttac agatccaagc tgtgaccggc   1560
gcctacgccg ccaccatgag gccctcaggc actgccgggg ccgccctcct ggccctgtta   1620
gccgctttgt gtccagcaag ccgcgccgga gtgcggaaat gtaagaaatg cgaaggaccc   1680
tgccggaagg tatgcaacgg cattgggatt ggcgaattca aggacagcct gagcattaat   1740
gctacaaaca tcaagcactt taagaattgc accagcatta gcggcgatct gcatatactg   1800
ccagtggctt ccgaggcga ctctttact catacccctc cgctggaccc tcaagagctg    1860
gacattctca agactgtgaa ggaaattacg gggtttctgc tcattcaggc ctggcctgaa   1920
aaccgcacgg atttgcatgc ctttgagaat ctggaaataa tcagaggccg gacgaaacag   1980
catggccagt tcagcctcgc ggtcgtctct ttgaatatta cgtcactcgg cctcaggtcc   2040
ctcaaagaga tttctgatgg cgatgtcatc atctctggta ataagaatct gtgttacgca   2100
aataccatca attggaagaa gctctttggg acctcaggtc aaaagactaa aattatctcc   2160
aaccgcggcg agaacagctg taaggctaca ggccaggttt gccacgcgct ctgctcccca   2220
gagggttgct ggggccctga gccaagggat tgcgtttcat gtcgcaacgt gtctcggggc   2280
agagaatgcg tggataaatg taacctctta gagggcgaac ctcgcgagtt tgttgagaac   2340
tcagaatgta tacagtgcca ccccgaatgt cttcctcagg ccatgaatat cacatgcacc   2400
ggacgcggac cagacaactg tatccaatgt gctcactaca ttgacggacc tcattgtgtg   2460
aaaacatgcc ccgcaggagt tatgggagaa acaacaccc tcgtttggaa atatgccgat    2520
gcaggtcacg tatgtcacct gtgccaccca aactgcactt atgggtgcac cgggccgggc   2580
ctggagggt gccctacgaa tggaccaaaa attcccagta ttgcaactgg gatggtcggg    2640
gcactgttgt tgctgcttgt ggttgccctc gggataggcc tgtttatgtc tggctccggc   2700
gccaccaatt tcagcctgct gaaacaggca ggcgacgtcg aagaaaatcc aggaccaatg   2760
cgaatatcaa aaccacactt gcgcagcatt tctatacagt gctatttgtg cttgttgctg   2820
aactctcact tcctcacaga ggctgggata cacgttttca tacttggatg ttttcagct   2880
gggctgccga agacagaggc gaattgggtg aatgtaattt cagacctcaa gaagatcgag   2940
gatctcatcc agtccatgca catcgacgct actctgtaca cagagagcga tgtccaccct   3000
tcttgtaagg ttaccgccat gaatgcttc cttttggaac tccaagtcat ctcattggaa    3060
tcaggggatg cgtccattca tgacaccgtg gaaaacctga taatactggc taacaacagc   3120
ttgtcaagta atgggaatgt tactgagtcc ggttgtaaag aatgtgaaga gctggaggag   3180
aagaacatta aggaattttt gcaatctttt gtacatattg ttcagatgtt tattaacaca   3240
agctgataaa acttgtttat tgcagcttat aatggttaca aataaagcaa tagcatcaca   3300
```

| | |
|---|---|
| aatttcacaa ataaagcatt tttttcactg cattctagtt gtggtttgtc caaactcatc | 3360 |
| aatgtatctt atcatgtctg taaggatcag ccccaaggta aaaaggccgg gaaagcatct | 3420 |
| taatttagcg tgcagtctca gctggtcctg ccattccaga taaacagaga aaccattctg | 3480 |
| aattggggat gggggtgagg atgggaacag gagtctgtgt cctgctgggg caggccattg | 3540 |
| gaagatgtga aagagttgtc tatttccttc caccggaggg agacttcagg tcagccaggt | 3600 |
| gtctggagta tgaaccatgt atcagcaccg aaaggttcta gaagtcagac tttcgggcag | 3660 |
| tgtgtcacta actctcagca tgctggcctg gctcggccca cagcaaggtc ttctcgcctc | 3720 |
| cctttgggta aatactgagg ggtgcctctg caggacggga cctctgccag actccactcc | 3780 |
| atacccagag aagcagggaa accaaaattg gagtcagcct tgaggtgtag ctgttgagcc | 3840 |
| ctcagcagct ggggagagct ggcggatgct gccctccccc cagtttccta atggtgttgt | 3900 |
| ttaaaaaggg tcaggggacg ggggaacaga tggtgggaag agcacagtgc agacacctgg | 3960 |
| caccggctct gaaggcagca tggcagctac accgttggct gggaagggtg tgcccctgaa | 4020 |
| gaagtcgttt acattctcga gtcaattttc ctggagtgta caatggacct gtgggaaagc | 4080 |
| ctgtatgaaa gggtaatgat gagggaccta gcacagtgtc caatattta taggaactgg | 4140 |
| aattgagctc ataggagctc aatttttattg gcattgctgt tgttggatgg ttaaaggggt | 4200 |
| ggtatccctt ttctcagact cccctgaaat gtatggtttg ctttgaaccc agagactgat | 4260 |
| gacaggtctg ccggtgtggt tgggtgcagc cttaagttgc tacgggaaag tgttggaggg | 4320 |
| ggagaagtca gaggtaacct tgcccccctcc ctcaattcca gatgaggaaa ttcaggcctg | 4380 |
| aaaagggaga tccaggctag gtggaggctc agtgatgata agtctgcgat ggtggatgca | 4440 |
| tgtgtcatgg tcatagctgt ttcctgtgtg aaattgttat ccgctcagag ggcacaatcc | 4500 |
| tattccgcgc tatccgacaa tctccaagac attaggtgga gttcagttcg gcgtatggca | 4560 |
| tatgtcgctg gaaagaacat gtgagcaaaa ggccagcaaa aggccaggaa ccgtaaaaag | 4620 |
| gccgcgttgc tggcgttttt ccataggctc cgccccctg acgagcatca aaaaatcga | 4680 |
| cgctcaagtc agaggtggcg aaacccgaca ggactataaa gataccaggc gtttccccct | 4740 |
| ggaagctccc tcgtgcgctc tcctgttccg accctgccgc ttaccggata cctgtccgcc | 4800 |
| tttctccctt cgggaagcgt ggcgctttct catagctcac gctgtaggta tctcagttcg | 4860 |
| gtgtaggtcg ttcgctccaa gctgggctgt gtgcacgaac ccccgttca gcccgaccgc | 4920 |
| tgcgccttat ccggtaacta tcgtcttgag tccaacccgg taagacacga cttatcgcca | 4980 |
| ctggcagcag ccactggtaa caggattagc agagcgaggt atgtaggcgg tgctacagag | 5040 |
| ttcttgaagt ggtggcctaa ctacggctac actagaagaa cagtatttgg tatctgcgct | 5100 |
| ctgctgaagc cagttacctt cggaaaaaga gttggtagct cttgatccgg caaacaaacc | 5160 |
| accgctggta gcggtggttt ttttgtttgc aagcagcaga ttacgcgcag aaaaaaagga | 5220 |
| tctcaagaag atcctttgat cttttctacg ggtctgacg ctctattcaa caaagccgcc | 5280 |
| gtcccgtcaa gtcagcgtaa atgggtaggg ggcttcaaat cgtcctcgtg ataccaattc | 5340 |
| ggagcctgct tttttgtaca aacttgttga taatggcaat tcaaggatct tcacctagat | 5400 |
| cctttaaat taaaaatgaa gttttaaatc aatctaaagt atatatgagt aaacttggtc | 5460 |
| tgacagttac caatgcttaa tcagtgaggc acctatctca gcgatctgtc tatttcgttc | 5520 |
| atccatagtt gcctgactcc ccgtcgtgta gataactacg atacgggagg gcttaccatc | 5580 |
| tggccccagt gctgcaatga taccgcgaga gccacgctca ccggctccag atttatcagc | 5640 |

```
aataaaccag ccagccggaa gggccgagcg cagaagtggt cctgcaactt tatccgcctc      5700
catccagtct attaattgtt gccgggaagc tagagtaagt agttcgccag ttaatagttt      5760
gcgcaacgtt gttgccattg ctacaggcat cgtggtgtca cgctcgtcgt ttggtatggc      5820
ttcattcagc tccggttccc aacgatcaag gcgagttaca tgatccccca tgttgtgcaa      5880
aaaagcggtt agctccttcg gtcctccgat cgttgtcaga agtaagttgg ccgcagtgtt      5940
atcactcatg gttatggcag cactgcataa ttctcttact gtcatgccat ccgtaagatg      6000
cttttctgtg actggtgagt actcaaccaa gtcattctga aatagtgta tgcggcgacc       6060 gagttgctct tgcccggcgt caatacggga taataccgcg ccacatagca gaactttaaa      6120
agtgctcatc attggaaaac gttcttcggg gcgaaaactc tcaaggatct taccgctgtt      6180
gagatccagt tcgatgtaac ccactcgtgc acccaactga tcttcagcat cttttacttt      6240
caccagcgtt tctgggtgag caaaaacagg aaggcaaaat gccgcaaaaa agggaataag      6300
ggcgacacgg aaatgttgaa tactcatact cttcctttt caatattatt gaagcattta       6360
tcagggttat tgtctcatga gcggatacat atttgaatgt atttagaaaa ataaacaaat      6420
aggggttccg cgcacatttc cccgaaaagt gccagatacc tgaaacaaaa cccatcgtac      6480
ggccaaggaa gtctccaata actgtgatcc accacaagcg ccagggtttt cccagtcacg      6540
acgttgtaaa acgacggcca gtcatgcata atccgcacgc atctggaata aggaagtgcc      6600
attc                                                                  6604

<210> SEQ ID NO 87
<211> LENGTH: 1042
<212> TYPE: DNA
<213> ORGANISM: Artificial Sequence
<220> FEATURE:
<223> OTHER INFORMATION: B2M targeting left homology arm

<400> SEQUENCE: 87
gcatataaaa cctcagcaga aataaagagg ttttgttgtt tggtaagaac ataccttggg        60
ttggttgggc acggtggctc gtgcctgtaa tcccaacact ttgggaggcc aaggcaggct       120
gatcacttga agttgggagt tcaagaccag cctggccaac atggtgaaat cccgtctcta       180
ctgaaaatac aaaaattaac caggcatggt ggtgtgtgcc tgtagtccca ggaatcactt       240
gaacccagga ggcggaggtt gcagtgagct gagatctcac cactgcacac tgcactccag       300
cctgggcaat ggaatgagat tccatcccaa aaataaaaa aataaaaaa taagaacat         360 accttgggtt gatccactta ggaacctcag ataataacat ctgccacgta tagagcaatt       420
gctatgtccc aggcactcta ctagacactt catacagttt agaaaatcag atgggtgtag       480
atcaaggcag gagcaggaac caaaaagaaa ggcataaaca taagaaaaaa aatgaagggg       540
gtggaaacag agtacaataa catgagtaat ttgatggggg ctattatgaa ctgagaaatg       600
aactttgaaa agtatcttgg ggccaaatca tgtagactct tgagtgatgt gttaaggaat       660
gctatgagtg ctgagagggc atcagaagtc cttgagagcc tccagagaaa ggctcttaaa       720
aatgcagcgc aatctccagt gacagaagat actgctagaa atctgctaga aaaaaaacaa       780
aaaaggcatg tatagaggaa ttatgaggga agataccaa gtcacggttt attcttcaaa        840
atggaggtgg cttgttggga aggtggaagc tcatttggcc agagtggaaa tggaattggg       900
agaaatcgat gaccaaatgt aaacacttgg tgcctgatat agcttgacac caagttagcc       960
ccaagtgaaa taccctggca atattaatgt gtcttttccc gatattcctc aggtactcca      1020
aagattcagg tttactcacg tc                                              1042
```

<210> SEQ ID NO 88
<211> LENGTH: 1023
<212> TYPE: DNA
<213> ORGANISM: Artificial Sequence
<220> FEATURE:
<223> OTHER INFORMATION: B2M targeting right homology arm

<400> SEQUENCE: 88

```
atccagcaga gaatggaaag tcaaatttcc tgaattgcta tgtgtctggg tttcatccat      60
ccgacattga agttgactta ctgaagaatg gagagagaat tgaaaaagtg gagcattcag     120
acttgtcttt cagcaaggac tggtctttct atctcttgta ctacactgaa ttcacccca     180
ctgaaaaaga tgagtatgcc tgccgtgtga accatgtgac tttgtcacag cccaagatag     240
ttaagtgggg taagtcttac attcttttgt aagctgctga aagttgtgta tgagtagtca     300
tatcataaag ctgctttgat ataaaaaagg tctatggcca tactaccctg aatgagtccc     360
atcccatctg atataaacaa tctgcatatt gggattgtca gggaatgttc ttaaagatca     420
gattagtggc acctgctgag atactgatgc acagcatggt ttctgaacca gtagtttccc     480
tgcagttgag cagggagcag cagcagcact tgcacaaata catatacact cttaacactt     540
cttacctact ggcttcctct agcttttgtg gcagcttcag gtatatttag cactgaacga     600
acatctcaag aaggtatagg cctttgtttg taagtcctgc tgtcctagca tcctataatc     660
ctggacttct ccagtacttt ctggctggat tggtatctga ggctagtagg aagggcttgt     720
tcctgctggg tagctctaaa caatgtattc atgggtagga acagcagcct attctgccag     780
ccttattcct aaccattta gacatttgtt agtacatggt attttaaaag taaaacttaa     840
tgtcttcctt ttttttctcc actgtctttt tcatagatcg agacatgtaa gcagcatcat     900
ggaggtaagt ttttgacctt gagaaaatgt ttttgtttca ctgtcctgag gactatttat     960
agacagctct aacatgataa ccctcactat gtggagaaca ttgacagagt aacattttag    1020
cag                                                                  1023
```

<210> SEQ ID NO 89
<211> LENGTH: 7813
<212> TYPE: DNA
<213> ORGANISM: Artificial Sequence
<220> FEATURE:
<223> OTHER INFORMATION: B2M Targeting Plasmid

<400> SEQUENCE: 89

```
gcatataaaa cctcagcaga aataaagagg ttttgttgtt tggtaagaac ataccttggg      60
ttggttgggc acgtggctc gtgcctgtaa tcccaacact tgggaggcc aaggcaggct      120
gatcacttga agttgggagt tcaagaccag cctggccaac atggtgaaat cccgtctcta     180
ctgaaaatac aaaaattaac caggcatggt ggtgtgtgcc tgtagtccca ggaatcactt     240
gaacccagga ggcggaggtt gcagtgagct gagatctcac cactgcacac tgcactccag     300
cctgggcaat ggaatgagat tccatcccaa aaaataaaaa aataaaaaaa taagaacat     360
accttgggtt gatccactta ggaacctcag ataataacat ctgccacgta tagagcaatt     420
gctatgtccc aggcactcta ctagacactt catacagttt agaaaatcag atgggtgtag     480
atcaaggcag gagcaggaac caaaagaaa ggcataaaca taagaaaaaa aatggaaggg     540
gtggaaacag agtacaataa catgagtaat ttgatggggg ctattatgaa ctgagaaatg     600
aactttgaaa agtatcttgg ggccaaatca tgtagactct tgagtgatgt gttaaggaat     660
```

```
gctatgagtg ctgagagggc atcagaagtc cttgagagcc tccagagaaa ggctcttaaa       720
aatgcagcgc aatctccagt gacagaagat actgctagaa atctgctaga aaaaaaacaa       780
aaaaggcatg tatagaggaa ttatgaggga aagataccaa gtcacggttt attcttcaaa       840
atggaggtgg cttgttggga aggtggaagc tcatttggcc agagtggaaa tggaattggg       900
agaaatcgat gaccaaatgt aaacacttgg tgcctgatat agcttgacac caagttagcc       960
ccaagtgaaa taccctggca atattaatgt gtcttttccc gatattcctc aggtactcca      1020
aagattcagg tttactcacg tcggcctcca acgcgtagat ctattgatta ttgactagtt      1080
attaatagta atcaattacg gggtcattag ttcatagccc atatatggag ttccgcgtta      1140
cataacttac ggtaaatggc ccgcctggct gaccgcccaa cgaccccgc ccattgacgt        1200 caataatgac gtatgttccc atagtaacgc caatagggac tttccattga cgtcaatggg      1260
tggactattt acggtaaact gcccacttgg cagtacatca agtgtatcat atgccaagta      1320
cgccccctat tgacgtcaat gacggtaaat ggcccgcctg gcattatgcc cagtacatga      1380
ccttatggga ctttcctact tggcagtaca tctacgtatt agtcatcgct attaccatgg      1440
gtcgaggtga gccccacgtt ctgcttcact ctccccatct ccccccctc cccacccca       1500 attttgtatt tatttatttt ttaattattt tgtgcagcga tggggggggg gggggggggg      1560
gcgcgcgcca gcggggcgg ggcggggcga gggcggggc gggggcgaggc ggagaggtgc       1620 ggcggcagcc aatcagagcg gcgcgctccg aaagtttcct tttatggcga ggcggcggcg      1680
gcggcggccc tataaaaagc gaagcgcgcg gcgggcggga gtcgctgcgt tgccttcgcc      1740
ccgtgccccg ctccgcgccg cctcgcgccg cccgccccgg ctctgactga ccgcgttact      1800
cccacaggtg agcgggcggg acggcccttc tcctccgggc tgtaattagc gcttggttta      1860 atgacgctc gtttctttc tgtggctgcg tgaaagcctt aaagggctcc gggagggccc        1920
tttgtgcggg gggagcggc tcgggggtg cgtgcgtgtg tgtgtgcgtg gggagcgccg        1980
cgtgcggccc gcgctgcccg gcggctgtga gcgctgcggg cgcggcgcgg gctttgtgc       2040 gctccgcgtg tgcgcgaggg gagcgcggcc ggggcggtg ccccgcggtg cgggggggct      2100
gcgaggggaa caaaggctgc gtgcgggtg tgtgcgtggg ggggtgagca ggggtgtgg       2160 gcgcggcggt cggctgtaa cccccccctg cacccccctc cccgagttgc tgagcacggc       2220
ccggcttcgg gtgcgggct ccgtgcgggg cgtggcgcgg ggctcgccgt gccgggcggg      2280
gggtggcggc aggtggggt gccgggcggg gcggggccgc ctcgggccgg ggagggctcg     2340 ggggagggc gcggcggccc cggagcgccg gcggctgtcg aggcgcggcg agccgcagcc      2400
attgcctttt atggtaatcg tgcgagaggg cgcagggact tcctttgtcc caaatctggc      2460
ggagccgaaa tctggggagggc gccgccgcac ccctctagc gggcgcgggc gaagcggtgc    2520
ggcgccggca ggaaggaaat gggcggggag ggccttcgtg cgtcgccgcg ccgccgtccc     2580
cttctccatc tccagcctcg gggctgccgc aggggacggg ctgccttcgg ggggacggg    2640 gcagggcggg gttcggcttc tggcgtgtga ccggcggat atctacgaag cggccgccct     2700
ctgctaacca tgttcatgcc ttcttctttt tcctacagct cctgggcaac gtgctggtta     2760
ttgtgctgtc tcatcattt ggcaaagtcg acgccaccat ggtggtcatg gcccctagaa      2820
cactgttcct gctgctgtct ggcgccctga cactgacaga gacatgggcc gtgatggccc     2880
ccagaaccct gatcctgggc ggcgtggtt caggcggagg aggttcagga ggagggggta      2940
gtggaggtgg tggttctatc cagcggaccc ctaagatcca ggtgtacagc agacacccccg    3000 ccgagaacgg caagagcaac ttcctgaact gctacgtgtc cggctttcac cccagcgaca     3060
```

```
ttgaggtgga cctgctgaag aacggcgagc ggatcgagaa ggtggaacac agcgatctga   3120
gcttcagcaa ggactggtcc ttctacctgc tgtactacac cgagttcacc cctaccgaga   3180
aggacgagta cgcctgcaga gtgaaccacg tgacactgag ccagcctaag atcgtgaagt   3240
gggatcgcga tatgggcgga ggcggatctg gtggcggagg aagtggcggc ggaggatctg   3300
gctcccactc cttgaagtat ttccacactt ccgtgtcccg gcccggccgc ggggagcccc   3360
gcttcatctc tgtgggctac gtggacgaca cccagttcgt gcgcttcgac aacgacgccg   3420
cgagtccgag gatggtgccg cgggcgccgt ggatggagca ggaggggtca gagtattggg   3480
accgggagac acggagcgcc aggacaccgc acagattttt ccgagtgaat ctgcggacgc   3540
tgcgcggcta ctacaatcag agcgaggccg ggtctcacac cctgcagtgg atgcatggct   3600
gcgagctggg gcccgacggg cgcttcctcc gcgggtatga acagttcgcc tacgacggca   3660
aggattatct cacccctgaat gaggacctgc gctcctggac cgcggtggac acggcggctc   3720
agatctccga gcaaaagtca aatgatgcct ctgaggcgga gcaccagaga gcctacctgg   3780
aagacacatg cgtggagtgg ctccacaaat acctggagaa ggggaaggag acgctgcttc   3840
acctggagcc cccaaagaca cacgtgactc accacccat ctctgaccat gaggccaccc   3900
tgaggtgctg ggccctgggc ttctaccctg cggagatcac actgacctgg cagcaggatg   3960
gggagggcca tacccaggac acggagctcg tggagaccag gcctgcaggg gatgaacct   4020
tccagaagtg ggcagctgtg gtggtgcctt ctggagagga gcagagatac acgtgccatg   4080
tgcagcatga gggctaccc gagcccgtca ccctgagatg gaagccggct tcccagccca   4140
ccatccccat cgtgggcatc attgctggcc tggttctcct tggatctgtg gtctctggag   4200
ctgtggttgc tgctgtgata tggaggaaga gagctcagg tggaaaagga gggagctact   4260
ctaaggctga gtggagcgac agtgcccagg ggtctgagtc tcacagcttg taatgaagcg   4320
gccgcgactc tagatcataa tcagccatac cacatttgta gaggttttac ttgctttaaa   4380
aaacctccca cacctccccc tgaacctgaa acataaaatg aatgcaattg ttgttgttaa   4440
cttgtttatt gcagcttata atggttacaa ataaagcaat agcatcacaa atttcacaaa   4500
taaagcattt ttttcactgc attctagttg tggtttgtcc aaactcatca atgtatctta   4560
tcatgtctga tccagcagag aatgaaagt caaatttcct gaattgctat gtgtctgggt   4620
tcatccatc cgacattgaa gttgacttac tgaagaatgg agagagaatt gaaaaagtgg   4680
agcattcaga cttgtctttc agcaaggact ggtctttcta tctcttgtac tacactgaat   4740
tcaccccac tgaaaagat gagtatgcct gccgtgtgaa ccatgtgact ttgtcacagc   4800
ccaagatagt taagtggggt aagtcttaca ttcttttgta agctgctgaa agttgtgtat   4860
gagtagtcat atcataaagc tgctttgata taaaaaaggt ctatggccat actccctga   4920
atgagtccca tcccatctga tataaacaat ctgcatattg ggattgtcag ggaatgttct   4980
taaagatcag attagtggca cctgctgaga tactgatgca cagcatggtt tctgaaccag   5040
tagtttccct gcagttgagc agggagcagc agcagcactt gcacaaatac atatacactc   5100
ttaacacttc ttacctactg gcttcctcta gcttttgtgg cagcttcagg tatatttagc   5160
actgaacgaa catctcaaga aggtataggc ctttgtttgt aagtcctgct gtcctagcat   5220
cctataatcc tggacttctc cagtactttc tggctggatt ggtatctgag gctagtagga   5280
agggcttgtt cctgctgggt agctctaaac aatgtattca tgggtaggaa cagcagccta   5340
ttctgccagc cttatttcta accatttag acatttgtta gtacatggta ttttaaaagt   5400
```

```
aaaacttaat gtcttccttt tttttctcca ctgtcttttt catagatcga gacatgtaag    5460
cagcatcatg gaggtaagtt tttgaccttg agaaaatgtt tttgtttcac tgtcctgagg    5520
actatttata gacagctcta acatgataac cctcactatg tggagaacat tgacagagta    5580
acattttagc agaggctagg tggaggctca gtgatgataa gtctgcgatg gtggatgcat    5640
gtgtcatggt catagctgtt tcctgtgtga aattgttatc cgctcagagg gcacaatcct    5700
attccgcgct atccgacaat ctccaagaca ttaggtggag ttcagttcgg cgtatggcat    5760
atgtcgctgg aaagaacatg tgagcaaaag gccagcaaaa ggccaggaac cgtaaaaagg    5820
ccgcgttgct ggcgtttttc cataggctcc gcccccctga cgagcatcac aaaaatcgac    5880
gctcaagtca gaggtggcga aacccgacag gactataaag ataccaggcg tttccccctg    5940
gaagctccct cgtgcgctct cctgttccga cctgccgct taccggatac ctgtccgcct    6000
ttctcccttc gggaagcgtg cgctttctc atagctcacg ctgtaggtat ctcagttcgg    6060
tgtaggtcgt tcgctccaag ctgggctgtg tgcacgaacc ccccgttcag cccgaccgct    6120
gcgccttatc cggtaactat cgtcttgagt ccaacccggt aagacacgac ttatcgccac    6180
tggcagcagc cactggtaac aggattagca gagcgaggta tgtaggcggt gctacagagt    6240
tcttgaagtg gtggcctaac tacggctaca ctagaagaac agtatttggt atctgcgctc    6300
tgctgaagcc agttaccttc ggaaaaagag ttggtagctc ttgatccggc aaacaaacca    6360
ccgctggtag cggtggtttt tttgtttgca agcagcagat tacgcgcaga aaaaaggat    6420 ctcaagaaga tcctttgatc ttttctacgg ggtctgacgc tctattcaac aaagccgccg    6480
tcccgtcaag tcagcgtaaa tgggtagggg gcttcaaatc gtcctcgtga taccaattcg    6540
gagcctgctt ttttgtacaa acttgttgat aatggcaatt caaggatctt cacctagatc    6600
cttttaaatt aaaaatgaag ttttaaatca atctaaagta tatatgagta aacttggtct    6660
gacagttacc aatgcttaat cagtgaggca cctatctcag cgatctgtct atttcgttca    6720
tccatagttg cctgactccc cgtcgtgtag ataactacga tacgggaggg cttaccatct    6780
ggccccagtg ctgcaatgat accgcgagag ccacgctcac cggctccaga tttatcagca    6840
ataaaccagc cagccggaag ggccgagcgc agaagtggtc ctgcaacttt atccgcctcc    6900
atccagtcta ttaattgttg ccgggaagct agagtaagta gttcgccagt taatagtttg    6960
cgcaacgttg ttgccattgc tacaggcatc gtggtgtcac gctcgtcgtt tggtatggct    7020
tcattcagct ccggttccca acgatcaagg cgagttacat gatccccat gttgtgcaaa    7080 aaagcggtta gctccttcgg tcctccgatc gttgtcagaa gtaagttggc cgcagtgtta    7140
tcactcatgg ttatggcagc actgcataat tctcttactg tcatgccatc cgtaagatgc    7200
ttttctgtga ctggtgagta ctcaaccaag tcattctgag aatagtgtat gcggcgaccg    7260
agttgctctt gcccggcgtc aatacgggat aataccgcgc cacatagcag aactttaaaa    7320
gtgctcatca ttggaaaacg ttcttcgggg cgaaaactct caaggatctt accgctgttg    7380
agatccagtt cgatgtaacc cactcgtgca cccaactgat cttcagcatc ttttactttc    7440
accagcgttt ctgggtgagc aaaaacagga aggcaaaatg ccgcaaaaaa gggaataagg    7500
gcgacacgga aatgttgaat actcatactc ttcctttttc aatattattg aagcatttat    7560
cagggttatt gtctcatgag cggatacata tttgaatgta tttagaaaaa taaacaaata    7620
ggggttccgc gcacatttcc ccgaaaagtg ccagatacct gaaacaaaac ccatcgtacg    7680
gccaaggaag tctccaataa ctgtgatcca ccacaagcgc cagggttttc ccagtcacga    7740
cgttgtaaaa cgacggccag tcatgcataa tccgcacgca tctggaataa ggaagtgcca    7800
```

<210> SEQ ID NO 90
<211> LENGTH: 1205
<212> TYPE: DNA
<213> ORGANISM: Artificial Sequence
<220> FEATURE:
<223> OTHER INFORMATION: AAVS1 targeting left homology arm

<400> SEQUENCE: 90

| | | |
|---|---|---|
| actctgcccc aggcctcctt accattcccc ttcgacctac tctcttccgc attggagtcg | 60 |
| ctttaactgg ccctggcttt ggcagcctgt gctgacccat gcagtcctcc ttaccatccc | 120 |
| tccctcgact tcccctcttc cgatgttgag cccctccagc cggtcctgga ctttgtctcc | 180 |
| ttccctgccc tgccctctcc tgaacctgag ccagctccca tagctcagtc tggtctatct | 240 |
| gcctggccct ggccattgtc actttgcgct gccctcctct cgcccccgag tgcccttgct | 300 |
| gtgccgccgg aactctgccc tctaacgctg ccgtctctct cctgagtccg gaccactttg | 360 |
| agctctactg gcttctgcgc cgcctctggc ccactgtttc ccttcccag gcaggtcctg | 420 |
| cttttctctga cctgcattct ctcccctggg cctgtgccgc tttctgtctg cagcttgtgg | 480 |
| cctgggtcac ctctacggct ggcccagatc cttccctgcc gcctccttca ggttccgtct | 540 |
| tcctccactc cctcttcccc ttgctctctg ctgtgttgct gcccaaggat gctctttccg | 600 |
| gagcacttcc ttctcggcgc tgcaccacgt gatgtcctct gagcggatcc tccccgtgtc | 660 |
| tgggtcctct ccgggcatct ctcctcccctc acccaacccc atgccgtctt cactcgctgg | 720 |
| gttcccttttt ccttctcctt ctggggcctg tgccatctct cgtttcttag gatggccttc | 780 |
| tccgacggat gtctcccttg cgtcccgcct ccccttcttg taggcctgca tcatcaccgt | 840 |
| ttttctggac aaccccaaag tacccgtct ccctggcttt agccacctct ccatcctctt | 900 |
| gctttctttg cctggacacc ccgttctcct gtggattcgg gtcacctctc actccttca | 960 |
| tttgggcagc tcccctaccc cccttacctc tctagtctgt gctagctctt ccagcccct | 1020 |
| gtcatggcat cttccagggg tccgagagct cagctagtct tcttcctcca acccgggccc | 1080 |
| ctatgtccac ttcaggacag catgtttgct gcctccaggg atcctgtgtc cccgagctgg | 1140 |
| gaccaccta tattcccagg gccggttaat gtggctctgg ttctgggtac ttttatctgt | 1200 |
| ccccct | 1205 |

<210> SEQ ID NO 91
<211> LENGTH: 1200
<212> TYPE: DNA
<213> ORGANISM: Artificial Sequence
<220> FEATURE:
<223> OTHER INFORMATION: AAVS1 targeting right homology arm

<400> SEQUENCE: 91

| | | |
|---|---|---|
| ccacccaca gtggggccac tagggacagg attggtgaca gaaaagcccc atccttaggc | 60 |
| ctcctccttc ctagtctcct gatattgggt ctaaccccca cctcctgtta ggcagattcc | 120 |
| ttatctggtg acacacccc atttcctgga gccatctctc tccttgccag aacctctaag | 180 |
| gtttgcttac gatggagcca gagaggatcc tgggaggag agcttggcag ggggtgggag | 240 |
| ggaagggggg gatgcgtgac ctgcccggtt ctcagtggcc accctgcgct accctctccc | 300 |
| agaacctgag ctgctctgac gcggccgtct ggtgcgtttc actgatcctg gtgctgcagc | 360 |
| ttccttacac ttcccaagag gagaagcagt ttggaaaaac aaaatcagaa taagttggtc | 420 |

```
ctgagttcta actttggctc ttcacctttc tagtccccaa tttatattgt tcctccgtgc    480
gtcagtttta cctgtgagat aaggccagta gccagccccg tcctggcagg gctgtggtga    540
ggaggggggt gtccgtgtgg aaaactccct tgtgagaat ggtgcgtcct aggtgttcac     600
caggtcgtgg ccgcctctac tccctttctc tttctccatc cttctttcct taaagagtcc    660
ccagtgctat ctgggacata ttcctccgcc cagagcaggg tcccgcttcc ctaaggccct    720
gctctgggct tctgggtttg agtccttggc aagcccagga gaggcgctca ggcttccctg    780 tccccctttcc tcgtccacca tctcatgccc ctggctctcc tgccccttcc ctacaggggt   840
tcctggctct gctcttcaga ctgagccccg ttccccctgca tccccgtacc cctgcatccc   900
ccttcccctg catcccccag aggccccagg ccacctactt ggcctggacc ccacgagagg    960
ccaccccagc cctgtctacc aggctgcctt ttgggtggat tctcctccaa ctgtggggtg   1020
actgcttggc aaactcactc ttcggggtat cccaggaggc ctggagcatt ggggtgggct   1080
ggggttcaga gaggagggat tcccttctca ggttacgtgg ccaagaagca ggggagctgg   1140
gtttgggtca ggtctgggtg tggggtgacc agcttatgct gtttgcccag gacagcctag   1200
```

<210> SEQ ID NO 92
<211> LENGTH: 7971
<212> TYPE: DNA
<213> ORGANISM: Artificial Sequence
<220> FEATURE:
<223> OTHER INFORMATION: AAVS1 Targeting plasmid

<400> SEQUENCE: 92

```
actctgcccc aggcctcctt accattcccc ttcgacctac tctcttccgc attggagtcg     60
ctttaactgg ccctggcttt ggcagcctgt gctgacccat gcagtcctcc ttaccatccc    120
tccctcgact tcccctcttc cgatgttgag ccctccagc cggtcctgga ctttgtctcc    180
ttccctgccc tgccctctcc tgaacctgag ccagctccca tagctcagtc tggtctatct    240 gcctggcccct ggccattgtc actttgcgct gccctcctct cgcccccgag tgcccttgct   300
gtgccgccgg aactctgccc tctaacgctg ccgtctctct cctgagtccg gaccactttg    360
agctctactg gcttctgcgc cgcctctggc ccactgtttc cccttcccag gcaggtcctg    420 cttttctctga cctgcattct ctcccctggg cctgtgccgc tttctgtctg cagcttgtgg    480
cctgggtcac ctctacggct ggcccagatc cttccctgcc gcctccttca ggttccgtct    540
tcctccactc cctcttcccc ttgctctctg ctgtgttgct gcccaaggat gctctttccg    600
gagcacttcc ttctcggcgc tgcaccacgt gatgtcctct gagcggatcc tccccgtgtc    660
tgggtcctct ccgggcatct ctcctccctc acccaacccc atgccgtctt cactcgctgg    720
gttccctttt ccttctcctt ctggggcctg tgccatctct cgtttcttag gatggccttc    780
tccgacggat gtctcccttg cgtcccgcct cccttcttg taggcctgca tcatcaccgt     840
ttttctggac aaccccaaag tacccgtct ccctggcttt agccacctct ccatcctctt    900
gctttctttg cctggacacc ccgttctcct gtggattcgg gtcacctctc actcctttca    960
tttgggcagc tcccctaccc cccttacctc tctagtctgt gctagctctt ccagcccct    1020 gtcatggcat cttccagggg tccgagagct cagctagtct tcttcctcca acccgggccc   1080
ctatgtccac ttcaggacag catgtttgct gcctccaggg atcctgtgtc cccgagctgg   1140 gaccaccttta tattcccagg gccggttaat gtggctctgg ttctgggtac ttttatctgt   1200
cccctgcggc cgcacgcgta gatcattga ttattgacta gttattaata gtaatcaatt    1260
acggggtcat tagttcatag cccatatatg gagttccgcg ttacataact tacggtaaat    1320
```

```
ggcccgcctg gctgaccgcc caacgacccc cgcccattga cgtcaataat gacgtatgtt    1380
cccatagtaa cgccaatagg gactttccat tgacgtcaat gggtggacta tttacggtaa    1440
actgcccact tggcagtaca tcaagtgtat catatgccaa gtacgccccc tattgacgtc    1500
aatgacggta aatggcccgc ctggcattat gcccagtaca tgaccttatg ggactttcct    1560
acttggcagt acatctacgt attagtcatc gctattacca tgggtcgagg tgagccccac    1620
gttctgcttc actctcccca tctcccccc ctccccaccc ccaattttgt atttatttat    1680 ttttaatta ttttgtgcag cgatggggg ggggggggg ggggcgcgcg ccaggcgggg    1740
cggggcgggg cgaggggcgg ggcggggcga ggcggagagg tgcggcggca gccaatcaga    1800
gcggcgcgct ccgaaagttt cctttatgg cgaggcggcg gcggcggcgg ccctataaaa    1860
agcgaagcgc gcggcgggcg ggagtcgctg cgttgccttc gccccgtgcc ccgctccgcg    1920
ccgcctcgcg ccgcccgccc cggctctgac tgaccgcgtt actcccacag gtgagcgggc    1980
gggacggccc ttctcctccg ggctgtaatt agcgcttggt ttaatgacgg ctcgtttctt    2040
ttctgtggct gcgtgaaagc cttaaagggc tccgggaggg ccctttgtgc gggggggagc    2100
ggctcggggg gtgcgtgcgt gtgtgtgtgc gtggggagcg ccgcgtgcgg cccgcgctgc    2160
ccggcggctg tgagcgctgc gggcgcggcg cggggctttg tgcgctccgc gtgtgcgcga    2220
ggggagcgcg gccgggggcg gtgccccgcg gtgcggggg gctgcgaggg gaacaaaggc    2280
tgcgtgcggg gtgtgtgcgt gggggggtga gcaggggtg tgggcgcggc ggtcgggctg    2340
taaccccccc ctgcaccccc ctccccgagt tgctgagcac ggcccggctt cgggtgcggg    2400
gctccgtgcg gggcgtggcg cggggctcgc cgtgccgggc gggggtggc ggcaggtggg    2460 ggtgccgggc ggggcggggc cgcctcgggc cgggagggc tcggggagg ggcgcggcgg    2520 ccccggagcg ccggcggctg tcgaggcgcg gcgagccgca gccattgcct tttatggtaa    2580
tcgtgcgaga gggcgcaggg acttcctttg tcccaaatct ggcggagccg aaatctggga    2640
ggcgccgccg cacccctct agcggcgcg ggcgaagcg tgcggcgccg gcaggaagga    2700
aatgggcggg gagggccttc gtgcgtcgcc gcgccgccgt cccttctcc atctccagcc    2760 tcggggctgc cgcaggggga cggctgcctt cggggggac ggggcagggc ggggttcggc    2820
ttctggcgtg tgaccggcgg gatatctacg aagcggccgc cctctgctaa ccatgttcat    2880
gccttcttct tttcctaca gctcctgggc aacgtgctgg ttattgtgct gtctcatcat    2940
tttggcaaag tcgacgccac catgctgctg ctggtcacat ctctgctgct gtgcgagctg    3000
ccccatcctg cctttctgct gatccccgac atccagatga cccagaccac aagcagcctg    3060
tctgccagcc tgggcgatag agtgaccatc agctgtagag ccagccagga catcagcaag    3120
tacctgaact ggtatcagca aaagcccgac ggcaccgtga agctgctgat ctaccacacc    3180
agcagactgc acagcggcgt gccaagcaga ttttctggca gcggctctgg caccgactac    3240
agcctgacaa tcagcaacct ggaacaagag gatatcgcta cctacttctg ccagcaaggc    3300
aacacccctg cttacacctt tggcggaggc accaagctgg aaatcaccgg ctctacaagc    3360
ggcagcggca aacctggatc tggcgaggga tctaccaagg cgaagtgaa actgcaagag    3420 tctggccctg gactggtggc cccatctcag tctctgagcg tgacctgtac agtcagcgga    3480
gtgtccctgc ctgattacgg cgtgtcctgg atcagacagc ctcctcggaa aggcctggaa    3540
tggctgggag tgatctgggg cagcgagaca acctactaca acagcgccct gaagtcccgg    3600
ctgaccatca tcaaggacaa ctccaagagc caggtgttcc tgaagatgaa cagcctgcag    3660
```

```
accgacgaca ccgccatcta ctattgcgcc aagcactact actacggcgg cagctacgcc    3720
atggattatt ggggccaggg caccagcgtg accgtgtcta gcacgacgac tcctgctcca    3780
aggcctccta cacctgcacc aaccattgca agtcagccgt tgagcctccg gccagaagca    3840
tgtcgcccag ccgcaggcgg ggctgtacac acgagaggct tggatttcgc atgtgacatc    3900
tatatctggg ccccactggc cggcacctgc ggcgtgctgc tgctgagcct ggtgatcacc    3960
aagcgaggcc gcaaaaaact cctttatata ttcaagcaac cttttatgag gcccgtccag    4020
accacgcaag aggaagatgg gtgctcttgc cgctttccag aggaagagga gggggctgc     4080 gaacttagag tgaagttcag cagatccgcc gatgctcccg cctatcagca gggccaaaac    4140
cagctgtaca acgagctgaa cctggggaga agagaagagt acgacgtgct ggacaagcgg    4200
agaggcagag atcctgaaat gggcggcaag cccagacgga agaatcctca agagggcctg    4260
tataatgagc tgcagaaaga caagatggcc gaggcctaca gcgagatcgg aatgaagggc    4320
gagcgcagaa gaggcaaggg acacgatgga ctgtaccagg gcctgagcac cgccaccaag    4380
gatacctatg atgccctgca catgcaggcc ctgcctccaa gataataaaa cttgtttatt    4440
gcagcttata atggttacaa ataaagcaat agcatcacaa atttcacaaa taaagcattt    4500
ttttcactgc attctagttg tggtttgtcc aaactcatca atgtatctta ccaccccaca    4560
gtggggccac tagggacagg attggtgaca gaaaagcccc atccttaggc ctcctccttc    4620
ctagtctcct gatattgggt ctaacccca cctcctgtta ggcagattcc ttatctggtg    4680
acacaccccc atttcctgga gccatctctc tccttgccag aacctctaag gtttgcttac    4740
gatggagcca gagaggatcc tgggagggag agcttggcag ggggtgggag ggaaggggg    4800 gatgcgtgac ctgcccggtt ctcagtggcc accctgcgct accctctccc agaacctgag    4860
ctgctctgac gcggccgtct ggtgcgtttc actgatcctg gtgctgcagc ttccttacac    4920
ttcccaagag gagaagcagt ttggaaaaac aaaatcagaa taagttggtc ctgagttcta    4980
actttggctc ttcacctttc tagtccccaa tttatattgt tcctccgtgc gtcagtttta    5040
cctgtgagat aaggccagta gccagccccg tcctggcagg gctgtggtga ggaggggggt    5100
gtccgtgtgg aaaactccct tgtgagaat ggtgcgtcct aggtgttcac caggtcgtgg    5160
ccgcctctac tcccttctc tttctccatc cttctttcct taaagagtcc ccagtgctat    5220
ctgggacata ttcctccgcc cagagcaggg tcccgcttcc ctaaggccct gctctgggct    5280
tctgggtttg agtccttggc aagcccagga gaggcgctca ggcttccctg tcccccttcc    5340
tcgtccacca tctcatgccc ctggctctcc tgcccttcc ctacaggggt tcctggctct    5400
gctcttcaga ctgagccccg ttcccctgca tccccgtacc cctgcatccc ccttcccctg    5460 catccccag aggccccagg ccacctactt ggcctggacc ccacgagagg ccaccccagc    5520
cctgtctacc aggctgcctt tgggtggat tctcctccaa ctgtggggtg actgcttggc    5580
aaactcactc ttcggggtat cccaggagc ctggagcatt ggggtgggct ggggttcaga    5640
gaggagggat tcccttctca ggttacgtgg ccaagaagca gggagctgg gtttgggtca    5700 ggtctgggtg tggggtgacc agcttatgct gtttgcccag acagcctag aggctaggtg    5760 gaggctcagt gatgataagt ctgcgatggt ggatgcatgt gtcatggtca tagctgtttc    5820
ctgtgtgaaa ttgttatccg ctcagagggc acaatcctat tccgcgctat ccgacaatct    5880
ccaagacatt aggtggagtt cagttcggcg tatggcatat gtcgctggaa agaacatgtg    5940
agcaaaaggc cagcaaaagg ccaggaaccg taaaaaggcc gcgttgctgg cgttttccca    6000
taggctccgc cccctgacg agcatcacaa aaatcgacgc tcaagtcaga ggtggcgaaa    6060
```

-continued

```
cccgacagga ctataaagat accaggcgtt tccccctgga agctccctcg tgcgctctcc    6120
tgttccgacc ctgccgctta ccggatacct gtccgccttt ctcccttcgg gaagcgtggc    6180
gctttctcat agctcacgct gtaggtatct cagttcggtg taggtcgttc gctccaagct    6240
gggctgtgtg cacgaacccc ccgttcagcc cgaccgctgc gccttatccg gtaactatcg    6300
tcttgagtcc aacccggtaa gacacgactt atcgccactg gcagcagcca ctggtaacag    6360
gattagcaga gcgaggtatg taggcggtgc tacagagttc ttgaagtggt ggcctaacta    6420
cggctacact agaagaacag tatttggtat ctgcgctctg ctgaagccag ttaccttcgg    6480
aaaaagagtt ggtagctctt gatccggcaa acaaaccacc gctggtagcg gtggtttttt    6540
tgtttgcaag cagcagatta cgcgcagaaa aaaaggatct caagaagatc ctttgatctt    6600
ttctacgggg tctgacgctc tattcaacaa agccgccgtc cgtcaagtc agcgtaaatg    6660 ggtaggggc ttcaaatcgt cctcgtgata ccaattcgga gcctgctttt ttgtacaaac    6720
ttgttgataa tggcaattca aggatcttca cctagatcct tttaaattaa aaatgaagtt    6780
ttaaatcaat ctaaagtata tgagtaaaa cttggtctga cagttaccaa tgcttaatca    6840
gtgaggcacc tatctcagcg atctgtctat ttcgttcatc catagttgcc tgactccccg    6900
tcgtgtagat aactacgata cgggagggct taccatctgg ccccagtgct gcaatgatac    6960
cgcgagagcc acgctcaccg gctccagatt tatcagcaat aaaccagcca gccggaaggg    7020
ccgagcgcag aagtggtcct gcaactttat ccgcctccat ccagtctatt aattgttgcc    7080
gggaagctag agtaagtagt tcgccagtta atagtttgcg caacgttgtt gccattgcta    7140
caggcatcgt ggtgtcacgc tcgtcgtttg gtatggcttc attcagctcc ggttcccaac    7200
gatcaaggcg agttacatga tcccccatgt tgtgcaaaaa agcggttagc tccttcggtc    7260
ctccgatcgt tgtcagaagt aagttggccg cagtgttatc actcatggtt atggcagcac    7320
tgcataattc tcttactgtc atgccatccg taagatgctt ttctgtgact ggtgagtact    7380
caaccaagtc attctgagaa tagtgtatgc ggcgaccgag ttgctcttgc ccggcgtcaa    7440
tacgggataa taccgcgcca catagcagaa ctttaaaagt gctcatcatt ggaaaacgtt    7500
cttcggggcg aaaactctca aggatcttac cgctgttgag atccagttcg atgtaaccca    7560
ctcgtgcacc caactgatct tcagcatctt ttactttcac cagcgtttct gggtgagcaa    7620
aaacaggaag gcaaaatgcc gcaaaaaagg gaataagggc gacacggaaa tgttgaatac    7680
tcatactctt cctttttcaa tattattgaa gcatttatca gggttattgt ctcatgagcg    7740
gatacatatt tgaatgtatt tagaaaaata aacaaatagg ggttccgcgc acatttcccc    7800
gaaaagtgcc agataccctga aacaaacccc atcgtacggc caaggaagtc tccaataact    7860
gtgatccacc acaagcgcca gggttttccc agtcacgacg ttgtaaaacg acggccagtc    7920
atgcataatc cgcacgcatc tggaataagg aagtgccatt ccgcctgacc t            7971
```

<210> SEQ ID NO 93
<211> LENGTH: 24
<212> TYPE: DNA
<213> ORGANISM: Artificial Sequence
<220> FEATURE:
<223> OTHER INFORMATION: B2M target gRNA

<400> SEQUENCE: 93
tttactcacg tcatccagca gaga    24

<210> SEQ ID NO 94

```
<211> LENGTH: 24
<212> TYPE: DNA
<213> ORGANISM: Artificial Sequence
<220> FEATURE:
<223> OTHER INFORMATION: AAVS1 target gRNA

<400> SEQUENCE: 94
tttatctgtc ccctccaccc caca                                            24

<210> SEQ ID NO 95
<211> LENGTH: 24
<212> TYPE: DNA
<213> ORGANISM: Artificial Sequence
<220> FEATURE:
<223> OTHER INFORMATION: CIITA target gRNA

<400> SEQUENCE: 95
tttaccttgg ggctctgaca ggta                                            24
```